United States Patent [19]
Tartaglia et al.

[11] Patent Number: 6,130,066
[45] Date of Patent: Oct. 10, 2000

[54] VECTORS HAVING ENHANCED EXPRESSION AND METHODS OF MAKING AND USES THEREOF

[75] Inventors: James Tartaglia, Schenectady; William I. Cox, Sand Lake; Russell Robert Gettig, Averill Park; Hector Martinez, Menands; Enzo Paoletti, Delmar; Steven E. Pincus, East Greenbush, all of N.Y.

[73] Assignee: Virogenetics Corporation, Troy, N.Y.

[21] Appl. No.: 09/079,587

[22] Filed: May 15, 1998

Related U.S. Application Data

[62] Division of application No. 08/816,155, Mar. 12, 1997, Pat. No. 5,990,091.

[51] Int. Cl.$^7$ ..................................................... C12P 21/06
[52] U.S. Cl. .................. 435/69.1; 435/320.1; 435/91.41; 536/23.72
[58] Field of Search ................................ 435/320.1, 69.1, 435/91.41; 514/44; 424/93.2; 536/23.72

[56] References Cited

U.S. PATENT DOCUMENTS

| | | | |
|---|---|---|---|
| 4,738,922 | 4/1988 | Haseltine et al. | 435/69.3 |
| 5,302,517 | 4/1994 | Rhode, III | 435/69.1 |

OTHER PUBLICATIONS

Orkin et al. Report and recommendations of the panel to assess the NIH investment in research on gene therapy. www.nih.gov/news/panelrep. html, 1995.

Park et al., Proc. Natl. Acad. Sci. USA 91:4713–4717 (1994).

*Primary Examiner*—John S. Brusca
*Attorney, Agent, or Firm*—Frommer Lawrence & Haug LLP; William S. Frommer; Thomas J. Kowalski

[57] ABSTRACT

Disclosed and claimed are vectors having enhanced expression and methods for making and using them. Enhancement of expression is from substantially co-temporal expression of at least one first nucleic acid molecule and at least one second nucleic acid molecule. The second nucleic acid molecule encodes a transcription factor or a translation factor or a transcription factor and a translation factor. The contemporaneous expression can be from operably linking the first and second nucleic molecules to a single promoter, or from operably linking the first nucleic acid molecule to a first promoter and the second nucleic molecule to a second promoter wherein the first and second promoters function substantially contemporaneously. Thus, the first and second nucleic acid molecules can be at the same locus in the vector, or at different loci. The second nucleic acid molecule can encode: one transcription factor or more than one transcription factor; or one translation factor or more than one translation factor; or at least one transcription factor and at least one translation factor. The transcription factor can be from vaccinia H4L, D6, A7, G8R, A1L, A2L, H5R, or combinations thereof. The translation factor can be from a K3L open reading frame, an E3L open reading frame, a VAI RNA, an EBER RNA, a sigma 3 open reading frame, a TRBP open reading frame, or combinations thereof. The vector can be a poxvirus such as an attenuated poxvirus, e.g., NYVAC, or ALVAC.

24 Claims, 30 Drawing Sheets

FIG. IA

Nucleotide sequence of the insert in vP1380 containing the mutagenized H4L orf and lacZ orf under the H6 promoter.

| Characteristic | Position(s) |
|---|---|
| Left arm | 1-798 |
| Right arm | 6636-7319 |
| H6 promoter | C3307-3184 and C6495-6372 |
| H4L orf | C3183-799 |
| T to C mutations | C2836 and C2839 |
| lacZ orf | C6371-3327 |

```
   1 GGATCCTGCC GTTCCTATTC TAGACCAAAA ATTCGGTTTC ATGTTTTCGA AGCGGTGTTC
  61 TGCAACAAGT CGGGGATCGT GTTCTACATA TTTGGCGGCA TTATCCAGTA TCTGCCTATT
 121 GATCTTCATT TCGTTTTCGA TTCTGGCTAT TTCAAAATAA AATCCCGATG ATAGACCTCC
 181 AGACTTTATA ATTTCATCTA CGATGTTCAG CGCCGTAGTA ACTCTAATAA TATAGGCTGA
 241 TAAGCTAACA TCATACCCTC CTGTATATGT GAATATGGTA TGATTTTTGT CCATTACAAG
 301 CTCGGTTTTA ACTTTATTGC CTGTAATAAT TTCTCTCATC TGTAGGATAT CTATTTTTTT
 361 GTCATGCATT GCCTTCAAGA CGGGACGAAG AAACGTAATA TCCTCAATAA CGTTATCGTT
 421 TTCTACAATA ACTACATATT CTACCTTTTT ATTTTCTAAC TGGTAAAAA AATTAGAATC
 481 CCATAGGGCT AAATGTCTAG CGATATTTCT TTTCGTTTCC TCTGTACACA TAGTGTTACA
 541 AAACCCTGAA AAGAAGTGAG TATACTTGTC ATCATTTCTA ATGTTTCCTC CAGTCCACTG
 601 TATAAACGCA TAATCCTTGT AATGATCTGG ATCATCCTTG ACTACCACAA CATTTCTTTT
 661 TTCTGGCATA ACTTCGTTGT CCTTTACATC ATCGAACTTC TGATCATTAA TATGCTCATG
 721 AACATTAGGA AATGTTTCTG ATGGAGGTCT ATCAATAACT GGCACAACAA TAACAGGAGT
 781 TTTCACCGCC GCCATTTAGT TATTGAAATT AATCATATAC AACTCTTTAA TACGAGTTAT
 841 ATTTTCGTCT ATCCATTGTT TCACATTTAC ATATTTCGAC AAAAAGATAT AAAATGCGTA
 901 TTCCAATGCT TCTCTGTTTA ATGAATTACT AAAATATACA AACACGTCAC TGTCTGGCAA
 961 TAAATGATAT CTTAGAATAT TGTAACAATT TATTTTGTAT TGCACATGTT CGTGATCTAT
1021 GAGTTCTTCT TCGAATGGCA TAGGATCTCC GAATCTGAAA ACGTATAAAT AGGAGTTAGA
1081 ATAATAATAT TTGAGAGTAT TGGTAATATA TAAACTCTTT AGCCGGTATAA TTAGTTTTTT
1141 TCTCTCAATT TCTATTTTTA GATGTGATGG AAAAATGACT AATTTTGTAG CATTAGTATC
1201 ATGAACTCTA ATCAAAATCT TAATATCTTC GTCACACGTT AGCTCTTTGA AGTTTTTAAG
1261 AGATGCATCA GTTGGTTCTA CAGATGGAGT AGGTGCAACA ATTTTTTGTT CTACACATGT
1321 ATGTACTGGA GCCATTGTTT TAACTATAAT GGTGCTTGTA TCGAAAAACT TAATGCAGA
1381 TAGCGGAAGC TCTTCGCCGC GACTTTCTAC ATCGTAATTG GGTTCTAACG CCGATCTCTG
1441 AATGGATACT AGTTTTCTAA GTTCTAATGT GATTCTCTGA AAATGTAAAT CCAATTCCTC
1501 CGGCATTATA GATGTGTATA CATCGGTAAA TAAAACTATA GTATCCAACG ATCCCTTCTC
1561 GCAAATTCTA GTCTTAACCA AAAAATCGTA TATAACCACG GAGATGGCGT ATTTAAGAGT
1621 GGATTCTTCT ACCGTTTTGT TCTTGGATGT CATATAGGAA ACTATAAAGT CCGCACTACT
1681 GTTAAGAATG ATTACTAACG CAACTATATA GTTCAAATTA AGCATTTTGG AAACATAAAA
1741 TAACTCTGTA GACGATACTT GACTTTCGAA TAAGTTTGCA GACAAACGAA GAAAGAACAG
1801 ACCTCTCTTA ATTTCAGAAG AAAACTTTTT TTCGTATTCC TGACGTCTAG AGTTTATATC
1861 AATAAGAAAG TTAAGAATTA GTCGGTTAAT GTTGTATTTC ATTACCCAAG TTTGAGATTT
1921 CATAATATTA TCAAAAGACA TGATAATATT AAAGATAAAG CGCTGACTAT GAACGAAATA
1981 GCTATATGGT TCGCTCAAAA ATATAGTCTT GTTAAACGTG GAAACGATAA CTGTATTTTT
2041 AATCACGTCA GCGGCATCTA AATTAAATAT AGGTATATTT ATTCCACACA CTCTACAATA
2101 TGCCACACCA TCTTCATAAT AAATAAATTC GTTAGCAAAA TTATTAATTT TAGTGAAATA
2161 GTTAGCGTCA ACTTTCATAG CTTCCTTCAA TCTAATTTGA TGCTCACACG GTGCGAATTC
2221 TACTCTAACA TCCCTTTTCC ATGCCTTCAG TTCATCGATC TCTATAATAT CTAGTTTTTT
2281 GCGTTTCACA AACACAGGCT CGTCTCTCGC GATGAGATCT GTATAGTAAC TATGTAAATG
2341 ATAACTAGAT AGAAAGATGT AGCTATATAG ATGACGATCC TTTAAGAGAG GTATAATAAC
2401 TTTACCCCAA TCAGATAGAC TGTTGTTATG GTCTTCGGAA AAAGAATTTT TATAAATTTT
```

FIG. 1B

```
2461 TCCAGTATTT TCCAAATATA CGTACTTAAC ATCTAAAAAA TCCTTAATGA TAATAGGAAT
2521 GGATAATCCG TCTATTTTAT AAAGAAATAC ATATCGCACA TTATACTTTT TTTTGGAAAT
2581 GGGAATACCG ATGTGTCTAC ATAAATATGC AAAGTCTAAA TATTTTTTAG AGAATCTTAG
2641 TTGGTCCAAA TTCTTTTCCA AGTACGGTAA TAGATTTTTC ATATTGAACG GTATCTTCTT
2701 AATCTCTGGT TCTAGTTCCG CATTAAATGA TGAAACTAAG TCACTATTTT TATAACTAAC
2761 GATTACATCA CCTCTAACAT CATCATTTAC CAGAATACTG ATCTTCTTTT GTCGTAAATA
2821 CATGTCTAAT GTGTTGAAGA AAAGATCATA CAAGTTATAC GTCATTTCAT CTGTGGTATT
2881 CTTGTCATTG AAGGATAAAC TCGTACTAAT CTCTTCTTTA ACAGCCTGTT CAAATTTATA
2941 TCCTATATAC GAAAAAATAG CAACCAGTGT TTGATCATCC GCGTCAATAT TCTGTTCTAT
3001 CGTAGTGTAT AACAATCGTA TATCTTCTTC TGTGATAGTC GATACGTTAT AAAGGTTGAT
3061 AACGAAAATA TTTTTATTTC GTGAAATAAA GTCATCGTAG GATTTTGGAC TTATATTCGC
3121 GTCTAGTAGA TATGCTTTTA TTTTTGGAAT GATCTCAATT AGAATAGTCT CTTTAGAGTC
3181 CATTACGATA CAAACTTAAC GGATATCGCG ATAATGAAAT AATTTATGAT TATTTCTCGC
3241 TTTCAATTTA ACACAACCCT CAAGAACCTT TGTATTTATT TTCACTTTTT AAGTATAGAA
3301 TAAAGAAGCT TCCCGGGGGA TCCTTATTTT TGACACCAGA CCAACTGGTA ATGGTAGCGA
3361 CCGGCGCTCA GCTGGAATTC CGCCGATACT GACGGGCTCC AGGAGTCGTC GCCACCAATC
3421 CCCATATGGA AACCGTCGAT ATTCAGCCAT GTGCCTTCTT CCGCGTGCAG CAGATGGCGA
3481 TGGCTGGTTT CCATCAGTTG CTGTTGACTG TAGCGGCTGA TGTTGAACTG GAAGTCGCCG
3541 CGCCACTGGT GTGGGCCATA ATTCAATTCG CGCGTCCCGC AGCGCAGACC GTTTTCGCTC
3601 GGGAAGACGT ACGGGTATA CATGTCTGAC AATGGCAGAT CCCAGCGGTC AAAACAGGCG
3661 GCAGTAAGGC GGTCGGGATA GTTTCTTGC GGCCCTAATC CGAGCCAGTT TACCCGCTCT
3721 GCTACCTGCG CCAGCTGGCA GTTCAGGCCA ATCCGCGCCG GATGCGGTGT ATCGCTCGCC
3781 ACTTCAACAT CAACGGTAAT CGCCATTTGA CCACTACCAT CAATCCGGTA GGTTTTCCGG
3841 CTGATAAATA AGGTTTTCCC CTGATGCTGC CACGCGTGAG CGGTCGTAAT CAGCACCGCA
3901 TCAGCAAGTG TATCTGCCGT GCACTGCAAC AACGCTGCTT CGGCCTGGTA ATGGCCCGCC
3961 GCCTTCCAGC GTTCGACCCA GGCGTTAGGG TCAATGCGGG TCGCTTCACT TACGCCAATG
4021 TCGTTATCCA GCGGTGCACG GGTGAACTGA TCGCGCAGCG GCGTCAGCAG TTGTTTTTTA
4081 TCGCCAATCC ACATCGTGTA AAGAAAGCCT GACTGGCGGT TAAATTGCCA ACGCTTATTA
4141 CCCAGCTCGA TGCAAAAATC CATTTCGCTG GTGGTCAGAT GCGGGATGGC GTGGGACGCG
4201 GCGGGGAGCG TCACACTGAG GTTTTCCGCC AGACGCCACT GCTGCCAGGC GCTGATGTGC
4261 CCGGCTTCTG ACCATGCGGT CGCGTTCGGT TGCACTACGC GTACTGTGAG CCAGAGTTGC
4321 CCGGCGCTCT CCGGCTGCGG TAGTTCAGGC AGTTCAATCA ACTGTTTACC TTGTGGAGCG
4381 ACATCCAGAG GCACTTCACC GCTTGCCAGC GGCTTACCAT CCAGCGCCAC CATCCAGTGC
4441 AGGAGCTCGT TATCGCTATG ACGGAACAGG TATTCGCTGG TCACTTCGAT GGTTTGCCCG
4501 GATAAACGGA ACTGGAAAAA CTGCTGCTGG TGTTTTGCTT CCGTCAGCGC TGGATGCGGC
4561 GTGCGGTCGG CAAAGACCAG ACCGTTCATA CAGAACTGGC GATCGTTCGG CGTATCGCCA
4621 AAATCACCGC CGTAAGCCGA CCACGGGTTG CCGTTTTCAT CATATTTAAT CAGCGACTGA
4681 TCCACCCAGT CCCAGACGAA GCCGCCCTGT AAACGGGGAT ACTGACGAAA CGCCTGCCAG
4741 TATTTAGCGA AACCGCCAAG ACTGTTACCC ATCGCGTGGG CGTATTCGCA AGGGATCAGC
4801 GGGCGCGTCT CTCCAGGTAG CGAAAGCCAT TTTTTGATGG ACCATTTCGG CACAGCCGGG
4861 AAGGGCTGGT CTTCATCCAC GCGCGCGTAC ATCGGCAAA TAATATCGGT GGCCGTGGTG
4921 TCGGCTCCGC CGCCTTCATA CTGCACCGGG CGGGAAGGAT CGACAGATTT GATCCAGCGA
4981 TACAGCGCGT CGTGATTAGC GCCGTGGCCT GATTCATTCC CCAGCGACCA GATGATCACA
5041 CTCGGGTGAT TACGATCGCG CTGCACCATT CGCGTTACGC GTTCGCTCAT CGCCGGTAGC
5101 CAGCGCGGAT CATCGGTCAG ACGATTCATT GGCACCATGC CGTGGGTTTC AATATTGGCT
5161 TCATCCACCA CATACAGGCC GTAGCGGTCG CACAGCGTGT ACCACAGCGG ATGGTTCGGA
5221 TAATGCGAAC AGCGCACGGC GTTAAAGTTG TTCTGCTTCA TCAGCAGGAT ATCCTGCACC
5281 ATCGTCTGCT CATCCATGAC CTGACCATGC AGAGGATGAT GCTCGTGACG GTTAACGCCT
5341 CGAATCAGCA ACGGCTTGCC GTTCAGCAGC AGCAGACCAT TTTCAATCCG CACCTCGCGG
5401 AAACCGACAT CGCAGGCTTC TGCTTCAATC AGCGTGCCGT CGGCGGTGTG CAGTTCAACC
5461 ACCGCACGAT AGAGATTCGG GATTTCGGCG CTCCACAGTT TCGGGTTTTC GACGTTCAGA
5521 CGTAGTGTGA CGCGATCGGC ATAACCACCA CGCTCATCGA TAATTTCACC GCCGAAAGGC
5581 GCGGTGCCGC TGGCGACCTG CGTTTCACCC TGCCATAAAG AAACTGTTAC CCGTAGGTAG
5641 TCACGCAACT CGCCGCACAT CTGAACTTCA GCCTCCAGTA CAGCGCGGCT GAAATCATCA
5701 TTAAAGCGAG TGGCAACATG GAAATCCGCT ATTTGTGTAG TCGGTTTATG CAGCAACGAG
5761 ACGTCACGCA AAATGCCGCT CATCCGCCAC ATATCCTGAT CTTCCAGATA ACTGCCGTCA
5821 CTCCAACGCA GCACCATCAC CGCGAGGCGG TTTTCTCCGG CGCGTAAAAA TGCGCTCAGG
5881 TCAAATTCAG ACGGCAAACG ACTGTCCTGG CCGTAACCGA CCCAGCGCCC GTTGCACCAC
5941 AGATGAAACG CCGAGTTAAC GCCATCAAAA ATAATTCGCG TCTGGCCTTC CTGTAGCCAG
6001 CTTTCATCAA CATTAAATGT GAGCGAGTAA CAACCCGTCG GATTCTCCGT GGGAACAAAC
6061 GGCGGATTGA CCGTAATGGG ATAGGTTACG TTGGTGTAGA TGGGCGCATC GTAACCGTGC
6121 ATCTGCCAGT TTGAGGGGAC GACGACAGTA TCGGCCTCAG GAAGATCGCA CTCCAGCCAG
```

FIG. 1C

```
6181 CTTTCCGGCA CCGCTTCTGG TGCCGGAAAC CAGGCAAAGC GCCATTCGCC ATTCAGGCTG
6241 CGCAACTGTT GGGAAGGGCG ATCGGTGCGG GCCTCTTCGC TATTACGCCA GCTGGCGAAA
6301 GGGGGATGTG CTGCAAGGCG ATTAAGTTGG GTAACGCCAG GGTTTTCCCA GTCACGACGT
6361 TGTAAAACCA TTACGATACA AACTTAACGG ATATCGCGAT AATGAAATAA TTTATGATTA
6421 TTTCTCGCTT TCAATTTAAC ACAACCCTCA AGAACCTTTG TATTTATTTT CACTTTTTAA
6481 GTATAGAATA AAGAACCCGG GAAGCTTGTC TAGCTGGTGC TGAGTTTCTA CGTGAGTTGA
6541 TTCGTCTCTT GCGTGCCTCT CGTGATCCAA TTGTCCCGAG ATATTCTCTT CTCTTCCGGT
6601 GCTTCTTATG AAACTTTCCC TGACGGTGGC GTTTTAAAGT TACAAACAAC TAGGAAATTG
6661 GTTTATGATG TATAATTTTT TTAGTTTTTA TAGATTCTTT ATTCTATACT TAAAAATGA
6721 AAATAAATAC AAAGGTTCTT GAGGGTTGTG TTAAATTGAA AGCGAGAAAT AATCATAAAT
6781 TATTTCATTA TCGCGATATC CGTTAAGTTT GTATCGTAAT GGCGTGGTCA ATTACAAATA
6841 AAGCGGATAC TAGTAGCTTC ACAAAGATGG CTGAAATCAG AGCTCATCTA AAAAATAGCG
6901 CTGAAAATAA AGATAAAAAC GAGGATATTT TCCCGGAAGA TGTAATAATT CCATCTACTA
6961 AGCCCAAAAC CAAACGAGCC ACTACTCCTC GTAAACCAGC GGCTACTAAA AGATCAACCA
7021 AAAAGGAGGA AGTGGAAGAA GAAGTAGTTA TAGAGGAATA TCATCAAACA ACTGAAAAAA
7081 ATTCTCCATC TCCTGGAGTC GGCGACATTG TAGAAAGCGT GGCTGCTGTA GAGCTCGATG
7141 ATAGCGACGG GGATGATGAA CCTATGGTAC AAGTTGAAGC TGGTAAAGTA AATCATAGTG
7201 CTAGAAGCGA TCTTTCTGAC CTAAGGTGG CTACCGACAA TATCGTTAAA GATCTTAAGA
7261 AAATTATTAC TAGAATCTCT GCAGTATCGA CGGTTCTAGA GGATGTTCAA GCAGGATCC
```

FIG. 2A

Nucleotide Sequence of the ALVAC C8 Insertion site containing the H6/H4L expression cassette

| Characteristic | Position(s)bp |
|---|---|
| Left Arm | 1-487 |
| Right Arm | 3016-4225 |
| H6 Promoter | 495-618 |
| H4L orf | 619-3003 |

```
   1 GAGCTCACTT ATTACATCCT ACTGACTATA TACAGCGAAT TAACCATAGG CGTAATTGTA
  61 CAGAAACCAG GAAATTATTA CCGCCTTTTA TAAGAAGTAT TAATAAAACA TGTAGCGTAT
 121 GTCTAGAAAG AATATACGAA AAAGAAATAA ATAAACAATA TTTCGGTATT TTACCAAATT
 181 GTAAACACGT GTTTTGTTTT TACTGTATAC AACGTTGGAT GTCTATAATA AAAGGTACGG
 241 ATACCGAAGG TACATGTCCT GTATGTAGAA CAGTTTCTGT ATTTATAGTG CCTAATAGGT
 301 ACTGGATAGA CGATAAATAT GAAAAGAGAT TAATTATAAA TAAATATAAG AATGACAGAA
 361 AGACTTATAA AGCGTTTAAA CATTATATAG GAAGATACGT ATTATTTTAT ACAGTAAACA
 421 ACAGTTTATT TGTTACTAAT GATTAAGGTA CGTGACTAAT TAGCTATAAA AAGGATCCAT
 481 CGATGATGGG AAGCTTCTTT ATTCTATACT TAAAAAGTGA AAATAAATAC AAAGGTTCTT
 541 GAGGGTTGTG TTAAATTGAA AGCGAGAAAT AATCATAAAT TATTTCATTA TCGCGATATC
 601 CGTTAAGTTT GTATCGTAAT GGACTCTAAA GAGACTATTC TAATTGAGAT CATTCCAAAA
 661 ATAAAAGCAT ATCTACTAGA CGCGAATATA AGTCCAAAAT CCTACGATGA CTTTATTTCA
 721 CGAAATAAAA ATATTTTCGT TATCAACCTT TATAACGTAT CGACTATCAC AGAAGAAGAT
 781 ATACGATTGT TATACACTAC GATAGAACAG AATATTGACG CGGATGATCA AACACTGGTT
 841 GCTATTTTTT CGTATATAGG ATATAAATTT GAACAGGCTG TTAAAGAAGA GATTAGTACG
 901 AGTTTATCCT TCAATGACAA GAATACCACA GATGAAATGA CGTATAACTT GTATGATCTT
 961 TTCTTCAACA CATTAGACAT GTATTTACGA CAAAAGAAGA TCAGTATTCT GGTAAATGAT
1021 GATGTTAGAG GTGATGTAAT CGTTAGTTAT AAAAATAGTG ACTTAGTTTC ATCATTTAAT
1081 GCGGAACTAG AACCAGAGAT TAAGAAGATA CCGTTCAATA TGAAAAATCT ATTACCGTAC
1141 TTGGAAAAGA ATTTGGACCA ACTAAGATTC TCTAAAAAAT ATTTAGACTT TGCATATTTA
1201 TGTAGACACA TCGGTATTCC CATTTCCAAA AAAAAGTATA ATGTGCGATA TGTATTTCTT
1261 TATAAAATAG ACGGATTATC CATTCCTATT ATCATTAAGG ATTTTTTAGA TGTTAAGTAC
1321 GTATATTTGG AAAATACTGG AAAAATTTAT AAAAATTCTT TTTCCGAAGA CCATAACAAC
1381 AGTCTATCTG ATTGGGGTAA AGTTATTATA CCTCTCTTAA AGGATCGTCA TCTATATAGC
1441 TACATCTTTC TATCTAGTTA TCATTTACAT AGTTACTATA CAGATCTCAT CGCGAGAGAC
1501 GAGCCTGTGT TTGTGAAACG CAAAAAACTA GATATTATAG AGATCGATGA ACCTGAGGCA
1561 TGGAAAAGGG ATGTTAGAGT AGAATTCGCA CCGTGTGAGC ATCAAATTAG ATTGAAGGAA
1621 GCTATGAAAG TTGACGCTAA CTATTTCACT AAAATTAATA ATTTTGCTAA CGAATTTATT
1681 TATTATGAAG ATGGTGTGGC ATATTGTAGA GTGTGTGGAA TAAATATACC TATATTTAAT
1741 TTAGATGCCG CTGACGTGAT TAAAAATACA GTTATCGTTT CCACGTTTAA CAAGACTATA
1801 TTTTTGAGCG AACCATATAG CTATTTCGTT CATAGTCAGC GCTTTATCTT TAATATTATC
1861 ATGTCTTTTG ATAATATTAT GAAATCTCAA ACTTGGGTAA TGAAATACAA CATTAACCGA
1921 CTAATTCTTA ACTTTCTTAT TGATATAAAC TCTAGACGTC AGGAATACGA AAAAAAGTTT
1981 TCTTCTGAAA TTAAGAGAGG TCTGTTCTTT CTTCGTTTGT CTGCAAACTT ATTCGAAAGT
2041 CAAGTATCGT CTACAGAGTT ATTTTATGTT TCCAAAATGC TTAATTTGAA CTATATAGTT
2101 GCGTTAGTAA TCATTCTTAA CAGTAGTGCG GACTTTATAG TTTCCTATAT GACATCCAAG
2161 AACAAAACGG TAGAAGAATC CACTCTTAAA TACGCCATCT CCGTGGTTAT ATACGATTTT
2221 TTGGTTAAGA CTAGAATTTG CGAGAAGGGA TCGTTGGATA CTATAGTTTT ATTTACCGAT
2281 GTATACACAT CTATAATGCC GGAGGAATTG GATTTACATT TTCAGAGAAT CACATTAGAA
2341 CTTAGAAAAC TAGTATCCAT TCAGAGATCG GCGTTAGAAC CCAATTACGA TGTAGAAAGT
2401 CGCGGCGAAG AGCTTCCGCT ATCTGCATTA AAGTTTTTCG ATACAAGCAC CATTATAGTT
2461 AAAACAATGG CTCCAGTACA TACATGTGTA GAACAAAAAA TTGTTGCACC TACTCCATCT
2521 GTAGAACCAA CTGATGCATC TCTTAAAAAC TTCAAAGAGC TAACGTGTGA CGAAGATATT
2581 AAGATTTTGA TTAGAGTTCA TGATACTAAT GCTACAAAAT TAGTCATTTT TCCATCACAT
2641 CTAAAAATAG AAATTGAGAG AAAAAAACTA ATTATACCGC TAAAGAGTTT ATATATTACC
2701 AATACTCTCA ATATTATTA TTCTAACTCC TATTTATACG TTTCAGATT CGGAGATCCT
2761 ATGCCATTCG AAGAAGAACT CATAGATCAC GAACATGTGC AATACAAAAT AAATTGTTAC
2821 AATATTCTAA GATATCATTT ATTGCCAGAC AGTGACGTGT TTGTATATTT TAGTAATTCA
2881 TTAAACAGAG AAGCATTGGA ATACGCATTT TATATCTTTT TGTCGAAATA TGTAAATGTG
2941 AAACAATGGA TAGACGAAAA TATAACTCGT ATTAAAGAGT TGTATATGAT TAATTTCAAT
3001 AACTAAAAGC TTCCCATCCT GCAGCTCGAG TTTTTATGAC TAGTTAATCA CGGCCGCTCA
```

FIG. 2B

```
3061 ATATTGTATT GGATGGTTAG AGATCAAAGG ATACAAGATA ACTGGGCTCA TTTCAGCTTT
3121 ACATTCATCC CTATAAGCTT TCATAATGGG ATTTTTCTCC ATAATGTCAA AATCACTTTG
3181 GATATATTCA AAATTTTCTA CAAAATGTTT TGGTTGTTCT GAGCTAAACA CGATGTTAGA
3241 TATTAATAAC TTTGCTATCT CAAGACCTTC TGAAGTATCA ACTTTGATAT TGGAAAGAGG
3301 TGTAAAATAA GGTGATGAAG CGATTGTTGT ATCTGCACAG AATGTTAACA GTATATCTAC
3361 TAATTCTACA TTTCCATCTG TCACAGCATG CCATAGAGGA GTATTCCAGT ACCTGTCCTT
3421 AGCATTTATA TCAGCACCGA ATTCCAAAAG CATAATAGTT ATCTTTACAG ATCCTATACA
3481 CACAGCATAA TGCAAAGGAG TCATCCTATG GCTATCTTTA ACGTTAGTAT ATGCTCCAGC
3541 TAGAAGTAAT TGCTCTATTA TCTCCATGTT TTCAGATTTA ACAGCATAAT GCAATGGATA
3601 CATATATCCT CTGTAACCAT AATTTATACT CGATCCAGCT TTTAGTAACA TACTCACAAT
3661 TTCCAAATTT TCTCTCTTTA TAGCCTCGAT TATGGGATGA TTTTCCCTGT ACTCATTGTC
3721 AACATCAGCG TTATACTCCA GAAGTAACTT TACAATTTCC ACATTCTCTA TAGAGACAGC
3781 ATACTGGAGT GGAGTCTTTA CTTTGTAGTC CTCATATGTA TCCACATTAG CGCCATGATC
3841 CAACAAGAGT TCACCAGAT CTATGTTCTG AACTTTGACA GCTCTATGCA ACGGAGAAGA
3901 TACTTGTTCG CTAGATATAT CAGGATCAGC TCCTGCTAAC AATAGAGCTT TGGCTATTTC
3961 AAATTTTTCA TTTTCTACAG CACAATGAAG GGGTGAGCAG CCATAATCGT TGAATACGTC
4021 CAGGTTAATG CCGGTTTTCA CAATATCTAG CACGCTAGAC AGAGATCCAG ATTCAATAGC
4081 TTCGAATAAG TATGCCTCCA TTTTGTGTAA TAGTAGTAAG TAATAATTTT CTGAAGAAAC
4141 TACTAACTTA CCGAGCTATA GTAGATAGTT ATAATTTCAT TTTTTTACAA GTAGTATCAC
4201 ATAGTGATTG CTTATTAAAG GTACC
```

FIG. 3A

Nucleotide sequence of the ALVAC C6 insertion site containing the H6 / K3L and E3L expression cassette.

| Characteristic | Position(s) |
|---|---|
| Left Arm | 1-385 |
| Right Arm | 3273-4434 |
| K3L orf | C727-464 |
| H6 Promoter | C850-728 |
| E3L | C2758-2188 |

```
   1 GAGCTCGCGG CCGCCTATCA AAAGTCTTAA TGAGTTAGGT GTAGATAGTA TAGATATTAC
  61 TACAAAGGTA TTCATATTTC CTATCAATTC TAAAGTAGAT GATATTAATA ACTCAAAGAT
 121 GATGATAGTA GATAATAGAT ACGCTCATAT AATGACTGCA AATTTGGACG GTTCACATTT
 181 TAATCATCAC GCGTTCATAA GTTTCAACTG CATAGATCAA AATCTCACTA AAAAGATAGC
 241 CGATGTATTT GAGAGAGATT GGACATCTAA CTACGCTAAA GAAATTACAG TTATAAATAA
 301 TACATAATGG ATTTTGTTAT CATCAGTTAT ATTTAACATA AGTACAATAA AAAGTATTAA
 361 ATAAAAATAC TTACTTACGA AAAAATGACT AATTAGCTAT AAAAACCCAG ATCTCTCGAG
 421 GTCGACGGTA TCGATAAGCT TGATATCGAA TTCATAAAAA TTATTGATGT CTACACATCC
 481 TTTTGTAATT GACATCTATA TATCCTTTTG TATAATCAAC TCTAATCACT TTAACTTTTA
 541 CAGTTTTCCC TACCAGTTTA TCCCTATATT CAACATATCT ATCCATATGC ATCTTAACAC
 601 TCTCTGCCAA GATAGCTTCA GAGTGAGGAT AGTCAAAAAG ATAAATGTAT AGAGCATAAT
 661 CCTTCTCGTA TACTCTGCCC TTTATTACAT CGCCCGCATT GGGCAACGAA TAACAAAATG
 721 CAAGCATACG ATACAAACTT AACGGATATC GCGATAATGA ATAATTTAT GATTATTTCT
 781 CGCTTTCAAT TTAACACAAC CCTCAAGAAC CTTTGTATTT ATTTTCACTT TTTAAGTATA
 841 GAATAAAGAA AGCTCTAATT AATTAATGAA CAGATTGTTT CGTTTTCCCC TTGGCGTATC
 901 ACTAATTAAT TAACCCGGGC TGCAGCTCGA GGAATTCAAC TATATCGACA TATTTCATTT
 961 GTATACACAT AACCATTACT AACGTAGAAT GTATAGGAAG AGATGTAACG GGAACAGGGT
1021 TTGTTGATTC GCAAACTATT CTAATACATA ATTCTTCTGT TAATACGTCT TGCACGTAAT
1081 CTATTATAGA TGCCAAGATA TCTATATAAT TATTTTGTAA GATGATGTTA ACTATGTGAT
1141 CTATATAAGT AGTGTAATAA TTCATGTATT TCGATATATG TTCCAACTCT GTCTTTGTGA
1201 TGTCTAGTTT CGTAATATCT ATAGCATCCT CAAAAAATAT ATTCGCATAT ATTCCCAAGT
1261 CTTCAGTTCT ATCTTCTAAA AAATCTTCAA CGTATGGAAT ATAATAATCT ATTTTACCTC
1321 TTCTGATATC ATTAATGATA TAGTTTTTGA CACTATCTTC TGTCAATTGA TTCTTATTCA
1381 CTATATCTAA GAAACGGATA GCGTCCCTAG GACGAACTAC TGCCATTAAT ATCTCTATTA
1441 TAGCTTCTGG ACATAATTCA TCTATTATAC CAGAATTAAT GGGAACTATT CCGTATCTAT
1501 CTAACATAGT TTTAAGAAAG TCAGAATCTA AGACCTGATG TTCATATATT GGTTCATACA
1561 TGAAATGATC TCTATTGATG ATAGTGACTA TTTCATTCTC TGAAAATTGG TAACTCATTG
1621 TATATATGCT TTCCTTGTTG ATGAAGGATA GAATTACTC AATAGAATTT GTACCAACAA
1681 ACTGTTCTCT TATGAATCGT ATATCATCAT CTGAAATAAT CATGTAAGGC ATACATTTAA
1741 CAATTAGAGA CTTGTCTCCT GTTATCAATA TACTATTCTT GTGATAATTT ATGTGTGAGG
1801 CAAATTTGTC CACGTTCTTT AATTTTGTTA TAGTAGATAT CAAATCCAAT GGAGCTACAG
1861 TTCTTGGCTT AAACAGATAT AGTTTTTCTG GAACAAATTC TACAACATTA TTATAAAGGA
1921 CTTGGGTAG ATAAGTGGGA TGAAATCCTA TTTTAATTAA TGCTATCGCA TTGTCCTCGT
1981 GCAAATATCC AAACGCTTTT GTGATAGTAT GGCATTCATT GTCTAGAAAC GCTCTACGAA
2041 TATCTGTGAC AGATATCATC TTTAGAGAAT ATACTAGTCG CGTTAATAGT ACTACAATTT
2101 GTATTTTTTA ATCTATCTCA ATAAAAAAAT TAATATGTAT GATTCAATGT ATAACTAAAC
2161 TACTAACTGT TATTGATAAC TAGAATCAGA ATCAATGAT GACGTAACCA AGAAGTTTAT
2221 CTACTGCCAA TTTAGCTGCA TTATTTTTAG CATCTCGTTT AGATTTTCCA TCTGCCTTAT
2281 CGAATACTCT TCCGTCGATG TCTACACAGG CATAAAATGT AGGAGAGTTA CTAGGCCCAA
2341 CTGATTCAAT ACGAAAGAC CAATCTCTCT TAGTTATTTG GCAGTACTCA TTAATAATGG
2401 TGACAGGGTT AGCATCTTTC CAATCAATAA TTTTTTTAGC CGGAATAACA TCATCAAAAG
2461 ACTTATGATC CTCTCTCATT GATTTTTCGC GGGATACATC ATCTATTATG ACGTCAGCCA
```

FIG. 3B

```
2521 TAGCATCAGC ATCCGGCTTA TCCGCCTCCG TTGTCATAAA CCAACGAGGA GGAATATCGT
2581 CGGAGCTGTA CACCATAGCA CTACGTTGAA GATCGTACAG AGCTTTATTA ACTTCTCGCT
2641 TCTCCATATT AAGTTGTCTA GTTAGTTGTG CAGCAGTAGC TCCTTCGATT CCAATGTTTT
2701 TAATAGCCGC ACACACAATC TCTGCGTCAG AACGCTCGTC AATATAGATC TTAGACATTT
2761 TTAGAGAGAA CTAACACAAC CAGCAATAAA ACTGAACCTA CTTTATCATT TTTTTATTCA
2821 TCATCCTCTG GTGGTTCGTC GTTTCTATCG AATGTAGCTC TGATTAACCC GTCATCTATA
2881 GGTGATGCTG GTTCTGGAGA TTCTGGAGGA GATGGATTAT TATCTGGAAG AATCTCTGTT
2941 ATTTCCTTGT TTTCATGTAT CGATTGCGTT GTAACATTAA GATTGCGAAA TGCTCTAAAT
3001 TTGGGAGGCT TAAAGTGTTG TTTGCAATCT CTACACGCGT GTCTAACTAG TGGAGGTTCG
3061 TCAGCTGCTC TAGTTTGAAT CATCATCGGC GTAGTATTCC TACTTTTACA GTTAGGACAC
3121 GGTGTATTGT ATTTCTCGTC GAGAACGTTA AAATAATCGT TGTAACTCAC ATCCTTTATT
3181 TTATCTATAT TGTATTCTAC TCCTTTCTTA ATGCATTTTA TACCGAATAA GAGATAGCGA
3241 AGGAATTCTT TTTATTGATT AACTAGTCAA ATGAGTATAT ATAATTGAAA AAGTAAAATA
3301 TAAATCATAT AATAATGAAA CGAAATATCA GTAATAGACA GGAACTGGCA GATTCTTCTT
3361 CTAATGAAGT AAGTACTGCT AAATCTCCAA AATTAGATAA AAATGATACA GCAAATACAG
3421 CTTCATTCAA CGAATTACCT TTTAATTTTT TCAGACACAC CTTATTACAA ACTAACTAAG
3481 TCAGATGATG AGAAAGTAAA TATAAATTTA ACTTATGGGT ATAATATAAT AAAGATTCAT
3541 GATATTAATA ATTTACTTAA CGATGTTAAT AGACTTATTC CATCAACCCC TTCAAACCTT
3601 TCTGGATATT ATAAAATACC AGTTAATGAT ATTAAAATAG ATTGTTTAAG AGATGTAAAT
3661 AATTATTTGG AGGTAAAGGA TATAAAATTA GTCTATCTTT CACATGGAAA TGAATTACCT
3721 AATATTAATA ATTATGATAG GAATTTTTTA GGATTTACAG CTGTTATATG TATCAACAAT
3781 ACAGGCAGAT CTATGGTTAT GGTAAAACAC TGTAACGGGA AGCAGCATTC TATGGTAACT
3841 GGCCTATGTT TAATAGCCAG ATCATTTTAC TCTATAAACA TTTTACCACA AATAATAGGA
3901 TCCTCTAGAT ATTTAATATT ATATCTAACA ACAACAAAAA AATTTAACGA TGTATGGCCA
3961 GAAGTATTTT CTACTAATAA AGATAAAGAT AGTCTATCTT ATCTACAAGA TATGAAAGAA
4021 GATAATCATT TAGTAGTAGC TACTAATATG GAAAGAAATG TATACAAAAA CGTGGAAGCT
4081 TTTATATTAA ATAGCATATT ACTAGAAGAT TTAAAATCTA GACTTAGTAT AACAAAACAG
4141 TTAAATGCCA ATATCGATTC TATATTTCAT CATAACAGTA GTACATTAAT CAGTGATATA
4201 CTGAAACGAT CTACAGACTC AACTATGCAA GGAATAAGCA ATATGCCAAT TATGTCTAAT
4261 ATTTTAACTT TAGAACTAAA ACGTTCTACC AATACTAAAA ATAGGATACG TGATAGGCTG
4321 TTAAAAGCTG CAATAAATAG TAAGGATGTA GAAGAAATAC TTTGTTCTAT ACCTTCGGAG
4381 GAAAGAACTT TAGAACAACT TAAGTTTAAT CAAACTTGTA TTTATGAAGG TACC
```

FIG. 4A

DNA sequence of the coding region of FHV gB with modified T5NT motifs.

1 ATGTCCACTC GTGGCGATCT TGGGAAGCGG CGACGAGGGA GTCGTTGGCA GGGACACAGT
61 GGCTATTTTC GACAGAGATG TTTTTTCCCT TCTCTACTCG GTATTGCAGC GACTGGCTCC
121 AGACATGGTA ACGGATCGTC GGGATTAACC AGACTAGCTA GATATGTTTC ATTTATCTGG
181 ATCGTACTAT TCTTAGTCGG TCCCCGTCCA GTAGAGGGTC AATCTGGAAG CACATCGGAA
241 CAACCCCGGC GGACTGTAGC TACCCCTGAG GTAGGGGGTA CACCACCAAA ACCAACTACA
301 GATCCCACCG ATATGTCGGA TATGAGGGAA GCTCTCCGTG CGTCCCAAAT AGAGGCTAAC
361 GGACCATCGA CTTTCTATAT GTGTCCACCA CCTTCAGGAT CTACTGTCGT GCGTTTAGAG
421 CCACCACGGG CCTGTCCAGA TTATAAACTA GGGAAAAATT TTACCGAGGG TATAGCTGTA
481 ATATTTAAAG AAAATATAGC GCCATATAAA TTCAAGGCAA ATATATACTA TAAAAACATT
541 ATTATGACAA CGGTATGGTC TGGGAGTTCC TATGCCGTTA CAACCAACCG ATATACAGAC
601 AGGGTTCCCG TGAAAGTTCA AGAGATTACA GATCTCATAG ATAGACGGGG TATGTGCCTC
661 TCGAAAGCTG ATTACGTTCG TAACAATTAT CAATTTACGG CCTTTGATCG AGACGAGGAT
721 CCCAGAGAAC TGCCTCTGAA ACCCTCCAAG TTCAACACTC CAGAGTCCCG TGGATGGCAC
781 ACCACCAATG AAACATACAC AAAGATCGGT GCTGCTGGAT TTCACCACTC TGGGACCTCT
841 GTAAATTGCA TCGTAGAGGA AGTGGATGCA AGATCTGTAT ATCCATATGA CTCATTTGCT
901 ATCTCCACTG GTGACGTGAT TCACATGTCT CCATTCTTTG GGCTGAGGGA TGGAGCCCAT
961 GTAGAACATA CTAGTTATTC TTCAGACAGA TTTCAACAAA TCGAGGGATA CTATCCAATA
1021 GACTTGGATA CGCGATTACA ACTGGGGGCA CCAGTTTCTC GCAATTTTTT GGAAACTCCG
1081 CATGTGACAG TGGCCTGGAA CTGGACCCCA AAGTCTGGTC GGGTATGTAC CTTAGCCAAA
1141 TGGAGGGAAA TAGATGAAAT GCTACGCGAT GAATATCAGG GCTCCTATAG ATTTACAGCC
1201 AAGACCATAT CCGCTACTTT CATCTCCAAT ACTTCACAAT TTGAAATCAA TCGTATCCGT
1261 TTGGGGGACT GTGCCACCAA GGAGGCAGCC GAAGCCATAG ACCGGATTTA TAAGAGTAAA
1321 TATAGTAAAA CTCATATTCA GACTGGAACC CTGGAGACCT ACCTAGCCCG TGGGGGATTT
1381 CTAATAGCTT TCCGTCCCAT GATCAGCAAC GAACTAGCAA AGTTATATAT CAATGAATTA

FIG. 4B

```
1441  GCACGTTCCA  ATCGCACGGT  AGATCTCAGT  GCACTCCTCA  ATCCATCTGG  GGAAACAGTA
1501  CAACGAACTA  GAAGATCGGT  CCCATCTAAT  CAACATCATA  GGTCGCGGCG  CAGCACAATA
1561  GAGGGGGTA   TAGAAACCGT  GAACAATGCA  TCACTCCTCA  AGACCACCTC  ATCTGTGGAA
1621  TTCGCAATGC  TACAATTTGC  CTATGACTAC  ATACAAGCCC  ATGTAAATGA  AATGTTGAGT
1681  CGGATAGCCA  CTGCCTGGTG  TACACTTCAG  AACCGCGAAC  ATGTGCTGTG  GACAGAGACC
1741  CTAAAACTCA  ATCCCGGTGG  GGTGGTCTCG  ATGGCCCTAG  AACGTCGTGT  ATCCGCGCGC
1801  CTACTTGGAG  ATGCCGTCGC  CGTAACACAA  TGTGTTAACA  TTTCTAGCGG  ACATGTCTAT
1861  ATCCAAAATT  CTATGCGGGT  GACGGTTCA   TCAACGACAT  GTTACAGCCG  CCCTCTTGTT
1921  TCCTTCCGTG  CCCTCAATGA  CTCCGAATAC  ATAGAAGGAC  AACTAGGGGA  AAACAATGAA
1981  CTTCTCGTGG  AACGAAAACT  AATTGAGCCT  TGCACTGTCA  ATAATAAGCG  GTATTTAAG
2041  TTTGGGCAG   ATTATGTATA  TTTTGAGGAT  TATGCGTATG  TCCGTAAAGT  CCCGCTATCG
2101  GAGATAGAAC  TGAAGTGC    GTATGTGAAT  TTAAATCTTA  CTCTCCTAGA  GGATCGTGAA
2161  TTTCTCCCAC  TCGAAGTTTA  TACACGAGCT  GAGCTGGAAG  ATACCGGCCT  TTTGGACTAC
2221  AGCGAGATTC  AACGCCGCAA  CCAACTCCAC  GCCCTAAAAT  TTTATGATAT  AGACAGCATA
2281  GTCAGAGTGG  ATAATAATCT  TGTCATCATG  CGTGGTATGG  CAAATTTCTT  TCAGGACTC
2341  GGGGATGTGG  GGGCTGGTTT  CGGCAAGGTG  GTCTTAGGGG  CTGCGAGTGC  GGTAATCTCA
2401  ACAGTATCAG  GCGTATCATC  ATTTCTAAAC  AACCCATTTG  GAGCATTGGC  CGTGGGACTG
2461  TTAATATTAG  CTGGCCATCGT CGCAGCATTC  CTGGCATATC  GCTATATATC  TAGATTACGT
2521  GCAAATCCAA  TGAAAGCCTT  ATATCCTGTG  ACGACTAGGA  ATTTGAAACA  GACGCTAAGA
2581  GCCCGCTCAA  CGGCTGGTGG  GGATAGCGAC  CCGGAGTCG   ATTGACTTCGA TGAGGAAAAG
2641  CTAATGCAGG  CAAGGGAGAT  GATAAAAATAT ATGTCCCTCG  TATCGGCTAT  TGAGCAACAA
2701  GAACATAAGG  CGATGAAAAA  GAATAAGGGC  CCAGCGGATCC TAACGAGTCA  TCTCACTAAC
2761  ATGGCCCTCC  GTCCGCGTGG  ACCTAAATAC  CAACGCCCTCA ATAATCTTGA  TAGCGGTGAT
2821  GATACTGAAA  CAAATCTTGT  CTAA
```

FIG. 5A

DNA sequence of the the H6 promoted FHV gB donor plasmid pC3H6FHVB.

H6 promoter: 3958 - 3835

FHV gB coding region: 3834 - 991

C3 left arm: 15 - 939

C3 right arm: 4056 - 6628

```
   1 GCGGCCGCGT CGACATGCAT TGTTAGTTCT GTAGATCAGT AACGTATAGC ATACGAGTAT
  61 AATTATCGTA GGTAGTAGGT ATCCTAAAAT AAATCTGATA CAGATAATAA CTTTGTAAAT
 121 CAATTCAGCA ATTTCTCTAT TATCATGATA ATGATTAATA CACAGCGTGT CGTTATTTTT
 181 TGTTACGATA GTATTTCTAA AGTAAAGAGC AGGAATCCCT AGTATAATAG AAATAATCCA
 241 TATGAAAAAT ATAGTAATGT ACATATTTCT AATGTTAACA TATTTATAGG TAAATCCAGG
 301 AAGGGTAATT TTTACATATC TATATACGCT TATTACAGTT ATTAAAAATA TACTTGCAAA
 361 CATGTTAGAA GTAAAAAGA AAGAACTAAT TTTACAAAGT GCTTTACCAA AATGCCAATG
 421 GAAATTACTT AGTATGTATA TAATGTATAA AGGTATGAAT ATCACAAACA GCAAATCGGC
 481 TATTCCCAAG TTGAGAAACG GTATAATAGA TATATTTCTA GATACCATTA ATAACCTTAT
 541 AAGCTTGACG TTTCCTATAA TGCCTACTAA GAAAACTAGA AGATACATAC ATACTAACGC
 601 CATACGAGAG TAACTACTCA TCGTATAACT ACTGTTGCTA ACAGTGACAC TGATGTTATA
 661 ACTCATCTTT GATGTGGTAT AAATGTATAA TAACTATATT ACACTGGTAT TTTATTTCAG
 721 TTATATACTA TATAGTATTA AAAATTATAT TTGTATAATT ATATTATTAT ATTCAGTGTA
 781 GAAAGTAAAA TACTATAAAT ATGTATCTCT TATTTATAAC TTATTAGTAA AGTATGTACT
 841 ATTCAGTTAT ATTGTTTTAT AAAAGCTAAA TGCTACTAGA TTGATATAAA TGAATATGTA
 901 ATAAATTAGT AATGTAGTAT ACTAATATTA ACTCACATTT GACTAATTAG CTATAAAAAC
 961 CCGGGCTGCA GCCCGGGAAG CTTACAAAAA TTAGACAAGA TTTGTTTCAG TATCATCACC
1021 GCTATCAAGA TTATTGAGGC GTTGGTATTT AGGTCCACGG CGACGGAGGG CCATGTTAGT
1081 GAGATGACTC GTTAGGATCG CTGGGCCCTT ATTCTTTTTC ATCGCCTTAT GTTCTTGTTG
1141 CTCCATAGCC GATACGAGGG ACATATATTT TATCCTCTCC CTTGCCTGCA TTAGCTTTTC
1201 CTCATCGAAG TCATCGACTC CCGGGTCGCT ATCCCCACCA GCCGTTGAGC GGGCTCTTAG
1261 CGTCTGTTTC AAATTCCTAG TCGTCACAGG ATATAAGGCT TTCATTGGAT TTGCACGTAA
1321 TCTAGATATA TAGCGATATG CCAGGAATGC TGCGACGATG CCAGCTAATA TTAACAGTCC
1381 CACGGCCAAT GCTCCAAATG GGTTGTTTAG AAATGATGAT ACGCCTGATA CTGTTGAGAT
1441 TACCGCACTC GCAGCCCCTA AGACCACCTT GCCGAAACCA GCCCCACAT CCCCGAGTCC
1501 CTGAAAGAAA TTTGCCATAC CACGCATGAT GACAAGATTA TTATCCACTC TGACTATGCT
1561 GTCTATATCA TAAAATTTTA AGGCGTGGAG TTGGTTGCGG CGTTGAATCT CGCTGTAGTC
1621 CAAAAGGCCG GTATCTTCCA GCTCAGCTCG TGTATAAACT TCGAGTGGGA GAAATTCACG
1681 ATCCTCTAGG AGAGTAAGAT TTAAATTCAC ATACGCACTT ATCAGTTCTA TCTCCGATAG
1741 CGGGACTTTA CGGACATACG CATAATCCTC AAAATATACA TAATCTGCCC CAAACTTAAA
1801 ATACCGCTTA TTATTGACAG TGCAAGGCTC AATTAGTTTT CGTTCACGA GAAGTTCATT
1861 GTTTTCCCCT AGTTGTCCTT CTATGTATTC GGAGTCATTG AGGGCACGGA AGGAAACAAG
1921 AGGGCGGCTG TAACATGTCG TTGATGAACC CGTCACCCGC ATAGAATTTT GGATATAGAC
1981 ATGTCCGCTA GAAATGTTAA CACATTGTGT TACGGCGACG GCATCTCCAA GTAGGCGCGC
2041 GGATACACGA CGTTCTAGGG CCATCGAGAC CACCCCACCG GGATTGAGTT TAGGGTCTC
2101 TGTCCACAGC ACATGTTCGC GGTTCTGAAG TGTACACCAG GCAGTGGCTA TCCGACTCAA
2161 CATTTCATTT ACATGGGCTT GTATGTAGTC ATAGGCAAAT TGTAGCATTG CGAATTCCAC
2221 AGATGAGGTG GTCTTGAGGA GTGATGCATT GTTCACGGTT TCTATACCCC CCTCTATTGT
```

FIG. 5B

```
2281 GCTGCGCCGC GACCTATGAT GTTGATTAGA TGGGACCGAT CTTCTAGTTC GTTGTACTGT
2341 TTCCCCAGAT GGATTGAGGA GTGCACTGAG ATCTACCGTG CGATTGGAAC GTGCTAATTC
2401 ATTGATATAT AACTTTGCTA GTTCGTTGCT GATCATGGGA CGGAAAGCTA TTAGAAATCC
2461 CCCACGGGCT AGGTAGGTCT CCAGGGTTCC AGTCTGAATA TGAGTTTTAC TATATTTACT
2521 CTTATAAATC CGGTCTATGG CTTCGGCTGC CTCCTTGGTG GCACAGTCCC CCAAACGGAT
2581 ACGATTGATT TCAAATTGTG AAGTATTGGA GATGAAAGTA GCGGATATGG TCTTGGCTGT
2641 AAATCTATAG GAGCCCTGAT ATTCATCGCG TAGCATTTCA TCTATTTCCC TCCATTTGGC
2701 TAAGGTACAT ACCCGACCAG ACTTTGGGGT CCAGTTCCAG GCCACTGTCA CATGCGGAGT
2761 TTCCAAAAAA TTGCGAGAAA CTGGTGCCCC CAGTTGTAAT CGCGTATCCA AGTCTATTGG
2821 ATAGTATCCC TCGATTTGTT GAAATCTGTC TGAAGAATAA CTAGTATGTT CTACATGGGC
2881 TCCATCCCTC AGCCCAAAGA ATGGAGACAT GTGAATCACG TCACCAGTGG AGATAGCAAA
2941 TGAGTCATAT GGATATACAG ATCTTGCATC CACTTCCTCT ACGATGCAAT TTACAGAGGT
3001 CCCAGAGTGG TGAAATCCAG CAGCACCGAT CTTTGTGTAT GTTTCATTGG TGGTGTGCCA
3061 TCCACGGGAC TCTGGAGTGT TGAACTTGGA GGGTTTCAGA GGCAGTTCTC TGGGATCCTC
3121 GTCTCGATCA AAGGCCGTAA ATTGATAATT GTTACGAACG TAATCAGCTT TCGAGAGGCA
3181 CATACCCCGT CTATCTATGA GATCTGTAAT CTCTTGAACT TTCACGGGAA CCCTGTCTGT
3241 ATATCGGTTG GTTGTAACGG CATAGGAACT CCCAGACCAT ACCGTTGTCA TAATAATGTT
3301 TTTATAGTAT ATATTTGCCT TGAATTTATA TGGCGCTATA TTTTCTTTAA ATATTACAGC
3361 TATACCCTCG GTAAAATTTT TCCCTAGTTT ATAATCTGGA CAGGCCCGTG GTGGCTCTAA
3421 ACGCACGACA GTAGATCCTG AAGGTGGTGG ACACATATAG AAAGTCGATG GTCCGTTAGC
3481 CTCTATTTGG GACGCACGGA GAGCTTCCCT CATATCCGAC ATATCGGTGG GATCTGTAGT
3541 TGGTTTTGGT GGTGTACCCC CTACCTCAGG GGTAGCTACA GTCCGCCGGG GTTGTTCCGA
3601 TGTGCTTCCA GATTGACCCT CTACTGGACG GGGACCGACT AAGAATAGTA CGATCCAGAT
3661 AAATGAAACA TATCTAGCTA GTCTGGTTAA TCCCGACGAT CCGTTACCAT GTCTGGAGCC
3721 AGTCGCTGCA ATACCGAGTA GAGAAGGGAA AAAACATCTC TGTCGAAAAT AGCCACTGTG
3781 TCCCTGCCAA CGACTCCCTC GTCGCCGCTT CCCAAGATCG CCACGAGTGG ACATTACGAT
3841 ACAAACTTAA CGGATATCGC GATAATGAAA TAATTTATGA TTATTTCTCG CTTTCAATTT
3901 AACACAACCC TCAAGAACCT TTGTATTTAT TTTCACTTTT TAAGTATAGA ATAAAGAAGC
3961 TCTAATTAAT TAAGCTACAA ATAGTTTCGT TTTCACCTTG TCTAATAACT AATTAATTAA
4021 CCCGGATCGA TCCCGATTTT TATGACTAGT TAATCAAATA AAAAGCATAC AAGCTATTGC
4081 TTCGCTATCG TTACAAAATG GCAGGAATTT TGTGTAAACT AAGCCACATA CTTGCCAATG
4141 AAAAAAATAG TAGAAAGGAT ACTATTTTAA TGGGATTAGA TGTTAAGGTT CCTTGGGATT
4201 ATAGTAACTG GCATCTGTT AACTTTTACG ACGTTAGGTT AGATACTGAT GTTACAGATT
4261 ATAATAATGT TACAATAAAA TACATGACAG GATGTGATAT TTTTCCTCAT ATAACTCTTG
4321 GAATAGCAAA TATGGATCAA TGTGATAGAT TTGAAAATTT CAAAAAGCAA ATAACTGATC
4381 AAGATTTACA GACTATTTCT ATAGTCTGTA AAGAAGAGAT GTGTTTTCCT CAGAGTAACG
4441 CCTCTAAACA GTTGGGAGCG AAAGGATGCG CTGTAGTTAT GAAACTGGAG GTATCTGATG
4501 AACTTAGAGC CCTAAGAAAT GTTCTGCTGA ATGCGGTACC CTGTTCGAAG GACGTGTTTG
4561 GTGATATCAC AGTAGATAAT CCGTGGAATC CTCACATAAC AGTAGGATAT GTTAAGGAGG
4621 ACGATGTCGA AAACAAGAAA CGCCTAATGG AGTGCATGTC CAAGTTTAGG GGGCAAGAAA
4681 TACAAGTTCT AGGATGGTAT TAATAAGTAT CTAAGTATTT GGTATAATTT ATTAAATAGT
4741 ATAATTATAA CAAATAATAA ATAACATGAT AACGGTTTTT ATTAGAATAA AATAGAGATA
4801 ATATCATAAT GATATATAAT ACTTCATTAC CAGAAATGAG TAATGGAAGA CTTATAAATG
4861 AACTGCATAA AGCTATAAGG TATAGAGATA TAAATTTAGT AAGGTATATA CTTAAAAAAT
4921 GCAAATACAA TAACGTAAAT ATACTATCAA CGTCTTTGTA TTTAGCCGTA AGTATTTCTG
4981 ATATAGAAAT GGTAAAATTA TTACTAGAAC ACGGTGCCGA TATTTAAAA TGTAAAAATC
5041 CTCCTCTTCA TAAAGCTGCT AGTTTAGATA ATACAGAAAT TGCTAAACTA CTAATAGATT
5101 CTGGCGCTGA CATAGAACAG ATACATTCTG GAAATAGTCC GTTATATATT TCTGTATATA
5161 GAAACAATAA GTCATTAACT AGATATTTAT TAAAAAAGG TGTTAATTGT AATAGATTCT
5221 TTCTAAATTA TTACGATGTA CTGTATGATA AGATATCTGA TGATATGTAT AAAATATTTA
5281 TAGATTTTAA TATTGATCTT AATATACAAA CTAGAAATTT TGAAACTCCG TTACATTACG
5341 CTATAAAGTA TAAGAATATA GATTTAATTA GGATATTGTT AGATAATAGT ATTAAAATAG
5401 ATAAAGTTT ATTTTTGCAT AAACAGTATC TCATAAAGGC ACTTAAAAAT AATTGTAGTT
5461 ACGATATAAT AGCGTTACTT ATAAATCACG GAGTGCCTAT AAACGAACAA GATGATTTAG
```

FIG. 5C

```
5521 GTAAAACCCC ATTACATCAT TCGGTAATTA ATAGAAGAAA AGATGTAACA GCACTTCTGT
5581 TAAATCTAGG AGCTGATATA AACGTAATAG ATGACTGTAT GGGCAGTCCC TTACATTACG
5641 CTGTTTCACG TAACGATATC GAAACAACAA AGACACTTTT AGAAAGAGGA TCTAATGTTA
5701 ATGTGGTTAA TAATCATATA GATACCGTTC TAAATATAGC TGTTGCATCT AAAAACAAAA
5761 CTATAGTAAA CTTATTACTG AAGTACGGTA CTGATACAAA GTTGGTAGGA TTAGATAAAC
5821 ATGTTATTCA CATAGCTATA GAAATGAAAG ATATTAATAT ACTGAATGCG ATCTTATTAT
5881 ATGGTTGCTA TGTAAACGTC TATAATCATA AAGGTTTCAC TCCTCTATAC ATGGCAGTTA
5941 GTTCTATGAA AACAGAATTT GTTAAACTCT TACTTGACCA CGGTGCTTAC GTAAATGCTA
6001 AAGCTAAGTT ATCTGGAAAT ACTCCTTTAC ATAAAGCTAT GTTATCTAAT AGTTTTAATA
6061 ATATAAAATT ACTTTTATCT TATAACGCCG ACTATAATTC TCTAAATAAT CACGGTAATA
6121 CGCCTCTAAC TTGTGTTAGC TTTTTAGATG ACAAGATAGC TATTATGATA ATATCTAAAA
6181 TGATGTTAGA AATATCTAAA AATCCTGAAA TAGCTAATTC AGAAGGTTTT ATAGTAAACA
6241 TGGAACATAT AAACAGTAAT AAAAGACTAC TATCTATAAA AGAATCATGC GAAAAAGAAC
6301 TAGATGTTAT AACACATATA AAGTTAAATT CTATATATTC TTTTAATATC TTTCTTGACA
6361 ATAACATAGA TCTTATGGTA AAGTTCGTAA CTAATCCTAG AGTTAATAAG ATACCTGCAT
6421 GTATACGTAT ATATAGGGAA TTAATACGGA AAAATAAATC ATTAGCTTTT CATAGACATC
6481 AGCTAATAGT TAAAGCTGTA AAAGAGAGTA AGAATCTAGG AATAATAGGT AGGTTACCTA
6541 TAGATATCAA ACATATAATA ATGGAACTAT TAAGTAATAA TGATTTACAT TCTGTTATCA
6601 CCAGCTGTTG TAACCCAGTA GTATAAAG
```

FIG.6A

```
POL/NEF epitopes
           10         20         30         40         50         60         70         80         90        100        110
           *          *          *          *          *          *          *          *          *          *          *
TTTTTTTCAT TATTTAGAAA TTATGCATTT TAGATCTTTA TAGGGGCCG TGATTAACTA GTCATAAAAA CCCGGATCG ATTCTAGACT CGAGGGTACC GGATCTTAAT
AAAAAAAGTA ATAAATCTTT AATACGTAAA ATCTAGAAAT ATTCGCCGGC ACTAATTGAT CAGTATTTTT GGGCCCTAGC TAAGATCTGA GCTCCCATGG CCTAGAATTA 120        130        140        150        160        170        180        190        200        210        220
           *          *          *          *          *          *          *          *          *          *          *
TAATTAGTCA TCAGGCAGGG CGAGAACGAG ACTATCTGCT CGTTAATTAA TTAGGTCGAC GGATCCCCCA ACAAAAACTA ATCAGCTATC GGGGTTAATT AATTAGTTAT
ATTAATCAGT AGTCCGTCCC GCTCTTGCTC TGATAGACGA GCAATTAATT AATCCAGCTG CCTAGGGGGT TGTTTTTGAT TAGTCGATAG CCCCAATTAA TTAATCAATA 230        240        250        260        270        280        290        300        310        320        330
           *          *          *          *          *          *          *          *          *          *          *
TAGACAAGGT GAAAACGAAA CTATTGTAG CTTAATTAAT TAGAGCTTCT TTATTCTATA CTTAAAAAGT GAAAATAAAT ACAAAGGTTC TTGAGGGTTG TGTTAAATTG
ATCTGTTCCA CTTTGCTTT GATAAACATC GAATTAATTA ATCTCGAAGA AATAAGATAT GAATTTTTCA CTTTTATTTA TGTTTCCAAG AACTCCCAAC ACAATTTAAC
                                                                                H6 promoter 340        350        360        370        380        390        400        410        420        430
           *          *          *          *          *          *          *          *          *          *
AAGGCGAGAA ATAATCATAA ATTATTTCAT TATCGGGATA TCCGTTAAGT TTGTATCGTA ATG CCA CTA ACA GAA GAA GCA GAG CTA GAA GCA GAA AAC
TTCGCTCTT TATTAGTATT TAATAAAGTA ATAGCCTAT AGGCAATTCA AACATAGCAT TAC GGT GAT TGT CTT CTT CGT CTC GAT CTT CGT CTT TTG
       H6 promoter                                                 > Met Pro Leu Thr Glu Glu Ala Glu Leu Glu Ala Glu Asn
                                                                                POL/NEF Epitopes
```

FIG. 6B

```
       440         450         460         470         480         490         500         510         520
        *           *           *           *           *           *           *           *           *
AGA GAG ATT CTA AAA GAA CCA CAT GGA GTG TAT TAT GAC CCA AAA TCA GAC TTA ATA GCA GAA ATA CAG AAG CAG GGG CAA GGC CAA
TCT CTC TAA GAT TTT CTT GGT GTA CCT CAC ATA ATA CTG GGT AGT TTT CTG AAT TAT CGT CGT CTT GTC TTC GTC CCC GTT CCG GTT
Arg Glu Ile Leu Lys Glu Pro His Gly Val Tyr Tyr Asp Pro Lys Ser Asp Leu Ile Ala Glu Ile Gln Lys Gln Gly Gln Gly Gln
                                                                    POL/NEF Epitopes 530         540         550         560         570         580         590         600         610
        *           *           *           *           *           *           *           *           *
TGG ACA TAT CAA ATT TAT CAA GAG CTC GGT AAA ACA GAG TGG ACC CTC AAA GAG TGG ACC CTC AGA TCT AGA TCT AAA GTA GTG CAT
ACC TGT ATA GTT TAA ATA GTT CTC GAG CCA TTT TGT CTC ACC TGG AGT TCT CTC ACC TGG AGT TCT AGA TCT AGA TTT CAT CAC GTA
Trp Thr Tyr Gln Ile Tyr Gln Glu Leu Gly Lys Thr Glu Trp Thr Leu Lys Glu Trp Thr Leu Arg Ser Arg Ser Lys Val Val His
                                                  POL/NEF Epitopes 620         630         640         650         660         670         680         690         700
        *           *           *           *           *           *           *           *           *
GCT AGA TCA CAT CCT GAA CTT AAA AAT TGT ACA TAT TTT AAA ATT TTA CAA AGT TCA AGT TCA TTC AAG CTT ATG GCA ATA TTC AAA ATC TTA GAG CCT TTT AGA
CGA TCT AGT GTA GGA CTT GAA TTT TTA ACA TGT ATA AAA TTT TAA AAT GTT TCA AGT TCA AAG TTC GAA TAC CGT TAT AAG TTT TAG AAT CTC GGA AAA TCT
Ala Arg Leu His Pro Glu Leu Lys Asn Cys Thr Tyr Phe Lys Ile Leu Gln Ser Ser Ser Met Thr Lys Ile Phe Leu Glu Pro Phe Arg
                                                                                      POL/NEF Epitopes 710         720         730         740         750         760         770         780         790
        *           *           *           *           *           *           *           *           *
AAA CAA AAT CCA GAC ATA GTT ATC TAT CAA TAC ATG GAT GAT TTG TAT GTA GGA TCT GAC TTG GAA GAA CAT CCC GTC TAT TCT TAT
TTT GTT TTA GGT CTG TAT CAA TAG ATA GTT ATG TAC CTA CTA AAC ATA CAT CCT AGA CTG AAC CTT CTT GTA GGG CAG TAG ATA ATA
Lys Gln Asn Pro Asp Ile Val Ile Tyr Gln Tyr Met Asp Asp Leu Tyr Val Gly Ser Asp Leu Glu Glu His Pro Val Tyr Ser Tyr
                                                                                     POL/NEF Epitopes 800         810         820         830         840         850         860         870         880
        *           *           *           *           *           *           *           *           *
GAG CTG AGA CAA CAT CTG TTG AGG GGA CTT GAA TCC ACC CCT GAC AAC ACC ATG GGT CTT CCA ACA CCT CAA GTA GGT CAT AGA CCA ATG ACT
CTC GAC TCT GTT GTA GAC AAC TCC CCT GAA CTT AGG TGG GGA CTG TTG TGG TAC CCA GAA GGT TGT GGA GTT CAT CCA GTA TCT GGT TAC TGA
Glu Leu Arg Gln His Leu Leu Arg Gly Leu Glu Trp Thr Tyr Thr Met Val Gly Phe Pro Gln Val Pro Leu Arg Pro Met Thr
                                                                             POL/NEF Epitopes
```

FIG. 6C

```
          890         900         910         920         930         940         950         960         970
           *           *           *           *           *           *           *           *           *
TAC AAA GCA GCT GTA GAT CTT TCT CAC TTT TTA AAA GAA AAA GGA GGT TTA GAA GGG CTA ATT CAT TCT CAA CGA AGA CAA GAT ATT CTT
ATG TTT CGT CGA CAT CTA GAA GTG AAA AAT TTT CTT CCT CCA AAT CTT CCC GAT TAA GTA AGA GTT GCT TCT GTT CTA TAA GAA
Tyr Lys Ala Ala Val Asp Leu Ser His Phe Leu Lys Glu Lys Gly Gly Leu Glu Gly Leu Ile His Ser Gln Arg Arg Gln Asp Ile Leu
                                                                              POL/NEF Epitopes 980         990        1000        1010        1020        1030        1040        1050        1060
           *           *           *           *           *           *           *           *           *
GAT TTG TGG ATT TAT ACA CAA GGA TAT CCT GAT TGG CAG AAT TAC ACA CCA GGA CCA GGG GTC AGA TAC CCA TTA ACC TTT GGT
CTA AAC ACC TAA ATA TGT GTT CCT ATA GGA CTA ACC GTC TTA ATG TGT GGT CCT GGT CCC CAG TCT ATG GGT AAT TGG AAA CCA
Asp Leu Trp Ile Tyr Thr Gln Gly Tyr Phe Pro Asp Trp Gln Asn Tyr Thr Pro Gly Pro Gly Val Arg Tyr Pro Leu Thr Phe Gly
                                                              POL/NEF Epitopes 1070        1080        1090        1100        1110        1120        1130        1140        1150
           *           *           *           *           *           *           *           *           *
TGG TGC TAC AAG CTA GTA CCA GTT GAG ACT GTA CCA GTA AAG TTA AAG CCA GGA ATG GAT GGC CCA AAA GTT AAA CAA TGG CCA TTG
ACC ACG ATG TTC GAT CAT CTC TGA CAT GGT CAA CTC TGA CAT TTC AAT TTC GGT CCT TAC CTA CCG GGT TTT CAA TTT GTT ACC GGT AAC
Trp Cys Tyr Lys Leu Val Pro Val Glu Thr Val Pro Val Lys Leu Lys Pro Gly Met Asp Gly Pro Lys Val Lys Gln Trp Pro Leu
                                                                     POL/NEF Epitopes 1160        1170        1180        1190        1200        1210        1220        1230        1240
           *           *           *           *           *           *           *           *           *
ACA GAA AAA ATA GCA TTT TTT CGT AAT CAT CTT TAA ACA TGT CTC TAC CTT CTT ACA GAG ATG GAA AAG GAA AAA ATT TCA AAA ATT GGG CCT TAA TTTTTCT
TGT CTT TTT TAT TTT TAT CGT AAT AGT CAT TTA AGT TGT TTT TAA AGT TTT TAA AGT TTT TAA AGT TTT TAA CCC GGA ATT AAAAAGA
Thr Glu Lys Ile Ala Leu Val Glu Ile Cys Thr Glu Met Glu Lys Glu Lys Glu Lys Ile Ser Lys Ile Gly Pro
                                                                POL/NEF Epitopes 1250        1260        1270        1280        1290        1300        1310        1320        1330        1340        1350
           *           *           *           *           *           *           *           *           *           *           *
GCAGCCCGGG GGATCCTTTT TATAGCTAAT TAGTCACGTA CCTTGAGAG TACCACTTCA GCTACCTCTT TTGTGTCTCA GAGTAACTTT CTTTAATCAA TTCCAAAACA
CGTCGGGCCC CCTAGGAAAA ATATCGATTA ATCAGTGCAT GGAAACTCTC ATGGTGAAGT CGATGGAGAA AACACAGAGT CTCATTGAAA GAAATTAGTT AAGGTTTTGT
```

FIG. 7A gag (+ pro) and gp120 (+ transmembrane)

| FEATURES | From | To/Span | Description |
|---|---|---|---|
| frag | 1 | 56 | C3 flanking arm |
| frag | 162 | 76 (C) | HIV1 (IIIB) env transmembrane region |
| frag | 1728 | 163 (C) | HIV1 (MN) gp120 gene |
| frag | 1853 | 1729 (C) | vaccinia H6 promoter |
| frag | 1925 | 1983 | vaccinia I3L promoter |
| frag | 1984 | 3746 | HIV1 (IIIB) gag/pro gene |
| frag | 3753 | 3808 | C3 flanking arm |

```
        10        20        30        40        50        60        70        80        90       100       110       120
TAATGTAGTATACTAATATTAACTCACATTTGACTAATTAGCTATAAAAACCCGGGATCGATTCTAGAATAAAAATTATCCCTGCCTAACTCTATTCACTACAGAGAGTACAGCAAAAAC
ATTACATCATATGATTATAATTGAGTGTAAACTGATTAATCGATATTTTTGGGCCCTAGCTAAGATCTTATTTTTAATAGGGACGGATTGAGATAAGTGATGTCTCTCATGTCGTTTTTG
                                                                                G  Q  R  V  R  N  V  V  S  L  V  A  F  V
____________________C3 FLANKING ARM_____________________>
                                                                           <____HIV1 (IIIB) ENV TRANSMEMBRANE REGION_____

130       140       150       160       170       180       190       200       210       220       230       240
TATTCTTAAACCTACCAAGCCTCCTACTATCATTATGAATAATCTTTTTTCTCTCTGCACCACTCTTCTCTTTGCCTTGGTGGGTGCTACTCCTAATGGTTCAATTGTTACTACTTTATA
ATAAGAATTTGGATGGTTCGGAGGATGATAGTAATACTTATTAGAAAAAAGAGAGACGTGGTGAGAAGAGAAACGGAACCACCCACGATGAGGATTACCAAGTTAACAATGATGAAATAT
 I  R  L  G  V  L  G  G  V  I  M  I  F  L  R  K  E  R  Q  V  V  R  R  K  A  K  T  P  A  V  G  L  P  E  I  T  V  V  K  Y
<__HIV1 (IIIB) ENV TRANSMEMBRANE REGION___
                                        <____________________________HIV1 (MN) GP120 GENE______________________________

250       260       270       280       290       300       310       320       330       340       350       360
TTTATATAATTCACTTCTCCAATTGTCCCTCATATCTCCTCCTCCAGGTCTGAAGATCTCGGTGTCGTTCGTGTCCGTGTCCTTACCACCATCTCTTGTTAATAGTAGCCCTGTAATATT
AAATATATTAAGTGAAGAGGTTAACAGGGAGTATAGAGGAGGAGGTCCAGACTTCTAGAGCCACAGCAAGCACAGGCACAGGAATGGTGGTAGAGAACAATTATCATCGGGACATTATAA
 K  Y  L  E  S  R  W  N  D  R  M  D  G  G  G  P  R  F  I  E  T  D  N  T  D  T  D  K  G  G  D  R  T  L  L  L  G  T  I  N
<_______________________________________________HIV1 (MN) GP120 GENE_________________________________________________

```
           970       980       990      1000      1010      1020      1030      1040      1050      1060      1070      1080
GACATTTTACATGATCCTTTCCACTGAACTTTTATCGTTACACTTTAGAATCGCAAAACCAGCCGGGCACAATAGTGTATGGGAATTGGCTCAAAGGATATCTTGGACAAGCTTG
CTGTAAAAATGTACTAGGAGAAAAGGTGACTTGAAATAGCAATGCGTTTGGTCGGCCCCGTGTTATCACATACCCTTAACCGAGTTTCCTATAGAAACCTGTTGAAC
 V  N  K  C  S  G  K  G  S  F  K  K  D  N  C  K  L  I  A  F  G  A  P  A  C  Y  H  I  P  I  P  E  F  S  I  K  P  C  A  Q
                                                      HIV1 (MN) GP120 GENE
V 1090      1100      1110      1120      1130      1140      1150      1160      1170      1180      1190      1200
TGTAATGACTGAGGTATTACAACTTATCAACCTATCATATCATTATTATTGATACTATATAGTTTATAAGAAGTGCATATTCTTTCTGCATCTATCTCTATGCTTGT
ACATTGACTGACTCCATAAGTTGAATATCGACCATAGTAGTTCAAATATTTCTTCACGTATAAGAAAGACGTAGAATACGAACA
 T  I  V  S  T  N  C  S  I  L  R  Y  S  T  S  D  N  N  I  S  V  I  D  L  K  Y  L  L  A  Y  E  K  Q  M  K  D  R  I  S  T
                                                      HIV1 (MN) GP120 GENE
V 1210      1220      1230      1240      1250      1260      1270      1280      1290      1300      1310      1320
TGTGATATTGAAAGAGCAGTTTTCATTTCTCCTATTGTCCCTCGCTATTACTATTGTTATTAGCAGTACTATTATTGGTATTAGTAGTATTCCTCAAATCAGTGCAATTTAA
CCACTATAACTTTCTGTCAAAAGTAAAGAGGAGGAAATAACAGGAGCGATAATGATAACATAACGTCATGATAATCATCATAAGGAGTTAGTCACGTTAAATT
 T  I  N  F  S  C  N  K  M  E  G  G  K  I  T  G  E  S  N  N  N  A  T  S  N  N  T  T  N  R  L  D  T  C  N  L
                                                      HIV1 (MN) GP120 GENE
V 1330      1340      1350      1360      1370      1380      1390      1400      1410      1420      1430      1440
AGTAACACAGAGTGGGTTAATTTTACACATGGCTTTAGGCTTTGATCCATAAACTGATTATATCCTCATGCATCGTTCTACCATGTACCATGTTAATTTTCTGTCAC
TCATTGTGTCTCACCCATTAAAATGTGTACCAGAATCCGAAATCTAGGGTATTTGACTAATAATAGAGGTACTAACAAGATGGTACAATAAAAGGTGTACAATTTAAAAGACAGTG
 T  V  C  L  P  T  L  K  V  C  P  K  L  S  Q  D  W  L  S  I  D  E  H  M  Q  E  V  H  N  K  W  M  N  F  N  E  T  V
                                                      HIV1 (MN) GP120 GENE
V 1450      1460      1470      1480      1490      1500      1510      1520      1530      1540      1550      1560
ATTTACCAATTCTACTTCTTGTGGGTTCTGTGGGTCTGTGGGTACACAGGCATGTGGCCCAAACATTAGTACCTCTGTATCATATGCTTTAGCATCTGATGCACAAAATAGAGTGTGGT
TAAATGGTTAAGATGAAGAACACCCAGGAGTTGTCGTAACACCATGGTCCGTAGCCCATGTGTAATACATGGAGAAATACGAGAGATACTACGTGTTTATCTCACCACCA
 N  V  L  E  V  E  Q  P  N  P  D  T  P  V  C  A  H  T  A  W  N  H  V  E  T  D  Y  A  K  A  D  S  A  C  F  L  T  T
                                                      HIV1 (MN) GP120 GENE
V
```

FIG. 7D

```
     1570      1580      1590      1600      1610      1620      1630      1640      1650      1660      1670      1680
TGCTTCTTTCCACACAGTACCCCATAATAGACTGTGACCACTGATCATCCAAGGAGCATGGTGCCCCATCTCCACAAGTG
ACGAAGAAAGGTGTGTCCATGGGGTATTACTCTGACACTGGGTTAAAAAGACTGTGAGTAGTAGTTGTAGGGTCCTGTACCACGGGTAGAGGTGGGGTAGAGGTGTCAC
 A  E  K  W  V  P  V  G  Y  Y  V  T  V  H  L  K  E  T  A  S  C  I  M  L  M  G  L  L  M  T  G  W  R  H  G  W  R  H  L  H
                                              HIV1 (MN) GP120 GENE 1690      1700      1710      1720      1730      1740      1750      1760      1770      1780      1790      1800
CTGATATTTCTCCTTCACTCTCTCATTGCCACTGTCTTCTGCTCTTTCATATACGATACAAACTTAACGCATATCGCGATAATGAAATTTATGATTATTTCTCGCTTTCAATTTAACAC
GACTATAAAGAGGAAGTGAGAGTAACGGTGACAGAAGACAGAGAAACATAATGCTATGTTGAATTGCGTATAGCGTATGGCTATAGCCTATTACTTATTAAATACTAATAAAGAGGAAAGTTAAATTGTG
 Q  Y  K  E  K  V  R  M  A  V  T  K  Q  E  K  M
        HIV1 (MN) GP120 GENE                                        VACCINIA H6 PROMOTER 1810      1820      1830      1840      1850      1860      1870      1880      1890      1900      1910      1920
AACCCTCAAGAACCTTGTATTATTTTCACTTTTCACTGGTAATAAAGAAGCTCTAATTAAGTACAACAATAGTTCGTTTCACCTTGTCTAATAACTAATAATTAACCCGG
TTGGGAGTTCTTGGAACATAAAGTGAAACATTCATATCTATTTCTTCGAGATTATTTCTTATCAAGCAAAGTGGAACAGATTATTGATTAATTAATTGGGCC
                                                        VACCINIA H6 PROMOTER 1930      1940      1950      1960      1970      1980      1990      2000      2010      2020      2030      2040
ATCTTGAGATAAAGTGAAATATATCATTATTACAAAGTACAATTATTTAGGTTAAATCATGGGTGCGAGAGCGTCAGTATTAAGCGGGGAGAATTAGATCGATGGGAAAAAATT
TAGAACTCTATTTCACTTTATATAGTAATAATGTTTCATGTAATAAATCCAATTAGTACCCAGCTCTCGCAGTCATAATTCGCCCCTCTTAATCTAGCTACCCTTTTTAA
                VACCINIA I3L PROMOTER                    > M  G  A  R  A  S  V  L  S  G  G  E  L  D  R  W  E  K  I
                                                                     HIV1 (IIIB) GAG/PRO GENE 2050      2060      2070      2080      2090      2100      2110      2120      2130      2140      2150      2160
CGGTTAAGGCCAGGGGAAAGAAAAAATATAAATTAAAACATATAGTATGGGCAAGCAGGGAGCTAGAACGATTCGCAGTTAATCCTGGCCTGTTAGAAACATCAGAAGGCTGTAGACAA
GCCAATTCCGGTCCCCTTTCTTTTTTATATTTAATTTTGTATATCATACCCGTTCGTCCCTCGATCTTGCTAAGGCGTCAATTAGGACGACATCTTTGTAGTCTTCCGACATCTGTT
 R  L  R  P  G  G  K  K  K  Y  K  L  K  H  I  V  W  A  S  R  E  L  E  R  F  A  V  N  P  G  L  L  E  T  S  E  G  C  R  Q
                        HIV1 (IIIB) GAG/PRO GENE 2170      2180      2190      2200      2210      2220      2230      2240      2250      2260      2270      2280
```

FIG. 7E

```
ATACTGGGACAGCTACAACCATCCCTCAGACAGGATCAGAAGAACTTAGATCATTATATAATACAGTAGCAACCCTCTATTGTGTGCATCAAAGGATAGAGATAAAAGACACCAAGGAA
TATGACCCTGTCGATGTTGGTAGGGAAGTCGTCCTAGTCTTCTTGAATCTAGTAATATATTATGTCATCGTTGGGAGATAACACGTAGTTCTTCCTATCTCTATTTTCTGTGGTTCCTT
 I  L  G  Q  L  Q  P  S  L  Q  T  G  S  E  E  L  R  S  L  Y  N  T  V  A  T  L  Y  C  V  H  Q  R  I  E  I  K  D  T  K  E
    2290      2300      2310      2320      2330      2340      2350      2360      2370      2380      2390      2400
                                            HIV1 (IIIB) GAG/PRO GENE

GCTTTAGACAAGATAGAGGAAGAGAGAACAAAAGTAAGAAAAAAAGCACAGCAAGCAGCAGCTGACAGCAGCAATCAGGTCAGCCAAATTACCCTATAGTGCAGAACATCCAG
CGAAATCTGTTCTATCTCCTTCTCTCTTGTTTCATTCTTTTTCGTGTCGTTCGTCGTCGACTGTCGTCGTCGTCGTTAGTCCAGTCGGTTTAATGGGATATCACGTCTTGTAGGTC
 A  L  D  K  I  E  E  E  Q  N  K  S  K  K  K  A  Q  Q  A  A  A  D  T  G  H  S  N  Q  V  S  Q  N  Y  P  I  V  Q  N  I  Q
    2410      2420      2430      2440      2450      2460      2470      2480      2490      2500      2510      2520
                                            HIV1 (IIIB) GAG/PRO GENE

GGGCAAATGGTACATCAGGCCATATCACTAGAACTTAAATGCATGGGTAAAAGTAGTAGAAGAGAAGGCTTTCAGCCCAGAAGTGATACCCATGTTTTCAGCATTATCAGAAGGAGCC
CCCGTTTACCATGTAGTCCGGTATAGTGATCTTGAAATTTACGTACCCATTTTCATCATCTTCTTCCGAAAGTCGGGTCTTCACTATGGGTACAAAAGTCGTAATAGTCTTCCTCGG
 G  Q  M  V  H  Q  A  I  S  P  R  T  L  N  A  W  V  K  V  V  E  E  K  A  F  S  P  E  V  I  P  M  F  S  A  L  S  E  G  A
    2530      2540      2550      2560      2570      2580      2590      2600      2610      2620      2630      2640
                                            HIV1 (IIIB) GAG/PRO GENE

ACCCCACAAGATTTAAACACCATGCTAAACACAGTGGGGGGACATCAAGCAGCCATGCAAATGTTAAAAGAGACCATCAATGAGGAAGCTGCAGAATGGGATAGAGTGCATCCAGTGCAT
TGGGGTGTTCTAAATTTGTGGTACGATTTGTGTCACCCCCCCTGTAGTTCGTCGGTACGTTTACATTTTCTGCGTAGTTACTCCTTCGACGTCTTACCCTATCTCACGTAGGTCACGTA
 T  P  Q  D  L  N  T  M  L  N  T  V  G  G  H  Q  A  A  M  Q  M  L  K  E  T  I  N  E  E  A  A  E  W  D  R  V  H  P  V  H
    2650      2660      2670      2680      2690      2700      2710      2720      2730      2740      2750      2760
                                            HIV1 (IIIB) GAG/PRO GENE

GCAGGGCCTATTGCACCAGGCCAGATGAGAGAACCAAGGGGAAGTGACATAGCAGGAACTACTAGTACCCTTCAGGAACAACATAGGATGACAAATAATCCACCTATCCCAGTAGGA
CGTCCCGGATAACGTGGTCCGGTCTACTCTCTTGGTTCCCCTTCACTGTATCGTCCTTGATGATCATGGGAAGTCCTTGTTGTATCCTACTGTTTATTAGGTGGATAGGGTCATCCT
 A  G  P  I  A  P  G  Q  M  R  E  P  R  G  S  D  I  A  G  T  T  S  T  L  Q  E  Q  I  G  W  M  T  N  N  P  P  I  P  V  G
    2650      2660      2670      2680      2690      2700      2710      2720      2730      2740      2750      2760
                                            HIV1 (IIIB) GAG/PRO GENE
```

FIG. 7F

```
      2770      2780      2790      2800      2810      2820      2830      2840      2850      2860      2870      2880
GAAATTTATAAAAGATGGGATAATCCTGGATTAAATAAAATAGTAAGAATGTATAGCCCTACCAGCATTCTGGACACATAAGACAAGGACCAAAAGAACCCTTTAGAGACTATGTAGACCGG
CTTTAAATATTTTCTACCTATTAGAGACCCTAATTTATTTATCATTTACATATCGGATGGTCGTGAAGACCTGTATTCTGTTCCTGGTTTCTTGGGAAATCTCTGATACATCTGGCC
 E  I  Y  K  R  W  I  I  L  G  L  N  K  I  V  R  M  Y  S  P  T  S  I  L  D  I  R  Q  G  P  K  E  P  F  R  D  Y  V  D  R
                                      HIV1 (IIIB) GAG/PRO GENE 2890      2900      2910      2920      2930      2940      2950      2960      2970      2980      2990      3000
TTCTATAAAACTCTAAGAGCCGAGCAAGCTTCACAGAGGAGTAAAAAAATTGGATGACAGAAACCTTGTTGGTCCAAAATGCAACCAGATTGTAAGACTATTTTAAAAGCATTGGGACCA
AAGATATTTGAGATTCTCGGCTCGTTCGAAGTGTCTCCTCATTTTTTAACCTACTGTCTTTGGAACAACCAGGTTTTACGTTGGTCTAACATTCTGATAAAATTTCGTAACCTGGT
 F  Y  K  T  L  R  A  E  Q  A  S  Q  E  V  K  N  W  M  T  E  T  L  L  V  Q  N  A  N  P  D  C  K  T  I  L  K  A  L  G  P
                                      HIV1 (IIIB) GAG/PRO GENE 3010      3020      3030      3040      3050      3060      3070      3080      3090      3100      3110      3120
GCGGCTACACTAGAAGAAATGATGACAGCATGTCAGGGAGTAGGAGGACCCGGCCATAAGGCAAGAATTTTGGCTGAAGCAAGTAACAAATTCAGTCACTACCATAATGATGCAG
CGCCGATGTGATCTTCTTGGTTTCTACTACTGTCGTACAGTCCCTCATCCTCCTGGGGCCGGTATTCCGTTCTTAAACCGACTTCGTTCATTGTTAAGTCGATGATGGTATTACTACGTC
 A  A  T  L  E  E  M  M  T  A  C  Q  G  V  G  G  P  G  H  K  A  R  V  L  A  E  A  M  S  Q  V  T  N  S  A  T  I  M  M  Q
                                      HIV1 (IIIB) GAG/PRO GENE 3130      3140      3150      3160      3170      3180      3190      3200      3210      3220      3230      3240
AGAGGCAATTTTAGGAACCAAAGAAAGATTGTTAAGTGTTTCAATTGTGGCAAAGAAGGGCACACAGCCAGAAATTGCAGGGCCCCTAGGAAAAAGGGCTGTTGGAAATGTGGAAAGGAA
TCTCCGTTAAAATCCTTGGTTTCTTTCTAACAATTCACAAAGTTAACACCGTTTCTTCCCGTGTGTCGGTCTTTAACGTCCCGGGGATCCTTTTCCGACAACCTTTACACCTTTCCTT
 R  G  N  F  R  N  Q  R  K  I  V  K  C  F  N  C  G  K  E  G  H  T  A  R  N  C  R  A  P  R  K  K  G  C  W  K  C  G  K  E
                                      HIV1 (IIIB) GAG/PRO GENE 3250      3260      3270      3280      3290      3300      3310      3320      3330      3340      3350      3360
GGACACCAAATGAAAGATTGTACTGAGAGACAGGCTAATTTTTTAGGGAAGATCTGGCCTTCCTACAAGGGAAGGCCAGGGAATTTCTTCAGAGCAGACCAGAGCCAACAGCCCCACCA
CCTGTGGTTTACTTTCTAACATGACTCGTCTGTCCGATTAAAAAATCCCTTCTAGACCGGAAGGATGTTCCCTTCCGGTCCCTTAAAGAAGTCTCGTCTGGTCTCGGTTGTCGGGGTGGT
 G  H  Q  M  K  D  C  T  E  R  Q  A  N  F  L  G  K  I  W  P  S  Y  K  G  R  P  G  N  F  L  Q  S  R  P  E  P  T  A  P  P
                                      HIV1 (IIIB) GAG/PRO GENE
```

10         20         30         40         50         60         70         80         90        100        110
             *          *          *          *          *          *          *          *          *          *          *
GAGCTCGCGG CCGCCTATCA AAAGTCTTAA TGAGTTAGGT GTAGATAGTA TAGATATTAC TACAAAGGTA TTCATATTTC CTATCAATTC TAAAGTAGAT GATATTAATA
CTCGAGCGCC GGCGGATAGT TTTCAGAATT ACTCAATCCA CATCTATCAT ATCTATAATG AAGTATAAAG GATAGTTAAG AGTATTAAG AATTCATCTA CTATAATTAT 120        130        140        150        160        170        180        190        200        210        220
             *          *          *          *          *          *          *          *          *          *          *
ACTCAAAGAT GATGATAGTA GATAATAGAT ACGCTCATAT AATGACTGCA AATTGGACG GTTCACATTT TAATCATCAC GGGTTCATCA GTTCAACTG CATAGATCAA
TGAGTTTCTA CTACTATCAT CTATTATCTA TGCGAGTATA TTACTGACGT TTAAACCTGC CAAGTGTAAA ATTAGTAGTG CGCAAGTATT CAAGTTGAC GTATCTAGTT 230        240        250        260        270        280        290        300        310        320        330
             *          *          *          *          *          *          *          *          *          *          *
AATCTCACTA AAAGATAGC CGATGTATTT GAGAGAGATT GGACACATCA CTACGCTAAA GAAATTACAG TTATAAATAA TACATAATGG ATTTTGTTAT CATCAGTTAT
TTAGAGTGAT TTTCTATCG GCTACATAAA CTCTCTCTAA CCTGTGTAGT GATGCGATTT CTTTAATGTC AATATTTATT ATGTATTACC TAAAACAATA GTAGTCAATA 340        350        360        370        380        390        400        410        420        430        440
             *          *          *          *          *          *          *          *          *          *          *
ATTAACATA AGTACAATAA AAAGTATTAA ATAAAAATAC TTACTTACGA AAAAATGACT AATTAGCTAT AAAAACCCAG ATCTCTCGAG GTCGACGGTA TCGATAAGCT
TAATTGTAT TCATGTTATT TTCATAATT TATTTTTATG AATGAATGCT TTTTTACTGA TTAATCGATA TTTTTTGGGTC TAGAGAGCTC CAGCTGCCAT AGCTATTCGA 450        460        470        480        490        500        510        520        530
             *          *          *          *          *          *          *          *          *
TGATATCGAA TTCATAAAAA TT A TTG ATG TCT ACA CAT CCT GTA ATT GAC ATC TAT ATA TCC TTT TGT ATA ATC AAC TCT AAT CAC TTT
ACTATAGCTT AAGTATTTTT AA T AAC TAC AGA TGT GTA GGA CAT TAA CTG TAG ATA TAT AGG AAA ACA TAT TAG TTG AGA TTA GTG AAA
                             <Q  H   R   C   M   R   K   Y   N   V   D   I   Y   G   K   T   Y   D   V   R   I   V   K
                            ------------------------------------------k3L------------------------------------------
```

```
            1150       1160       1170       1180       1190       1200       1210       1220       1230       1240       1250
              *          *          *          *          *          *          *          *          *          *          *
CTATATAAGT AGTGTAATAA TTCATGTATT TCGATATATG TTCCAACTCT GTCTTTGTGA TGCTTAGTTT CGTATATCT ATAGCATCCT CAAAAATAT ATTCGCATAT
GATATATTCA TCACATTATT AAGTACATAA AGCTATATAC AAGGTTGAGA CAGAAACACT ACAGATCAAA GCATTATAGA TATCGTAGGA GTTTTTATA TAAGCGTATA 1260       1270       1280       1290       1300       1310       1320       1330       1340       1350       1360
              *          *          *          *          *          *          *          *          *          *          *
ATTCCCAAGT CTTCAGTTCT ATCTTCTAAA AAATCTTCAA CGTATGGAAT ATAATAATCT ATTTTACCTC TTCTATATC ATTAATGATA TAGTTTTTGA CACTATCTTC
TAAGGGTTCA GAAGTCAAGA TAGAAGATTT TTTAGAAGTT GCATACCTTA TATTATTAGA TAAAATGGAG AAGACTATAG TAATTACTAT ATCAAAACT GTGATAGAAG 1370       1380       1390       1400       1410       1420       1430       1440       1450       1460       1470
              *          *          *          *          *          *          *          *          *          *          *
TGTCAATTGA TTCTTATTCA CTATATCTAA GAAACGGATA GCGTCCCTAG GACGAACTAC TGCCATTAAT ATCTCTATTA TAGCTTCTGG ACATAATTCA TCTATTATAC
ACAGTTAACT AAGAATAAGT GATATAGATT CTTTGCCTAT CGCAGGGATC CTGCTTGATG ACGGTAATTA TAGAGATAAT ATCGAAGACC TGTATTAAGT AGATAATATG 1480       1490       1500       1510       1520       1530       1540       1550       1560       1570       1580
              *          *          *          *          *          *          *          *          *          *          *
CAGAATTAAT GGGAACTATT CCGTATCTAT CTAACATAGT TTTAAGAAAG TCAGAATCTA AGACCTGATG TTCATATATT GGTTCATACA TGAAATGATC TCTATTGATG
GTCTTAATTA CCCTTGATAA GGCATAGATA GATTGTATCA AAATTCTTTC AGTCTTAGAT TCTGGACTAC AAGTAGATAT CCAAGTATGT ACTTACTAG AGATAACTAC 1590       1600       1610       1620       1630       1640       1650       1660       1670       1680       1690
              *          *          *          *          *          *          *          *          *          *          *
ATAGTGACTA TTTCATTCTC TGAAAATTGG TAACTCATTC TATATATGCT TTCCTTGTTG ATGAAGGATA GAATACTC AATAGAATTT GTACCAACAA ACTGTTCT
TATCACTGAT AAAGTAAGAG ACTTTTAACC ATTGAGTAAG ATATATACGA AAGGAACAAC TACTTCCTAT CTTATATGAG TTATCTTAAA CATGGTTGTT TGACAAGAGA 1700       1710       1720       1730       1740       1750       1760       1770       1780       1790       1800
              *          *          *          *          *          *          *          *          *          *          *
TATGAATCGT ATATCATCAT CTGAAATAAT CATGTAAGGC ATACATTTAA CAATTAGAGA CTTGTCTCCT GTTATCAATA TACTATTCTT GTGATAATTT ATGTGTGAGG
ATACTTAGCA TATAGTAGTA GACTTTATTA GTACATTCCG TATGTAAATT GTTAATCTCT GAACAGAGGA CAATAGTTAT ATGATAAGAA CACTATTAAA TACACACTCC
```

FIG. 8D

```
          1810       1820       1830       1840       1850       1860       1870       1880       1890       1900       1910
            *          *          *          *          *          *          *          *          *          *          *
CAAATTGTC CACGTTCTTT AATTTTGTTA TAGTAGATAT CAAATCCAAT GGAGCTACAG TTCTTGGCTT AAACAGATAT AGTTTTCTG GAACAAATTC TACAACATTA
GTTTAAACAG GTGCAAGAAA TTAAAACAAT ATCATCTATA GTTTAGGTTA CCTCGATGTC AAGAACCGAA TTTGTCTATA TCAAAAAGAC CTTGTTTAAG ATGTTGTAAT 1920       1930       1940       1950       1960       1970       1980       1990       2000       2010       2020
            *          *          *          *          *          *          *          *          *          *          *
TTATAAAGGA CTTTGGGTAG ATAAGTGGGA TGAAATCCTA TTTTAATTAA TGCTATCGCA TTGTCCTCGT GCAAATATCC AAACGCTTTT GTGATAGTAT GGCATTCATT
AATATTTCCT GAAACCCATC TATTCACCCT ACTTTAGGAT AAAATTAATT ACGATAGCGT AACAGGAGCA CGTTTATAGG TTTGCGAAAA CACTATCATA CCGTAAGTAA 2030       2040       2050       2060       2070       2080       2090       2100       2110       2120       2130
            *          *          *          *          *          *          *          *          *          *          *
GTCTAGAAAC GCTCTACGAA TATCTGTGAC AGATATCATC TTTAGAGAAT ATACTAGTCG GTTAATAGT ACTACAATTT GTATTTTTA ATCTATCTCA ATAAAAAAAT
CAGATCTTTG CGAGATGCTT ATAGACACTG TCTATAGTAG AAATCTCTTA TATGATCAGC GCAATTATCA TGATGTTAAA CATAAAAAAT TAGATAGAGT TATTTTTTA 2140       2150       2160       2170       2180       2190       2200       2210       2220       2230
            *          *          *          *          *          *          *          *          *          *
TAATATGTAT GATTCAATGT ATAACTAAAC TACTAACTGT TATTGATAAC TAGAATCA GAA TCT AGA TTA CTA CTG CAT TGG TTC TTC AAA TAG ACG GTT
ATTATACATA CTAAGTTACA TATTGATTTG ATGATTGACA ATAACTATTG ATCTTAGT   CTT AGA TCT AAT GAT GAC GTA ACC AAG AAG TTT ATC TAC CAA
                                                               <F  R   I   I   V   Y   G   L   L   K   D   V   A   L
                                                               ----- E3L --------------------------------------------

2240       2250       2260       2270       2280       2290       2300       2310       2320
            *          *          *          *          *          *          *          *          *
TTT AGC TGC ATT ATT TTT AGC ATC TCG TTT AGA TTT TCC ATC TGC CTT ATC GAA TAC TCT TCC GTC GAT GTC TAC ACA GGC ATA AAA TGT
AAA TCG ACG TAA TAA AAA TCG TAG AGC AAA TCT AAA AGG TAG AGA AGG TAG CTT ATG AGA AGG CAG CTA CAG ATG TGT CCG TAT TTT ACA
<K   A   A   N   N   K   A   D   R   K   S   K   G   D   A   K   D   F   V   R   G   D   I   D   V   C   A   Y   F   T
--------------------------------------------------------------- E3L ---------------------------------------------
```

FIG. 8E

```
      2330         2340         2350         2360         2370         2380         2390         2400         2410
        *            *            *            *            *            *            *            *            *
     AGG AGA GTT ACT AGG CCC AAC TGA TTC AAT ACG AAA AGA CCA ATC TCT CTT AGT TAT TTG GCA GTA CTC ATT AAT GGT GAC AGG GTT
     TCC TCT CAA TGA TCC GGG TTG ACT AAG TTA TGC TTT TCT GGT TAG AGA GAA TCA ATA AAC CGT CAT GAG TAA TTA TTA CCA CTG TCC AA
     <P  S   N   S   P   G   V   S   E   I   R   F   S   W   D   R   K   T   I   Q   C   Y   E   N   I   T   V   P   N
     ----------------------------------------------------------------------------E3L---------------------------------

2420         2430         2440         2450         2460         2470         2480         2490         2500
        *            *            *            *            *            *            *            *            *
     AGC ATC TTT CCA ATC AAT AAT TTT TTT AGC CGG AAT AAC ATC AAA AGA CTT GAA ATC CTC ATG ATC TCT CAT TGA TTT TTC GCG GGA TAC ATC
     TCG TAG AAA GGT TAG TTA TTA AAA AAA TCG GCC TTA TTG TAG TTT TCT GAA CTT TAG GAG TAC TAG AGA GTA ACT AAA AAG CGC CCT ATG TAG
     <A  D   K   W   D   I   I   K   K   A   P   I   V   D   D   F   S   K   H   D   E   R   M   S   K   E   R   S   V   D
     ----------------------------------------------E3L---------------------------------------------------------------

2510         2520         2530         2540         2550         2560         2570         2580         2590
        *            *            *            *            *            *            *            *            *
     ATC TAT TAT GAC GTC AGC CAT AGC ATC ATC CGC CTT ATC CGT TGT CAT AAA CCA ACG AGG AAT ATC GTC GGA GCT GTA
     TAG ATA ATA CTG CAG TCG GTA TCG TAG TAG GCG GAA TAG GCA ACA GTA TTT GGT TGC TCC TTA TAG CAG CCT CGA CAT
     <D  I   I   V   D   A   M   A   D   D   P   K   D   A   E   T   T   M   F   W   R   P   I   D   D   S   Y
     ----------------------------------------------E3L---------------------------------------------------------------

2600         2610         2620         2630         2640         2650         2660         2670         2680
        *            *            *            *            *            *            *            *            *
     CAC CAT AGC ACT ACG TTG AAG ATC GTA CAG AGC TTT ATT AAC TTC TCG CTT CTC CAT ATT AAG TTG TCT AGT TAG TTG TGC AGT AGC
     GTG GTA TCG TGA TGC AAC TTC TAG CAT GTC TCG AAA TAA TTG AAG AGC GAA GAG GTA TAA TTC AAC AGA TCA ATC AAC ACG TCG TCA TCG
     <V  M   A   S   R   Q   L   D   Y   L   A   K   N   V   E   R   K   E   M   N   L   Q   R   T   L   Q   A   T   A
     ----------------------------------------------E3L---------------------------------------------------------------

2690         2700         2710         2720         2730         2740         2750         2760         2770
        *            *            *            *            *            *            *            *            *
     TCC TTC GAT TCC AAT GTT TTT AAT AGC CGC AAT CTC TGC GTC AAT ATA GAT CTT AGA CAT TT TTAGAGAGAA
     AGG AAG CTA AGG TTA CAA AAA TTA TCG GCG TGT GTG TTA GAG CAG TCT CTA GAA TCT GTA AA AATCTCTCTT
     <G  E   I   G   N   K   I   A   A   C   V   I   E   A   D   S   R   E   D   I   Y   I   K   S   M
     ----------------------------------------------E3L---------------------------------------------------------------
```

FIG. 8F

```
         2780       2790       2800       2810       2820       2830       2840       2850       2860       2870       2880
           *          *          *          *          *          *          *          *          *          *          *
CTAACACAAC CAGCAATAAA ACTGAACCTA CTTTATCATT TTTTATTCA TCATCCCTCTG GTGGTTCGTC GTTCTATCG AATGTAGCTC TGATTAACCC GTCATCTATA
GATTGTGTTG GTCGTTATTT TGACTTGGAT GAAATAGTAA AAAAATAAGT AGTAGGAGAC CACCAACCAG CAAAGATAGC TTACATCGAG ACTAATTGGG CAGTAGATAT 2890       2900       2910       2920       2930       2940       2950       2960       2970       2980       2990
           *          *          *          *          *          *          *          *          *          *          *
GGTGATGCTG GTTCTGGAGA TTCTGGAGGA GATGGATTAT TATCTGGAAG AATCTCTGTT ATTTCCTTGT TTTCATGTAT CGATTGCGTT GTAACATTAA GATTGCGAAA
CCACTACGAC CAAGACCTCT AAGACCTCCT CTACCTAATA ATAGACCTTC TTAGAGACAA TAAAGGAACA AAAGTACATA GCTAACGCAA CATTGTAATT CTAACGCTTT 3000       3010       3020       3030       3040       3050       3060       3070       3080       3090       3100
           *          *          *          *          *          *          *          *          *          *          *
TGCTCTAAAT TTGGGAGGCT TAAAGTGTTG TTTGCAATCT CTACACGCGT GTCTAACTAG TGGAGGTTCG TCAGCTGCTC TAGTTTGAAT CATCATCGGC GTAGTATTCC
ACGAGATTTA AACCCTCCGA ATTTCACAAC AAACGTTAGA GATGTGCGCA CAGATTGATC ACCTCCAAGC AGTCGACGAG ATCAAACTTA GTAGTAGCCG CATCATAAGG 3110       3120       3130       3140       3150       3160       3170       3180       3190       3200       3210
           *          *          *          *          *          *          *          *          *          *          *
TACTTTACA GTTAGGACAC GGTGTATTGT ATTTCCGTC GAGAACGTTA AAATAATCGT TGTAACTCAC ATCCTTTATT TTATCTATAT TGTATTCTAC TCCTTTCTTA
ATGAAATGT CAATCCTGTG CCACATAACA CTCTTGCAAT TTTATTAGCA ACATTGAGTG TAGGAAATAA AATAGATATA ACATAAGATG AGGAAAGAAT 3220       3230       3240       3250       3260       3270       3280       3290       3300       3310       3320
           *          *          *          *          *          *          *          *          *          *          *
ATGCATTTTA TACGAATAA GAGATAGCCA AGGAATTCTT TTTATTGATT AACTAGTCAA ATGAGTATAT AATAATTGAAA AAGTAAAATA TAAATCATAT AATAATGAAA
TACGTAAAAT ATGGCTTATT CTCTATCGGT TCCTTAAGAA AAATAACTAA TTGATCAGTT TACTCATATA TTATTAACTTT TTCATTTTAT ATTTAGTATA TTATTACTTT
```

FIG. 8G

```
          3330       3340       3350       3360       3370       3380       3390       3400       3410       3420       3430
            *          *          *          *          *          *          *          *          *          *          *
CGAAATATCA GTAATAGACA GGAACTGGCA GATTCTTCTT CTAATGAAGT AAGTACTGCT AAATCTCCAA AATTAGATACA AAATGATACA GCAAATACAG CTTCATTCAA
GCTTTATAGT CATTATCTGT CCTTGACCGT CTAAGAAGAA GATTACTTCA TTCATGACGA TTCAGAGGTT TTAATCTATT TTTACTATGT CGTTTATGTC GAAGTAAGTT 3440       3450       3460       3470       3480       3490       3500       3510       3520       3530       3540
            *          *          *          *          *          *          *          *          *          *          *
CGAATTACCT TTTAATTTTT TCAGACACAC CTTATTACAA ACTAACTAAG TCAGATGATG AGAAAGTAAA TATAAATTTA ACTTATGGGT ATAATATAAT AAAGATTCAT
GCTTAATGGA AAATTAAAAA AGTCTGTGTG GAATAATGTT TGATTGATTC AGTCTACTAC TCTTTCATTT ATATTTAAAT TGAATACCCA TATTATATTA TTTCTAAGTA 3550       3560       3570       3580       3590       3600       3610       3620       3630       3640       3650
            *          *          *          *          *          *          *          *          *          *          *
GATATTAATA ATTACTTAA CGATGTAAT AGACTTATTC ATCAACCCCC TTCAAACCTT TCTGGATATT ATAAAATACC AGTTAATGAT ATTAAAATAG ATTGTTAAG
CTATAATTAT TAATGAATT GCTACAATTA TCTGAATAAG GTAGTTGGGG AAGTTTGGAA AGACCTATAA TATTTTATGG TCAATTACTA TAATTTATC TAACAAATTC 3660       3670       3680       3690       3700       3710       3720       3730       3740       3750       3760
            *          *          *          *          *          *          *          *          *          *          *
AGATGTAAAT AATTATTGG AGGTAAAGGA TATAAAATTA GTCTATCTTT CACATGGAAA TGAATTACCT AATATAATA ATATGATAG GAATTTTTA GGATTACAG
TCTACATTTA TTAATAAACC TCCATTTCCT ATATTTTAAT CAGATAGAAA GTGTACCTTT ACTTAATGGA TTATAATTAT TATACTATC CTTAAAAAAT CCTAAATGTC 3770       3780       3790       3800       3810       3820       3830       3840       3850       3860       3870
            *          *          *          *          *          *          *          *          *          *          *
CTGTTATATG TATCAACAAT ACAGGCAGAT CTATGGTTAT GGTAAAACAC TGTAACGGGA AGCAGCATTC TATGGTAACT GGCCTATGTT TAATAGCCAG ATCATTTTAC
GACAATATAC ATAGTTGTTA TGTCCGTCTA GATACCAATA CCATTTGTG ACATTGCCCT TCGTCGTAAG ATACCATTGA CCGGATACAA ATTATCGGTC TAGTAAAATG
```

FIG. 8H

```
          3880       3890       3900       3910       3920       3930       3940       3950       3960       3970       3980
            *          *          *          *          *          *          *          *          *          *          *
TCTATAAACA TTTACCACA AATAATAGGA TCCTCTAGAT ATTTAATATT ATATCTAACA ACAACAAAAA AATTTAACGA TGTATGGCCA GAAGTATTT CTACTAATAA
AGATATTGT AAAATGGTGT TTATTATCCT AGGAGATCTA TAAATTATAA TATAGATTGT TGTTGTTTT TTAAATTGCT ACATACCGGT CTTCATAAAA GATGATTATT 3990       4000       4010       4020       4030       4040       4050       4060       4070       4080       4090
            *          *          *          *          *          *          *          *          *          *          *
AGATAAAGAT AGTCTATCTT ATCTACAAGA TATGAAAGAA GATAATCATT TAGTAGTAGC TACTAATATG GAAAGAAATG TATACAAAAA CGTGGAAGCT TTTATATTAA
TCTATTTCTA TCAGATAGAA TAGATGTTCT ATACTTTCTT CTATTAGTAA ATCATCATCG ATGATTATAC CTTTCTTTAC ATATGTTTT GCACCTTCGA AAATATAATT 4100       4110       4120       4130       4140       4150       4160       4170       4180       4190       4200
            *          *          *          *          *          *          *          *          *          *          *
ATAGCATATT ACTAGAAGAT TTAAAATCTA GACTTAGTAT AACAAAACAG TTAAATGCCA ATATCGATTC TATATTTCAT CATAACAGTA GTACATTAAT CAGTGATATA
TATCGTATAA TGATCTTCTA AATTTTAGAT CTGAATCATA TTGTTTTGTC AATTTACGGT TATAGCTAAG ATATAAAGTA GTATTGTCAT CATGTAATTA GTCACTATAT 4210       4220       4230       4240       4250       4260       4270       4280       4290       4300       4310
            *          *          *          *          *          *          *          *          *          *          *
CTGAAACGAT CTACAGACTC AACTATGCAA GGAATAAGCA ATATGCCAAT TATGTCTAAT ATTTAACTT TAGAACTAAA ACGTTCTACC AATACTAAAA ATAGGATACG
GACTTTGCTA GATGTCTGAG TTGATACGTT CCTTATTCGT TATACGGTTA ATACAGATTA TAAAATTGAA ATCTTGATTT TGCAAGATGG TTATGATTTT TATCCTATGC 4320       4330       4340       4350       4360       4370       4380       4390       4400       4410       4420
            *          *          *          *          *          *          *          *          *          *          *
TGATAGGCTG TTAAAAGCTG CAATAAATAG TAAGGATGTA GAAGAAATAC TTTGTTCTAT ACCTTCGGAG GAAAGAACTT TAGAACACAT TAAGTTTAAT CAAACTTGTA
ACTATCCGAC AATTTTCGAC GTTATTTATC ATTCCTACAT CTTCTTTATG AAACAAGATA TGGAAGCCTC CTTTCTTGAA ATCTGTTGA ATTCAAATTA GTTTGAACAT

4430
            *
TTTATGAAGG TACC
AAATACTTCC ATGG
```

VECTORS HAVING ENHANCED EXPRESSION AND METHODS OF MAKING AND USES THEREOF

This is a divisional application of U.S. Ser. No. 08/816,155 filed Mar. 12, 1997, U.S. Pat. No. 5,990,091.

RELATED APPLICATIONS

Reference is made to the concurrently filed application of Tartaglia et al., "Vectors Having Enhanced Expression, And Methods of Making and Uses Thereof", U.S. Pat. No. 6,004,777, incorporated herein by reference. Reference is also made to the copending applications of Paoletti et al., U.S. Pat. Nos. 5,863,542, 5,766,598, 5,762,938, 5,833,975, Ser. Nos. 08/709,209, 08/184,009 (incorporating by reference U.S. Pat. No. 5,378,457) and 08/521,016 and to U.S. Pat. Nos. 5,378,457, 5,225,336, 5,453,364, 5,494,807, 5,505,941, and 5,110,587, all of which are incorporated herein by reference.

FIELD OF THE INVENTION

The present invention relates to enhanced vectors, and methods for making and using them. The vectors can have enhanced transcription or translation or enhanced transcription and translation and/or expression, e.g., enhanced transcription or translation or transcription and translation and/or expression from a nucleotide sequence of interest.

Several publications are referenced in this application. Full citation to these publications is found where cited or at the end of the specification, immediately preceding the claims or where the publication is mentioned; and each of these publications is hereby incorporated by reference. These publications relate to the state of the art to which the invention pertains; however, there is no admission that any of these publications is indeed prior art.

BACKGROUND OF THE INVENTION

DNA such as plasmids or naked DNA, and other vectors, such as viral vectors, e.g., vaccinia virus and more recently other poxviruses, have been used for the insertion and expression from foreign genes. The basic technique of inserting foreign genes into live infectious poxvirus involves recombination between pox DNA sequences flanking a foreign genetic element in a donor plasmid and homologous sequences present donor plasmid and homologous sequences present in the rescuing poxvirus (Piccini et al., 1987). Recombinant poxviruses are constructed in steps known as in or analogous to methods in U.S. Pat. Nos. 4,769,330, 4,772,848, 4,603,112, 5,505,941, and 5,494,807, incorporated herein by reference. A desire in vector development is attenuated vectors, e.g., for enhanced safety; for instance, so that the vector may be employed in an immunological or vaccine composition.

For instance, the NYVAC vector, derived by deletion of specific virulence and host-range genes from the Copenhagen strain of vaccinia (Tartaglia et al., 1992) has proven useful as a recombinant vector in eliciting a protective immune response against an expressed foreign antigen. Likewise, the ALVAC vector, a vaccine strain of canarypox virus, has also proven effective as a recombinant viral vaccine vector (Perkus et al., 1995). In non-avian hosts, both these vectors do not productively replicate (with some exceptions as to NYVAC). Since all poxviruses replicate in the cytoplasm and encode most, if not all of the proteins required for viral transcription (Moss 1990), appropriately engineered foreign coding sequences under the control of poxvirus promoters are transcribed and translated in the absence of productive viral replication.

It would be an improvement over the state of the art to provide enhanced vectors, e.g., vectors having enhanced transcription or translation or transcription and translation and/or expression, for instance such vectors which are attenuated; especially since attenuation may raise issues of expression levels and/or persistence, and it would be an advancement to address such issues.

OBJECTS AND SUMMARY OF THE INVENTION

Recent studies on vaccinia replication have revealed certain poxvirus-encoded functions which play a role in the regulation of viral transcription and translation (reviewed in Moss, 1990; Moss, 1992). Some of these vaccinia encoded functions (e.g., E3L, K3L, H4L, and combinations thereof) have now surprisingly been utilized to increase the levels and persistence of gene expression (e.g., foreign gene expression) in vectors (e.g., the NYVAC and ALVAC vectors); and, are exemplary of the inventive vectors and methods.

Objects of the present invention may include at least one of: providing a method for increasing transcription or translation or transcription and translation and/or expression from at least one nucleotide sequence of interest by a vector, such as a coding nucleotide sequence by a vector; a vector having enhanced transcription or translation or transcription and translation; providing a method for preparing a vector having enhanced transcription or translation or transcription and translation and/or expression; providing a method for enhancing transcription or translation or transcription and translation and/or expression from a vector; providing an improved vector, such as poxvirus vectors, e.g., improved NYVAC, ALVAC or TROVAC vectors; and, products therefrom.

The invention thus provides a vector for enhanced expression of at least one first nucleotide sequence. The vector is modified to comprise at least one second nucleotide sequence encoding a transcription factor or translation factor or a transcription factor and a translation factor. The vector also can be modified to comprise the first nucleotide sequence. There is substantially co-temporal or substantially contemporaneous expression from the first and second nucleotide sequences. The expression is in a cell having a particular phenotype, and preferably the expression of the first and second nucleotide sequences is with respect to the phenotype of the cell. Thus, expression of the second nucleotide sequence enhances expression of the first nucleotide sequence by enhancing transcription or translation or transcription and translation.

The first nucleotide sequence can be operably linked to a first promoter and the second nucleotide sequence can be operably linked to a second promoter, and the first and second promoters are preferably functional substantially co-temporally or contemporaneously. Thus, the first and second nucleotide sequences can be at different loci within the vector. The first and second nucleotide sequences also can be at the same locus within the vector, using the first and second promoters; or, by the first nucleotide sequence and the second nucleotide sequence being operably linked to a promoter.

The transcription factor can be of poxvirus origin, e.g., from a vaccinia virus. The transcription factor can be from an open reading frame selected from the group consisting of H4L, D6, A7, G8R, A1L, A2L, H5R, and combinations thereof. The translation factor can effect inhibition of eIF-2α phosphorylation or inhibition of PKR phosphorylation or otherwise sequester dsRNA which actually increases the concentration required to activate PKR. The translation factor can be selected from the group consisting of: a K3L open reading frame, an E3L open reading frame, a viral associated RNA I (VAI), an EBER RNA, a sigma 3 open reading frame, a TRBP open reading frame, and combinations thereof.

The first nucleotide sequence can be exogenous, e.g., encoding an epitope of interest, a biological response modulator, a growth factor, a recognition sequence, a therapeutic gene, a fusion protein or combinations thereof.

The vector can be a recombinant virus, such as a poxvirus; for instance, an orthopoxvirus or an avipoxvirus, e.g., a vaccinia virus, a fowlpox virus, a canarypox virus; preferably an attenuated virus such as an attenuated poxvirus, e.g., NYVAC, ALVAC, or TROVAC.

The invention further provides a method for preparing a an inventive vector comprising modifying the vector to comprise the at least one second nucleotide sequence. The method can also include modifying the vector so that it comprises at the at least one first nucleotide sequence. Preferably the vector is so modified that there is substantially co-temporal or contemporaneous expression of the first and second nucleotide sequences; and, more preferably, the vector is also so modified that the expression is with respect to the phenotype of the cell.

The method can comprise operably linking the first nucleotide sequence to a first promoter and the second nucleotide sequence to a second promoter, wherein the first and second promoters are functional substantially co-temporally or contemporaneously. The method can also comprise operably linking the first and second nucleotide sequences to a promoter.

The invention further provides an immunological, vaccine or therapeutic composition comprising at least one inventive vector and a pharmaceutically acceptable carrier or diluent.

The invention even still further provides a method for generating an immunological or therapeutic response in a host (animal, human, vertebrate, mammal, etc.) comprising administering to the host at least one inventive composition.

The invention additionally provides a method for increasing expression of at least one first nucleotide sequence by a vector comprising the first nucleotide sequence. The method comprises modifying the vector to comprise at least one second nucleotide sequence encoding a transcription factor or a translation factor or a transcription factor and a translation factor. There is preferably substantially co-temporal or contemporaneous expression of the first and second nucleotide sequences. Expression can be in a cell having a particular phenotype; and it is more preferred to have expression be with respect to the phenotype of the cell. Expression of the second. nucleotide sequence enhances expression of the first nucleotide sequence by enhancing transcription or translation or transcription and translation. The method can additionally comprise modifying the vector to comprise the first nucleotide sequence of interest.

The invention in yet another embodiment provides a method for expressing at least one gene product in vitro comprising infecting, or transfecting, a suitable cell with at least one inventive vector. The products therefrom can be an immunogen or epitope of interest, which can be useful in formulating therapeutic, immunological or vaccine compositions; or, for generating antibodies such as monoclonal antibodies; or, in assays, kits, tests and the like, such as diagnostic compositions, e.g., for detection of antibodies.

Thus, the invention can provide compositions and methods for in vitro transcription or translation or transcription and translation and/or expression involving at least one inventive vector, e.g., methods for producing a gene product (which can be used as an immunogen or epitope in a therapeutic, immunological or vaccine composition, or in a diagnostic or detection kit, assay or method, e.g., to ascertain the presence or absence of antibodies, or to generate antibodies, such as monoclonal antibodies, e.g., for use in a diagnostic or detection kit, assay or method), and/or for ex vivo transcription or translation or transcription and translation and/or expression involving at least one inventive vector, e.g., methods for producing a gene product for stimulating cells for reinfusion into a host (e.g., animal, mammal, vertebrate, human).

Additionally, in a further embodiment the invention provides a method for expressing at least one nucleotide sequence (e.g., the at least one first nucleotide sequence) in vivo comprising administering at least one inventivie vector to a host (human, animal, vertebrate, mammal, etc.). The nucleotide sequence can encode an immunogen or epitope of interest. The method can obtain antibodies. From generating antibodies one can generate monoclonal antibodies; or, antibodies are useful in assays, kits, tests or diagnostic compositions, e.g., for detection of antigens.

The invention can thus provide methods and compositions for in vivo transcription or translation or transcription and translation and/or expression involving the inventive vectors, e.g., administering at least one inventive vector or a composition comprising at least one inventive vector, for instance, therapeutic, immunological or vaccine compositions comprising at least one inventive vector and a suitable carrier or diluent (e.g., suitable for veterinary and human medicine).

These and other embodiments are disclosed or are obvious from and encompassed by, the following Detailed Description.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which:

FIGS. 1A–1C show the nucleotide sequence of the insert in vP1380 containing the mutagenized H4L orf and lacZ orf under the H6 promoter (SEQ ID NO: 1);

FIGS. 2A–2B show the nucleotide sequence of the ALVAC C8 Insertion site containing the H6/H42 expression cassette (SEQ ID NO: 2);

FIGS. 3A–3B show the nucleotide sequence of the ALVAC C6 insertion site containing the H6/K3L and E3L expression cassette (SEQ ID NO: 3);

FIGS. 4A–4B show the DNA sequence of the coding region of FHV gB with modified T5NT motifs (SEQ ID NO: 4);

FIGS. 5A–5C show the DNA sequence of the H6 promoted FHV gB donor plasmid pC3H6FHVB (SEQ ID NO: 5);

Figure 7B:
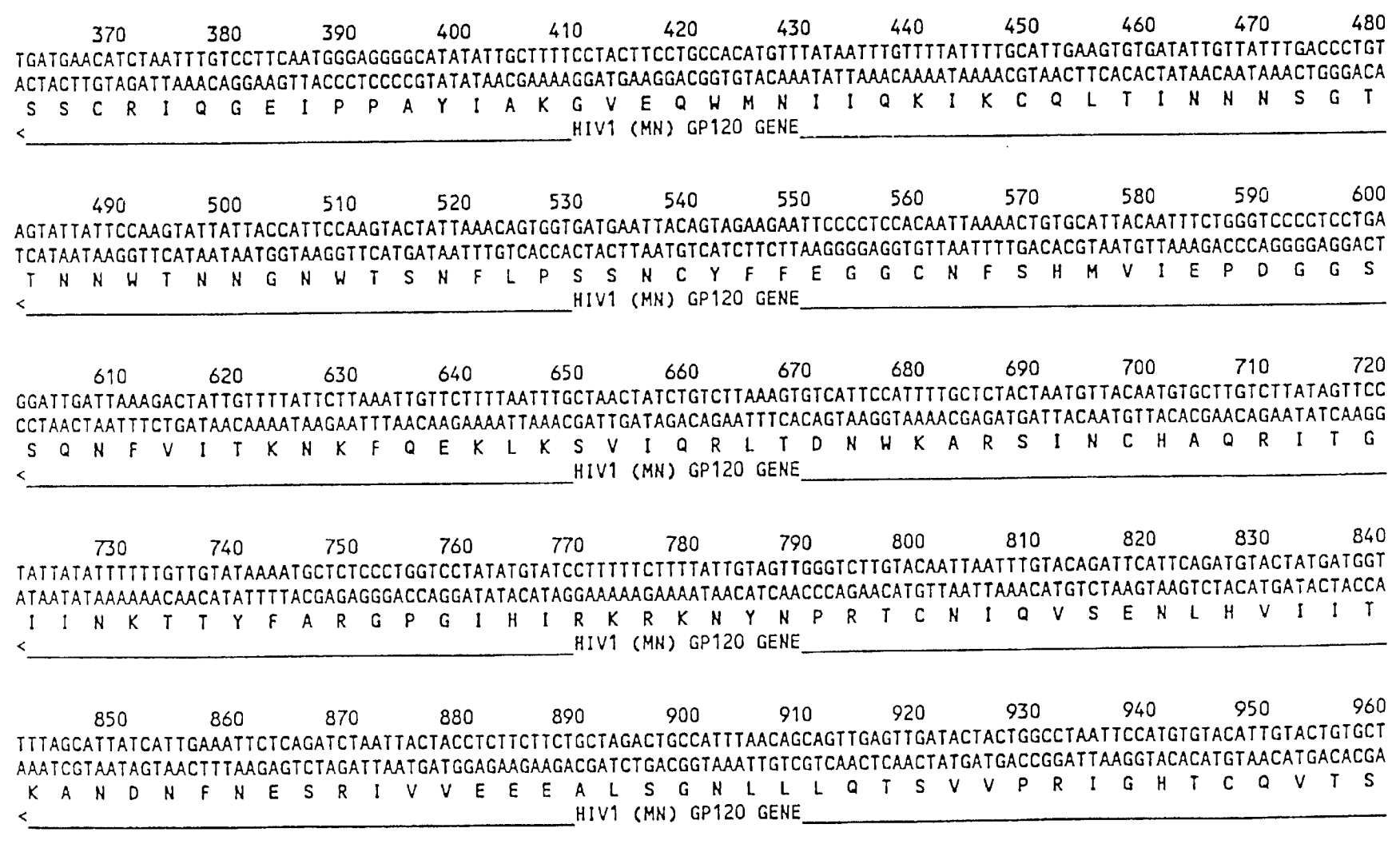
Figure 7G:
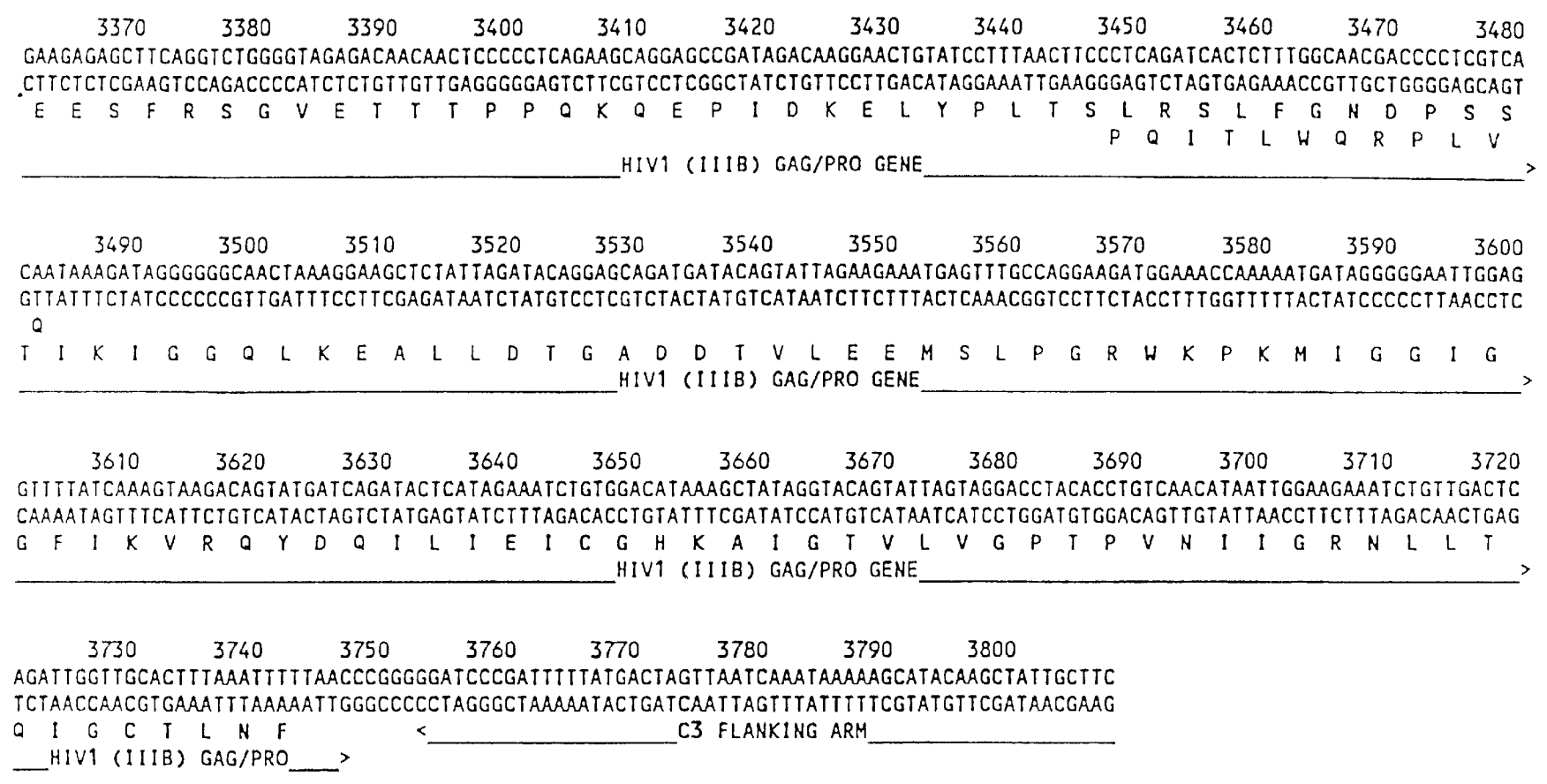

FIGS. 6A–6C and 7A–7G show DNA and amino acid sequences (SEQ ID NOS: 6, 7, 43, 44, 45 and 46) of inserts in vCP1433 and vCP1452; and FIGS. 8A–8H show the DNA sequence (SEQ ID NOS: 8, 47 and 48) of K3L E3L in vCP1452.

DETAILED DESCRIPTION

U.S. Pat. No. 5,494,807, to Paoletti et al., hereby incorporated herein by reference, relates to a modified recombinant virus having inactivated virus-encoded genetic functions so that the recombinant virus has attenuated virulence and enhanced safety. The viruses disclosed in Paoletti et al. can be poxviruses, e.g., a vaccinia virus or an avipox virus, such as fowlpox virus and canarypox virus, e.g., NYVAC, ALVAC and TROVAC. ALVAC was deposited under the terms of the Budapest Treaty with the American Type Culture Collection (ATCC), 10801 University Boulevard, Manassas, Va. 20110-2209, USA, ATCC accession number VR-2547. TROVAC was likewise deposited under the terms of the Budapest Treaty with the ATCC, accession number 2553. And, NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

Like the Paoletti et al. issued U.S. Patent, Falkner et al., WO 95/30018, published Nov. 9, 1995, based on U.S. application Ser. No. 08/235,392, filed Apr. 24, 1994 (both incorporated herein by reference), relates to poxviruses wherein loci for genetic functions associated with virulence (i.e., loci for "essential" functions) are employed for insertion of exogenous DNA.

Further, recombinants can be made from early (DNA$^-$) and late defective mutants (see Condit and Niles, "Orthopoxvirus Genetics," pp 1–39, In: *Poxviruses*, Edited by R. W. Moyer and P. C. Turner (Springer-Verlag, 1990), and documents cited therein, hereby incorporated herein by reference)), or from MVA which is said to be abortive late. Recombinants from defective mutants, abortive late viruses, viruses having essential genetic functions deleted or interrupted, or viruses having expression without productive replication (e.g., ALVAC in mammalian systems) may be said to be attenuated.

Certain vectors, such as attenuated vectors, e.g., NYVAC and ALVAC vectors, are blocked or limited in late gene expression in mammalian cells. Thus, early promoters are routinely employed in such vectors, e.g., NYVAC- or ALVAC-based recombinants, for expression from the foreign gene products.

Vaccinia encodes an open reading frame (ORF) designated H4L which has been shown to be required for early viral transcription (Ahn and Moss 1992, Zhang et al, 1994). The H4L ORF encodes an essential protein of 94 kDa which is expressed after the start of viral DNA replication (late function). The H4L protein has been found to be tightly associated with the viral RNA polymerase complex and is believed to act in conjunction with the vaccinia early transcription factor (VETF) to initiate and transcribe early viral message (Ahn and Moss, 1992).

H4L is expressed late, but required early. This is consistent with the protein being packaged in the viral particles similar to that which is observed with VETF. This suggested that the amount of H4L present at early times post infection is low and perhaps limiting. Hence, one approach to increase foreign gene expression in an abortive, early vector-, e.g., virus-host interaction would be to increase the amount of H4L protein available during the early phase by expressing the H4L ORF using a vaccinia early/late promoter rather than the endogenous late promoter. Early expression from H4L may not only increase the level of foreign gene transcripts, but also increase levels of other vaccinia early genes (e.g. E3L) which may also increase total protein levels.

There are other viral transcription factors; for instance, early and/or late viral transcription factors of poxvirus origin; e.g., from: vaccinia D6, vaccinia A7, vaccinia G8R, vaccinia A1L, vaccinia A2L, or vaccinia H5R (VLTF-1, -2, -3, -4, P3, VLTF-X; see Kovacs et al., J. Virology, October 1996, 70(10):6796–6802, and documents cited therein, incorporated herein by reference). These and other transcription factors, and nucleotide sequences therefor or for homologs thereof, e.g., from another poxvirus, are useful in the practice of the invention.

The selection of a suitable transcription factor is within the ambit of the skilled artisan from this disclosure and knowledge in the art; for instance, the skilled artisan can select a transcription factor based on an abortive phenotype of the vector, e.g., MVA is said to be abortive late, and a late or early or early/late transcription factor may be employed with this vector; ALVAC is abortive early and an early or early/late transcription factor may be employed with this vector; and, the vector can also be a ts (temperature sensitive) mutant (with respect to early (DNA$^-$) and late defective mutants which can be also used in the practice of this invention, reference is made to Condit and Niles, supra). Thus, it is preferred that the transcription and/or translation factor and the at least one nucleotide sequence of interest be expressed early, late (including intermediate), or early/late, relative to the phenotype of the vector.

Another means to increase foreign gene expression involves enhancing the overall efficiency of translation, e.g., mRNA translation, such as viral mRNA translation. Two vaccinia encoded functions (E3L and K3L) have recently been identified as playing a role in the regulation of viral translation (Beattie et al., 1995a, 1995b, 1991; Chang et al., 1992; Davies et al., 1993). Both are capable of inhibiting the action of a cellular protein kinase (PKR) which, when activated by double stranded RNA (dsRNA), phosphorylates the translational initiation factor eIF-2$\alpha$, leading to an inhibition of initiation of mRNA translation (reviewed in Jacobs and Langland, 1996). Vaccinia virus, which produces dsRNA during viral transcription, has thus evolved mechanisms to block the negative action of PKR on eIF-2$\alpha$ and allow for efficient translation of viral mRNA. (Asymetric transcription gives rise to dsRNA; any viral infection or plasmid derived expression gives rise to it; dsRNA activates PKR; PKR becomes autophosphorylated, leading to phosphorylation of eIF-2$\alpha$.)

The vaccinia K3L ORF has been shown to have significant amino acid homology to eIF-2$\alpha$ (Goebel et al., 1990; Beattie et al., 1991; U.S. Pat. No. 5,378,457; see also Beattie et al., 1995a, 1995b). This protein is believed to act as a pseudosubstrate for PKR and competes for the eIF-2$\alpha$ binding site (Carroll et al., 1993; Davies et al., 1992). The K3L gene product can bind to activated PKR and thus prevent phosphorylation of eIF-2$\alpha$ with its resultant negative effect on translation initiation.

The vaccinia E3L gene codes for a protein which is capable of specifically binding to dsRNA (Watson and Jacobs, 1991; Chang et al., 1992). This would tend to lower the amounts of dsRNA in the infected cell, and thus reduce the level of activated PKR. When E3L was deleted from vaccinia, the resulting virus lost this kinase inhibitory function and further allowed activation of the 2' 5' oligoadenylate synthetase/RNase L pathway resulting in increased degradation of rRNA (Beattie et al., 1995a, 1995b). Thus, E3L appears to be critical for efficient mRNA translation in vaccinia infected cells at two levels; mRNA stability and limiting eIF-2$\alpha$ phosphorylation.

The ALVAC genome has been sequenced and searched for any homology to E3L/K3L or to any known dsRNA binding motif. Results have revealed no significant homology of any ALVAC ORFS to these two vaccinia ORFs, nor the presence of any dsRNA binding motifs.

Thus, an approach to improving expression levels in recombinant ALVAC vectors was to express the vaccinia E3L/K3L ORFs in ALVAC under the control of early vaccinia promoters. Through inhibition of PKR in the infected cells, the levels and persistence of foreign gene expression could be enhanced.

Hence, NYVAC and ALVAC recombinants as discussed herein were generated in order to enhance foreign gene expression at the transcriptional or translational or transcriptional and translational levels, as examples of the vectors and methods of the present invention.

Thus, exemplified herein is NYVAC recombinants having an early expressed H4L ORF and ALVAC recombinants having expression from the vaccinia E3L/K3L genes for enhancing or increasing the levels or persistence of expression of an inserted foreign gene. The up-regulation of foreign gene expression can have a profound effect on the induction of a therapeutic or immunological response in a host administered or inoculated with recombinants derived from these new vectors, thereby leading to an enhanced immunological, e.g., protective, response, or an enhanced therapeutic response.

The scope of the invention, i.e., to manipulate expression from any of a transcription and/or translation factor, e.g., H4L, E3L and K3L, to thereby enhance transcriptional or translational or transcriptional and translational and/or expression efficiency, can be extended to other eukaryotic vector systems (i.e. DNA, viruses).

In fact, viruses in other families have also evolved mechanisms to overcome the cellular anti-viral response of translational down-regulation through PKR activation. In adenoviruses, the VAI RNA, transcribed by RNA pol III, has been well characterized and shown to bind directly to PKR, and thus, prevent its activation by dsRNA (Mathews and Shenk, 1991). Deletion of VAI from the adenovirus genome results in a mutant that replicates poorly and is deficient in levels of late gene expression (Thimmappaya et al., 1982). Similarly, Epstein-Barr virus, a herpesvirus, has an analogous RNA, called EBER, which also acts to prevent PKR activation by directly binding to the kinase (Clark et al., 1991; Sharp et al., 1993). The reovirus sigma 3 gene product has been shown to act in a similar manner as vaccinia E3L in binding dsRNA and thus preventing activation of PKR (Imani and Jacobs, 1988; see also Beattie et al. 1995a). Indeed, one study has shown that the reovirus sigma 3 gene can partially compensate a vaccinia recombinant deleted of E3L (Beattie et al., 1995a). Further, a cellular protein activated upon HIV infection (TRBP) has been shown to inhibit the activity of PKR (Park et al., 1994).

Thus, the present invention broadly relates to manipulation of expression, preferably by employing at least one transcription factor, e.g., at least one early and/or late viral transcription factor, or at least one translation factor, e.g., a nucleotide sequence encoding a product for overcoming the cellular anti-viral response of translational down-regulation through PKR activation in any eukaryotic vector system, or at least one transcription factor and at least one translation factor; for instance, to increase or enhance expression. And, the invention can pertain to any vector system, including, plasmid or naked DNA vectors, viral vectors, such as poxvirus, adenovirus, herpesvirus, baculovirus, and the like. Thus, the nucleotide sequences can be RNA or DNA, for instance, as is suitable in view of the vector system.

Accordingly, the invention can relate to a vector modified to comprise at least one nucleotide sequence encoding at least one transcription factor, at least one translation factor, or at least one transcription factor and at least one translation factor; a method for increasing transcription and/or translation and/or expression by a vector or for preparing an inventive vector, e.g., by modifying the vector to comprise the at least one nucleotide sequence.

These methods can include substantially co-temporal expression from: (i) a first nucleotide sequence comprising at least one nucleotide sequence of interest, and (ii) a second nucleotide sequence comprising at least one nucleotide sequence encoding a transcription factor, or at least one nucleotide sequence encoding a translation factor or at least one nucleotide sequence encoding a transcription factor and a translation factor. The vector also can be modified to comprise the at least one nucleotide sequence of interest. The at least one nucleotide sequence of interest can be at least one coding nucleotide sequence. The vector preferably has substantially co-temporal or contemporaneous expression of the first and second nucleotide sequences.

The substantially co-temporal expression can occur by employing promoters for the first and second nucleotide sequences which are functional at approximately the same time or stage of infection. Thus, the nucleotide sequence of interest and the nucleotide sequences encoding the factor(s) can be positioned at different loci in the vector. Alternatively, substantially co-temporal expression can occur by positioning the first and second nucleotide sequences within the same loci. Thus, substantially co-temporal expression can occur by operably linking to the nucleotide sequence of interest and/or to a promoter operably linked to the nucleotide sequence of interest, a nucleotide sequence encoding a transcription factor, a nucleotide sequence encoding a translation factor, or a nucleotide sequence encoding a transcription factor and a translation factor.

The transcription factor can be from any suitable system. Preferably, the transcription factor is of poxvirus origin, e.g., from a vaccinia virus. The transcription factor can be from expression from an open reading frame selected from the group consisting of H4L, D6, A7, G8R, A1L, A2L, H5R, a homolog thereof and combinations thereof. It is also preferred that embodiments including a nucleotide sequence encoding a transcription factor comprise a poxvirus vector system.

The translation factor can likewise be from any suitable system. Preferably the translation factor can effect inhibition of eIF-2α phosphorylation or inhibition of PKR phosphorylation or otherwise decreases cellular dsRNA content which increases the effective concentration of dsRNA. The translation factor can be selected from expression from the group consisting of: a K3L open reading frame, an E3L open reading frame, a VAI RNA, an EBER RNA, a sigma 3 open reading frame, a TRBP open reading frame, a homolog thereof, and combinations thereof. The term "effective" with respect to dsRNA concentration means the amount of dsRNA to activate PKR and/or eIF-2α phosphorylation (the dsRNA being in a form therefor). With respect to RNA-based factors, e.g., VAI RNA, EBER RNA, the skilled artisan can obtain suitable DNA from the RNA for use in a DNA vector system without undue experimentation. And, with respect to DNA-based factors, the skilled artisan can obtain suitable RNA therefrom for use in a RNA vector system, without undue experimentation.

The term "substantially co-temporal expression" or the term "substantially contemporaneous expression" means that the nucleotide sequence(s) encoding the transcription or translation or transcription and translation factor(s) are expressed during approximately the same stage of infection as is the at least one nucleotide sequence of interest.

For instance, poxvirus genes are regulated in a temporal manner (Coupar, et al., Eur. J. Immunol., 1986, 16:1479–1487, at 1479). Thus, immediately after infection, a class of "early" genes is expressed (Id.). "Early genes" cease being expressed (i.e., early promoters cease functioning) at a time after infection prior to the "later" stage of infection (DNA replication commencement). The thymidine kinase ("TK") gene and TK promoter is an example of an immediate "early" gene and promoter (Hruby et al., J. Virol., 1982, 43(2):403–409, at 403). The TK gene is switched "off" about four hours after infection.

"Late genes" are a class of genes not expressed until DNA replication has commenced (Coupar et al., supra). The PL11 promoter employed by Coupar et al. is an example of a "late" promoter. Thus, in Coupar et al., HA gene expression regulated by the PL11 promoter was not until after DNA replication, despite being in the TK region.

In contrast to canonical "early" genes and "late" genes the 7.5 kD gene and 7.5 kD promoter, is an example of an "early and late" gene and promoter. An "apparent exception to regulated transcription" (Davison and Moss, "Structure of Vaccinia Virus Early Promoters" J. Mol. Biol., 210–69, 249–69 (1989) at 749), the 7.5 kD promoter "contains regulatory signal for both early and late transcription" (Coupar et al., supra). Indeed, there are "independent early and late RNA start sites within the promoter region of the 7.5-kD gene" (Cochran et al., J. Virol., 59(1): 30–37 (April, 1985).

Coupar et al. observed "that temporal regulation of HA expression by the promoters PF [early], P7.5 [early and late] and PL11 [late] was maintained when the promoters were transposed to interrupt the TK gene of [vaccinia virus]" (Id., at 1482). That is, Coupar et al. observed that foreign gene expression under the control of an early vaccinia promoter occurred "early", foreign gene expression under control of a late vaccinia promoter occurred "late", and foreign gene expression under the control of the early and late vaccinia 7.5 kD promoter occurred both early and late (See also id. at 1479: "[p]romoter sequences transposed to within the thymidine kinase (TK) gene continue to function in a temporally regulated manner" (citations omitted)).

Thus, the nucleotide sequence(s) encoding the transcription or translation or transcription and translation factor(s) can be under the control of a first type of promoter and the at least one nucleotide sequence of interest or the coding nucleotide sequence can be under the control of a second type of promoter, wherein the first and second promoters are both early, both late (including intermediate), or both early and late; or, the first promoter can be early or late and the second promoter early and late; or the first promoter can be early and late and the second promoter early or late. The nucleotide sequence of interest and the nucleotide sequence(s) encoding the transcription or translation or transcription and translation factor(s) can be at the same locus or at different loci; or under the control of the same promoter.

Accordingly, the invention can relate to a method for preparing a vector having enhanced transcription or translation or transcription and translation and/or expression, or to a method for increasing or enhancing transcription or translation or transcription and translation and/or expression in a vector comprising operably linking to at least one nucleotide sequence of interest, or to a promoter operably linked thereto, at least one nucleotide sequence for at least one transcription and/or at least one translation factor; e.g., at least one nucleotide sequence for a transcription transcription factor, or at least one nucleotide sequence for a translation factor or at least one nucleotide sequence for a transcription factor and a translation factor. Preferably the translation factor effects an inhibition of eIF-2α phosphorylation and/or effects an inhibition of phosphorylation of PKR and/or a cellular kinase responsible for phosphorylation of eIF-2α and/or effects the effective concentration of dsRNA. The invention also can thus relate to vectors from such methods.

Alternatively, the inventive methods can comprise operably linking at least one nucleotide sequence of interest to a first type of promoter and operably linking at least one second nucleotide sequence encoding at least one transcription and/or translation factor to a second type of promoter, within a vector, wherein the first and second promoters are both functional at the same time or same stage of infection, e.g., the first and second promoters are both early, both late (including intermediate), or both early and late; or, the first promoter is early or late and the second promoter is early and late; or the first promoter is early and late and the second promoter is early or late. Of course, the first and second promoters can be the same promoter at two or more different loci, or the same promoter at one locus. And, the invention thus relates to vectors from such methods.

And, the term "nucleotide sequence" as used herein can mean nucleic acid molecule. Thus, a nucleotide sequence can be an isolated nucleic acid molecule, e.g., exogenous DNA.

Accordingly, the present invention can provide vectors modified to contain at least one exogenous nucleotide sequence, preferably encoding at least one epitope of interest, and at least one transcription factor or at least one translation factor or at least one transcription factor and at least one translation factor, wherein there is substantially temporal co-expression (or substantially co-temporal expression or substantially contemporaneous expression) of the exogenous nucleotide sequence and the factor(s); and, methods for making and using such vectors and products therefrom. Enhanced or improved expression is obtained by the vectors and methods of the invention; and, enhanced or improved expression can mean enhanced levels and/or persistence of expression.

The invention can thus provide vectors, for instance, poxvirus vectors, which are abortive early, e.g., NYVAC, ALVAC or TROVAC recombinants, having an early expressed transcription factor, e.g., an early expressed H4L open reading frame (or a homolog thereof, e.g., from another vector system, such as poxviruses other than vaccinia, herpesvirus, such as Epstein-Barr, adenovirus, plasmid or naked DNA, and the like) as a means for enhancing and/or increasing the levels and/or persistence of an inserted nucleotide sequence, e.g., a foreign gene. The invention can also provide vectors, for instance, poxvirus vectors, which are abortive late (which includes abortive intermediate), e.g., MVA recombinants, having a late expressed transcription factor, e.g., an expressed G8R, A1L, A2L, H5R (VLTF-1, -2, -3, -4, P3, VLTF-X) open reading frame (or a homolog thereof, e.g., from another vector system, such as poxviruses other than vaccinia, herpesvirus, such as Epstein-Barr, adenovirus, plasmid or naked DNA, and the like) as a means for enhancing and/or increasing the levels and/or persistence of expression from an inserted nucleotide sequence, e.g., a foreign gene.

The invention can additionally provide vectors, for instance, poxvirus vectors, e.g., NYVAC, ALVAC or TRO- VAC recombinants, having expression from the vaccinia E3L and/or K3L (or a homolog thereof, e.g., from another vector system, such as poxviruses other than vaccinia, herpesvirus, such as Epstein-Barr, adenovirus, plasmid or naked DNA, and the like, note discussion supra of viral mechanisms to overcome the cellular anti-viral response of translational down-regulation through PKR activation) as a means for enhancing and/or increasing the levels and persistence of an inserted nucleotide sequence, e.g., a foreign gene.

Even further still, the invention can provide vectors, for instance, poxvirus vectors, e.g., NYVAC, ALVAC or TROVAC recombinants, having an early expressed transcription factor, e.g., an early expressed H4L open reading frame (or a homolog thereof) and/or a late expressed transcription factor, e.g., an expressed G8R, A1L, A2L, H5R (VLTF-1, -2, -3, -4, P3, VLTF-X) (or a homolog thereof), for instance abortive late (which includes abortive intermediate), e.g., MVA, recombinants, and expression from the vaccinia E3L and/or K3L (or a homolog thereof) as a means for enhancing and/or increasing the levels and persistence of expression from an inserted nucleotide sequence, e.g., a foreign gene.

As shown in the Examples below, ALVAC-HIV recombinant vCP1452 containing the K3L/E3L factors had enhanced expression on human cells in comparison to vCP1433 or vCP300. Indeed, enhanced expression is observed with the E3L/K3L translational factors in human and canine cells.

Enhanced expression by translational factors such as E3L/K3L may be cell type dependent. For instance, while enhanced expression with E3L/K3L is observed in human and canine cells it is not observed in murine and feline cells. From this disclosure and the knowledge in the art, the skilled artisan can select an appropriate translational factor for use with a particular cell type, without undue experimentation. For example, it should go without saying that the skilled artisan knows the differences between cells. Thus it is preferred that the translational factor be expressed in a cell in which enhanced expression is observed, e.g., that the translational factor employed be with respect to the cell.

Further, preliminary immunogenicity studies in mice show no evidence of enhanced immunogenicity by the E3L/K3L translational factor. This corresponds to no observed enhanced expression in murine cells. Accordingly, the skilled artisan from this disclosure and the knowledge in the art can select a translational factor which will provide enhanced immunogenicity in a desired animal, without undue experimentation. If enhanced expression is observed in vitro in a particular cell line by a particular translational factor, e.g., E3L/K3L in human or canine cells, the skilled artisan can thus expect enhanced immunogenicity in vivo in the animal (including human) from which the cells were derived by that particular translational factor, e.g., enhanced immunogenicity in humans and canines from the E3L/K3L translational factor.

Furthermore, in murine cells, the limiting factor of ALVAC expression is at the transcription level. Accordingly, use of an appropriate transcription factor can overcome the inability to observe enhanced expression in the murine system. Thus, the origin of the cell may be a factor in in vitro or in vivo applications of the invention (note H4 data), as may be the nature of the vector, e.g., the phenotype of the vector; but, appropriate selection of a cell and vector phenotype and of time of expression from factor(s) and foreign and/or exogenous DNA are within the ambit of the skilled artisan, from this disclosure and the knowledge in the art, without undue experimentation.

Also, the Examples below show that NYVAC recombinant vP1380 has enhanced expression levels in comparison to vP994. Possibly, part of the enhanced levels in vP1380 are due to enhanced transcription and expression from viral specific products such as E3L, such that there is enhanced transcription and translation involved in expression in vP1380. There is more expression from the exogenous DNA and at more persistent levels in vP1380, in accordance with the invention wherein vectors obtain greater levels of expression and more persistent levels of expression.

Enhanced expression profiles in the murine system provided enhanced immunogenicity in mice, as shown by vP1380 being more immunogenic in mice than vP994. Another observation is that enhancement profiles are seen in restrictive early cells in the abortive early NYVAC recombinants herein, whereas the profiles were not observed in cells where there was productive replication, e.g., VERO or CEF, suggesting that it may be preferred that the factor and the foreign DNA be expressed substantially co-temporally or contemporaneously, i.e., that preferably there be co-expression at substantially the same time or stage, and that the time of expression, e.g., early, late, early and late, should be matched with the phenotype of the vector (e.g., abortive early, abortive late), i.e., that in a system in which viral replication is not impaired (a permissive system) or in a system in which replication is aborted at a time when expression is not matched with the phenotype of the vector may not obtain optimal expression. Thus, in an abortive early system such as ALVAC or NYVAC, one preferably expresses exogenous DNA and the transcriptional or translational or transcriptional and translational factor(s) early; in an abortive late system, one preferably expresses exogenous DNA and the transcriptional or translational or transcriptional and translational factor late or early and late (as expression only early may be akin to expression in a permissive system, i.e., one may not necessarily obtain optimal expression).

The methods for making a vector or recombinant can be by or analogous to the methods disclosed in U.S. Pat. Nos. 4,603,112, 4,769,330, 5,174,993, 5,505,941, 5,338,683, 5,494,807, and 4,722,848, WO 95/30018, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirusbased expression vectors: Strategies and applications," PNAS USA 93:11371–11377, October 1996, Kitson et al., J. Virol. 65, 3068–3075, 1991; U.S. Pat. Nos. 5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259:1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591, 639, 5,589,466, and 5,580,859 relating to DNA expression vectors, inter alia. See also U.S. applications Ser. Nos. 08/675,566 and 08/675,556, relating to vectors, including adenovirus vectors.

As to the inserted nucleic acid molecule in a vector of the invention, e.g., the foreign gene, the heterologous or exogenous nucleic acid molecule, e.g., DNA, in vectors of the instant invention, preferably encodes an expression product comprising: an epitope of interest, a biological response modulator, a growth factor, a recognition sequence, a therapeutic gene or a fusion protein. With respect to these terms, reference is made to the following discussion, and generally to Kendrew, THE ENCYCLOPEDIA OF MOLECULAR BIOLOGY (Blackwell Science Ltd., 1995) and Sambrook, Fritsch and Maniatis, *Molecular Cloning, A Laboratory Manual*, 2nd Ed., Cold Spring Harbor Laboratory Press, 1982.

An epitope of interest is an immunologically relevant region of an antigen or immunogen or immunologically active fragment thereof, e.g., from a pathogen or toxin of veterinary or human interest.

An epitope of interest can be prepared from an antigen of a pathogen or toxin, or from another antigen or toxin which elicits a response with respect to the pathogen, or from another antigen or toxin which elicits a response with respect to the pathogen, such as, for instance: a Morbillivirus antigen, e.g., a canine distemper virus or measles or rinderpest antigen such as HA or F; a rabies glycoprotein, e.g., rabies glycoprotein G; an avian influenza antigen, e.g., turkey influenza HA, Chicken/Pennsylvania/1/83 influenza antigen such as a nudeoprotein (NP); a bovine leukemia virus antigen, e.g., gp51,30 envelope; a Newcastle Disease Virus (NDV) antigen, e.g., HN or F; a feline leukemia virus antigen (FeLV), e.g., FeLV envelope protein; RAV-1 env; matrix and/or preplomer of infectious bronchitis virus; a Herpesvirus glycoprotein, e.g., a glycoprotein from feline herpesvirus, equine herpesvirus, bovine herpesvirus, pseudorabies virus, canine herpesvirus, HSV, Marek's Disease Virus, or cytomegalovirus; a flavivirus antigen, e.g., a Japanese encephalitis virus (JEV) antigen, a Yellow Fever antigen, or a Dengue virus antigen; a malaria (Plasmodium) antigen, an immunodeficiency virus antigen, e.g., a feline immunodeficiency virus (FIV) antigen or a simian immunodeficiency virus (SIV) antigen or a human immunodeficiency virus antigen (HIV); a parvovirus antigen, e.g., canine parvovirus; an equine influenza antigen; an poxvirus antigen, e.g., an ectromelia antigen, a canarypox virus antigen or a fowlpox virus antigen; or an infectious bursal disease virus antigen, e.g., VP2, VP3, VP4.

An epitope of interest can be from an antigen of a human pathogen or toxin, or from another antigen or toxin which elicits a response with respect to the pathogen, or from another antigen or toxin which elicits a response with respect to the pathogen, such as, for instance: a Morbillivirus antigen, e.g., a measles virus antigen such as HA or F; a rabies glycoprotein, e.g., rabies virus glycoprotein G; an influenza antigen, e.g., influenza virus HA or N; a Herpesvirus antigen, e.g., a glycoprotein of a herpes simplex virus (HSV), a human cytomegalovirus (HCMV), Epstein-Barr; a flavivirus antigen, a JEV, Yellow Fever virus or Dengue virus antigen; a Hepatitis virus antigen, e.g., HBsAg; an immunodeficiency virus antigen, e.g., an HIV antigen such as gp120, gp160; a Hantaan virus antigen; a C. tetani antigen; a mumps antigen; a pneumococcal antigen, e.g., PspA; a Borrelia antigen, e.g., OspA, OspB, OspC of Borrelia associated with Lyme disease such as *Borrelia burgdorferi*, *Borrelia afzelli* and *Borrelia garinii*; a chicken pox (varicella zoster) antigen; or a Plasmodium antigen.

Of course, the foregoing lists are intended as exemplary, as the epitope of interest can be derived from any antigen of any veterinary or human pathogen; and, to obtain an epitope of interest, one can express an antigen of any veterinary or human pathogen (such that the invention encompasses the exogenous or foreign nucleic acid molecule(s) of interest encoding at least one antigen).

Since the heterologous DNA can be a growth factor or therapeutic gene, the inventive recombinants can be used in gene therapy. Gene therapy involves transferring genetic information; and, with respect to gene therapy and immunotherapy, reference is made to U.S. Pat. No. 5,252, 479, which is incorporated herein by reference, together with the documents cited in it and on its face, and to WO 94/16716 and allowed U.S. Pat. No. 5,833,975, filed Jan. 19, 1994, each of which is also incorporated herein by reference, together with the documents cited therein. The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin, macrophage colony stimulating factor, granulocyte colony stimulating factor, erythropoietin, mast cell growth factor, tumor suppressor p53, retinoblastoma, interferon, melanoma associated antigen or B7.

The invention further relates to an immunogenic, immunological or vaccine composition containing the inventive vector and an acceptable carrier or diluent( e.g., veterinary acceptable or pharmaceutically acceptable). An immunological composition containing the vector (or an expression product thereof) elicits an immunological response—local or systemic. The response can, but need not be protective. An immunogenic composition containing the inventive recombinants (or an expression product thereof) likewise elicits a local or systemic immunological response which can, but need not be, protective. A vaccine composition elicits a local or systemic protective response. Accordingly, the terms "immunological composition" and "immunogenic composition" include a "vaccine composition" (as the two former terms can be protective compositions).

The invention therefore also provides a method for inducing an immunological response in a host vertebrate comprising administering to the host an immunogenic, immunological or vaccine composition comprising the inventive recombinant virus or vector and an acceptable carrier or diluent. For purposes of this specification, "animal" includes all vertebrate species, except humans; and "vertebrate" includes all vertebrates, including animals (as "animal" is used herein) and humans. And, of course, a subset of "animal" is "mammal", which for purposes of this specification includes all mammals, except humans.

For human administration, the inventive recombinants or vectors, can provide the advantage of expression without productive replication. This thus provides the ability to use recombinants of the invention in immunocompromised individuals; and, provides a level of safety to workers in contact with recombinants of the invention. Therefore, the invention comprehends methods for amplifying or expressing a protein by administering or inoculating a host with a recombinant virus or vector, whereby the host is not a natural host of the recombinant virus or vector, and there is expression without productive replication.

The exogenous or heterologous DNA (or DNA foreign to vaccine virus) can be DNA encoding any of the aforementioned epitopes of interest, as listed above. In this regard, with respect to Borrelia DNA, reference is made to U.S. Pat. No. 5,523,089, WO93/08306, PCT/US92/08697, Molecular Microbiology (1989), 3(4), 479–486, and PCT publications WO 93/04175, and WO 96/06165, incorporated herein by reference.

With respect to pneumococcal epitopes of interest, reference is made to Briles et al. WO 92/14488, incorporated herein by reference, with respect to tumor viruses reference is made to *Molecular Biology of Tumor Viruses, RNA TUMOR VIRUSES* (Second Edition, Edited by Weiss et al., Cold Spring Harbor Laboratory 1982) (e.g., page 44 et seq.—Taxonomy of Retroviruses), incorporated herein by reference.

With respect to DNA encoding epitopes of interest, attention is directed to documents cited herein, see, e.g., documents cited supra and documents cited infra, for instance: U.S. Pat. Nos. 5,174,993 and 5,505,941 (e.g., recombinant avipox virus, vaccinia virus; rabies glycoprotein (G), gene, turkey influenza hemagglutinin gene, gp51,30 envelope gene of bovine leukemia virus, Newcastle Disease Virus (NDV) antigen, FeLV envelope gene, RAV-1 env gene, NP (nudeoprotein gene of Chicken/Pennsylvania/1/83 influenza virus), matrix and preplomer gene of infectious bronchitis virus; HSV gD), U.S. Pat. No. 5,338,683 (e.g., recombinant vaccinia virus, avipox virus; DNA encoding Herpesvirus glycoproteins, inter alia), U.S. Pat. No. 5,494,807 (e.g., recombinant vaccinia, avipox; exogenous DNA encoding antigens from rabies, Hepatitis B, JEV, YF, Dengue, measles, pseudorabies, Epstein-Barr, HSV, HIV, SIV, EHV, BHV, HCMV, canine parvovirus, equine influenza, FeLV, FHV, Hantaan, *C. tetani*, avian influenza, mumps, NDV, inter alia), U.S. Pat. No. 5,503,834 (e.g., recombinant vaccinia, avipox, Morbillivirus, e.g., measles F, hemagglutinin, inter alia), U.S. Pat. No. 4,722,848 (e.g., recombinant vaccinia virus; HSV tk, HSV glycoproteins, e.g., gB, gD, influenza HA, Hepatitis B, e.g., HBsAg, inter alia), U.K. Patent GB 2 269 820 B and U.S. Pat. No. 5,514,375 (recombinant poxvirus; flavivirus structural proteins); WO 92/22641 and U.S. Pat. No. 5,863,542 and U.S. application Ser. No. 08/372,664 (e.g., recombinant poxvirus; immunodeficiency virus, HTLV, inter alia), WO 93/03145 and U.S. Pat. Nos. 5,658,572 and 5,641,490 (e.g., recombinant poxvirus; IBDV, inter alia), WO 94/16716 and U.S. Pat. No. 5,833,975 (e.g., recombinant poxvirus; cytokine and/or tumor associated antigens, inter alia), U.S. application Ser. No. 08/469,969 (rabies combination compositions), U.S. application Ser. No. 08/746,668 (lentivirus, retrovirus and/or immunodeficiency virus, including feline immunodeficiency virus, inter alia), U.S. Pat. Nos. 5,529,780 and 5,688,920 (canine herpesvirus), 5,989,561 (calicivirus), WO 96/3941 and U.S. Pat. No. 5,997,878 (cytomegalovirus), and PCT/US94/06652 (Plasmodium antigens such as from each stage of the Plasmodium life cycle).

As to antigens for use in vaccine or immunological compositions, reference is made to the documents and discussion set forth in the documents cited herein (see, e.g., documents cited supra); see also Stedman's Medical Dictionary (24th edition, 1982, e.g., definition of vaccine (for a list of antigens used in vaccine formulations; such antigens or epitopes of interest from those antigens can be used in the invention, as either an expression product of an inventive recombinant virus or vector, or in a multivalent composition containing an inventive recombinant virus or vector or an expression product therefrom).

As to epitopes of interest, one skilled in the art can determine an epitope or immunodominant region of a peptide or polypeptide and ergo the coding DNA therefor from the knowledge of the amino acid and corresponding DNA sequences of the peptide or polypeptide, as well as from the nature of particular amino acids (e.g., size, charge, etc.) and the codon dictionary, without undue experimentation.

A general method for determining which portions of a protein to use in an immunological composition focuses on the size and sequence of the antigen of interest. "In general, large proteins, because they have more potential determinants are better antigens than small ones. The more foreign an antigen, that is the less similar to self configurations which induce tolerance, the more effective it is in provoking an immune response." Ivan Roitt, *Essential Immunology*, 1988.

As to size: the skilled artisan can maximize the size of the protein encoded by the DNA sequence to be inserted into the viral vector (keeping in mind the packaging limitations of the vector). To minimize the DNA inserted while maximizing the size of the protein expressed, the DNA sequence can exclude introns (regions of a gene which are transcribed but which are subsequently excised from the primary RNA transcript).

At a minimum, the DNA sequence can code for a peptide at least 8 or 9 amino acids long. This is the minimum length that a peptide needs to be in order to stimulate a CD8+ T cell response (which recognizes virus infected cells or cancerous cells). A minimum peptide length of 13 to 25 amino acids is useful to stimulate a CD4+ T cell response (which recognizes special antigen presenting cells which have engulfed the pathogen). See Kendrew, supra. However, as these are minimum lengths, these peptides are likely to generate an immunological response, i.e., an antibody or T cell response; but, for a protective response (as from a vaccine composition), a longer peptide is preferred.

With respect to the sequence, the DNA sequence preferably encodes at least regions of the peptide that generate an antibody response or a T cell response. One method to determine T and B cell epitopes involves epitope mapping. The protein of interest "is fragmented into overlapping peptides with proteolytic enzymes. The individual peptides are then tested for their ability to bind to an antibody elicited by the native protein or to induce T cell or B cell activation. This approach has been particularly useful in mapping T-cell epitopes since the T cell recognizes short linear peptides complexed with MHC molecules. The method is less effective for determining B-cell epitopes" since B cell epitopes are often not linear amino acid sequence but rather result from the tertiary structure of the folded three dimensional protein. Janis Kuby, *Immunology*, (1992) pp. 79–80.

Another method for determining an epitope of interest is to choose the regions of the protein that are hydrophilic. Hydrophilic residues are often on the surface of the protein and are therefore often the regions of the protein which are accessible to the antibody. Janis Kuby, *Immunology*, (1992) p. 81

Yet another method for determining an epitope of interest is to perform an X-ray crystallographic analysis of the antigen (full length)-antibody complex. Janis Kuby, *Immunology*, (1992) p. 80.

Still another method for choosing an epitope of interest which can generate a T cell response is to identify from the protein sequence potential HLA anchor binding motifs which are peptide sequences which are known to be likely to bind to the MHC molecule.

The peptide which is a putative epitope of interest, to generate a T cell response, should be presented in a MHC complex. The peptide preferably contains appropriate anchor motifs for binding to the MHC molecules, and should bind with high enough affinity to generate an immune response. Factors which can be considered are: the HLA type of the patient (vertebrate, animal or human) expected to be immunized, the sequence of the protein, the presence of appropriate anchor motifs and the occurrence of the peptide sequence in other vital cells.

An immune response is generated, in general, as follows: T cells recognize proteins only when the protein has been cleaved into smaller peptides and is presented in a complex called the "major histocompatability complex MHC" located on another cell's surface. There are two classes of MHC complexes—class I and class II, and each class is made up of many different alleles. Different patients have different types of MHC complex alleles; they are said to have a 'different HLA type.'

Class I MHC complexes are found on virtually every cell and present peptides from proteins produced inside the cell. Thus, Class I MHC complexes are useful for killing cells which when infected by viruses or which have become cancerous and as the result of expression of an oncogene. T cells which have a protein called CD8 on their surface, bind specifically to the MHC class I/peptide complexes via the T cell receptor. This leads to cytolytic effector activities.

Class II MHC complexes are found only on antigen-presenting cells and are used to present peptides from circulating pathogens which have been endocytosed by the antigen-presenting cells. T cells which have a protein called CD4 bind to the MHC class II/peptide complexes via the T cell receptor. This leads to the synthesis of specific cytokines which stimulate an immune response.

Some guidelines in determining whether a protein is an epitopes of interest which will stimulate a T cell response, include: Peptide length—the peptide should be at least 8 or 9 amino acids long to fit into the MHC class I complex and at least 13–25 amino acids long to fit into a class II MHC complex. This length is a minimum for the peptide to bind to the MHC complex. It is preferred for the peptides to be longer than these lengths because cells may cut the expressed peptides. The peptide should contain an appropriate anchor motif which will enable it to bind to the various class I or class II molecules with high enough specificity to generate an immune response (See Bocchia, M. et al, *Specific Binding of Leukemia Oncogene Fusion Protein Peptides to HLA Class I Molecules*, Blood 85:2680–2684; Englehard, VH, *Structure of peptides associated with class I and class II MHC molecules* Ann. Rev. Immunol. 12:181 (1994)). This can be done, without undue experimentation, by comparing the sequence of the protein of interest with published structures of peptides associated with the MHC molecules. Protein epitopes recognized by T cell receptors are peptides generated by enzymatic degradation of the protein molecule and are presented on the cell surface in association with class I or class II MHC molecules.

Further, the skilled artisan can ascertain an epitope of interest by comparing the protein sequence with sequences listed in the protein data base.

Even further, another method is simply to generate or express portions of a protein of interest, generate monoclonal antibodies to those portions of the protein of interest, and then ascertain whether those antibodies inhibit growth in vitro of the pathogen from which the from which the protein was derived. The skilled artisan can use the other guidelines set forth in this disclosure and in the art for generating or expressing portions of a protein of interest for analysis as to whether antibodies thereto inhibit growth in vitro. For example, the skilled artisan can generate portions of a protein of interest by: selecting 8 to 9 or 13 to 25 amino acid length portions of the protein, selecting hydrophylic regions, selecting portions shown to bind from X-ray data of the antigen (full length)-antibody complex, selecting regions which differ in sequence from other proteins, selecting potential HLA anchor binding motifs, or any combination of these methods or other methods known in the art.

Epitopes recognized by antibodies are expressed on the surface of a protein. To determine the regions of a protein most likely to stimulate an antibody response one skilled in the art can preferably perform an epitope map, using the general methods described above, or other mapping methods known in the art.

As can be seen from the foregoing, without undue experimentation, from this disclosure and the knowledge in the art, the skilled artisan can ascertain the amino acid and corresponding DNA sequence of an epitope of interest for obtaining a T cell, B cell and/or antibody response. In addition, reference is made to Gefter et al., U.S. Pat. No. 5,019,384, issued May 28, 1991, and the documents it cites, incorporated herein by reference (Note especially the "Relevant Literature" section of this patent, and column 13 of this patent which discloses that: "A large number of epitopes have been defined for a wide variety of organisms of interest. Of particular interest are those epitopes to which neutralizing antibodies are directed. Disclosures of such epitopes are in many of the references cited in the Relevant Literature section.")

With respect to expression of a biological response modulator, reference is made to Wohlstadter, "Selection Methods," WO 93/19170, published Sep. 30, 1993, and the documents cited therein, incorporated herein by reference.

For instance, a biological response modulator modulates biological activity; for instance, a biological response modulator is a modulatory component such as a high molecular weight protein associated with non-NMDA excitatory amino acid receptors and which allosterically regulates affinity of AMPA binding (See Kendrew, supra). The recombinant of the present invention can express such a high molecular weight protein.

More generally, nature has provided a number of precedents of biological response modulators. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

Table 2 of Neidhardt et al *Physiology of the Bacterial Cell* (Sinauer Associates Inc., Publishers, 1990), at page 73, lists chemical modifications to bacterial proteins. As is noted in that table, some modifications are involved in proper assembly and other modifications are not, but in either case such modifications are capable of causing modulation of function. From that table, analogous chemical modulations for proteins of other cells can be determined, without undue experimentation.

In some instances modulation of biological functions may be mediated simply through the proper/improper localization of a molecule. Molecules may function to provide a growth advantage or disadvantage only if they are targeted to a particular location. For example, a molecule may be typically not taken up or used by a cell, as a function of that molecule being first degraded by the cell by secretion of an enzyme for that degradation. Thus, production of the enzyme by a recombinant can regulate use or uptake of the molecule by a cell. Likewise, the recombinant can express a molecule which binds to the enzyme necessary for uptake or use of a molecule, thereby similarly regulating its uptake or use.

Localization targeting of proteins carried out through cleavage of signal peptides another type of modulation or regulation. In this case, a specific endoprotease catalytic activity can be expressed by the recombinant.

Other examples of mechanisms through which modulation of function may occur are RNA virus poly-proteins, allosteric effects, and general covalent and non-covalent steric hindrance. HIV is a well studied example of an RNA virus which expresses non-functional poly-protein constructs. In HIV "the gag, pol, and env poly-proteins are processed to yield, respectively, the viral structural proteins p17, p24, and p15—reverse transcriptase and integrase—and the two envelope proteins gp41 and gp120" (Kohl et al., PNAS USA 85:4686–90 (1988)). The proper cleavage of the poly-proteins is crucial for replication of the virus, and virions carrying inactive mutant HIV protease are non-infectious (id.). This is another example of the fusion of proteins down-modulating their activity. Thus, it is possible to construct recombinant viruses which express molecules which interfere with endoproteases, or which provide endoproteases, for inhibiting or enhancing the natural expression of certain proteins (by interfering with or enhancing cleavage).

The functional usefulness of enzymes may also be modulated by altering their capability of catalyzing a reaction. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation (see Table 1 of Neidhardt, supra, at page 315 and Table 2 at page 73).

Zymogens are examples of naturally occurring protein fusions which cause modulation of enzymatic activity. Zymogens are one class of proteins which are converted into their active state through limited proteolysis. See Table 3 of Reich, *Proteases and Biological Control*, Vol. 2, (1975) at page 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$–$10^6$ times lower than those of the corresponding enzyme" (See Table 3 of Reich, supra at page 54).

It is therefore possible to down-modulate the function of certain enzymes simply by the addition of a peptide sequence to one of its termini. For example, with knowledge of this property, a recombinant can express peptide sequences containing additional amino acids at one or both termini.

The formation or disassociation of multi-subunit enzymes is another way through which modulation may occur. Different mechanisms may be responsible for the modulation of activity upon formation or disassociation of multi-subunit enzymes.

Therefore, sterically hindering the proper specific subunit interactions will down-modulate the catalytic activity. And accordingly, the recombinant of the invention can express a molecule which sterically hinders a naturally occurring enzyme or enzyme complex, so as to modulate biological functions.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (Fritsch, *Enzyme Structure and Mechanism*, 2d ed; Freeman & Co. Publishers, 1984)). This type of modulation is possible by the recombinant expressing a suitable suicide substrate, to thereby modulate biological responses (e.g., by limiting enzyme activity).

There are also examples of non-covalent steric hindrance including many repressor molecules. The recombinant can express repressor molecules which are capable of sterically hindering and thus down-modulating the function of a DNA sequence by preventing particular DNA-RNA polymerase interactions.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (Fritsch, supra). Using methods of the invention, molecules can be expressed which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Table 2 of Neidhardt, supra, at page 73, lists different bacterial enzymes which undergo such modifications. From that list, one skilled in the art can ascertain other enzymes of other systems which undergo the same or similar modifications, without undue experimentation. In addition, many proteins which are implicated in human disease also undergo such chemical modifications. For example, many oncogenes have been found to be modified by phosphorylation or to modify other proteins through phosphorylation or dephosphorylation. Therefore, the ability afforded by the invention to express modulators which can modify or alter function, e.g., phosphorylation, is of importance.

From the foregoing, the skilled artisan can use the present invention to express a biological response modulator, without any undue experimentation.

With respect to expression of fusion proteins by inventive recombinants, reference is made to Sambrook, Fritsch, Maniatis, *Molecular Cloning, A LABORATORY MANUAL* (2d Edition, Cold Spring Harbor Laboratory Press, 1989) (especially Volume 3), and Kendrew, supra, incorporated herein by reference. The teachings of Sambrook et al., can be suitably modified, without undue experimentation, from this disclosure, for the skilled artisan to generate recombinants or vectors expressing fusion proteins.

With regard to gene therapy and immunotherapy, reference is made to U.S. Pat. Nos. 4,690,915 and 5,252,479, which are incorporated herein by reference, together with the documents cited therein it and on their face, and to WO 94/16716 and U.S. Pat. No. 5,833,975, each of which is also incorporated herein by reference, together with the documents cited therein.

A growth factor can be defined as multifunctional, locally acting intercellular signalling peptides which control both ontogeny and maintenance of tissue and function (see Kendrew, supra, especially at page 455 et seq.).

The growth factor or therapeutic gene, for example, can encode a disease-fighting protein, a molecule for treating cancer, a tumor suppressor, a cytokine, a tumor associated antigen, or interferon; and, the growth factor or therapeutic gene can, for example, be selected from the group consisting of a gene encoding alpha-globin, beta-globin, gamma-globin, granulocyte macrophage-colony stimulating factor, tumor necrosis factor, an interleukin (e.g., an interleukin selected from interleukins 1 to 14, or 1 to 11, or any combination thereof), macrophage colony stimulating factor, granulocyte colony stimulating factor, erythropoietin, mast cell growth factor, tumor suppressor p53, retinoblastoma, interferon, melanoma associated antigen or B7. U.S. Pat. No. 5,252,479 provides a list of proteins which can be expressed in an adenovirus system for gene therapy, and the skilled artisan is directed to that disclosure. WO 94/16716 and U.S. Pat. No. 5,833,975, provide genes for cytokines and tumor associated antigens and immunotherapy methods, including ex vivo methods, and the skilled artisan is directed to those disclosures.

Thus, one skilled in the art can create recombinants or vectors expressing a growth factor or therapeutic gene and use the recombinants or vectors, from this disclosure and the knowledge in the art, without undue experimentation.

Moreover, from the foregoing and the knowledge in the art, no undue experimentation is required for the skilled artisan to construct an inventive recombinant or vector which expresses an epitope of interest, a biological response modulator, a growth factor, a recognition sequence, a therapeutic gene, or a fusion protein; or for the skilled artisan to use such a recombinant or vector.

As the recombinants or vectors of the invention can be used for expression of gene products in vitro, techniques for protein purification can be employed in the practice of the invention, and such techniques, in general, include:

Briefly, the cells are disrupted and the protein of interest is released into an aqueous "extract". There are many methods of cellular disintegration, which vary from relatively gentle to vigorous conditions, and the choice of one method over the other is dependent upon the source material. Animal tissues vary from the very easily broken erythrocytes to tough collagenous material such as found in blood vessels and other smooth-muscle containing tissue. Bacteria vary from fairly fragile organisms that can be broken up by digestive enzymes or osmotic shock to more resilient species with thick cell walls, needing vigorous mechanical treatment for disintegration.

Gentle techniques include cell lysis, enzymatic digestion, chemical solubilization, hand homogenization and mincing (or grinding); moderate techniques of cell disintegration include blade homogenization and grinding with abrasive materials, i.e., sand or alumina; and vigorous techniques include french press, ultrasonication, bead mill or Manton-Gaulin homogenization. Each of the aforementioned techniques are art-recognized, and it is well within the scope of knowledge of the skilled artisan to determine the appropriate method for cell disintegration based upon the starting material, and the teachings herein and in the art.

Following cell disintegration, the extract is prepared by centrifuging off insoluble material. At this stage, one may proceed with the purification method, as an extract containing as much of the protein of interest as possible has been prepared, and, where appropriate, particulate and most non-protein materials have been removed.

Standard techniques of protein purification may be employed to further purify the protein of interest, including: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immuno affinity or dye-ligand chromatography; immunoprecipitation and the use of gel filtration, electrophoretic methods, ultrafiltration and isoelectric focusing. Each of the above-identified methods are well within the knowledge of the skilled artisan, and no undue experimentation is required to purify the proteins or epitopes of interest from expression of a recombinant or vector of the invention, using the standard methodologies outlined hereinabove, and in the literature, as well as the teachings in the Examples below.

As the expression products can provide an antigenic, immunological, or protective (vaccine) response, the invention further relates to products therefrom; namely, antibodies and uses thereof. More in particular, the expression products can elicit antibodies by administration of those products or of recombinants or vectors expressing the products. The antibodies can be monoclonal antibodies; and, the antibodies or expression products can be used in kits, assays, tests, and the like involving binding, so that the invention relates to these uses too. Additionally, since the recombinants or vectors of the invention can be used to replicate DNA, the invention relates to the inventive recombinants as vectors and methods for replicating DNA by infecting or transfecting cells with the recombinant and harvesting DNA therefrom. The resultant DNA can be used as probes or primers or for amplification.

The administration procedure for the inventive recombinants or vectors or expression products thereof, compositions of the invention such as immunological, antigenic or vaccine compositions or therapeutic compositions can be via a parenteral route (intradermal, intramuscular or subcutaneous). Such an administration enables a systemic immune response. The administration can be via a mucosal route, e.g., oral, nasal, genital, etc. Such an administration enables a local immune response.

More generally, the inventive antigenic, immunological or vaccine compositions or therapeutic compositions can be prepared in accordance with standard techniques well known to those skilled in the pharmaceutical, medical or veterinary arts. Such compositions can be administered in dosages and by techniques well known to those skilled in the medical or veterinary arts taking into consideration such factors as the breed or species, age, sex, weight, and condition of the particular patient, and the route of administration. The compositions can be administered alone, or can be co-administered or sequentially administered with other compositions of the invention or with other immunological, antigenic or vaccine or therapeutic compositions. Such other compositions can include purified native antigens or epitopes or antigens or epitopes from expression by an inventive recombinant or vector or another vector system; and are administered taking into account the aforementioned factors.

Examples of compositions of the invention include liquid preparations for orifice, e.g., oral, nasal, anal, genital, e.g., vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant or vector may be in admixture with a suitable carrier, diluent, or excipient such as sterile water, physiological saline, glucose or the like.

Antigenic, immunological or vaccine compositions typically can contain an adjuvant and an amount of the recombinant or vector or expression product to elicit the desired response. In human applications, alum (aluminum phosphate or aluminum hydroxide) is a typical adjuvant. Saponin and its purified component Quil A, Freund's complete adjuvant and other adjuvants used in research and veterinary applications have toxicities which limit their potential use in human vaccines. Chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the protein within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) can also be used.

The composition may be packaged in a single dosage form for immunization by parenteral (i.e., intramuscular, intradermal or subcutaneous) administration or orifice administration, e.g., perlingual (i.e., oral), intragastric, mucosal including intraoral, intraanal, intravaginal, and the like administration. And again, the effective dosage and route of administration are determined by the nature of the composition, by the nature of the expression product, by expression level if the recombinant is directly used, and by known factors, such as breed or species, age, sex, weight, condition and nature of host, as well as $LD_{50}$ and other screening procedures which are known and do not require undue experimentation. Dosages of expressed product can range from a few to a few hundred micrograms, e.g., 5 to 500 μg. The inventive recombinant or vector can be administered in any suitable amount to achieve expression at these dosage levels. The viral recombinants of the invention can be administered in an amount of about $10^{3.5}$ pfu; thus, the inventive viral recombinant is preferably administered in at least this amount; more preferably about $10^4$ pfu to about $10^6$ pfu; however higher dosages such as about $10^4$ pfu to about $10^{10}$ pfu, e.g., about $10^5$ pfu to about $10^9$ pfu, for instance about $10^6$ pfu to about $10^8$ pfu can be employed. Suitable quantities of inventive plasmid or naked DNA in plasmid or naked DNA compositions can be 1 ug to 100 mg, preferably 0.1 to 10 mg, but lower levels such as 0.1 to 2 mg or preferably 1–10 ug may be employed Other suitable carriers or diluents can be water or a buffered saline, with or without a preservative. The expression product or recombinant or vector may be lyophilized for resuspension at the time of administration or can be in solution.

The carrier may also be a polymeric delayed release system. Synthetic polymers are particularly useful in the formulation of a composition having controlled release. An early example of this was the polymerization of methyl methacrylate into spheres having diameters less than one micron to form so-called nano particles, reported by Kreuter, J., *Microcapsules and Nanoparticles in Medicine and Pharmacology*, M. Donbrow (Ed). CRC Press, p. 125–148.

Microencapsulation has been applied to the injection of microencapsulated pharmaceuticals to give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters and polyamides, particularly those that are biodegradable.

A frequent choice of a carrier for pharmaceuticals and more recently for antigens is poly (d,1-lactide-co-glycolide) (PLGA). This is a biodegradable polyester that has a long history of medical use in erodible sutures, bone plates and other temporary prostheses where it has not exhibited any toxicity. A wide variety of pharmaceuticals including peptides and antigens have been formulated into PLGA microcapsules. A body of data has accumulated on the adaption of PLGA for the controlled release of antigen, for example, as reviewed by Eldridge, J. H., et al. *Current Topics in Microbiology and Immunology* 1989, 146:59–66. The entrapment of antigens in PLGA microspheres of 1 to 10 microns in diameter has been shown to have a remarkable adjuvant effect when administered orally. The PLGA microencapsulation process uses a phase separation of a water-in-oil emulsion. The compound of interest is prepared as an aqueous solution and the PLGA is dissolved in a suitable organic solvents such as methylene chloride and ethyl acetate. These two immiscible solutions are co-emulsified by high-speed stirring. A non-solvent for the polymer is then added, causing precipitation of the polymer around the aqueous droplets to form embryonic microcapsules. The microcapsules are collected, and stabilized with one of an assortment of agents (polyvinyl alcohol (PVA), gelatin, alginates, polyvinylpyrrolidone (PVP), methyl cellulose) and the solvent removed by either drying in vacuo or solvent extraction.

Thus, solid, including solid-containing-liquid, liquid, and gel (including "gel caps") compositions are envisioned.

Furthermore, the inventive vectors or recombinants can be used in any desired immunization or administration regimen; e.g., as part of periodic vaccinations such as annual vaccinations as in the veterinary arts or as in periodic vaccinations as in the human medical arts, or as in a prime-boost regimen wherein an inventive vector or recombinant is administered either before or after the administration of the same or of a different epitope of interest or recombinant or vector expressing such a same or different epitope of interest (including an inventive recombinant or vector expressing such a same or different epitope of interest), see, e.g., documents cited herein such as U.S. application Ser. No. 08/746,668.

Additionally, the inventive vectors or recombinants and the expression products therefrom can stimulate an immune or antibody response in animals. From those antibodies, by techniques well-known in the art, monoclonal antibodies can be prepared and, those monoclonal antibodies, can be employed in well known antibody binding assays, diagnostic kits or tests to determine the presence or absence of antigen(s) and therefrom the presence or absence of the natural causative agent of the antigen or, to determine whether an immune response to that agent or to the antigen (s) has simply been stimulated.

Monoclonal antibodies are immunoglobulin produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Furthermore, the inventive recombinants or vectors or expression products therefrom can be used to stimulate a response in cells in vitro or ex vivo for subsequent reinfusion into a patient. If the patient is seronegative, the reinfusion is to stimulate an immune response, e.g., an immunological or antigenic response such as active immunization. In a seropositive individual, the reinfusion is to stimulate or boost the immune system against a pathogen.

The recombinants or vectors of the invention are also useful for generating DNA for probes or for PCR primers which can be used to detect the presence or absence of hybridizable DNA or to amplify DNA, e.g., to detect a pathogen in a sample or for amplifying DNA.

Since viruses require translation of viral mRNAs in order to generate viral proteins required for replication, it is evident that any function which blocks the action of PKR in the infected cell will have a positive effect on viral protein expression. Thus, co-expression, in some fashion, of the vaccinia E3L/K3L gene products, or a homolog of E3L and/or K3L, may provide a general mechanism for enhancing the expression levels of heterologous gene products by vectors in general. The E3L/K3L or homologous functions may enhance or augment native anti-PKR mechanisms, and thus increase protein expression levels and/or persistence. This provides a useful element towards optimizing the efficiency of eukaryotic virus systems as immunization vehicles. This approach could be further extended for improvement of DNA-based immunogens, e.g., naked DNA or plasmid DNA vector systems. Further, employing a nucleotide sequence for a transcription factor, e.g., for an early and/or late viral transcription factor, in conjunction with enhancing translation by employing a nucleotide sequence for a translation factor, can even further enhance or increase expression by increasing or enhancing transcription and translation; and thus, increasing or enhancing levels or persistence of expression can be obtained.

A better understanding of the present invention and of its many advantages will be had from the following non-limiting Examples, given by way of illustration.

EXAMPLES

Example 1

NYVAC Recombinants Containing H4L

The plasmids placZH6H4L and placZH6H4Lreverse (ATCC Deposit No. ATCC-97913) were used as donor plasmids for in vivo recombination with the rescue virus vP994 (ATCC Deposit No. VR-2558; U.S. Pat. No. 5,494,807, incorporated herein by reference; vaccinia H6 promoter/HIV1 MN env-noncleavable, secreted gp140, in HA insertion site). The donor plasmids were designed to replace the endogenous promoter and coding sequences of H4L by homologous recombination. The resulting recombinant viruses were designated vP1379 and vP1380; vP1379 contains the H61acZ/H6H4L cassette in a head-to-head configuration; vP1380 contains the H61acZ/H6H4L cassette in a head-to-tail configuration (SEQ ID NO: 1; FIG. 1).

The plasmids were constructed as follows:

H4L Expression Cassette

The H4L open reading frame (orf) as delineated in Goebel et al. 1990 corresponds to positions 94830–92446 in the Copenhagen (vaccine) strain vaccinia virus genomic sequence. pSD404VC contains a clone of the 8.6 Kb HindIII H fragment of Copenhagen vaccinia virus inserted into the pUC vector background. pSD404VC was digested with PvuII to isolate a 3860 bp fragment containing the H4L coding sequences and flanking sequences. The 3860 bp fragment was inserted into the blunted BamHI site of pBSecogpt (E. coli gpt gene (ATCC No. 37145) under the control of Copenhagen B13R promoter in the pBS SK vector (Stratagene La Jolla, Calif.)) resulting in plasmid pRW935.

pRW935 was linearized with EcoRI and partially digested with DraI to remove a 970 bp fragment containing the 5' end of the H4L coding sequence. Using a series of Polymerase Chain Reactions (PCRs) the H4L coding sequence was reengineered to be under the control of the modified vaccinia H6 promoter (Perkus et: al. 1989). Using the plasmid template pRW935 and primer pairs RW500/RW502 and RW501/RW503 in the PCR amplifications, the 5' H4L sequences were regenerated. In addition, the oligonucleotide, RW502, modifies the H4L coding sequences (position 341–348 from the A of the ATG) from TTTTTTTT to TTTTCTTC without altering the predicted amino acid sequence to remove an early transcriptional stop signal (Yuan, L. and Moss, B., 1987). The modified H6 promoter was amplified from the plasmid template pRW936 using oligonucleotides RW504 and RW507. Oligonucleotides RW505 and RW506 having complementary sequences were PCR amplified directly. The four PCR reactions were pooled and further amplified using primer pair RW500 and RW505. The resulting PCR fragment was digested with DraI and EcoRI and cloned into DraI and EcoRI digested pRW935 generating pRW939. A PCR introduced error in the 5' end of the coding region of pRW939 was corrected, resulting in plasmid pRW947. Specifically, the PCR error introduced in pRW939 (H4L codon 155 is AAA—correct codon should be GAA) was corrected by replacement of the 600 bp pRW939 AflIII-EcoRI fragment with the equivalent fragment from pRW935 to generate pRW939. The oligonucleotide sequences for each of the above-identified oligonucleotides (RW500 and RW501 to RW507; SEQ ID NOS: 9 to 16) are:

```
RW500 5'- GAAATAGTTAGCGTCAAC -3'

RW501 5'- TGTCTAATGTGTTGAAGAAAAGATCATACAAGTTATAC -3'

RW502 5'- AACTTGTATGATCTTTTCTTCAACACATTAGACATGTATTTAC -3'

RW503 5'- TAAGTTTGTATCGTAATGGACTCTAAAGAGACTATTC -3'

RW504 5'- AGTCTCTTTAGAGTCCATTACGATACAAACTTAAC -3'

RW505
5'-CCGACGATTTTAAAACGCCACCGTCAGGGAAAGTTTCATAAGAAGCACCGGAAGAGAAGAGA
ATTCTCGGGACAATTGGATC -3'

RW506
5'-
GTCTAGCTGGTGCTGAGTTTCTACGTGAGTTGATTCGTCTCTTGCGTGCCTCTCGTGATCCAATT
GTCCCGAGATATTCTC -3'

RW507
5'-
GTAGAAACTCAGCACCAGCTAGACAAGCTTCTTTATTCTATACTTAAAAAGTGAAAATAAATAC
-3'
```

The plasmid pRW947 was digested with XhoI to generate two fragments. The 7036 bp fragment containing the H6 promoted H4L in the pBSSK vector background was purified and self-ligated, resulting in the plasmid pH6H4L. The plasmid pRW973A, containing a LacZ expression cassette under the control of the vaccinia H6 promoter, was digested with HindIII. The 3.3 Kbp fragment was purified and ligated into the HindIII digested pH6H4L, thereby generating pLACZH6H4Lreverse (H6 promoted LacZ gene and H6 promoted H4L gene in head-to-tail configuration), and placZH6H4L (H6 promoted lacZ gene and H6 promoted H4L gene in a head-to-head configuration).

Example 2

ALVAC Recombinants pMPC6H6K3E3 (ATCC No. ATCC 97912) was used as a donor plasmic in in vivo recombination (Piccini et al., 1987) with rescuing virus vCP205 (ATCC No. VR-2557; U.S. Pat. No. 5,863,542, incorporated herein by reference; HIV expression cassette—vaccinia H6 promoter/HIV truncated env MN strain, I3L gag with protease in ALVAC C3 insertion site); and the resulting recombinant virus was designated vCP1431A (vaccinia H6/K3L and E3L cassette in the C6 locus).

pC8H6H4 was used as the donor plasmid in in vivo recombination with vCP205 and the resulting recombinant virus designated vCP1435 (HIV cassette at C3 locus and the vaccinia H6/H4L expression cassette at C8 locus; H6/H4L expression cassette flanked by ALVAC C8 insertion site sequences (SEQ ID NO: 2) shown in FIG. 2).

vCP1431A was also used as a rescuing virus in in vivo recombination using plasmid pC8H6H4, generating the recombinant designated vCP1437A (HIV cassette at the C3 locus, the H6/K3L and E3L cassette at the C6 locus, and the vaccinia H6/H4L cassette at the C8 locus). With respect to the H6/K3L expression cassette and the vaccinia E3L gene with the endogenous promoter flanked by the ALVAC C6 insertion site sequences reference is made to FIG. 3 (SEQ ID NO: 3).

pC3H6FHVB (ATCC No. ; FIG. 5, SEQ ID NO: ; H6 promoted FHV gB ORF with early transcriptional and translational stop signals at both 5' and 3' ends flanked by the left and right arms of the ALVAC C3 locus) was used in in vivo recombination with the ALVAC (ATCC No. VR-2547) to generate vCP1459 (H6 promoted FHV gB expression cassette in deorfed C3 insertion locus). With respect to the FHV-1 gB coding region in which the two internal $T_5NT$ motifs have been mutated, see FIG. 4 (SEQ ID NO: 4).

pC3H6FHVB was used in in vivo recombination with vCP1431A to generate vCP1460 (H6 promoted FHV gB expression cassette in the deorfed C3 insertion locus and vaccinia E3L/K3L genes in C6 locus).

pC3H6FHVB was used in in vivo recombination with vCP1437 to generate vCP1464 (H6 promoted FHV gB expression cassette in deorfed C3 insertion locus, vaccinia E3L/K3L genes in C6 locus and H6 promoted vaccinia H4L ORF in C8 locus).

pMPC5H6PN (HIV pol/nef "string of beads" cassette in the ALVAC C5 locus) was used in recombination with vCP205 to obtain vCP1433 (ATCC Deposit No. VR-2556). Thus, recombinant ALVAC-MN120TMGNPst (vCP1433) was generated by insertion of an expression cassette encoding a synthetic polypeptide containing all of the known Pol CTL epitopes (Nixon and McMichael; 1991) and all of the known human Nef CTL epitopes into vCP205 at the insertion site known as C5.

pMPC6H6K3E3 (ATCC Deposit No. ATCC-97912; containing vaccinia H6/K3L expression cassette and vaccinia E3L gene with endogenous promoter flanked by the ALVAC C6 insertion site sequences) was used in recombination with vCP1433 to obtain vCP1452. FIGS. 6 and 7 show the nucleotide and amino acid sequences of the vCP1433 and vCP1452 inserts. FIG. 8 shows the K3L E3L in C6 in vCP1452. vCP1452 contains the HIV type 1 gag and protease genes derived from the IIIB isolate, the gp120 envelope sequences derived from the MN isolate, and sequences encoding a polypeptide encompassing the known human CTL epitopes from HIV-1 Nef and Pol (Nef1 and Nef2 CTL epitopes, and Poll, Pol2 and Pol3 CTL epitopes). The expressed gp120 moiety is linked to the transmembrane (TM) anchor sequence (28 amino acids) of the envelope glycoprotein. In addition to the HIV coding sequences vCP1452 contains the vaccinia virus E3L and K3L coding sequences inserted into the C6 site. The insertion sites and promoter linkages for this construct are shown in the Table below.

TABLE

Insertion sites and promoter linkages in vCP1452

| Insert | Insertion Site | Promoter |
|---|---|---|
| HIV1 MN gp120 + TM | C3 | HG |
| HIV1 IIIB gag (+ pro) | C3 | I3L |
| Pol3/Nef C term/Pol2/Nef central/Pol1 | C5 | H6 |
| Vaccinia virus E3L | C6 | endogenous |
| Vaccinia Virus K3L | C6 | H6 | vCP300 is an ALVAC recombinant containing HIV gp120TM (MN), gag/pro (IIIB) (C3 locus), Nef (C6 locus), and Pol (C5 locus), as described in U.S. Pat. No. 5,863,542, incorporated herein by reference.

Plasmids for preparing these recombinants were prepared as follows:

Vaccinia H4L Expression Cassette Into ALVAC pCPM6LDEL was generated by using primer pair H4A and H4B to amplify a 900 bp fragment from pBAMM11.6 (ALVAC 11.6 kb BamHI M fragment in pBSSK bector background), and primer pair H4C and H4D (SEQ ID NOS: 17 and 18) to amplify a 940 bp fragment from pBAMM11.6 (H4C 5'ACTACTAATTAGCTATAAAAACCCGGGATTAGTTT-TTATTACTAACTAATTACTATACTG3') (H4D 5'ATCATCGGATCCTTTAATAATCTTATGAACTTTTAT-AAATATGAG3'). A fusion PCR reaction using the PCR products from the amplifications and primer pair H4A and H4D obrained an 1840 bp PCR fusion fragment which was then cloned into the T/A Cloning vector for sequence confirmation. The sequence was found to have a PCR deletion at position 8054. The 1840 bp fragment was removed from the T/A vector by digestion with BamHI. The fragment was then cloned into the BamHI digested pBSSK ΔEcoRI-SmaI vector. The deletion was repaired by digesting the construct with HindIII to remove a 250 bp fragment of the right arm and religating to obtain pCPM6LDEL.

placZH6H4Lreverse was digested with PspAI and Asp700 resulting in a 1920 bp fragment containing the H6 promoter and the 5' 1780 bp of the H4L gene. The remaining 590 bp of the H4L gene were generated using PCR amplification from the plasmid template placZH6H4Lreverse using primer pair H4A and H4B. The oligonucleotide sequences for primer pair H4A and H4B (SEQ ID NOS: 19 and 20) are:

Oligonucleotide Sequences

H4A
5'-ATCATCGAAGAGCTTCCGCTATCTGCATTAA-AGTTT-3'

H4B
5'-ATCATCCCCGGGAAGCTTTTAGTTATTGAAA-TTAATCATATA-3'

The 590 bp PCR fragment was gel purified and cloned into the TA Cloning vector (Invitrogen San Diego, Calif. 92121) for sequence confirmation. The 590 bp insert containing the 3' H4L sequences was excised from the TA vector by digestion with PspAI and Asp700. The 1920 bp and the 590 bp fragments were directionally cloned into the PspAI digested pCPM6LDEL plasmid vector (containing the deorfed ALVAC M6L insertion site) to generate the plasmid pM6LDELH6H4 containing the H6/H4L expression cassette flanked by ALVAC sequences at the M6L insertion site.

ALVAC pC8 insertion vector was generated as follows: PCR J36, containing the C8 ORF and flanking sequences, was generated using JP121 (CAT-CAT-GAG-CTC-ACT-TAT-TAC-ATC-CTA-CT) and JP122 (TAC-TAC-GGT-ACC-TTT-AAT-AAG-CAA-TCA-CT) (SEQ ID NOS: 21 and 22) on ALVAC DNA. The resulting approximately 1.7 kb band was digested with Asp718/SacI and ligated into Asp718/SacI digested pBSSK+. After confirmation by sequence analysis, the resulting plasmid was designated pCPF85S3L. To remove most of the C8 ORF and introduce transcriptional and translational stops along with a MCS into pCPF85S3L, the plasmid was digested with SnaBI/HindIII and ligated to ~115 bp PCR J618I SnaBI/HindIII fragment, yielding pC8. PCR J618I is a fusion PCR product of PCRs J616 and J617 using primers JP516 (TAG-GAA-GAT-ACG-TAT-TAT-TTT-ATA-C) and JP519 (ATC-CCA-TTA-TGA-AAG-CTT-ATA-G) (SEQ ID NOS: 39 and 40). PCR J616 was generated using primers JP516 and JP517 (CTC-GAG-CTG-CAG-GAT-ATC-ATC-GAT-GGA-TCC-TTT-TTA-TAG-CTA-ATT-AGT-CAC-GTA-CCT-TTA-TCA-TTA-GTA-ACA-AAT) (SEQ ID NO: 41) on plasmid pCPF85S3L. PCR J617 was generated using primers JP518 (GGA-TCC-ATC-GAT-GAT-ATC-CTG-CAG-CTC-GAG-TTT-TTA-TGA-CTA-GTT-AAT-CAC-GGC-CGC-TCA-ATA-TTG-TAT-TGG-ATG-GTT-AG) (SEQ ID NO: 42) and JP519 on plasmid pCPF85S3L. Plasmid pC8, the C8 insertion plasmid, was confirmed by sequence analysis and contains a ~440 bp left arm, a ~1162 bp right arm, a MCS with unique BamHI, ClaI, EcoRV, PstI, and XhoI sites, flanked by both transcriptional and. translational stop sequences.

From the plasmid pM6LDELH6H4, the 2.5 Kbp H6/H4 expression cassette was excised with SmaI, and the resulting 2.5 Kbp SmaI fragment was purified and inserted into the ALVAC pC8 insertion vector at the EcoRV site generating pC8H6H4.

K3L Expression Cassette

The K3L coding sequences were synthesized by PCR amplification using pSD407VC containing Copenhagen vaccinia HindIII K fragment as template, as described in U.S. Pat. No. 5,378,457. The oligonucleotides MPSYN 763 and MPSYN 764 (SEQ ID NOS: 23 and 24) were used as primers for the PCR reaction.

MPSYN 763
5'-CCCTCTAGATCGCGATATCCGTTAAGTTTGTA-TCGTAATGCTTGCATTTTGTTATTCGT-3'

MPSYN 764
5'-CCCGAATTCATAAAAATTATTGATGTCTACA-3'

The approximately 325 bp PCR fragment was digested with XbaI and EcoRI yielding a 315 bp fragment. This 315 bp fragment was purified by isolation from an agarose gel and ligated with XbaI and EcoRI digested pBSSK+ vector (from Stratagene LA Jolla, Calif.). The nucleic acid sequence was confirmed directly from alkali denatured plasmid template as described in Hattori, M. and Sakaki, Y., 1986, using the modified T7 polymerase (Tabor, S. and Richardson, C. C. 1987) and Sequenase (from U.S. Biochemicals Cleveland, Ohio). This plasmid was designated pBS 763/764. Digesting pBS 763/764 with NruI and XhoI, a 340 bp fragment was isolated for cloning into the plasmid vector pMM154 containing a cassette with the vaccinia H6 promoter controlling an irrelevant gene in the NYVAC tk⁻ insertion vector background, which was prepared by digestion with NruI (partially) and XhoI, such that the 340 bp fragment from pBS 763/764 containing the K3L gene could be directionally oriented next to the H6 promoter generating pMPTKH6K3L. The plasmid pMP42GPT containing the dominant selectable marker Eco gpt gene (Pratt D. and Subramani S. 1983) under the control of the Entomopox 42k promoter, was digested with SmaI and BamHI to yield a 0.7 Kbp 42k-Eco gpt expression cassette. This 0.7 Kbp fragment was purified and ligated into SmaI and BamHI cut pMPTKH6K3L generating the plasmid pMPTKH6K3Lgpt. This plasmid was digested with XhoI, generating a 1.2 Kbp fragment containing the H6/K3L and the 42k/Ecogpt expression cassette, which was then gel purified. The 1.2 Kbp XhoI fragment was inserted into the XhoI site of the ALVAC C6 insertion plasmid pC6L (described in U.S. Pat. No. 5,494,807), generating pMPC6H6K3Lgpt.

E3L/K3L ALVAC Expression Cassette

The entire E3L gene is contained within a 2.3 Kbp EcoRI fragment isolated from pSD401VC, which contained a clone of the HindIII E fragment from Copenhagen vaccinia. The 2.3 Kbp EcoRI fragment was inserted into pMPC6H6K3Lgpt that had been partially digested with EcoRI, generating the plasmid pMPC6H6K3E3gpt. The plasmid pMPC6H6K3E3gpt was digested with XhoI and the resulting 6.8 Kbp vector fragment was purified and self-ligated, resulting in the plasmid pMPC6E3. The plasmid pMPTKH6K3L was digested with PspAI and the resulting 560 bp fragment containing the H6/K3L expression cassette was ligated into PspAI digested pMPC6E3 resulting in the plasmid construct pMPC6H6K3E3.

Construction of the H6-promoted FHV gB donor plasmid

The entire coding region of the Feline Herpesvirus 1 glycoprotein gB (FHV-1 gB) was obtained by digestion of pJCA079 (FHV gB coding region in which 5' and 3' $T_5NT$ sequences were mutated to change the early transcriptional stop signal without affecting amino acid sequences; the I3L vaccinia promoter has been coupled to the 5' end of the gB ORF; see FIG. 4, SEQ ID NO: 4) with PstI and isolating a 3 Kbp fragment from an agarose gel. The purified PstI fragment was cloned into an ALVAC C3 insertion plasmid (pVQH6CP3LSA) also digested with PstI (the unique BamHI site in pVQH6CP3LSA was previously inactivated by digestion with BamHI, blunting the ends with Klenow polymerase and religation; pVQH6CP3LSA was obtained by digesting pVQH6CP3L, discussed in U.S. Pat. No. 5,494,807, with NotI and NsiI, from which a 6623 bp fragment was isolated and ligated to annealed oligonucleotides CP34 (5'GGCCGCGTCGACATGCA3') and CP35 (5'TGTCGACGC3') (SEQ ID NOS: 25 and 26). The resulting plasmid, pRAC5, was screened for proper orientation of the gB coding region with respect to the H6 promoter. To properly link the H6 promoter to the FHV gB initiation codon, an 800 bp PCR fragment was amplified from pJCA079 using oligonucleotides RG789 (SEQ ID NO: 27) (5'-TTTCATTATCGCGATATC-CGTTAAGTTTGTATCGTAATGTCCACTCGTGGCGA-TC-3') and RG787 (SEQ ID NO: 28) (5'-GGAGGGTTTCAGAGGCAG-3'). This purified fragment was digested with NruI/BamHI and ligated into pRAC5 also digested with NruI/BamHI. The resulting plasmid was the FHV gB donor plasmid, pC3H6FHVB.

"String of Beads" Cassette

The "string of beads" expression cassette for the nef and pol CTL epitopes (H6/Pol 3/Nef C term/Pol 2/Nef central/Pol 1) was generated by PCR (polymerase chain reaction) as detailed below, using template pHXBD2 for pol epitopes and template 2-60-HIV.3 for Nef epitopes. Initial assembly was in two parts: (1) H6(partial promoter)/Pol 3/Nef C term(Nef 2); (2) Pol 2/Nef central (Nef 1)/Pol 1 in pBSSK. These were combined, then moved to pBSH6-11 for the assembly of the entire H6 promoter, then the H6/HIV cassette was moved to a C5 insertion plasmid.

(1) H6/Pol 3/Nef C term(Nef 2)

A 230 bp fragment (A) was derived by PCR to obtain the H6 linkage and Pol3 using synthetic oligonucleotides MPSYN783 and MPSYN784 (SEQ ID NOS: 29 and 30) and template pHXBD2. pHXBD2 was derived at the NIH/NCI (Dr. Nancy Miller) from a recombinant phage library of XbaI digested DNA from HTLV-III infected H9 cells cloned in lambda-J1 (Shaw et al., 1994). This plasmid contains the entire proviral DNA sequence of the HIV IIIB isolate.

A 110 bp fragment (B) was derived by PCR to obtain Nef2 using oligonucleotides MPSYN785/MPSYN786 (SEQ ID NOS: 31 and 32) and template p2-60-HIV.3 (described in U.S. Pat. No. 5,863,542).

PCR fragments A and B were combined in a PCR as template to obtain a 300 bp fragment containing H6 linkage/Pol3/Nef2 using external primers MPSYN783/MPSYN786 (SEQ ID NOS: 29 and 32). The 300 bp fragment was digested with XhoI/HindIII and a 290 bp fragment was isolated and ligated with similarly digested pBSSK to generate pBS783/786. The sequence was confirmed.

(2) Pol 2/Nef central (Nef 1)/Pol 1

A 210 bp fragment (C) containing Pol2 was derived by PCR using synthetic oligonucleotides MPSYN787/MPSYN788 (SEQ ID NOS: 33 and 34) and template pHXBD2.

A 270 bp fragment (D) containing Nef1 was derived by PCR using synthetic oligonucleotides MPSYN789/MPSYN790 (SEQ ID NOS: 35 and 36) and template p2-60-HIV.3 (described in U.S. Pat. No. 5,863,542).

A 170 bp fragment (E) containing Pol1 was derived by PCR using primers MPSYN791/MPSYN792 (SEQ ID NOS: 37 and 38) and template pHXBD2.

Fragments C and D were combined as template in a PCR for Pol 2/Nef 1 using external primers MPSYN787/MPSYN790 (SEQ ID NOS: 33 and 36) resulting in a 460 bp PCR product (C+D).

Fragments D and E were combined as template in a PCR for Nef 1/Pol 1 using external primers MPSYN789/MPSYN792 (SEQ ID NOS: 35 and 38), resulting in isolation of a 420 bp fragment (D+E).

Fragments (C+D) and (D+E) were combined as template in a PCR with external primers MPSYN787/MPSYN792 (SEQ ID NOS: 33 and 38) to obtain a 610 bp fragment containing Pol 2/Nef 1/Pol 1. This 610 bp fragment was digested with HindIII/PstI. The resulting 590 bp fragment was ligated with pBSSK cut with HindIII/PstI to generate pBS787/792. The sequence was confirmed.

MPSYN783: 5' CCC CTC GAG TCG CGA TAT CCG TTA AGT TTG TAT CGT AAT GCC ACT AAC AGA AGA AGC A 3' (58 mer)

MPSYN784: 5' AAA TCT CCA CTC CAT CCT TGT TTT CAG ATT TTT AAA 3' (36 mer)

MPSYN785: 5' AAT CTG AAA ACA GGA ATG GAG TGG AGA TTT GAT TCT 3' (36 mer)

MPSYN786: 5' CCC AAG CTT ACA ATT TTT AAA ATA TTC AGG 3' (30 mer)

MPSYN787: 5' CCC AAG CTT ATG GCA ATA TTC CAA AGT AGC 3' (30 mer)

MPSYN788: 5' TGG AAA ACC TAC CAT GGT TGT AAG TCC CCA CCT CAA 3' (36 mer)

MPSYN789: 5' TGG GGA CTT ACA ACC ATG GTA GGT TTT CCA GTA ACA 3' (36 mer)

MPSYN790: 5' TAC AGT CTC AAT CAT TGG TAC TAG CTT GTA GCA CCA 3' (36 mer)

MPSYN791: 5' TAC AAG CTA GTA CCA ATG ATT GAG ACT GTA CCA GTA 3' (36 mer)

MPSYN792: 5' CCC CCT GCA GAA AAA TTA AGG CCC AAT TTT TGA AAT 3' (36 mer)

(SEQ ID NOS: 29 to 38)

Assembly of entire cassette:

A 590 bp HindIII/PstI fragment was isolated from pBS787/792 and ligated with vector pBS783/786 cut with HindIII/PstI to generate pBS783/792. pBS783/792 was cut with EcoRV and PstI, to generate an 880 bp fragment which was then ligated with similarly digested vector pBSH6-1 to generate pBSH6PN. Plasmid pBSH6PN was digested with BamHI and a 1060 bp fragment was isolated. pVQC5LSP1, a generic C5 donor plasmid, was digested with BamHI and ligated with the 1060 bp fragment from pBSH6PN. The resulting plasmid, pMPC5H6PN, contains the HIV pol/nef "string of beads" cassette in the ALVAC C5 locus.

Example 3

Expression Studies

Example 3.1

NYVAC Expression Results

Dishes containing confluent monolayers of cells were infected at a multiplicity of infection (moi) of 2. After incubation for specified time periods, cells were incubated in labeling medium for 1 hour. At the end of the incubation, cells were harvested for immunoprecipitation analysis as described (Harlow, E and Lane, D (1988); Langone, J. (1982)).

Cells were infected at an moi of 2 pfu/cell and incubated for specified time periods. At the appropriate time post-infection, cell lysates were prepared for RNA analysis. The medium was aspirated and cells were harvested. RNA was isolated and prepared using the TRI-Reagent (Molecular Research Center Inc. Cincinnati, Ohio 45212) as per manufacture instructions and analyzed by slot blot. Radiolabelled DNA probes were used to detect specific RNA species.

The effect of vP1379 and vP1380 compared to the parental virus vP994 on the expression of HIV env truncated MN strain was studied by radiolabeling at specific times post-infection on CEF cells. IP analysis with monoclonal antibody against HIV env truncated MN strain (mAb K3A) revealed a significant increase in de novo synthesis for vP1380 infected cells at early times post infection compared to either vP994 parental virus or vP1379. A similar trend is observed at late times post infection. IP analysis with rabbit anti H4L antiserum (provided by Dr. S. Shuman, Sloan-Kettering Institute, NY) show that only vP1380 infected cells expressed H4L product early in infection. Neither vP994 nor vP1379 infected cells expressed H4L, early in infection. All samples show de novo synthesis of H4L late in infection, but expression rates are higher for vP1380 infected cells than for either vP994 or vP1379 infected cells. IP analysis of E3L product, a constitutive vaccinia protein, show that de novo synthesis occurs at a higher rate at all times post infection in vP1380 infected cells than in either vP994 or vP1379 infected cells.

These results indicate that vP1379 is a defective recombinant with a pattern of expression identical to the parental virus unlike vP1380 recombinant which expresses H4L at early and late times post-infection. This early H4 expression clearly correlates with the enhanced expression of the proteins under study (HIV env and E3L) at early times post-infection.

The following studies were conducted with vP1380 and vP994 since vP1379 does not express H4L product at early times post-infection. The rate of expression at different times post infection in HeLa cells (non permissive system) was studied by IP analysis. IP analysis with anti-H4L shows that vP1380 infected cells expressed H4L product at all times post-infection (3, 6, 24 and 48 Hrs.). No product was detected in vP994 infected cells at any time post infection. Sustained de novo synthesis is observed that increases with time. Analysis of HIV Env product shows that, although product expression levels are higher at all times for vP1380 infected cells vs. vP994's, the most significant difference is seen at late times, 24 and 48 Hrs., suggesting that expression of H4L must have an impact at some level on expression of HIV Env product. Expression of E3L product is also increased in vP1380 infected cells compared to vP994.

Experiments performed on L929 cells gave similar results. The most significant difference was that expression rates of the H4L product at all times post infection was very low, however there was a dramatic difference in the de novo synthesis rate of HIV Env component. Differences in the rates of Env synthesis peaked at 24 hours with a 5 to 10 fold increase in vP1380 infected cells compared to vP994.

Since H4L product is an early transcription factor, it is of interest to determine if the results obtained at the expression level correlate with an increase in H4L message in vP1380 infected cells. RNA analysis by slot blots indicate that H4L message is detectable at all times post infection in vP1380 infected cells and achieved a steady state at 6 Hrs. post infection.

HIV Env message levels increase rapidly to steady state levels at 3 Hrs post infection and remained at those levels for all time points in vP1380 infected cells. On the other hand, vP994 infected cells show a peak of HIV env message at 6 hours post infection and a decline starting at 12 hours. E3L message in vP1380 infected cells is present at higher levels for all times post infection compared to vP994 infected cells. This pattern of RNA levels is consistent with the pattern of de novo synthesis rate at the protein level.

Mice were immunized by the intraperitoneal route on day 0 and 28. Starting prior to the first immunization and at two week intervals following the immunization, mice were bled from the retroorbital plexus. Sera were prepared from the collected blood by standard clotting techniques and stored frozen at −20° C. until use in kinetics ELISA for antibodies reactive to the HIV envelope glycoprotein.

High doses of vP994 or vP1380 elicited similar levels of antibodies (Table below). However, at the lowest dose, $5\times10^6$ pfu, only vP1380 was capable of generating HIV antibodies. Moreover, the level of antibodies induced by the low dose was comparable to the levels of antibodies elicited by the highest dose, $5\times10^7$ pfu.

At a dose too low for vP994, lacking vaccinia H4 but identical in all other respects to vP1380, to elicit an antibody response, vP1380 induced antibody responses equivalent to those elicited by the highest doses tested. Thus, the overexpression of vaccinia H4L in NYVAC may result in increased potency for inducing humoral responses.

TABLE

Antibody responses to recombinant HIV-1 MN/BRU gp160.

| VIRUS | DOSE | MOUSE | KINETICS (mOD/min) WEEKS | | | | | | | |
|---|---|---|---|---|---|---|---|---|---|---|
| | | | 0 | 2 | 4 | 6 | 8 | 10 | 12 | 14 |
| NYAC | HI | a | 0 | 1 | 0 | 1 | 2 | 2 | 1 | 2 |
| | | b | 0 | 0 | 0 | 2 | 2 | 2 | 2 | 2 |
| | | c | 0 | 0 | 0 | 2 | 1 | 1 | 1 | 1 |
| vP994 | HI | a | 0 | 6 | 8 | 42 | 45 | 44 | 44 | 45 |
| | | b | 0 | 1 | 1 | 34 | 42 | 35 | 24 | 23 |
| | | c | 3 | 1 | 3 | 34 | 40 | 31 | 33 | 34 |
| vP994 | LO | a | 0 | 1 | 2 | 4 | 3 | 3 | 5 | 6 |
| | | b | 1 | 1 | 0 | 2 | 2 | 3 | 3 | 3 |
| | | c | 1 | 0 | 1 | 14 | 16 | 17 | 12 | 13 |
| vP1380 | HI | a | 2 | 8 | 39 | 41 | 49 | 47 | 52 | 50 |
| | | b | 3 | 12 | 45 | 49 | 46 | 51 | 54 | 49 |
| | | c | 1 | 7 | 35 | 42 | 41 | 43 | 40 | 39 |
| vP1380 | LO | a | 1 | 2 | 3 | 49 | 45 | 47 | 46 | 44 |
| | | b | 0 | 1 | 2 | 30 | 30 | 34 | 36 | 40 |
| | | c | 0 | 3 | 14 | 54 | 48 | 51 | 51 | 54 |

Mice were inoculated during weeks 0 and 4.
vP994, HIV 1 MN gp140, noncelevable, secreted envelope glycoprotein.
vP1380, HIV 1 MN gp140 + vaccinia H4L transcription factor.
vCP125, HIV 1 MN gp160.
HI dose, $5 \times 10^7$ pfu.
LO dose, $5 \times 10^6$ pfu.

As discussed above, possibly, part of the enhanced levels in vP1380 are due to enhanced transcription and expression of viral specific products such as E3L, such that there is enhanced transcription and translation involved in expression in vP1380. There was more expression of the exogenous DNA and at more persistent levels in vP1380, in accordance with the invention wherein vectors obtain greater levels of expression and more persistent levels of expression. Enhanced expression profiles in the murine system provided enhanced immunogenicity in mice, as shown by vP1380 being more immunogenic in mice than vP994. Another observation is that enhancement profiles are seen in restrictive early cells in the abortive early ALVAC recombinants herein, whereas the profiles were not observed in cells where there was productive replication, e.g., VERO or CEF, suggesting that the factor and the foreign DNA preferably should be expressed substantially co-temporally or contemporaneously, i.e., that preferably there should be co-expression at substantially the same time or stage, and that the time of expression, e.g., early, late, early and late, should be matched with the phenotype of the vector (e.g., abortive early, abortive late), i.e., that in a system in which viral replication is not impaired (a permissive system) or in a system in which replication is aborted at a time when expression is not matched with the phenotype of the vector may not obtain optimal expression. Thus, in an abortive early system such as ALVAC or NYVAC, one preferably expresses exogenous DNA and a transcriptional or transcriptional and translational factor early; in an abortive late system, one preferably expresses exogenous DNA and a transcriptional or transcriptional and translational factor late or early and late (as expression only early may be akin to expression in a permissive system, i.e., one may not necessarily obtain optimal expression).

Example 3.2

ALVAC Expression Results
ALVAC-HIV Recombinants

Immunoprecipitation (IP) was used to provide a semiquantitative comparison of the temporal expression of the HIV-I cassette contained in the ALVAC recombinants in MRC-5 infected cells. Heat inactivated sera from HIV patients was obtained and used for the IP as described in the methods. The antiserum will precipitate the 120 KDa env protein and the various cleavage products from the gag protein precursor. In the analysis of the IP data it is apparent that the ALVAC recombinants vCP1431A and vCP1437A containing the E3L/K3L cassette had a significant increase in the level of expression at all times post infection when compared to the ALVAC recombinant vCP205 without the E3L/K3L cassette.

Interestingly vCP1431A and vCP1437A had similar expression profiles; insertion of H6/H4L into an ALVAC E3L/K3L background did not enhance expression above E3L/K3L, suggesting that vaccinia H4L is not necessarily functional in ALVAC; but, manipulation of ALVAC transcriptional factors would lead to enhanced expression. Although there are homologs of vaccinia transcriptional factors in canarypox, the requirements in canarypox may be biochemically different; but, these differences can be ascertained by the skilled artisan without undue experimentation from this disclosure and the knowledge in the art. Furthermore, the present invention provides in vitro systems for transcriptional analysis in canarypox or fowlpox using vaccinia virus.

RNA slot blots were used to evaluate temporal transcriptional expression in MRC-5 cells infected with the ALVAC recombinants vCP205 and vCP1431A and vCP1437A. In this analysis comparisons were made to the levels of mRNA transcribed from the HIV-I cassette encoding the env and gag proteins. ALVAC recombinants containing the E3L/K3L cassette (vCP1431A and vCP1437A) did not exhibit a significant increase in the level of mRNA for the env and gag genes above that of the ALVAC recombinant vCP205.

The previously discussed role E3L/K3L plays in the down regulation of PKR in vaccinia infected cells thereby modulating translation seems to be operative in the ALVAC recombinants containing the vaccinia E3L/K3L functions. The data has shown that translation is significantly enhanced in cells infected with ALVAC recombinants containing the E3L/K3L genes, while no significant increase in the level of transcription has been detected. This exemplifies the impact of E3L/K3L expression on translation efficiency in poxvirus infected cells.

Immunoprecipitation analyses were also performed using radiolabeled lysates derived from CEF cells infected with ALVAC parental virus, ALVAC-MN120TMG (vCP205), ALVAC-MN120TMGNPst (vCP1433), vCP1452 and vCP300, as described previously (Taylor et al., 1990), with human serum derived from HIV-seropositive individuals (anti-HIV). The analysis confirmed the expression of the envelope sequences with a molecular weight of 120 kDa and the Gag precursor protein with a molecular weight of 55 kDa in the recombinants but not in the parental virus. However, vCP300 exhibits diminished expression in comparison to vCP1452, i.e., vCP1452 surprisingly demonstrates enhanced expression due to expression of transcription and/or translation factors, in accordance with the invention.

FAC scan analysis with the Human anti-HIV antibody demonstrated expression of gp120 on the surface of HeLa cells infected with ALVAC-MN120TMGNPst (vCP1433). No fluorescence was detected on cells infected with ALVAC parental virus.

Appropriate expression of the inserted HIV genes was further confirmed by immunoprecipitation analysis (using polyclonal serum pool from HIV infected individuals) performed on a radiolabelled lysate of MRC5 cells infected with vCP1433 or vCP1452. The analysis confirmed the expression of the envelope sequences with a molecular weight of 120 KDa and the Gag precursor protein with a molecular weight of 55 KDa in vCP1452.

vCP1452 had enhanced expression on human cells in comparison to vCP1433 and vCP300. Indeed, enhanced expression was observed with the E3L/K3L translational factor in human and canine cells.

Preliminary immunogenicity studies in mice showed no evidence of enhanced immunogenicity by the E3L/K3L translational factor. This corresponds to no observed enhanced expression in murine cells.

Furthermore, in murine cells, the limiting factor of ALVAC expression is at the transcription level. Accordingly, use of an appropriate transcription factor can overcome the inability to observe enhanced expression in the murine system. Thus, the origin of the cell may be an important factor in in vitro or in vivo applications of the invention (note H4 data above), as may be the nature of the vector, e.g., the phenotype of the vector (e.g., abortive, and when abortive such as abortive early, abortive late); but, appropriate selection of a cell and vector phenotype and of time of expression of factor(s) and foreign and/or exogenous DNA are within the ambit of the skilled artisan, from this disclosure and the knowledge in the art, without undue experimentation.

ALVAC-FHV gB Recombinants

Analysis of the expression for vCP1459, vCP1460 and vCP1464 was accomplished by immunoprecipitation analysis using a sheep anti-FHV gB polyclonal sera. Human MRC-5 cells were inoculated at an moi=5 at time 0, and then pulsed for 1 hour with $^{35}S$ labelled methionine at times 3, 6, 24, 48 and 72 h p.i. The precipitated protein was separated on SDS-PAGE gels. Autoradiographs of these IPs were scanned using a densitometer. The methods used provide a semi-quantitative analysis of FHV gB expression at the specific time points.

Results show that all recombinants express the proper sized full-length, glycosylated FHV gB polypeptide (apparent MW of approximately 115 kDa). However, recombinants vCP1460 and vCP1464 show significant increase in the amount of gB protein (about 5 times) compared to vCP1459. In addition, these expression levels persist even at 72 hr p.i. Thus, it appears that the expression of vaccinia E3L/K3L in ALVAC has a significant effect on the level and persistence of FHV gB expression.

Example 4

Additional Vectors

Using the documents cited herein and the teaching herein, including in the foregoing Examples, plasmid and naked DNA vectors, and additional viral vectors, including poxvirus, e.g., NYVAC, TROVAC, ALVAC, MVA, ts (temperature sensitive) mutants, or early ($DNA^-$) and late defective mutants, adenovirus, e.g., CAV such as CAV2, herpesvirus, e.g., Epstein Barr, are generated with enhanced transcription or translation or transcription and translation, e.g., by using H4L, vaccinia D6, vaccinia A7, vaccinia G8R, vaccinia A1L, vaccinia A2L, vaccinia H5R (VLTF-1, -2, -3, -4, P3, VLTF-X) E3L, K3L, VAI, EBER, sigma 3, TRBP, or combinations thereof to modify the vector to contain at least one transcritpion factor or at least one translation factor or at least one transcription factor and at least one translation factor; and accordingly, enhanced expression, of exogenous coding nucleic acid molecules (such exogenous coding nucleic acid molecules including from documents cited herein or as otherwise known in the art, or from applying those teachings in conjunction with teachings herein) is obtained.

Having thus described in detail preferred embodiments of the present invention, it is to be understood that the invention defined by the appended claims is not to be limited to particular details set forth in the above description as many apparent variations thereof are possible without departing from the spirit or scope of the present invention.

References

Ahn, B- Y. and Moss, B. 1992. RNA polymerase-associated transcription specificity factor encoded by vaccinia virus. Proc. Natl. Acad. Sci. 89: 3536–3540.

Beattie, E., Denzler, K., Tartaglia, J., Paoletti, E. and Jacobs, B. L. 1995. Reversal of the interferon-sensitive phenotype of and E3L-minus vaccinia virus by expression of the reovirus S4 gene. J. Virol. 69: 499–505 ("Beattie et al. 1995a").

Beattie, E., Paoletti, E., and Tartaglia, J. 1995. Distinct Patterns of IFN Sensitivity Observed in Cells Infected with Vaccinia $K3L^-$ and $E3L^-$ Mutant Viruses. Virology 210:254–263 ("Beattie et al 1995b")

Beattie, E., Tartaglia, J. and Paoletti, E. 1991. Vaccinia virus-encoded eIF-2a homologue abrogates the antiviral effect of interferon. Virology 183: 419–422.

Carroll, K., Elroy Stein, O., Moss, B. and Jagus, R. 1993. Recombinant vaccinia virus K3L gene product prevents activation of double-stranded RNA-dependent, initiation factor 2 alpha-specific protein kinase. J. Biol. Chem. 268: 12837–12842.

Chang, H- W., Watson, J. and Jacobs, B. L. 1992. The vaccinia virus E3L gene encodes a double-stranded RNA-binding protein with inhibitory activity for the interferon-induced protein kinase. Proc. Natl. Acad. Sci. USA 89: 4825–4829.

Clark, P. A., Schwemmle, M., Schickinger, J., Hilse, K., and Clemens, M. J. 1991. Binding of Epstein-Barr virus small RNA EBER-1 to double-stranded RNA-activated protein kinase DAI. Nucleic Acids Res. 19:243–248.

Davies, M. V., Chang, H. W. , Jacobs, B. L. and Kaufman, R. J. 1993. The E3L and K3L vaccinia virus gene products stimulate translation through inhibition of the double-stranded RNA-dependent protein kinase by different mechanisms. J. Virol. 67: 1688–1692.

Davies, M. V., Elroy Stein, O., Jagus, R., Moss, B. and Kaufman, R. J. 1992. The vaccinia K3L gene product potentiates translation by inhibiting double-stranded-RNA-activated protein kinase and phosphorylation of the alpha subunit of eukaryotic initiation factor 2. J. Virol. 66: 1943–1950.

Goebel, S. J., Johnson, G. P., Perkus, M. E., Davis, S. W., Winslow, J. P. and Paoletti, E. 1990. The complete DNA sequence of vaccinia virus. Virology 179: 247–266.

Harlow, E. and Lane, D. (1988). Antibodies, A Laboratory Manual. Cold Spring Harbor Laboratory. 421–470.

Hattori, M., and Sakaki, Y. (1986). Dideoxy sequencing method using denatured plasmid templates. Anal. Biochem. 152, 232–237.

Imani, F. and Jacobs, B. L. 1988. Inhibitory activity for the interferon induced protein kinase is associated with the reovirus serotype 1 s3 protein. Proc. Natl. Acad. Sci. USA 85: 7887–7891.

Jacobs, B. L. and Langland, J. O. 1996. When two strands are better than one: the mediators and modulators of the cellular responses to double-stranded RNA. Virology 219: 339–349.

Langone, J. (1982). Applications of immobilized protein A in immunochemical techniques. J. Immunol. Methods. 55. 277–296.

Mathews, M. B. and Shenk, T. 1991. Adenovirus virus-associated RNA and translation control. J. Virol. 65: 5657–5662.

Moss, B. 1990. Regulation of vaccinia virus transcription. Annu. Rev. Biochem. 59: 661–688.

Moss, B. 1992. Molecular biology of poxviruses. In *Recombinant Poxviruses*. Binns M. M., Smith, G. L. (eds). Boca Raton, Fla.: CRC Press; pg. 45–80.

Park, H., Davies, M. V., Langland, L. O., Chang, H- W., Nam, Y. S., Tartaglia, J., Paoletti, E., Jacobs, B. L., Kaufman, R. J. and Venkatesan, S. 1994. A cellular protein that binds several structured viral RNAs is an inhibitor of the interferon induced PKR protein kinase in vitro and in vivo. Proc. Natl. Acad. Sci. USA 91: 4713–4717.

Perkus, M., Limbach, K., Paoletti, E. (1989). Cloning and expression of foreign genes in vaccinia virus, using a host range selection system. J. Virology 63. 3829–3836.

Perkus, M. E., Tartaglia, J., and Paoletti, E. 1995. Poxvirus-based vaccine candidates for cancer, AIDS and other infectious diseases. J. of Leukocyte Biology 58: 1–13.

Sharp, T. V. , Schwemmle, M., Jeffrey, I., Laing, K., Mellor, H., Proud, C. G., Hilse, K. and Clemens, M. J. 1993. Comparative analysis of the regulation of the interferon-inducible protein kinase PKR by Epstein-Barr virus RNAs EBER-1 and EBER-2 and adenovirus VAI RNA. Nucleic Acids Res. 21: 4483–4490.

Tabor, S., and Richardson, C. C. (1987). DNA sequence analysis with a modified bacteriophage T7 polymerase. Proc. Natl. Acad. Sci. USA 84, 4767–4771.

Tartaglia, J., Perkus, M. E., Taylor, J. et al. 1992. NYVAC: A highly attenuated strain of vaccinia virus. Virology 188: 217–32.

Thimmappaya, B. C., Weinberger, C., Schneider, R. J. and Shenk, T. 1982. Adenovirus VAI RNA is required for efficient translation of viral mRNAs at late times after infection. Cell 31: 543–551.

Watson, J., Chang, H- W. and Jacobs, B. L. 1991. Characterization of a vaccinia virus-induced dsRNA-binding protein that may be the inhibitor of the dsRNA-dependent protein kinase. Virology 185: 206–216.

Yuen, L, and Moss, B. (1987). Oligonucleotide sequence signaling transcriptional termination of vaccinia virus early genes. Proc. Natl. Acad. Sci. USA 84, 6417–6421.

Zhang, Y., Ahn, B- Y. and Moss, B. 1994. Targeting of a multicomponent transcription apparatus into assembling vaccinia virus particles requires RAP94, an RNA polymerase-associated protein. J. Virol. 68: 1360–1370.

What is claimed is:

1. A vector for enhanced expression of at least one first nucleic acid molecule in a cell having a particular phenotype, said vector modified to comprise the first nucleic acid molecule and at least one second nucleic acid molecule encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation; and the first nucleic acid molecule is a gene encoding a therapeutic.

2. A vector for enhanced expression of at least one first nucleic acid molecule in a cell having a particular phenotype, said vector is modified to comprise the first nucleic acid molecule and at least one second nucleic acid molecule encoding a transcription factor or encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation; and, wherein the first nucleic molecule encodes a therapeutic.

3. The vector of claim 1 or 2 wherein the first nucleic acid molecule is operably linked to a first promoter and the second nucleic acid molecule is operably linked to a second promoter, and the first and second promoters function substantially co-temporally.

4. The vector of claim 3 wherein the first and second nucleic acid molecules are at different loci within the vector.

5. The vector of claim 3 wherein the first and second nucleic acid molecules are at the same locus within the vector.

6. The vector of claim 1 or 2 wherein the first nucleic acid molecule and the second nucleic acid molcule are operably linked to the same promoter.

7. The vector of claim 1 or 2 wherein the transcription factor is of poxvirus origin.

8. The vector of claim 7 wherein the transcription factor is from a vaccinia virus.

9. The vector of claim 8 wherein the transcription factor is from an open reading frame selected from the group consisting of H4L, D6, A7, G8R, A1L, A2L, H5R, and combinations thereof.

10. The vector of claim 1 or 2 wherein the translation factor effects inhibition of cIF-2α phosphorylation or inhibition of PKR phosphorylation or otherwise sequesters dsRNA.

11. The vector of claim 10 wherein said at least one second molecule is selected from the group consisting of: a K3L open reading frame, an E3L open reading frame, a VAI RNA open reading frame, an EBER RNA open reading frame, a sigma 3 open reading frame, a TRBP open reading frame, and combinations thereof.

12. The vector of claim 1 or 2 which is a recombinant poxvirus.

13. The vector of claim 12 which is a recombinant poxvirus.

14. The vector of claim 1 or 2 wherein the first nucleic acid molecule encodes alpha-globin, beta-globin, gamma-globin, granulocyte macrophage-colony stimulating factor, tumor necrosis factor, an interleukin, macropliage colony stimulating factor, granulocyte colony stimulating factor, etythropoietin, mast cell growth factor, tumor suppressor p53, retinoblastoma, interferon, melanoma associated antigen or B7.

15. A method for preparing a vector as claimed in claim 1 or 2 comprising modifying the vector to comprise the at least one second nucleic acid molecule, and optionally also modifying the vector to comprise the first nucleic acid molecule, so that there is substantially co-temporal expression of the first and second nucleic acid molecules with respect to the phenotype of the cell.

16. The method for claim 15 comprising operably linking the first nucleic acid molecule to a first promoter and the second nucleic acid molecule to a second promoter, wherein the first and second promoters are functional substantially co-temporally.

17. The method for claim 15 comprising operably linking the first and second nucleic acid molecules to a promoter.

18. A therapeutic composition comprising the vector of claim 1 or 2 and a pharmaceutically acceptable carrier or diluent.

19. A method for expressing a gene product in vitro comprising infecting, or transfecting, a suitable cell with a vector as claimed in claim 1 or 2.

20. The vector of claim 1 or 2 wherein the transcription factor is a viral transcription factor.

21. The vector of claim 1 or 2 wherein the translation factor is a viral translation factor.

22. The vector of claim 21 wherein the transcription factor is a viral transcription factor.

23. A method for increasing expression of at least one first nucleic acid molecule by a vector comprising the first nucleic acid molecule, wherein the expression is in a cell having a particular phenotype, and the method comprises modifying the vector to comprise at least one second nucleic acid molecule encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation; wherein the first nucleic acid molecule encodes a therapeutic.

24. A method for increasing expression of at least one first nucleic acid molecule by a vector comprising the first nucleic acid molecule, wherein the expression is in a cell having a particular phenotype, and the method comprises modifying the vector to comprise at least one second nucleic acid molecule encoding a transcription factor or encoding a transcription factor and a translation factor, wherein there is substantially co-temporal expression of the first and second nucleic acid molecules with respect to the phenotype of the cell, whereby expression of the second nucleic acid molecule enhances expression of the first nucleic acid molecule by enhancing transcription or transcription and translation; wherein the first nucleic acid molecule encodes a therapeutic.

* * * * *

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
        (A) LENGTH: 10281 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GCTCTTCTAG TTAGAACTTC AACTTCTTAG TATCACCTTC TATCACACCC AGCTTTCATC      60

AACATTAAAT GTGAGCGAGT AACAACCCGT CGGATTCTCC GTGGGAACAA ACGGCGGATT     120

GACCGTAATG GGATAGGTTA CGTTGGTGTA GATGGGCGCA TCGTAACCGT GCATCTGCCA     180

GTTTGAGGGG ACGACGACAG TATCGGCCTC AGGAAGATCG CACTCCAGCC AGCTTTCCGG     240

CACCGCTTCT GGTGCCGGAA ACCAGGCAAA GCGCCATTCG CCATTCAGGC TGCGCAACTG     300

TTGGGAAGGG CGATCGGTGC GGGCCTCTTC GCTATTACGC CAGCTGGCGA AAGGGGGATG     360

TGCTGCAAGG CGATTAAGTT GGGTAACGCC AGGGTTTTCC CAGTCACGAC GTTGTAAAAC     420

CATTACGATA CAAACTTAAC GGATATCGCG ATAATGAAAT AATTTATGAT TATTTCTCGC     480

TTTCAATTTA ACACAACCCT CAAGAACCTT TGTATTTATT TTCACTTTTT AAGTATAGAA     540

TAAAGAACCC GGGAAGCTTC TTTATTCTAT ACTTAAAAAG TGAAAATAAA TACAAAGGTT     600

CTTGAGGGTT GTGTTAAATT GAAAGCGAGA AATAATCATA AATTATTTCA TTATCGCGAT     660

ATCCGTTAAG TTTGTATCGT AATGGACTCT AAAGAGACTA TTCTAATTGA GATCATTCCA     720

AAAATAAAAG CATATCTACT AGACGCGAAT ATAAGTCCAA AATCCTACGA TGACTTTATT     780

TCACGAAATA AAAATATTTT CGTTATCAAC CTTTATAACG TATCGACTAT CACAGAAGAA     840
```

```
                                        -continued
GATATACGAT TGTTATACAC TACGATAGAA CAGAATATTG ACGCGGATGA TCAAACACTG      900

GTTGCTATTT TTTCGTATAT AGGATATAAA TTTGAACAGG CTGTTAAAGA AGAGATTAGT      960

ACGAGTTTAT CCTTCAATGA CAAGAATACC ACAGATGAAA TGACGTATAA CTTGTATGAT     1020

CTTTTCTTCA ACACATTAGA CATGTATTTA CGACAAAAGA AGATCAGTAT TCTGGTAAAT     1080

GATGATGTTA GAGGTGATGT AATCGTTAGT TATAAAAATA GTGACTTAGT TTCATCATTT     1140

AATGCGGAAC TAGAACCAGA GATTAAGAAG ATACCGTTCA ATATGAAAAA TCTATTACCG     1200

TACTTGGAAA AGAATTTGGA CCAACTAAGA TTCTCTAAAA AATATTTAGA CTTTGCATAT     1260

TTATGTAGAC ACATCGGTAT TCCCATTTCC AAAAAAAAGT ATAATGTGCG ATATGTATTT     1320

CTTTATAAAA TAGACGGATT ATCCATTCCT ATTATCATTA AGGATTTTTT AGATGTTAAG     1380

TACGTATATT TGGAAAATAC TGGAAAAATT TATAAAAATT CTTTTCCGA  AGACCATAAC     1440

AACAGTCTAT CTGATTGGGG TAAAGTTATT ATACCTCTCT TAAAGGATCG TCATCTATAT     1500

AGCTACATCT TTCTATCTAG TTATCATTTA CATAGTTACT ATACAGATCT CATCGCGAGA     1560

GACGAGCCTG TGTTTGTGAA ACGCAAAAAA CTAGATATTA TAGAGATCGA TGAACCTGAG     1620

GCATGGAAAA GGGATGTTAG AGTAGAATTC GCACCGTGTG AGCATCAAAT TAGATTGAAG     1680

GAAGCTATGA AAGTTGACGC TAACTATTTC ACTAAAATTA ATAATTTTGC TAACGAATTT     1740

ATTTATTATG AAGATGGTGT GGCATATTGT AGAGTGTGTG GAATAAATAT ACCTATATTT     1800

AATTTAGATG CCGCTGACGT GATTAAAAAT ACAGTTATCG TTTCCACGTT TAACAAGACT     1860

ATATTTTTGA GCGAACCATA TAGCTATTTC GTTCATAGTC AGCGCTTTAT CTTTAATATT     1920

ATCATGTCTT TTGATAATAT TATGAAATCT CAAACTTGGG TAATGAAATA CAACATTAAC     1980

CGACTAATTC TTAACTTTCT TATTGATATA AACTCTAGAC GTCAGGAATA CGAAAAAAAG     2040

TTTTCTTCTG AAATTAAGAG AGGTCTGTTC TTTCTTCGTT TGTCTGCAAA CTTATTCGAA     2100

AGTCAAGTAT CGTCTACAGA GTTATTTTAT GTTTCCAAAA TGCTTAATTT GAACTATATA     2160

GTTGCGTTAG TAATCATTCT TAACAGTAGT GCGGACTTTA TAGTTTCCTA TATGACATCC     2220

AAGAACAAAA CGGTAGAAGA ATCCACTCTT AAATACGCCA TCTCCGTGGT TATATACGAT     2280

TTTTTGGTTA AGACTAGAAT TTGCGAGAAG GGATCGTTGG ATACTATAGT TTTATTTACC     2340

GATGTATACA CATCTATAAT GCCGGAGGAA TTGGATTTAC ATTTTCAGAG AATCACATTA     2400

GAACTTAGAA AACTAGTATC CATTCAGAGA TCGGCGTTAG AACCCAATTA CGATGTAGAA     2460

AGTCGCGGCG AAGAGCTTCC GCTATCTGCA TTAAAGTTTT TCGATACAAG CACCATTATA     2520

GTTAAAACAA TGGCTCCAGT ACATACATGT GTAGAACAAA AAATTGTTGC ACCTACTCCA     2580

TCTGTAGAAC CAACTGATGC ATCTCTTAAA AACTTCAAAG AGCTAACGTG TGACGAAGAT     2640

ATTAAGATTT TGATTAGAGT TCATGATACT AATGCTACAA AATTAGTCAT TTTTCCATCA     2700

CATCTAAAAA TAGAAATTGA GAGAAAAAAA CTAATTATAC CGCTAAAGAG TTTATATATT     2760

ACCAATACTC TCAAATATTA TTATTCTAAC TCCTATTTAT ACGTTTTCAG ATTCGGAGAT     2820

CCTATGCCAT TCGAAGAAGA ACTCATAGAT CACGAACATG TGCAATACAA AATAAATTGT     2880

TACAATATTC TAAGATATCA TTTATTGCCA GACAGTGACG TGTTTGTATA TTTTAGTAAT     2940

TCATTAAACA GAGAAGCATT GGAATACGCA TTTTATATCT TTTTGTCGAA ATATGTAAAT     3000

GTGAAACAAT GGATAGACGA AAATATAACT CGTATTAAAG AGTTGTATAT GATTAATTTC     3060

AATAACTAAA TGGCGGCGGT GAAAACTCCT GTTATTGTTG TGCCAGTTAT TGATAGACCT     3120

CCATCAGAAA CATTTCCTAA TGTTCATGAG CATATTAATG ATCAGAAGTT CGATGATGTA     3180

AAGGACAACG AAGTTATGCC AGAAAAAAGA AATGTTGTGG TAGTCAAGGA TGATCCAGAT     3240
```

```
CATTACAAGG ATTATGCGTT TATACAGTGG ACTGGAGGAA ACATTAGAAA TGATGACAAG    3300

TATACTCACT TCTTTTCAGG GTTTTGTAAC ACTATGTGTA CAGAGGAAAC GAAAAGAAAT    3360

ATCGCTAGAC ATTTAGCCCT ATGGGATTCT AATTTTTTTA CCGAGTTAGA AAATAAAAAG    3420

GTAGAATATG TAGTTATTGT AGAAAACGAT AACGTTATTG AGGATATTAC GTTTCTTCGT    3480

CCCGTCTTGA AGGCAATGCA TGACAAAAAA ATAGATATCC TACAGATGAG AGAAATTATT    3540

ACAGGCAATA AAGTTAAAAC CGAGCTTGTA ATGGACAAAA ATCATACCAT ATTCACATAT    3600

ACAGGAGGGT ATGATGTTAG CTTATCAGCC TATATTATTA GAGTTACTAC GGCGCTGAAC    3660

ATCGTAGATG AAATTATAAA GTCTGGAGGT CTATCATCGG GATTTTATTT TGAAATAGCC    3720

AGAATCGAAA ACGAAATGAA GATCAATAGG CAGATACTGG ATAATGCCGC CAAATATGTA    3780

GAACACGATC CCCGACTTGT TGCAGAACAC CGCTTCGAAA ACATGAAACC GAATTTTTGG    3840

TCTAGAATAG AACGGCAGG ATCCACTAGT TCTAGAGCGG CCGCCACCGC GGTGGAGCTC    3900

CAGCTTTTGT TCCCTTTAGT GAGGGTTAAT TCCGAGCTTG GCGTAATCAT GGTCATAGCT    3960

GTTTCCTGTG TGAAATTGTT ATCCGCTCAC AATTCCACAC AACATACGAG CCGGAAGCAT    4020

AAAGTGTAAA GCCTGGGGTG CCTAATGAGT GAGCTAACTC ACATTAATTG CGTTGCGCTC    4080

ACTGCCCGCT TTCCAGTCGG GAAACCTGTC GTGCCAGCTG CATTAATGAA TCGGCCAACG    4140

CGCGGGGAGA GGCGGTTTGC GTATTGGGCG CTCTTCCGCT TCCTCGCTCA CTGACTCGCT    4200

GCGCTCGGTC GTTCGGCTGC GGCGAGCGGT ATCAGCTCAC TCAAAGGCGG TAATACGGTT    4260

ATCCACAGAA TCAGGGGATA ACGCAGGAAA GAACATGTGA GCAAAAGGCC AGCAAAAGGC    4320

CAGGAACCGT AAAAAGGCCG CGTTGCTGGC GTTTTTCCAT AGGCTCCGCC CCCCTGACGA    4380

GCATCACAAA AATCGACGCT CAAGTCAGAG GTGGCGAAAC CCGACAGGAC TATAAAGATA    4440

CCAGGCGTTT CCCCCTGGAA GCTCCCTCGT GCGCTCTCCT GTTCCGACCC TGCCGCTTAC    4500

CGGATACCTG TCCGCCTTTC TCCCTTCGGG AAGCGTGGCG CTTTCTCATA GCTCACGCTG    4560

TAGGTATCTC AGTTCGGTGT AGGTCGTTCG CTCCAAGCTG GGCTGTGTGC ACGAACCCCC    4620

CGTTCAGCCC GACCGCTGCG CCTTATCCGG TAACTATCGT CTTGAGTCCA ACCCGGTAAG    4680

ACACGACTTA TCGCCACTGG CAGCAGCCAC TGGTAACAGG ATTAGCAGAG CGAGGTATGT    4740

AGGCGGTGCT ACAGAGTTCT TGAAGTGGTG GCCTAACTAC GGCTACACTA GAAGGACAGT    4800

ATTTGGTATC TGCGCTCTGC TGAAGCCAGT TACCTTCGGA AAAAGAGTTG GTAGCTCTTG    4860

ATCCGGCAAA CAAACCACCG CTGGTAGCGG TGGTTTTTTT GTTTGCAAGC AGCAGATTAC    4920

GCGCAGAAAA AAAGGATCTC AAGAAGATCC TTTGATCTTT TCTACGGGGT CTGACGCTCA    4980

GTGGAACGAA AACTCACGTT AAGGGATTTT GGTCATGAGA TTATCAAAAA GGATCTTCAC    5040

CTAGATCCTT TTAAATTAAA AATGAAGTTT TAAATCAATC TAAAGTATAT ATGAGTAAAC    5100

TTGGTCTGAC AGTTACCAAT GCTTAATCAG TGAGGCACCT ATCTCAGCGA TCTGTCTATT    5160

TCGTTCATCC ATAGTTGCCT GACTCCCCGT CGTGTAGATA ACTACGATAC GGGAGGGCTT    5220

ACCATCTGGC CCCAGTGCTG CAATGATACC GCGAGACCCA CGCTCACCGG CTCCAGATTT    5280

ATCAGCAATA AACCAGCCAG CCGGAAGGGC CGAGCGCAGA AGTGGTCCTG CAACTTTATC    5340

CGCCTCCATC CAGTCTATTA ATTGTTGCCG GGAAGCTAGA GTAAGTAGTT CGCCAGTTAA    5400

TAGTTTGCGC AACGTTGTTG CCATTGCTAC AGGCATCGTG GTGTCACGCT CGTCGTTTGG    5460

TATGGCTTCA TTCAGCTCCG GTTCCCAACG ATCAAGGCGA GTTACATGAT CCCCCATGTT    5520

GTGCAAAAAA GCGGTTAGCT CCTTCGGTCC TCCGATCGTT GTCAGAAGTA AGTTGGCCGC    5580
```

-continued

```
AGTGTTATCA CTCATGGTTA TGGCAGCACT GCATAATTCT CTTACTGTCA TGCCATCCGT    5640

AAGATGCTTT TCTGTGACTG GTGAGTACTC AACCAAGTCA TTCTGAGAAT AGTGTATGCG    5700

GCGACCGAGT TGCTCTTGCC CGGCGTCAAT ACGGGATAAT ACCGCGCCAC ATAGCAGAAC    5760

TTTAAAAGTG CTCATCATTG GAAAACGTTC TTCGGGGCGA AAACTCTCAA GGATCTTACC    5820

GCTGTTGAGA TCCAGTTCGA TGTAACCCAC TCGTGCACCC AACTGATCTT CAGCATCTTT    5880

TACTTTCACC AGCGTTTCTG GGTGAGCAAA AACAGGAAGG CAAAATGCCG CAAAAAAGGG    5940

AATAAGGGCG ACACGGAAAT GTTGAATACT CATACTCTTC CTTTTTCAAT ATTATTGAAG    6000

CATTTATCAG GGTTATTGTC TCATGAGCGG ATACATATTT GAATGTATTT AGAAAAATAA    6060

ACAAATAGGG GTTCCGCGCA CATTTCCCCG AAAAGTGCCA CCTGGGACGC GCCCTGTAGC    6120

GGCGCATTAA GCGCGGCGGG TGTGGTGGTT ACGCGCAGCG TGACCGCTAC ACTTGCCAGC    6180

GCCCTAGCGC CCGCTCCTTT CGCTTTCTTC CCTTCCTTTC TCGCCACGTT CGCCGGCTTT    6240

CCCCGTCAAG CTCTAAATCG GGGGCTCCCT TTAGGGTTCC GATTTAGTGC TTTACGGCAC    6300

CTCGACCCCA AAAAACTTGA TTAGGGTGAT GGTTCACGTA GTGGGCCATC GCCCTGATAG    6360

ACGGTTTTTC GCCCTTTGAC GTTGGAGTCC ACGTTCTTTA ATAGTGGACT CTTGTTCCAA    6420

ACTGGAACAA CACTCAACCC TATCTCGGTC TATTCTTTTG ATTTATAAGG GATTTTGCCG    6480

ATTTCGGCCT ATTGGTTAAA AAATGAGCTG ATTTAACAAA AATTTAACGC GAATTTTAAC    6540

AAAATATTAA CGTTTACAAT TTCGCGCCAT TCGCCATTCA GGCTGCGCAA CTGTTGGGAA    6600

GGGCGATCGG TGCGGGCCTC TTCGCTATTA CGCCAGCTGG CGAAAGGGGG ATGTGCTGCA    6660

AGGCGATTAA GTTGGGTAAC GCCAGGGTTT TCCCAGTCAC GACGTTGTAA AACGACGGCC    6720

AGTGAATTGT AATACGACTC ACTATAGGGC GAATTGGGTA CCGGGCCCCC CCTCGAGGGA    6780

TCCTGCTTGA ACATCCTCTA GAACCGTCGA TACTGCAGAG ATTCTAGTAA TAATTTTCTT    6840

AAGATCTTTA ACGATATTGT CGGTAGCCAC CTTTAGGTCA GAAAGATCGC TTCTAGCACT    6900

ATGATTTACT TTACCAGCTT CAACTTGTAC CATAGGTTCA TCATCCCCGT CGCTATCATC    6960

GAGCTCTACA GCAGCCACGC TTTCTACAAT GTCGCCGACT CCAGGAGATG GAGAATTTTT    7020

TTCAGTTGTT TGATGATATT CCTCTATAAC TACTTCTTCT TCCACTTCCT CCTTTTTGGT    7080

TGATCTTTTA GTAGCCGCTG GTTTACGAGG AGTAGTGGCT CGTTTGGTTT TGGGCTTAGT    7140

AGATGGAATT ATTACATCTT CCGGGAAAAT ATCCTCGTTT TTATCTTTAT TTTCAGCGCT    7200

ATTTTTTAGA TGAGCTCTGA TTTCAGCCAT CTTTGTGAAG CTACTAGTAT CCGCTTTATT    7260

TGTAATTGAC CACGCCATTA CGATACAAAC TTAACGGATA TCGCGATAAT GAAATAATTT    7320

ATGATTATTT CTCGCTTTCA ATTTAACACA ACCCTCAAGA ACCTTTGTAT TTATTTTCAT    7380

TTTTTAAGTA TAGAATAAAG AATCTATAAA AACTAAAAAA ATTATACATC ATAAACCAAT    7440

TTCCTAGTTG TTTTGTAACTT TAAAACGCCA CCGTCAGGGA AAGTTTCATA AGAAGCACCG    7500

GAAGAGAAGA GAATATCTCG GGACAATTGG ATCACGAGAG GCACGCAAGA GACGAATCAA    7560

CTCACGTAGA AACTCAGCAC CAGCTAGACA AGCTTCCCGG GGGATCCTTA TTTTTGACAC    7620

CAGACCAACT GGTAATGGTA GCGACCGGCG CTCAGCTGGA ATTCCGCCGA TACTGACGGG    7680

CTCCAGGAGT CGTCGCCACC AATCCCCATA TGGAAACCGT CGATATTCAG CCATGTGCCT    7740

TCTTCCGCGT GCAGCAGATG GCGATGGCTG GTTTCCATCA GTTGCTGTTG ACTGTAGCGG    7800

CTGATGTTGA ACTGGAAGTC GCCGCGCCAC TGGTGTGGGC CATAATTCAA TTCGCGCGTC    7860

CCGCAGCGCA GACCGTTTTC GCTCGGGAAG ACGTACGGGG TATACATGTC TGACAATGGC    7920

AGATCCCAGC GGTCAAAACA GGCGGCAGTA AGGCGGTCGG GATAGTTTTC TTGCGGCCCT    7980
```

-continued

```
AATCCGAGCC AGTTTACCCG CTCTGCTACC TGCGCCAGCT GGCAGTTCAG GCCAATCCGC      8040

GCCGGATGCG GTGTATCGCT CGCCACTTCA ACATCAACGG TAATCGCCAT TTGACCACTA      8100

CCATCAATCC GGTAGGTTTT CCGGCTGATA AATAAGGTTT TCCCCTGATG CTGCCACGCG      8160

TGAGCGGTCG TAATCAGCAC CGCATCAGCA AGTGTATCTG CCGTGCACTG CAACAACGCT      8220

GCTTCGGCCT GGTAATGGCC CGCCGCCTTC CAGCGTTCGA CCCAGGCGTT AGGGTCAATG      8280

CGGGTCGCTT CACTTACGCC AATGTCGTTA TCCAGCGGTG CACGGGTGAA CTGATCGCGC      8340

AGCGGCGTCA GCAGTTGTTT TTTATCGCCA ATCCACATCT GTGAAAGAAA GCCTGACTGG      8400

CGGTTAAATT GCCAACGCTT ATTACCCAGC TCGATGCAAA AATCCATTTC GCTGGTGGTC      8460

AGATGCGGGA TGGCGTGGGA CGCGGCGGGG AGCGTCACAC TGAGGTTTTC CGCCAGACGC      8520

CACTGCTGCC AGGCGCTGAT GTGCCCGGCT TCTGACCATG CGGTCGCGTT CGGTTGCACT      8580

ACGCGTACTG TGAGCCAGAG TTGCCCGGCG CTCTCCGGCT GCGGTAGTTC AGGCAGTTCA      8640

ATCAACTGTT TACCTTGTGG AGCGACATCC AGAGGCACTT CACCGCTTGC CAGCGGCTTA      8700

CCATCCAGCG CCACCATCCA GTGCAGGAGC TCGTTATCGC TATGACGAA CAGGTATTCG       8760

CTGGTCACTT CGATGGTTTG CCCGGATAAA CGGAACTGGA AAAACTGCTG CTGGTGTTTT      8820

GCTTCCGTCA GCGCTGGATG CGGCGTGCGG TCGGCAAAGA CCAGACCGTT CATACAGAAC      8880

TGGCGATCGT TCGGCGTATC GCCAAAATCA CCGCCGTAAG CCGACCACGG GTTGCCGTTT      8940

TCATCATATT TAATCAGCGA CTGATCCACC CAGTCCCAGA CGAAGCCGCC CTGTAAACGG      9000

GGATACTGAC GAAACGCCTG CCAGTATTTA GCGAAACCGC CAAGACTGTT ACCCATCGCG      9060

TGGGCGTATT CGCAAAGGAT CAGCGGGCGC GTCTCTCCAG GTAGCGAAAG CCATTTTTTG      9120

ATGGACCATT TCGGCACAGC CGGGAAGGGC TGGTCTTCAT CCACGCGCGC GTACATCGGG      9180

CAAATAATAT CGGTGGCCGT GGTGTCGGCT CCGCCGCCTT CATACTGCAC CGGGCGGGAA      9240

GGATCGACAG ATTTGATCCA GCGATACAGC GCGTCGTGAT TAGCGCCGTG GCCTGATTCA      9300

TTCCCCAGCG ACCAGATGAT CACACTCGGG TGATTACGAT CGCGCTGCAC CATTCGCGTT      9360

ACGCGTTCGC TCATCGCCGG TAGCCAGCGC GGATCATCGG TCAGACGATT CATTGGCACC      9420

ATGCCGTGGG TTTCAATATT GGCTTCATCC ACCACATACA GGCCGTAGCG GTCGCACAGC      9480

GTGTACCACA GCGGATGGTT CGGATAATGC GAACAGCGCA CGGCGTTAAA GTTGTTCTGC      9540

TTCATCAGCA GGATATCCTG CACCATCGTC TGCTCATCCA TGACCTGACC ATGCAGAGGA      9600

TGATGCTCGT GACGGTTAAC GCCTCGAATC AGCAACGGCT TGCCGTTCAG CAGCAGCAGA      9660

CCATTTTCAA TCCGCACCTC GCGGAAACCG ACATCGCAGG CTTCTGCTTC AATCAGCGTG      9720

CCGTCGGCGG TGTGCAGTTC AACCACCGCA CGATAGAGAT TCGGGATTTC GGCGCTCCAC      9780

AGTTTCGGGT TTTCGACGTT CAGACGTAGT GTGACGCGAT CGGCATAACC ACCACGCTCA      9840

TCGATAATTT CACCGCCGAA AGGCGCGGTG CCGCTGGCGA CCTGCGTTTC ACCCTGCCAT      9900

AAAGAAACTG TTACCCGTAG GTAGTCACGC AACTCGCCGC ACATCTGAAC TTCAGCCTCC      9960

AGTACAGCGC GGCTGAAATC ATCATTAAAG CGAGTGGCAA CATGGAAATC GCTGATTGT      10020

GTAGTCGGTT TATGCAGCAA CGAGACGTCA CGGAAAATGC CGCTCATCCG CCACATATCC      10080

TGATCTTCCA GATAACTGCC GTCACTCCAA CGCAGCACCA TCACCGCGAG GCGGTTTTCT      10140

CCGGCGCGTA AAAATGCGCT CAGGTCAAAT TCAGACGGCA AACGACTGTC CTGGCCGTAA      10200

CCGACCCAGC GCCCGTTGCA CCACAGATGA AACGCCGAGT TAACGCCATC AAAAATAATT      10260

CGCGTCTGGC CTTCCTGTAG C                                                10281
```

(2) INFORMATION FOR SEQ ID NO:2:

(i) SEQUENCE CHARACTERISTICS:
        (A) LENGTH: 4259 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
GCTCTAACCT TCTAGTCATT CAACTTCTTA GTATGAGCTC ACTTATTACA TCCTACTGAC      60

TATATACAGC GAATTAACCA TAGGCGTAAT TGTACAGAAA CCAGGAAATT ATTACCGCCT     120

TTTATAAGAA GTATTAATAA AACATGTAGC GTATGTCTAG AAAGAATATA CGAAAAAGAA     180

ATAAATAAAC AATATTTCGG TATTTTACCA AATTGTAAAC ACGTGTTTTG TTTTTACTGT     240

ATACAACGTT GGATGTCTAT AATAAAAGGT ACGGATACCG AAGGTACATG TCCTGTATGT     300

AGAACAGTTT CTGTATTTAT AGTGCCTAAT AGGTACTGGA TAGACGATAA ATATGAAAAG     360

AGATTAATTA TAAATAAATA TAAGAATGAC AGAAAGACTT ATAAAGCGTT TAAACATTAT     420

ATAGGAAGAT ACGTATTATT TTATACAGTA AACAACAGTT TATTTGTTAC TAATGATTAA     480

GGTACGTGAC TAATTAGCTA TAAAAAGGAT CCATCGATGA TGGGAAGCTT CTTTATTCTA     540

TACTTAAAAA GTGAAAATAA ATACAAAGGT TCTTGAGGGT TGTGTTAAAT TGAAAGCGAG     600

AAATAATCAT AAATTATTTC ATTATCGCGA TATCCGTTAA GTTTGTATCG TAATGGACTC     660

TAAAGAGACT ATTCTAATTG AGATCATTCC AAAAATAAAA GCATATCTAC TAGACGCGAA     720

TATAAGTCCA AAATCCTACG ATGACTTTAT TTCACGAAAT AAAAATATTT TCGTTATCAA     780

CCTTTATAAC GTATCGACTA TCACAGAAGA AGATATACGA TTGTTATACA CTACGATAGA     840

ACAGAATATT GACGCGGATG ATCAAACACT GGTTGCTATT TTTTCGTATA TAGGATATAA     900

ATTTGAACAG GCTGTTAAAG AAGAGATTAG TACGAGTTTA TCCTTCAATG ACAAGAATAC     960

CACAGATGAA ATGACGTATA ACTTGTATGA TCTTTTCTTC AACACATTAG ACATGTATTT    1020

ACGACAAAAG AAGATCAGTA TTCTGGTAAA TGATGATGTT AGAGGTGATG TAATCGTTAG    1080

TTATAAAAAT AGTGACTTAG TTTCATCATT TAATGCGGAA CTAGAACCAG AGATTAAGAA    1140

GATACCGTTC AATATGAAAA ATCTATTACC GTACTTGGAA AAGAATTTGG ACCAACTAAG    1200

ATTCTCTAAA AAATATTTAG ACTTTGCATA TTTATGTAGA CACATCGGTA TTCCCATTTC    1260

CAAAAAAAAG TATAATGTGC GATATGTATT TCTTTATAAA ATAGACGGAT TATCCATTCC    1320

TATTATCATT AAGGATTTTT TAGATGTTAA GTACGTATAT TTGGAAAATA CTGGAAAAAT    1380

TTATAAAAAT TCTTTTTCCG AAGACCATAA CAACAGTCTA TCTGATTGGG GTAAAGTTAT    1440

TATACCTCTC TTAAAGGATC GTCATCTATA TAGCTACATC TTTCTATCTA GTTATCATTT    1500

ACATAGTTAC TATACAGATC TCATCGCGAG AGACGAGCCT GTGTTTGTGA AACGCAAAAA    1560

ACTAGATATT ATAGAGATCG ATGAACCTGA GGCATGGAAA AGGGATGTTA GAGTAGAATT    1620

CGCACCGTGT GAGCATCAAA TTAGATTGAA GGAAGCTATG AAAGTTGACG CTAACTATTT    1680

CACTAAAATT AATAATTTTG CTAACGAATT TATTTATTAT GAAGATGGTG TGGCATATTG    1740

TAGAGTGTGT GGAATAAATA TACCTATATT TAATTTAGAT GCCGCTGACG TGATTAAAAA    1800

TACAGTTATC GTTTCCACGT TTAACAAGAC TATATTTTTG AGCGAACCAT ATAGCTATTT    1860

CGTTCATAGT CAGCGCTTTA TCTTTAATAT TATCATGTCT TTTGATAATA TTATGAAATC    1920

TCAAACTTGG GTAATGAAAT ACAACATTAA CCGACTAATT CTTAACTTTC TTATTGATAT    1980
```

```
AAACTCTAGA CGTCAGGAAT ACGAAAAAAA GTTTTCTTCT GAAATTAAGA GAGGTCTGTT      2040

CTTTCTTCGT TTGTCTGCAA ACTTATTCGA AAGTCAAGTA TCGTCTACAG AGTTATTTTA      2100

TGTTTCCAAA ATGCTTAATT TGAACTATAT AGTTGCGTTA GTAATCATTC TTAACAGTAG      2160

TGCGGACTTT ATAGTTTCCT ATATGACATC CAAGAACAAA ACGGTAGAAG AATCCACTCT      2220

TAAATACGCC ATCTCCGTGG TTATATACGA TTTTTTGGTT AAGACTAGAA TTTGCGAGAA      2280

GGGATCGTTG GATACTATAG TTTTATTTAC CGATGTATAC ACATCTATAA TGCCGGAGGA      2340

ATTGGATTTA CATTTTCAGA GAATCACATT AGAACTTAGA AAACTAGTAT CCATTCAGAG      2400

ATCGGCGTTA GAACCCAATT ACGATGTAGA AAGTCGCGGC GAAGAGCTTC CGCTATCTGC      2460

ATTAAAGTTT TTCGATACAA GCACCATTAT AGTTAAAACA ATGGCTCCAG TACATACATG      2520

TGTAGAACAA AAAATTGTTG CACCTACTCC ATCTGTAGAA CCAACTGATG CATCTCTTAA      2580

AAACTTCAAA GAGCTAACGT GTGACGAAGA TATTAAGATT TTGATTAGAG TTCATGATAC      2640

TAATGCTACA AAATTAGTCA TTTTTCCATC ACATCTAAAA ATAGAAATTG AGAGAAAAAA      2700

ACTAATTATA CCGCTAAAGA GTTTATATAT TACCAATACT CTCAAATATT ATTATTCTAA      2760

CTCCTATTTA TACGTTTTCA GATTCGGAGA TCCTATGCCA TTCGAAGAAG AACTCATAGA      2820

TCACGAACAT GTGCAATACA AAATAAATTG TTACAATATT CTAAGATATC ATTTATTGCC      2880

AGACAGTGAC GTGTTTGTAT ATTTTAGTAA TTCATTAAAC AGAGAAGCAT GGAATACGC      2940

ATTTTATATC TTTTTGTCGA AATATGTAAA TGTGAAACAA TGGATAGACG AAAATATAAC      3000

TCGTATTAAA GAGTTGTATA TGATTAATTT CAATAACTAA AAGCTTCCCA TCCTGCAGCT      3060

CGAGTTTTTA TGACTAGTTA ATCACGGCCG CTCAATATTG TATTGGATGG TTAGAGATCA      3120

AAGGATACAA GATAACTGGG CTCATTTCAG CTTTACATTC ATCCCTATAA GCTTTCATAA      3180

TGGGATTTTT CTCCATAATG TCAAAATCAC TTTGGATATA TTCAAAATTT CTACAAAAT      3240

GTTTTGGTTG TTCTGAGCTA AACACGATGT TAGATATTAA TAACTTTGCT ATCTCAAGAC      3300

CTTCTGAAGT ATCAACTTTG ATATTGGAAA GAGGTGTAAA ATAAGGTGAT GAAGCGATTG      3360

TTGTATCTGC ACAGAATGTT AACAGTATAT CTACTAATTC TACATTTCCA TCTGTCACAG      3420

CATGCCATAG AGGAGTATTC CAGTACCTGT CCTTAGCATT TATATCAGCA CCGAATTCCA      3480

AAAGCATAAT AGTTATCTTT ACAGATCCTA TACACAGC ATAATGCAAA GGAGTCATCC       3540

TATGGCTATC TTTAACGTTA GTATATGCTC CAGCTAGAAG TAATTGCTCT ATTATCTCCA      3600

TGTTTTCAGA TTTAACAGCA TAATGCAATG GATACATATA TCCTCTGTAA CCATAATTTA      3660

TACTCGATCC AGCTTTTAGT AACATACTCA CAATTTCCAA ATTTTCTCTC TTTATAGCCT      3720

CGATTATGGG ATGATTTTCC CTGTACTCAT TGTCAACATC AGCGTTATAC TCCAGAAGTA      3780

ACTTTACAAT TTCCACATTC TCTATAGAGA CAGCATACTG GAGTGGAGTC TTTACTTTGT      3840

AGTCCTCATA TGTATCCACA TTAGCGCCAT GATCCAACAA GAGTTTCACC AGATCTATGT      3900

TCTGAACTTT GACAGCTCTA TGCAACGGAG AAGATACTTG TTCGCTAGAT ATATCAGGAT      3960

CAGCTCCTGC TAACAATAGA GCTTTGGCTA TTTCAAATTT TTCATTTTCT ACAGCACAAT      4020

GAAGGGGTGA GCAGCCATAA TCGTTGAATA CGTCCAGGTT AATGCCGGTT TTCACAATAT      4080

CTAGCACGCT AGACAGAGAT CCAGATTCAA TAGCTTCGAA TAAGTATGCC TCCATTTTGT      4140

GTAATAGTAG TAAGTAATAA TTTTCTGAAG AAACTACTAA CTTACCGAGC TATAGTAGAT      4200

AGTTATAATT TCATTTTTTT ACAAGTAGTA TCACATAGTG ATTGCTTATT AAAGGTACC       4259

(2) INFORMATION FOR SEQ ID NO:3:
```

(i) SEQUENCE CHARACTERISTICS:
    (A) LENGTH: 4472 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

```
GCTCTAACCT TCTAGTACAT TCAACTTCTT AGTACTCCGA GCTCGCGGCC GCCTATCAAA      60

AGTCTTAATG AGTTAGGTGT AGATAGTATA GATATTACTA CAAAGGTATT CATATTTCCT     120

ATCAATTCTA AAGTAGATGA TATTAATAAC TCAAAGATGA TGATAGTAGA TAATAGATAC     180

GCTCATATAA TGACTGCAAA TTTGGACGGT TCACATTTTA ATCATCACGC GTTCATAAGT     240

TTCAACTGCA TAGATCAAAA TCTCACTAAA AAGATAGCCG ATGTATTTGA GAGAGATTGG     300

ACATCTAACT ACGCTAAAGA AATTACAGTT ATAAATAATA CATAATGGAT TTGTTATCA      360

TCAGTTATAT TTAACATAAG TACAATAAAA AGTATTAAAT AAAAATACTT ACTTACGAAA     420

AAATGACTAA TTAGCTATAA AAACCCAGAT CTCTCGAGGT CGACGGTATC GATAAGCTTG     480

ATATCGAATT CATAAAAATT ATTGATGTCT ACACATCCTT TTGTAATTGA CATCTATATA     540

TCCTTTTGTA TAATCAACTC TAATCACTTT AACTTTTACA GTTTTCCCTA CCAGTTTATC     600

CCTATATTCA ACATATCTAT CCATATGCAT CTTAACACTC TCTGCCAAGA TAGCTTCAGA     660

GTGAGGATAG TCAAAAAGAT AAATGTATAG AGCATAATCC TTCTCGTATA CTCTGCCCTT     720

TATTACATCG CCCGCATTGG GCAACGAATA ACAAAATGCA AGCATACGAT ACAAACTTAA     780

CGGATATCGC GATAATGAAA TAATTTATGA TTATTTCTCG CTTTCAATTT AACACAACCC     840

TCAAGAACCT TTGTATTTAT TTTCACTTTT AAGTATAGA  ATAAAGAAAG CTCTAATTAA     900

TTAATGAACA GATTGTTTCG TTTTCCCCTT GGCGTATCAC TAATTAATTA ACCCGGGCTG     960

CAGCTCGAGG AATTCAACTA TATCGACATA TTTCATTTGT ATACACATAA CCATTACTAA    1020

CGTAGAATGT ATAGGAAGAG ATGTAACGGG AACAGGGTTT GTTGATTCGC AAACTATTCT    1080

AATACATAAT TCTTCTGTTA ATACGTCTTG CACGTAATCT ATTATAGATG CCAAGATATC    1140

TATATAATTA TTTTGTAAGA TGATGTTAAC TATGTGATCT ATATAAGTAG TGTAATAATT    1200

CATGTATTTC GATATATGTT CCAACTCTGT CTTTGTGATG TCTAGTTTCG TAATATCTAT    1260

AGCATCCTCA AAAAATATAT TCGCATATAT TCCCAAGTCT TCAGTTCTAT CTTCTAAAAA    1320

ATCTTCAACG TATGGAATAT AATAATCTAT TTTACCTCTT CTGATATCAT TAATGATATA    1380

GTTTTTGACA CTATCTTCTG TCAATTGATT CTTATTCACT ATATCTAAGA AACGGATAGC    1440

GTCCCTAGGA CGAACTACTG CCATTAATAT CTCTATTATA GCTTCTGGAC ATAATTCATC    1500

TATTATACCA GAATTAATGG GAACTATTCC GTATCTATCT AACATAGTTT TAAGAAAGTC    1560

AGAATCTAAG ACCTGATGTT CATATATTGG TTCATACATG AAATGATCTC TATTGATGAT    1620

AGTGACTATT TCATTCTCTG AAAATTGGTA ACTCATTCTA TATATGCTTT CCTTGTTGAT    1680

GAAGGATAGA ATATACTCAA TAGAATTTGT ACCAACAAAC TGTTCTCTTA TGAATCGTAT    1740

ATCATCATCT GAAATAATCA TGTAAGGCAT ACATTTAACA ATTAGAGACT TGTCTCCTGT    1800

TATCAATATA CTATTCTTGT GATAATTTAT GTGTGAGGCA AATTTGTCCA CGTTCTTTAA    1860

TTTTGTTATA GTAGATATCA AATCCAATGG AGCTACAGTT CTTGGCTTAA ACAGATATAG    1920

TTTTTCTGGA ACAAATTCTA CAACATTATT ATAAAGGACT TGGGTAGAT  AAGTGGGATG    1980

AAATCCTATT TTAATTAATG CTATCGCATT GTCCTCGTGC AAATATCCAA ACGCTTTGT     2040

GATAGTATGG CATTCATTGT CTAGAAACGC TCTACGAATA TCTGTGACAG ATATCATCTT    2100
```

-continued

```
TAGAGAATAT ACTAGTCGCG TTAATAGTAC TACAATTTGT ATTTTTTAAT CTATCTCAAT    2160

AAAAAAATTA ATATGTATGA TTCAATGTAT AACTAAACTA CTAACTGTTA TTGATAACTA    2220

GAATCAGAAT CTAATGATGA CGTAACCAAG AAGTTTATCT ACTGCCAATT TAGCTGCATT    2280

ATTTTTAGCA TCTCGTTTAG ATTTTCCATC TGCCTTATCG AATACTCTTC CGTCGATGTC    2340

TACACAGGCA TAAAATGTAG GAGAGTTACT AGGCCCAACT GATTCAATAC GAAAAGACCA    2400

ATCTCTCTTA GTTATTTGGC AGTACTCATT AATAATGGTG ACAGGGTTAG CATCTTTCCA    2460

ATCAATAATT TTTTTAGCCG GAATAACATC ATCAAAAGAC TTATGATCCT CTCTCATTGA    2520

TTTTTCGCGG GATACATCAT CTATTATGAC GTCAGCCATA GCATCAGCAT CCGGCTTATC    2580

CGCCTCCGTT GTCATAAACC AACGAGGAGG AATATCGTCG GAGCTGTACA CCATAGCACT    2640

ACGTTGAAGA TCGTACAGAG CTTTATTAAC TTCTCGCTTC TCCATATTAA GTTGTCTAGT    2700

TAGTTGTGCA GCAGTAGCTC CTTCGATTCC AATGTTTTTA ATAGCCGCAC ACACAATCTC    2760

TGCGTCAGAA CGCTCGTCAA TATAGATCTT AGACATTTTT AGAGAGAACT AACACAACCA    2820

GCAATAAAAC TGAACCTACT TTATCATTTT TTTATTCATC ATCCTCTGGT GGTTCGTCGT    2880

TTCTATCGAA TGTAGCTCTG ATTAACCCGT CATCTATAGG TGATGCTGGT TCTGGAGATT    2940

CTGGAGGAGA TGGATTATTA TCTGGAAGAA TCTCTGTTAT TTCCTTGTTT TCATGTATCG    3000

ATTGCGTTGT AACATTAAGA TTGCGAAATG CTCTAAATTT GGGAGGCTTA AAGTGTTGTT    3060

TGCAATCTCT ACACGCGTGT CTAACTAGTG GAGGTTCGTC AGCTGCTCTA GTTTGAATCA    3120

TCATCGGCGT AGTATTCCTA CTTTTACAGT TAGGACACGG TGTATTGTAT TTCTCGTCGA    3180

GAACGTTAAA ATAATCGTTG TAACTCACAT CCTTTATTTT ATCTATATTG TATTCTACTC    3240

CTTTCTTAAT GCATTTTATA CCGAATAAGA GATAGCGAAG GAATTCTTTT TATTGATTAA    3300

CTAGTCAAAT GAGTATATAT AATTGAAAAA GTAAAATATA AATCATATAA TAATGAAACG    3360

AAATATCAGT AATAGACAGG AACTGGCAGA TTCTTCTTCT AATGAAGTAA GTACTGCTAA    3420

ATCTCCAAAA TTAGATAAAA ATGATACAGC AAATACAGCT TCATTCAACG AATTACCTTT    3480

TAATTTTTTC AGACACACCT TATTACAAAC TAACTAAGTC AGATGATGAG AAAGTAAATA    3540

TAAATTTAAC TTATGGGTAT AATATAATAA AGATTCATGA TATTAATAAT TTACTTAACG    3600

ATGTTAATAG ACTTATTCCA TCAACCCCTT CAAACCTTTC TGGATATTAT AAAATACCAG    3660

TTAATGATAT TAAAATAGAT TGTTTAAGAG ATGTAAATAA TTATTTGGAG GTAAAGGATA    3720

TAAAATTAGT CTATCTTTCA CATGGAAATG AATTACCTAA TATTAATAAT TATGATAGGA    3780

ATTTTTTAGG ATTTACAGCT GTTATATGTA TCAACAATAC AGGCAGATCT ATGGTTATGG    3840

TAAAACACTG TAACGGGAAG CAGCATTCTA TGGTAACTGG CCTATGTTTA ATAGCCAGAT    3900

CATTTTACTC TATAAACATT TTACCACAAA TAATAGGATC CTCTAGATAT TTAATATTAT    3960

ATCTAACAAC AACAAAAAAA TTTAACGATG TATGGCCAGA AGTATTTTCT ACTAATAAAG    4020

ATAAAGATAG TCTATCTTAT CTACAAGATA TGAAAGAAGA TAATCATTTA GTAGTAGCTA    4080

CTAATATGGA AAGAAATGTA TACAAAAACG TGGAAGCTTT TATATTAAAT AGCATATTAC    4140

TAGAAGATTT AAAATCTAGA CTTAGTATAA CAAAACAGTT AAATGCCAAT ATCGATTCTA    4200

TATTTCATCA TAACAGTAGT ACATTAATCA GTGATATACT GAAACGATCT ACAGACTCAA    4260

CTATGCAAGG AATAAGCAAT ATGCCAATTA TGTCTAATAT TTTAACTTTA GAACTAAAAC    4320

GTTCTACCAA TACTAAAAAT AGGATACGTG ATAGGCTGTT AAAAGCTGCA ATAAATAGTA    4380

AGGATGTAGA AGAAATACTT TGTTCTATAC CTTCGGAGGA AAGAACTTTA GAACAACTTA    4440
```

```
AGTTTAATCA AACTTGTATT TATGAAGGTA CC                                    4472
```

(2) INFORMATION FOR SEQ ID NO:4:

(i) SEQUENCE CHARACTERISTICS:
        (A) LENGTH: 2856 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GACTCGGGTT TTATGTCCAC TCGTGGCGAT CTTGGGAAGC GGCGACGAGG GAGTCGTTGG          60

CAGGGACACA GTGGCTATTT TCGACAGAGA TGTTTTTTCC CTTCTCTACT CGGTATTGCA         120

GCGACTGGCT CCAGACATGG TAACGGATCG TCGGGATTAA CCAGACTAGC TAGATATGTT         180

TCATTTATCT GGATCGTACT ATTCTTAGTC GGTCCCCGTC CAGTAGAGGG TCAATCTGGA         240

AGCACATCGG AACAACCCCG GCGGACTGTA GCTACCCCTG AGGTAGGGGG TACACCACCA         300

AAACCAACTA CAGATCCCAC CGATATGTCG GATATGAGGG AAGCTCTCCG TGCGTCCCAA         360

ATAGAGGCTA ACGGACCATC GACTTTCTAT ATGTGTCCAC CACCTTCAGG ATCTACTGTC         420

GTGCGTTTAG AGCCACCACG GGCCTGTCCA GATTATAAAC TAGGGAAAAA TTTTACCGAG         480

GGTATAGCTG TAATATTTAA AGAAAATATA GCGCCATATA AATTCAAGGC AAATATATAC         540

TATAAAAACA TTATTATGAC AACGGTATGG TCTGGGAGTT CCTATGCCGT TACAACCAAC         600

CGATATACAG ACAGGGTTCC CGTGAAAGTT CAAGAGATTA CAGATCTCAT AGATAGACGG         660

GGTATGTGCC TCTCGAAAGC TGATTACGTT CGTAACAATT ATCAATTTAC GGCCTTTGAT         720

CGAGACGAGG ATCCCAGAGA ACTGCCTCTG AAACCCTCCA AGTTCAACAC TCCAGAGTCC         780

CGTGGATGGC ACACCACCAA TGAAACATAC ACAAAGATCG GTGCTGCTGG ATTTCACCAC         840

TCTGGGACCT CTGTAAATTG CATCGTAGAG GAAGTGGATG CAAGATCTGT ATATCCATAT         900

GACTCATTTG CTATCTCCAC TGGTGACGTG ATTCACATGT CTCCATTCTT TGGGCTGAGG         960

GATGGAGCCC ATGTAGAACA TACTAGTTAT TCTTCAGACA GATTTCAACA AATCGAGGGA        1020

TACTATCCAA TAGACTTGGA TACGCGATTA CAACTGGGGG CACCAGTTTC TCGCAATTTT        1080

TTGGAAACTC CGCATGTGAC AGTGGCCTGG AACTGGACCC CAAAGTCTGG TCGGGTATGT        1140

ACCTTAGCCA AATGGAGGGA AATAGATGAA ATGCTACGCG ATGAATATCA GGGCTCCTAT        1200

AGATTTACAG CCAAGACCAT ATCCGCTACT TTCATCTCCA ATACTTCACA ATTTGAAATC        1260

AATCGTATCC GTTTGGGGGA CTGTGCCACC AAGGAGGCAG CCGAAGCCAT AGACCGGATT        1320

TATAAGAGTA AATATAGTAA AACTCATATT CAGACTGGAA CCCTGGAGAC CTACCTAGCC        1380

CGTGGGGGAT TTCTAATAGC TTTCCGTCCC ATGATCAGCA ACGAACTAGC AAAGTTATAT        1440

ATCAATGAAT TAGCACGTTC CAATCGCACG GTAGATCTCA GTGCACTCCT CAATCCATCT        1500

GGGGAAACAG TACAACGAAC TAGAAGATCG GTCCCATCTA ATCAACATCA TAGGTCGCGG        1560

CGCAGCACAA TAGAGGGGGG TATAGAAACC GTGAACAATG CATCACTCCT CAAGACCACC        1620

TCATCTGTGG AATTCGCAAT GCTACAATTT GCCTATGACT ACATACAAGC CCATGTAAAT        1680

GAAATGTTGA GTCGGATAGC CACTGCCTGG TGTACACTTC AGAACCGCGA ACATGTGCTG        1740

TGGACAGAGA CCCTAAAACT CAATCCCGGT GGGGTGGTCT CGATGGCCCT AGAACGTCGT        1800

GTATCCGCGC GCCTACTTGG AGATGCCGTC GCCGTAACAC AATGTGTTAA CATTTCTAGC        1860

GGACATGTCT ATATCCAAAA TTCTATGCGG GTGACGGGTT CATCAACGAC ATGTTACAGC        1920
```

-continued

```
CGCCCTCTTG TTTCCTTCCG TGCCCTCAAT GACTCCGAAT ACATAGAAGG ACAACTAGGG    1980

GAAAACAATG AACTTCTCGT GGAACGAAAA CTAATTGAGC CTTGCACTGT CAATAATAAG    2040

CGGTATTTTA AGTTTGGGGC AGATTATGTA TATTTTGAGG ATTATGCGTA TGTCCGTAAA    2100

GTCCCGCTAT CGGAGATAGA ACTGATAAGT GCGTATGTGA ATTTAAATCT TACTCTCCTA    2160

GAGGATCGTG AATTTCTCCC ACTCGAAGTT TATACACGAG CTGAGCTGGA AGATACCGGC    2220

CTTTTGGACT ACAGCGAGAT TCAACGCCGC AACCAACTCC ACGCCTTAAA ATTTTATGAT    2280

ATAGACAGCA TAGTCAGAGT GGATAATAAT CTTGTCATCA TGCGTGGTAT GGCAAATTTC    2340

TTTCAGGGAC TCGGGGATGT GGGGGCTGGT TTCGGCAAGG TGGTCTTAGG GGCTGCGAGT    2400

GCGGTAATCT CAACAGTATC AGGCGTATCA TCATTTCTAA ACAACCCATT TGGAGCATTG    2460

GCCGTGGGAC TGTTAATATT AGCTGGCATC GTCGCAGCAT TCCTGGCATA TCGCTATATA    2520

TCTAGATTAC GTGCAAATCC AATGAAAGCC TTATATCCTG TGACGACTAG GAATTTGAAA    2580

CAGACGCTAA GAGCCCGCTC AACGGCTGGT GGGGATAGCG ACCCGGGAGT CGATGACTTC    2640

GATGAGGAAA AGCTAATGCA GGCAAGGGAG ATGATAAAAT ATATGTCCCT CGTATCGGCT    2700

ATGGAGCAAC AAGAACATAA GGCGATGAAA AAGAATAAGG GCCCAGCGAT CCTAACGAGT    2760

CATCTCACTA ACATGGCCCT CCGTCGCCGT GGACCTAAAT ACCAACGCCT CAATAATCTT    2820

GATAGCGGTG ATGATACTGA AACAAATCTT GTCTAA                             2856
```

(2) INFORMATION FOR SEQ ID NO:5:

(i) SEQUENCE CHARACTERISTICS:
        (A) LENGTH: 6649 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GACTTTGACT GCGGCTACGT AGCGGCCGCG TCGACATGCA TTGTTAGTTC TGTAGATCAG      60

TAACGTATAG CATACGAGTA TAATTATCGT AGGTAGTAGG TATCCTAAAA TAAATCTGAT     120

ACAGATAATA ACTTTGTAAA TCAATTCAGC AATTTCTCTA TTATCATGAT AATGATTAAT     180

ACACAGCGTG TCGTTATTTT TTGTTACGAT AGTATTTCTA AAGTAAAGAG CAGGAATCCC     240

TAGTATAATA GAAATAATCC ATATGAAAAA TATAGTAATG TACATATTTC TAATGTTAAC     300

ATATTTATAG GTAAATCCAG GAAGGGTAAT TTTTACATAT CTATATACGC TTATTACAGT     360

TATTAAAAAT ATACTTGCAA ACATGTTAGA AGTAAAAAAG AAAGAACTAA TTTTACAAAG     420

TGCTTTACCA AAATGCCAAT GGAAATTACT TAGTATGTAT ATAATGTATA AAGGTATGAA     480

TATCACAAAC AGCAAATCGG CTATTCCCAA GTTGAGAAAC GGTATAATAG ATATATTTCT     540

AGATACCATT AATAACCTTA TAAGCTTGAC GTTTCCTATA ATGCCTACTA AGAAAACTAG     600

AAGATACATA CATACTAACG CCATACGAGA GTAACTACTC ATCGTATAAC TACTGTTGCT     660

AACAGTGACA CTGATGTTAT AACTCATCTT TGATGTGGTA TAAATGTATA ATAACTATAT     720

TACACTGGTA TTTTATTTCA GTTATATACT ATATAGTATT AAAAATTATA TTTGTATAAT     780

TATATTATTA TATTCAGTGT AGAAAGTAAA ATACTATAAA TATGTATCTC TTATTTATAA     840

CTTATTAGTA AAGTATGTAC TATTCAGTTA TATTGTTTTA TAAAAGCTAA ATGCTACTAG     900

ATTGATATAA ATGAATATGT AATAAATTAG TAATGTAGTA TACTAAATATT AACTCACATT     960

TGACTAATTA GCTATAAAAA CCCGGGCTGC AGCCCGGGAA GCTTACAAAA ATTAGACAAG    1020
```

-continued

```
ATTTGTTTCA GTATCATCAC CGCTATCAAG ATTATTGAGG CGTTGGTATT TAGGTCCACG    1080

GCGACGGAGG GCCATGTTAG TGAGATGACT CGTTAGGATC GCTGGGCCCT TATTCTTTTT    1140

CATCGCCTTA TGTTCTTGTT GCTCCATAGC CGATACGAGG GACATATATT TTATCATCTC    1200

CCTTGCCTGC ATTAGCTTTT CCTCATCGAA GTCATCGACT CCCGGGTCGC TATCCCCACC    1260

AGCCGTTGAG CGGGCTCTTA GCGTCTGTTT CAAATTCCTA GTCGTCACAG GATATAAGGC    1320

TTTCATTGGA TTTGCACGTA ATCTAGATAT ATAGCGATAT GCCAGGAATG CTGCGACGAT    1380

GCCAGCTAAT ATTAACAGTC CCACGGCCAA TGCTCCAAAT GGGTTGTTTA GAAATGATGA    1440

TACGCCTGAT ACTGTTGAGA TTACCGCACT CGCAGCCCCT AAGACCACCT TGCCGAAACC    1500

AGCCCCCACA TCCCCGAGTC CCTGAAAGAA ATTTGCCATA CCACGCATGA TGACAAGATT    1560

ATTATCCACT CTGACTATGC TGTCTATATC ATAAAATTTT AAGGCGTGGA GTTGGTTGCG    1620

GCGTTGAATC TCGCTGTAGT CCAAAAGGCC GGTATCTTCC AGCTCAGCTC GTGTATAAAC    1680

TTCGAGTGGG AGAAATTCAC GATCCTCTAG GAGAGTAAGA TTTAAATTCA CATACGCACT    1740

TATCAGTTCT ATCTCCGATA GCGGGACTTT ACGGACATAC GCATAATCCT CAAAATATAC    1800

ATAATCTGCC CCAAACTTAA AATACCGCTT ATTATTGACA GTGCAAGGCT CAATTAGTTT    1860

TCGTTCCACG AGAAGTTCAT TGTTTTCCCC TAGTTGTCCT TCTATGTATT CGGAGTCATT    1920

GAGGGCACGG AAGGAAACAA GAGGGCGGCT GTAACATGTC GTTGATGAAC CCGTCACCCG    1980

CATAGAATTT TGGATATAGA CATGTCCGCT AGAAATGTTA ACACATTGTG TTACGGCGAC    2040

GGCATCTCCA AGTAGGCGCG CGGATACACG ACGTTCTAGG GCCATCGAGA CCACCCCACC    2100

GGGATTGAGT TTTAGGGTCT CTGTCCACAG CACATGTTCG CGGTTCTGAA GTGTACACCA    2160

GGCAGTGGCT ATCCGACTCA ACATTTCATT TACATGGGCT TGTATGTAGT CATAGGCAAA    2220

TTGTAGCATT GCGAATTCCA CAGATGAGGT GGTCTTGAGG AGTGATGCAT TGTTCACGGT    2280

TTCTATACCC CCCTCTATTG TGCTGCGCCG CGACCTATGA TGTTGATTAG ATGGGACCGA    2340

TCTTCTAGTT CGTTGTACTG TTTCCCCAGA TGGATTGAGG AGTGCACTGA GATCTACCGT    2400

GCGATTGGAA CGTGCTAATT CATTGATATA TAACTTTGCT AGTTCGTTGC TGATCATGGG    2460

ACGGAAAGCT ATTAGAAATC CCCCACGGGC TAGGTAGGTC TCCAGGGTTC CAGTCTGAAT    2520

ATGAGTTTTA CTATATTTAC TCTTATAAAT CCGGTCTATG GCTTCGGCTG CCTCCTTGGT    2580

GGCACAGTCC CCCAAACGGA TACGATTGAT TTCAAATTGT GAAGTATTGG AGATGAAAGT    2640

AGCGGATATG GTCTTGGCTG TAAATCTATA GGAGCCCTGA TATTCATCGC GTAGCATTTC    2700

ATCTATTTCC CTCCATTTGG CTAAGGTACA TACCCGACCA GACTTTGGGG TCCAGTTCCA    2760

GGCCACTGTC ACATGCGGAG TTTCCAAAAA ATTGCGAGAA ACTGGTGCCC CCAGTTGTAA    2820

TCGCGTATCC AAGTCTATTG GATAGTATCC CTCGATTTGT TGAAATCTGT CTGAAGAATA    2880

ACTAGTATGT TCTACATGGG CTCCATCCCT CAGCCCAAAG AATGGAGACA TGTGAATCAC    2940

GTCACCAGTG GAGATAGCAA ATGAGTCATA TGGATATACA GATCTTGCAT CCACTTCCTC    3000

TACGATGCAA TTTACAGAGG TCCCAGAGTG GTGAAATCCA GCAGCACCGA TCTTTGTGTA    3060

TGTTTCATTG GTGGTGTGCC ATCCACGGGA CTCTGGAGTG TTGAACTTGG AGGGTTTCAG    3120

AGGCAGTTCT CTGGGATCCT CGTCTCGATC AAAGGCCGTA AATTGATAAT TGTTACGAAC    3180

GTAATCAGCT TTCGAGAGGC ACATACCCCG TCTATCTATG AGATCTGTAA TCTCTTGAAC    3240

TTTCACGGGA ACCCTGTCTG TATATCGGTT GGTTGTAACG GCATAGGAAC TCCCAGACCA    3300

TACCGTTGTC ATAATAATGT TTTTATAGTA TATATTTGCC TTGAATTTAT ATGGCGCTAT    3360

ATTTTCTTTA AATATTACAG CTATACCCTC GGTAAAATTT TCCCTAGTT TATAATCTGG     3420
```

```
ACAGGCCCGT GGTGGCTCTA AACGCACGAC AGTAGATCCT GAAGGTGGTG GACACATATA    3480

GAAAGTCGAT GGTCCGTTAG CCTCTATTTG GGACGCACGG AGAGCTTCCC TCATATCCGA    3540

CATATCGGTG GGATCTGTAG TTGGTTTTGG TGGTGTACCC CCTACCTCAG GGGTAGCTAC    3600

AGTCCGCCGG GGTTGTTCCG ATGTGCTTCC AGATTGACCC TCTACTGGAC GGGGACCGAC    3660

TAAGAATAGT ACGATCCAGA TAAATGAAAC ATATCTAGCT AGTCTGGTTA ATCCCGACGA    3720

TCCGTTACCA TGTCTGGAGC CAGTCGCTGC AATACCGAGT AGAGAAGGGA AAAAACATCT    3780

CTGTCGAAAA TAGCCACTGT GTCCCTGCCA ACGACTCCCT CGTCGCCGCT TCCCAAGATC    3840

GCCACGAGTG GACATTACGA TACAAACTTA ACGGATATCG CGATAATGAA ATAATTTATG    3900

ATTATTTCTC GCTTTCAATT TAACACAACC CTCAAGAACC TTTGTATTTA TTTTCACTTT    3960

TTAAGTATAG AATAAAGAAG CTCTAATTAA TTAAGCTACA AATAGTTTCG TTTTCACCTT    4020

GTCTAATAAC TAATTAATTA ACCCGGATCG ATCCGATTT TTATGACTAG TTAATCAAAT    4080

AAAAAGCATA CAAGCTATTG CTTCGCTATC GTTACAAAAT GGCAGGAATT TTGTGTAAAC    4140

TAAGCCACAT ACTTGCCAAT GAAAAAAATA GTAGAAAGGA TACTATTTTA ATGGGATTAG    4200

ATGTTAAGGT TCCTTGGGAT TATAGTAACT GGGCATCTGT TAACTTTTAC GACGTTAGGT    4260

TAGATACTGA TGTTACAGAT TATAATAATG TTACAATAAA ATACATGACA GGATGTGATA    4320

TTTTTCCTCA TATAACTCTT GGAATAGCAA ATATGGATCA ATGTGATAGA TTTGAAAATT    4380

TCAAAAAGCA ATAACTGAT CAAGATTTAC AGACTATTTC TATAGTCTGT AAAGAAGAGA    4440

TGTGTTTTCC TCAGAGTAAC GCCTCTAAAC AGTTGGGAGC GAAAGGATGC GCTGTAGTTA    4500

TGAAACTGGA GGTATCTGAT GAACTTAGAG CCCTAAGAAA TGTTCTGCTG AATGCGGTAC    4560

CCTGTTCGAA GGACGTGTTT GGTGATATCA CAGTAGATAA TCCGTGGAAT CCTCACATAA    4620

CAGTAGGATA TGTTAAGGAG GACGATGTCG AAAACAAGAA ACGCCTAATG GAGTGCATGT    4680

CCAAGTTTAG GGGGCAAGAA ATACAAGTTC TAGGATGGTA TTAATAAGTA TCTAAGTATT    4740

TGGTATAATT TATTAAATAG TATAATTATA ACAAATAATA AATAACATGA TAACGGTTTT    4800

TATTAGAATA AAATAGAGAT AATATCATAA TGATATATAA TACTTCATTA CCAGAAATGA    4860

GTAATGGAAG ACTTATAAAT GAACTGCATA AAGCTATAAG GTATAGAGAT ATAAATTTAG    4920

TAAGGTATAT ACTTAAAAAA TGCAAATACA ATAACGTAAA TATACTATCA ACGTCTTTGT    4980

ATTTAGCCGT AAGTATTTCT GATATAGAAA TGGTAAAATT ATTACTAGAA CACGGTGCCG    5040

ATATTTTAAA ATGTAAAAAT CCTCCTCTTC ATAAAGCTGC TAGTTTAGAT AATACAGAAA    5100

TTGCTAAACT ACTAATAGAT TCTGGCGCTG ACATAGAACA GATACATTCT GGAAATAGTC    5160

CGTTATATAT TTCTGTATAT AGAAACAATA AGTCATTAAC TAGATATTTA TTAAAAAAAG    5220

GTGTTAATTG TAATAGATTC TTTCTAAATT ATTACGATGT ACTGTATGAT AAGATATCTG    5280

ATGATATGTA TAAAATATTT ATAGATTTTA ATATTGATCT TAATATACAA ACTAGAAATT    5340

TTGAAACTCC GTTACATTAC GCTATAAAGT ATAAGAATAT AGATTTAATT AGGATATTGT    5400

TAGATAATAG TATTAAAATA GATAAAAGTT TATTTTGCA TAAACAGTAT CTCATAAAGG    5460

CACTTAAAAA TAATTGTAGT TACGATATAA TAGCGTTACT TATAAATCAC GGAGTGCCTA    5520

TAAACGAACA AGATGATTTA GGTAAAACCC CATTACATCA TTCGGTAATT AATAGAAGAA    5580

AAGATGTAAC AGCACTTCTG TTAAATCTAG GAGCTGATAT AAACGTAATA GATGACTGTA    5640

TGGGCAGTCC CTTACATTAC GCTGTTTCAC GTAACGATAT CGAAACAACA AAGACACTTT    5700

TAGAAAGAGG ATCTAATGTT AATGTGGTTA ATAATCATAT AGATACCGTT CTAAATATAG    5760
```

-continued

| | |
|---|---|
|CTGTTGCATC TAAAAACAAA ACTATAGTAA ACTTATTACT GAAGTACGGT ACTGATACAA|5820|
|AGTTGGTAGG ATTAGATAAA CATGTTATTC ACATAGCTAT AGAAATGAAA GATATTAATA|5880|
|TACTGAATGC GATCTTATTA TATGGTTGCT ATGTAAACGT CTATAATCAT AAAGGTTTCA|5940|
|CTCCTCTATA CATGGCAGTT AGTTCTATGA AAACAGAATT TGTTAAACTC TTACTTGACC|6000|
|ACGGTGCTTA CGTAAATGCT AAAGCTAAGT TATCTGGAAA TACTCCTTTA CATAAAGCTA|6060|
|TGTTATCTAA TAGTTTTAAT AATATAAAAT TACTTTTATC TTATAACGCC GACTATAATT|6120|
|CTCTAAATAA TCACGGTAAT ACGCCTCTAA CTTGTGTTAG CTTTTTAGAT GACAAGATAG|6180|
|CTATTATGAT AATATCTAAA ATGATGTTAG AAATATCTAA AAATCCTGAA ATAGCTAATT|6240|
|CAGAAGGTTT TATAGTAAAC ATGGAACATA TAAACAGTAA TAAAAGACTA CTATCTATAA|6300|
|AAGAATCATG CGAAAAAGAA CTAGATGTTA TAACACATAT AAAGTTAAAT TCTATATATT|6360|
|CTTTTAATAT CTTTCTTGAC AATAACATAG ATCTTATGGT AAAGTTCGTA ACTAATCCTA|6420|
|GAGTTAATAA GATACCTGCA TGTATACGTA TATATAGGGA ATTAATACGG AAAAATAAAT|6480|
|CATTAGCTTT TCATAGACAT CAGCTAATAG TTAAAGCTGT AAAAGAGAGT AAGAATCTAG|6540|
|GAATAATAGG TAGGTTACCT ATAGATATCA AACATATAAT AATGGAACTA TTAAGTAATA|6600|
|ATGATTTACA TTCTGTTATC ACCAGCTGTT GTAACCCAGT AGTATAAAG|6649|

(2) INFORMATION FOR SEQ ID NO:6:

(i) SEQUENCE CHARACTERISTICS:
        (A) LENGTH: 10962 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

| | |
|---|---|
|CCTTTTTTTT TCATTATTTA GAAATTATGC ATTTTAGATC TTTATAAGCG GCCGTGATTA|60|
|ACTAGTCATA AAAACCCGGG ATCGATTCTA GACTCGAGGG TACCGGATCT TAATAAAAAA|120|
|AGTAATAAAT CTTTAATACG TAAAATCTAG AAATATTCGC CGGCACTAAT TGATCAGTAT|180|
|TTTTGGGCCC TAGCTAAGAT CTGAGCTCCC ATGGCCTAGA ATTATAATTA GTCATCAGGC|240|
|AGGGCGAGAA CGAGACTATC TGCTCGTTAA TTAATTAGGT CGACGGATCC CCCAACAAAA|300|
|ACTAATCAGC TATCGGGGTT AATTAATTAG TTATATTAAT CAGTAGTCCG TCCCGCTCTT|360|
|GCTCTGATAG ACGAGCAATT AATTAATCCA GCTGCCTAGG GGGTTGTTTT TGATTAGTCG|420|
|ATAGCCCCAA TTAATTAATC AATATAGACA AGGTGAAAAC GAAACTATTT GTAGCTTAAT|480|
|TAATTAGAGC TTCTTTATTC TATACTTAAA AAGTGAAAAT AAATACAAAG GTTCTTGAGG|540|
|GTTGTGTTAA ATTGATCTGT TCCACTTTTG CTTTGATAAA CATCGAATTA ATTAATCTCG|600|
|AAGAAATAAG ATATGAATTT TTCACTTTTA TTTATGTTTC CAAGAACTCC CAACACAATT|660|
|TAACTAAAGC GAGAAATAAT CATAAATTAT TTCATTATCG CGATATCCGT TAAGTTTGTA|720|
|TCGTAATGCC ACTAACAGAA GAAGCAGAGC TAGAACTGGA AGAAAACTTT CGCTCTTTAT|780|
|TAGTATTTAA TAAAGTAATA GCGCTATAGG CAATTCAAAC ATAGCATTAC GGTGATTGTC|840|
|TTCTTCGTCT CGATCTTGAC CGTCTTTTGT TTGGAAGGAA GATAGAGAGA TTCTAAAAGA|900|
|ACCAGTACAT GGAGTGTATT ATGACCCATC AAAAGACTTA ATAGCAGAAA TACAGAAGCA|960|
|GGGGCAAGGC CAATCTCTCT AAGATTTTCT TGGTCATGTA CCTCACATAA TACTGGGTAG|1020|
|TTTTCTGAAT TATCGTCTTT ATGTCTTCGT CCCCGTTCCG GTTAGGGAGA TTAAAAGGGG|1080|

-continued

```
GGGTTGGACA TATCAAATTT ATCAAGAGCC ATTTAAAAAT CTGAAAACAG GAATGGAGTG    1140

GAGATTTGAT TCTAGATTAG CATTTCATCA CGTAACCTGT ATAGTTTAAA TAGTTCTCGG    1200

TAAATTTTTA GACTTTTGTC CTTACCTCAC CTCTAAACTA AGATCTAATC GTAAAGTAGT    1260

GCATTTTGTG GATGTGTAGA AGAAATGCTA GAGAATTACA TCCTGAATAT TTTAAAAATT    1320

GTAAGCTTAT GGCAATATTC CAAAGTAGCA TGACAAAAAT CTTAGAGCCT TTTAGACGAT    1380

CTCTTAATGT AGGACTTATA AAATTTTTAA CATTCGAATA CCGTTATAAG GTTTCATCGT    1440

ACTGTTTTTA GAATCTCGGA AAATCTAAAG GGTACTAAGT TGAGTAAACA AAATCCAGAC    1500

ATAGTTATCT ATCAATACAT GGATGATTTG TATGTAGGAT CTGACTTAGA AATAGGGCAG    1560

CATAGAACAA AAATATTTGT TTTAGGTCTG TATCAATAGA TAGTTATGTA CCTACTAAAC    1620

ATACATCCTA GACTGAATCT TTATCCCGTC GTATCTTGTT TTTATGAAAT GTTAATAGAG    1680

GGAGTTGAGG AGCTGAGACA ACATCTGTTG AGGTGGGGAC TTACAACCAT GGTAGGTTTT    1740

CCAGTAACAC CTCAAGTACC TTTAAGACCA ATGACTCTCC TCGACTCTGT TGTAGACAAC    1800

TCCACCCCTG AATGTTGGTA CCATCCAAAA GGTCATTGTG GAGTTCATGG AAATTCTGGT    1860

TACTGAGGAG GAGTGTTTAG ATGAAGTTTT ACAAAGCAGC TGTAGATCTT TCTCACTTTT    1920

TAAAAGAAAA AGGAGGTTTA GAAGGGCTAA TTCATTCTCA ACGAAGACAA GATATTCTTA    1980

TGTTTCGTCG ACATCTAGAA AGAGTGAAAA ATTTTCTTTT TCCTCCAAAT CTTCCCGATT    2040

AAGTAAGAGT TGCTTCTGTT CTATAAGAAT AAAAAAGGGG GGAGAGGATG ATTTGTGGAT    2100

TTATCATACA CAAGGATATT TTCCTGATTG GCAGAATTAC ACACCAGGAC CAGGAGTCAG    2160

ATACCCATTA ACCTTTGGTC TAAACACCTA AATAGTATGT GTTCCTATAA AAGGACTAAC    2220

CGTCTTAATG TGTGGTCCTG GTCCTCAGTC TATGGGTAAT TGGAAACCAA TTTGGTATGA    2280

TTGGAAGTTG TTGGTGCTAC AAGCTAGTAC CAATGATTGA GACTGTACCA GTAAAATTAA    2340

AGCCAGGAAT GGATGGCCCA AAAGTTAAAC AATGGCCATT GACCACGATG TTCGATCATG    2400

GTTACTAACT CTGACATGGT CATTTTAATT TCGGTCCTTA CCTACCGGGT TTTCAATTTG    2460

TTACCGGTAA CTCTATGTAA GTAGAGTTAC AGAAGAAAAA ATAAAAGCAT TAGTAGAAAT    2520

TTGTACAGAG ATGGAAAAGG AAGGGAAAAT TTCAAAAATT GGGCCTTAAT TTTTCTTGTC    2580

TTCTTTTTTA TTTTCGTAAT CATCTTTAAA CATGTCTCTA CCTTTTCCTT CCCTTTTAAA    2640

GTTTTTAACC CGGAATTAAA AAGATGGAAA GCTGTGGGGT GCAGCCCGGG GGATCCTTTT    2700

TATAGCTAAT TAGTCACGTA CCTTTGAGAG TACCACTTCA GCTACCTCTT TTGTGTCTCA    2760

GAGTAACTTT CTTTAATCAA TTCCAAAACA CGTCGGGCCC CCTAGGAAAA ATATCGATTA    2820

ATCAGTGCAT GGAAACTCTC ATGGTGAAGT CGATGGAGAA AACACAGAGT CTCATTGAAA    2880

GAAATTAGTT AAGGTTTTGT GAGAGTAAAT TACTAGCAGA AGCTAAGAGC GGAGCACCAT    2940

AGACCATAGG AGGAGCAGAT AATGTAGTAT ACTAATATTA ACTCACATTT GACTAATTAG    3000

CTATAAAAAC CCGGGATCGA TTCTAGAATA AAAATTATCC CTGCCTAACT CTATTCACTA    3060

CAGAGAGTAC AGCAAAAACA TTACATCATA TGATTATAAT TGAGTGTAAA CTGATTAATC    3120

GATATTTTTG GGCCCTAGCT AAGATCTTAT TTTTAATAGG GACGGATTGA GATAAGTGAT    3180

GTCTCTCATG TCGTTTTTGC AGAGATAAGT ATTCTTAAAC CTACCAAGCC TCCTACTATC    3240

ATTATGAATA ATCTTTTTTC TCTCTGCACC ACTCTTCTCT TTGCCTTGGT GGGTGCTACT    3300

CCTAATGGTT CAATTGTTAC TACTTTATAA TAAGAATTTG GATGGTTCGG AGGATGATAG    3360

TAATACTTAT TAGAAAAAAG AGAGACGTGG TGAGAAGAGA AACGGAACCA CCCACGATGA    3420

GGATTACCAA GTTAACAATG ATGAAATATG GGATAGTTAA GGGTTTATAT AATTCACTTC    3480
```

```
TCCAATTGTC CCTCATATCT CCTCCTCCAG GTCTGAAGAT CTCGGTGTCG TTCGTGTCCG    3540

TGTCCTTACC ACCATCTCTT GTTAATAGTA GCCCTGTAAT ATTAAATATA TTAAGTGAAG    3600

AGGTTAACAG GGAGTATAGA GGAGGAGGTC CAGACTTCTA GAGCCACAGC AAGCACAGGC    3660

ACAGGAATGG TGGTAGAGAA CAATTATCAT CGGGACATTA TAAGGGTTTG GTGTGGTGAT    3720

GAACATCTAA TTTGTCCTTC AATGGGAGGG GCATATATTG CTTTTCCTAC TTCCTGCCAC    3780

ATGTTTATAA TTTGTTTTAT TTTGCATTGA AGTGTGATAT TGTTATTTGA CCCTGTACTA    3840

CTTGTAGATT AAACAGGAAG TTACCCTCCC CGTATATAAC GAAAAGGATG AAGGACGGTG    3900

TACAAATATT AAACAAAATA AAACGTAACT TCACACTATA ACAATAAACT GGGACACGAA    3960

GCTGTGGAGT ATTATTCCAA GTATTATTAC CATTCCAAGT ACTATTAAAC AGTGGTGATG    4020

AATTACAGTA GAAGAATTCC CCTCCACAAT TAAAACTGTG CATTACAATT TCTGGGTCCC    4080

CTCCTGATCA TAATAAGGTT CATAATAATG GTAAGGTTCA TGATAATTTG TCACCACTAC    4140

TTAATGTCAT CTTCTTAAGG GGAGGTGTTA ATTTTGACAC GTAATGTTAA AGACCCAGGG    4200

GAGGACTTTG TCGGCGGGGG GATTGATTAA AGACTATTGT TTTATTCTTA AATTGTTCTT    4260

TTAATTTGCT AACTATCTGT CTTAAAGTGT CATTCCATTT TGCTCTACTA ATGTTACAAT    4320

GTGCTTGTCT TATAGTTCCC CTAACTAATT TCTGATAACA AAATAAGAAT TTAACAAGAA    4380

AATTAAACGA TTGATAGACA GAATTTCACA GTAAGGTAAA ACGAGATGAT TACAATGTTA    4440

CACGAACAGA ATATCAAGGT TACATGGGTA TTATATTTTT TGTTGTATAA AATGCTCTCC    4500

CTGGTCCTAT ATGTATCCTT TTTCTTTTAT TGTAGTTGGG TCTTGTACAA TTAATTTGTA    4560

CAGATTCATT CAGATGTACT ATGATGGTAT AATATAAAAA ACAACATATT TTACGAGAGG    4620

GACCAGGATA TACATAGGAA AAAGAAAATA ACATCAACCC AGAACATGTT AATTAAACAT    4680

GTCTAAGTAA GTCTACATGA TACTACCATT AGGTCTGGTT TAGCATTATC ATTGAAATTC    4740

TCAGATCTAA TTACTACCTC TTCTTCTGCT AGACTGCCAT TTAACAGCAG TTGAGTTGAT    4800

ACTACTGGCC TAATTCCATG TGTACATTGT ACTGTGCTAA ATCGTAATAG TAACTTTAAG    4860

AGTCTAGATT AATGATGGAG AAGAAGACGA TCTGACGGTA AATTGTCGTC AACTCAACTA    4920

TGATGACCGG ATTAAGGTAC ACATGTAACA TGACACGAAA GTGTCTGGGA CATTTTTACA    4980

TGATCCTTTT CCACTGAACT TTTTATCGTT ACACTTTAGA ATCGCAAAAC CAGCCGGGGC    5040

ACAATAGTGT ATGGGAATTG GCTCAAAGGA TATCTTTGGA CAAGCTTGCT GTAAAAATGT    5100

ACTAGGAAAA GGTGACTTGA AAAATAGCAA TGTGAAATCT TAGCGTTTTG GTCGGCCCCG    5160

TGTTATCACA TACCCTTAAC CGAGTTTCCT ATAGAAACCT GTTCGAACCG GCAGAACCAG    5220

GTGTAATGAC TGAGGTATTA CAACTTATCA ACCTATAGCT GGTACTATCA TTATTTATTG    5280

ATACTATATC AAGTTTATAA AGAAGTGCAT ATTCTTTCTG CATCTTATCT CTTATGCTTG    5340

TACATTACTG ACTCCATAAT GTTGAATAGT TGGATATCGA CCATGATAGT AATAAATAAC    5400

TATGATATAG TTCAAATATT TCTTCACGTA TAAGAAAGAC GTAGAATAGA GAATACGAAC    5460

ATTCTATGGG GTGATATTGA AAGAGCAGTT TTTCATTTCT CCTCCCTTTA TTGTTCCCTC    5520

GCTATTACTA TTGTTATTAG CAGTACTATT ATTGGTATTA GTAGTATTCC TCAAATCAGT    5580

GCAATTTAAC CACTATAACT TTCTCGTCAA AAAGTAAAGA GGAGGGAAAT AACAAGGGAG    5640

CGATAATGAT AACAATAATC GTCATGATAA TAACCATAAT CATCATAAGG AGTTTAGTCA    5700

CGTTAAATTT CGGTGATTTT TCGGAGTAAC ACAGAGTGGG GTTAATTTTA CACATGGCTT    5760

TAGGCTTTGA TCCCATAAAC TGATTATATC CTCATGCATC TGTTCTACCA TGTTATTTTT    5820
```

-continued

```
CCACATGTTA AAATTTTCTG TCACTCATTG TGTCTCACCC CAATTAAAAT GTGTACCGAA    5880

ATCCGAAACT AGGGTATTTG ACTAATATAG GAGTACGTAG ACAAGATGGT ACAATAAAAA    5940

GGTGTACAAT TTTAAAAGAC AGTGTCTCTG GATTTACCAA TTCTACTTCT TGTGGGTTGG    6000

GGTCTGTGGG TACACAGGCA TGTGTGGCCC AAACATTATG TACCTCTGTA TCATATGCTT    6060

TAGCATCTGA TGCACAAAAT AGAGTGGTGG TTAAATGGTT AAGATGAAGA ACACCCAACC    6120

CCAGACACCC ATGTGTCCGT ACACACCGGG TTTGTAATAC ATGGAGACAT AGTATACGAA    6180

ATCGTAGACT ACGTGTTTTA TCTCACCACC ATCATATAAA CTTTGGTGCT TCTTTCCACA    6240

CAGGTACCCC ATAATAGACT GTGACCCACA ATTTTTCTGT AGCACTACAG ATCATCAACA    6300

TCCCAAGGAG CATGGTGCCC CATCTCCACC CCCATCTCCA CAAGTGACGA AGAAAGGTGT    6360

GTCCATGGGG TATTATCTGA CACTGGGTGT TAAAAAGACA TCGTGATGTC TAGTAGTTGT    6420

AGGGTTCCTC GTACCACGGG GTAGAGGTGG GGGTAGAGGT GTTCACAGTT ACGTGGGGCT    6480

GATATTTCTC CTTCACTCTC ATTGCCACTG TCTTCTGCTC TTTCATATAC GATACAAACT    6540

TAACGCATAT CGCGATAATG AAATAATTTA TGATTATTTC TCGCTTTCAA TTAACACGA    6600

CTATAAAGAG GAAGTGAGAG TAACGGTGAC AGAAGACGAG AAAGTATATG CTATGTTTGA    6660

ATTGCGTATA GCGCTATTAC TTTATTAAAT ACTAATAAAG AGCGAAAGTT AAATTGTGAT    6720

GGACCATAAC CCTCAAGAAC CTTTGTATTT ATTTTCACTT TTAAGTATA GAATAAAGAA     6780

GCTCTAATTA ATTAAGCTAC AAATAGTTTC GTTTTCACCT TGTCTAATAA CTAATTAATT    6840

AACCCGGTTG GGAGTTCTTG GAAACATAAA TAAAAGTGAA AAATTCATAT CTTATTTCTT    6900

CGAGATTAAT TAATTCGATG TTTATCAAAG CAAAAGTGGA ACAGATTATT GATTAATTAA    6960

TTGGGCCACC ATATCTTGAG ATAAAGTGAA AATATATATC ATTATATTAC AAAGTACAAT    7020

TATTTAGGTT TAATCATGGG TGCGAGAGCG TCAGTATTAA GCGGGGGAGA ATTAGATCGA    7080

TGGGAAAAAA TTTAGAACTC TATTTCACTT TTATATATAG TAATATAATG TTTCATGTTA    7140

ATAAATCCAA ATTAGTACCC ACGCTCTCGC AGTCATAATT CGCCCCCTCT TAATCTAGCT    7200

ACCCTTTTTT AAACCATGAA GGGAGGCGGT TAAGGCCAGG GGGAAAGAAA AAATATAAAT    7260

TAAAACATAT AGTATGGGCA AGCAGGGAGC TAGAACGATT CGCAGTTAAT CCTGGCCTGT    7320

TAGAAACATC AGAAGGCTGT AGACAAGCCA ATTCCGGTCC CCCTTTCTTT TTTATATTTA    7380

ATTTTGTATA TCATACCCGT TCGTCCCTCG ATCTTGCTAA GCGTCAATTA GGACCGGACA    7440

ATCTTTGTAG TCTTCCGACA TCTGTTGGAA GTGCGAGGAT ACTGGGACAG CTACAACCAT    7500

CCCTTCAGAC AGGATCAGAA GAACTTAGAT CATTATATAA TACAGTAGCA ACCCTCTATT    7560

GTGTGCATCA AAGGATAGAG ATAAAAGACA CCAAGGAATA TGACCCTGTC GATGTTGGTA    7620

GGGAAGTCTG TCCTAGTCTT CTTGAATCTA GTAATATATT ATGTCATCGT TGGGAGATAA    7680

CACACGTAGT TTCCTATCTC TATTTTCTGT GGTTCCTTGT GTATCTGAGG CTTTAGACA    7740

AGATAGAGGA AGAGCAAAAC AAAAGTAAGA AAAAGCACA GCAAGCAGCA GCTGACACAG     7800

GACACAGCAA TCAGGTCAGC CAAAATTACC CTATAGTGCA GAACATCCAG CGAAATCTGT    7860

TCTATCTCCT TCTCGTTTTG TTTTCATTCT TTTTTCGTGT CGTTCGTCGT CGACTGTGTC    7920

CTGTGTCGTT AGTCCAGTCG GTTTTAATGG GATATCACGT CTTGTAGGTC AAAAATGGAG    7980

GGGGCAAATG GTACATCAGG CCATATCACC TAGAACTTTA AATGCATGGG TAAAAGTAGT    8040

AGAAGAGAAG GCTTTCAGCC CAGAAGTGAT ACCCATGTTT TCAGCATTAT CAGAAGGAGC    8100

CCCCGTTTAC CATGTAGTCC GGTATAGTGG ATCTTGAAAT TTACGTACCC ATTTTCATCA    8160

TCTTCTCTTC CGAAAGTCGG GTCTTCACTA TGGGTACAAA AGTCGTAATA GTCTTCCTCG    8220
```

-continued

```
GGATAAAGAG AGGACCCCAC AAGATTTAAA CACCATGCTA AACACAGTGG GGGGACATCA    8280

AGCAGCCATG CAAATGTTAA AAGAGACCAT CAATGAGGAA GCTGCAGAAT GGGATAGAGT    8340

GCATCCAGTG CATTGGGGTG TTCTAAATTT GTGGTACGAT TTGTGTCACC CCCCTGTAGT    8400

TCGTCGGTAC GTTTACAATT TTCTCTGGTA GTTACTCCTT CGACGTCTTA CCCTATCTCA    8460

CGTAGGTCAC GTATTTGGAA TAAGAGGGCA GGGCCTATTG CACCAGGCCA GATGAGAGAA    8520

CCAAGGGGAA GTGACATAGC AGGAACTACT AGTACCCTTC AGGAACAAAT AGGATGGATG    8580

ACAAATAATC CACCTATCCC AGTAGGACGT CCCGGATAAC GTGGTCCGGT CTACTCTCTT    8640

GGTTCCCCTT CACTGTATCG TCCTTGATGA TCATGGGAAG TCCTTGTTTA TCCTACCTAC    8700

TGTTTATTAG GTGGATAGGG TCATCCTAGA GGAGTTTGTG GAGGGAAATT TATAAAAGAT    8760

GGATAATCCT GGGATTAAAT AAAATAGTAA GAATGTATAG CCCTACCAGC ATTCTGGACA    8820

TAAGACAAGG ACCAAAAGAA CCCTTTAGAG ACTATGTAGA CCGGCTTTAA ATATTTTCTA    8880

CCTATTAGGA CCCTAATTTA TTTTATCATT CTTACATATC GGGATGGTCG TAAGACCTGT    8940

ATTCTGTTCC TGGTTTTCTT GGGAAATCTC TGATACATCT GGCCGTGGAG GTTCTATAAA    9000

ACTCTAAGAG CCGAGCAAGC TTCACAGGAG GTAAAAAATT GGATGACAGA AACCTTGTTG    9060

GTCCAAAATG CGAACCCAGA TTGTAAGACT ATTTTAAAAG CATTGGGACC AAAGATATTT    9120

TGAGATTCTC GGCTCGTTCG AAGTGTCCTC CATTTTTTAA CCTACTGTCT TTGGAACAAC    9180

CAGGTTTTAC GCTTGGGTCT AACATTCTGA TAAAATTTTC GTAACCCTGG TTAATTACTA    9240

GGAGGGCGGC TACACTAGAA GAAATGATGA CAGCATGTCA GGGAGTAGGA GGACCCGGCC    9300

ATAAGGCAAG AGTTTTGGCT GAAGCAATGA GCCAAGTAAC AAATTCAGCT ACCATAATGA    9360

TGCAGCGCCG ATGTGATCTT CTTTACTACT GTCGTACAGT CCCTCATCCT CCTGGGCCGG    9420

TATTCCGTTC TCAAAACCGA CTTCGTTACT CGGTTCATTG TTTAAGTCGA TGGTATTACT    9480

ACGTCAATTA CGGGGAAATA TGAGGAGAGG CAATTTTAGG AACCAAAGAA AGATTGTTAA    9540

GTGTTTCAAT TGTGGCAAAG AAGGGCACAC AGCCAGAAAT TGCAGGGCCC CTAGGAAAAA    9600

GGGCTGTTGG AAATGTGGAA AGGAATCTCC GTTAAAATCC TTGGTTTCTT TCTAACAATT    9660

CACAAAGTTA ACACCGTTTC TTCCCGTGTG TCGGTCTTTA ACGTCCCGGG GATCCTTTTT    9720

CCCGACAACC TTTACACCTT TCCTTGCCGG TACAGCCGGA GGGGACACCA AATGAAAGAT    9780

TGTACTGAGA GACAGGCTAA TTTTTTAGGG AAGATCTGGC CTTCCTACAA GGGAAGGCCA    9840

GGGAATTTTC TTCAGAGCAG ACCAGAGCCA ACAGCCCCAC CACCTGTGGT TTACTTTCTA    9900

ACATGACTCT CTGTCCGATT AAAAAATCCC TTCTAGACCG GAAGGATGTT CCCTTCCGGT    9960

CCCTTAAAAG AAGTCTCGTC TGGTCTCGGT TGTCGGGGTG GTGCTAGGGT AGAGGGAAGA    10020

GAGCTTCAGG TCTGGGGTAG AGACAACAAC TCCCCCTCAG AAGCAGGAGC CGATAGACAA    10080

GGAACTGTAT CCTTTAACTT CCCTCAGATC ACTCTTTGGC AACGACCCCT CGTCACTTCT    10140

CTCGAAGTCC AGACCCCATC TCTGTTGTTG AGGGGGAGTC TTCGTCCTCG GCTATCTGTT    10200

CCTTGACATA GGAAATTGAA GGGAGTCTAG TGAGAAACCG TTGCTGGGGA GCAGTGTTTT    10260

GTGAGGCAAT AAAGATAGGG GGGCAACTAA AGGAAGCTCT ATTAGATACA GGAGCAGATG    10320

ATACAGTATT AGAAGAAATG AGTTTGCCAG GAAGATGGAA ACCAAAAATG ATAGGGGAA    10380

TTGGAGGTTA TTTCTATCCC CCCGTTGATT TCCTTCGAGA TAATCTATGT CCTCGTCTAC    10440

TATGTCAATA TCTTCTTTAC TCAAACGGTC CTTCTACCTT TGGTTTTTAC TATCCCCCTT    10500

AACCTCTGGA TGATGGGGA GGGTTTTATC AAAGTAAGAC AGTATGATCA GATACTCATA    10560
```

```
GAAATCTGTG GACATAAAGC TATAGGTACA GTATTAGTAG GACCTACACC TGTCAACATA    10620

ATTGGAAGAA ATCTGTTGAC TCCAAAATAG TTTCATTCTG TCATACTAGT CTATGAGTAT    10680

CTTTAGACAC CTGTATTTCG ATATCCATGT CATAATCATC CTGGATGTGG ACAGTTGTAT    10740

TAACCTTCTT TAGACAACTG AGGCGAGTGT GTGAGGAGAT TGGTTGCACT TTAAATTTTT    10800

AACCCGGGGG ATCCCGATTT TTATGACTAG TTAATCAAAT AAAAAGCATA CAAGCTATTG    10860

CTTCTCTAAC CAACGTGAAA TTTAAAAATT GGGCCCCCTA GGGCTAAAAA TACTGATCAA    10920

TTAGTTTATT TTTCGTATGT TCGATAACGA AGGCTCAGAG AG                      10962

(2) INFORMATION FOR SEQ ID NO:7:

(i) SEQUENCE CHARACTERISTICS:
        (A) LENGTH: 7797 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GAGAGTAAAT TACTAGCAGA AGCTAAGAGC GGAGCACCAT AGACCATAGG AGGAGCAGAT      60

AATGTAGTAT ACTAATATTA ACTCACATTT GACTAATTAG CTATAAAAAC CCGGGATCGA     120

TTCTAGAATA AAAATTATCC CTGCCTAACT CTATTCACTA CAGAGAGTAC AGCAAAAACA     180

TTACATCATA TGATTATAAT TGAGTGTAAA CTGATTAATC GATATTTTTG GGCCCTAGCT     240

AAGATCTTAT TTTTAATAGG GACGGATTGA GATAAGTGAT GTCTCTCATG TCGTTTTTGC     300

AGATAAGTAT TCTTAAACCT ACCAAGCCTC CTACTATCAT TATGAATAAT CTTTTTTCTC     360

TCTGCACCAC TCTTCTCTTT GCCTTGGTGG GTGCTACTCC TAATGGTTCA ATTGTTACTA     420

CTTTATAATA AGAATTTGGA TGGTTCGGAG GATGATAGTA ATACTTATTA GAAAAAAGAG     480

AGACGTGGTG AGAAGAGAAA CGGAACCACC CACGATGAGG ATTACCAAGT TAACAATGAT     540

GAAATATTAA GGGTTTATAT AATTCACTTC TCCAATTGTC CCTCATATCT CCTCCTCCAG     600

GTCTGAAGAT CTCGGTGTCG TTCGTGTCCG TGTCCTTACC ACCATCTCTT GTTAATAGTA     660

GCCCTGTAAT ATTAAATATA TTAAGTGAAG AGGTTAACAG GGAGTATAGA GGAGGAGGTC     720

CAGACTTCTA GAGCCACAGC AAGCACAGGC ACAGGAATGG TGGTAGAGAA CAATTATCAT     780

CGGGACATTA TAAGGTGATG AACATCTAAT TTGTCCTTCA ATGGGAGGGG CATATATTGC     840

TTTTCCTACT TCCTGCCACA TGTTTATAAT TTGTTTTATT TTGCATTGAA GTGTGATATT     900

GTTATTTGAC CCTGTACTAC TTGTAGATTA ACAGGAAGT TACCCTCCCC GTATATAACG      960

AAAAGGATGA AGGACGGTGT ACAAATATTA AACAAAATAA AACGTAACTT CACACTATAA    1020

CAATAAACTG GGACAGGAGT ATTATTCCAA GTATTATTAC CATTCCAAGT ACTATTAAAC    1080

AGTGGTGATG AATTACAGTA GAAGAATTCC CCTCCACAAT TAAAACTGTG CATTACAATT    1140

TCTGGGTCCC CTCCTGATCA TAATAAGGTT CATAATAATG GTAAGGTTCA TGATAATTTG    1200

TCACCACTAC TTAATGTCAT CTTCTTAAGG GGAGGTGTTA ATTTTGACAC GTAATGTTAA    1260

AGACCCAGGG GAGGACTGGG GATTGATTAA AGACTATTGT TTTATTCTTA AATTGTTCTT    1320

TTAATTTGCT AACTATCTGT CTTAAAGTGT CATTCCATTT TGCTCTACTA ATGTTACAAT    1380

GTGCTTGTCT TATAGTTCCC CTAACTAATT TCTGATAACA AAATAAGAAT TTAACAAGAA    1440

AATTAAACGA TTGATAGACA GAATTTCACA GTAAGGTAAA ACGAGATGAT TACAATGTTA    1500

CACGAACAGA ATATCAAGGG GTATTATATT TTTTGTTGTA TAAAATGCTC TCCCTGGTCC    1560
```

-continued

```
TATATGTATC CTTTTTCTTT TATTGTAGTT GGGTCTTGTA CAATTAATTT GTACAGATTC    1620

ATTCAGATGT ACTATGATGG TATAATATAA AAAACAACAT ATTTTACGAG AGGGACCAGG    1680

ATATACATAG GAAAAAGAAA ATAACATCAA CCCAGAACAT GTTAATTAAA CATGTCTAAG    1740

TAAGTCTACA TGATACTACC AGGTTTAGCA TTATCATTGA AATTCTCAGA TCTAATTACT    1800

ACCTCTTCTT CTGCTAGACT GCCATTTAAC AGCAGTTGAG TTGATACTAC TGGCCTAATT    1860

CCATGTGTAC ATTGTACTGT GCTAAATCGT AATAGTAACT TTAAGAGTCT AGATTAATGA    1920

TGGAGAAGAA GACGATCTGA CGGTAAATTG TCGTCAACTC AACTATGATG ACCGGATTAA    1980

GGTACACATG TAACATGACA CGAGGGACAT TTTTACATGA TCCTTTTCCA CTGAACTTTT    2040

TATCGTTACA CTTTAGAATC GCAAAACCAG CCGGGGCACA ATAGTGTATG GAATTGGCT     2100

CAAAGGATAT CTTTGGACAA GCTTGCTGTA AAAATGTACT AGGAAAAGGT GACTTGAAAA    2160

ATAGCAATGT GAAATCTTAG CGTTTTGGTC GGCCCCGTGT TATCACATAC CCTTAACCGA    2220

GTTTCCTATA GAAACCTGTT CGAACGGTGT AATGACTGAG GTATTACAAC TTATCAACCT    2280

ATAGCTGGTA CTATCATTAT TTATTGATAC TATATCAAGT TTATAAAGAA GTGCATATTC    2340

TTTCTGCATC TTATCTCTTA TGCTTGTACA TTACTGACTC CATAATGTTG AATAGTTGGA    2400

TATCGACCAT GATAGTAATA AATAACTATG ATATAGTTCA AATATTTCTT CACGTATAAG    2460

AAAGACGTAG AATAGAGAAT ACGAACAGGG GTGATATTGA AAGAGCAGTT TTTCATTTCT    2520

CCTCCCTTTA TTGTTCCCTC GCTATTACTA TTGTTATTAG CAGTACTATT ATTGGTATTA    2580

GTAGTATTCC TCAAATCAGT GCAATTTAAC CACTATAACT TTCTCGTCAA AAAGTAAAGA    2640

GGAGGGAAAT AACAAGGGAG CGATAATGAT AACAATAATC GTCATGATAA TAACCATAAT    2700

CATCATAAGG AGTTTAGTCA CGTTAAATTG GAGTAACACA GAGTGGGGTT AATTTTACAC    2760

ATGGCTTTAG GCTTTGATCC CATAAACTGA TTATATCCTC ATGCATCTGT TCTACCATGT    2820

TATTTTTCCA CATGTTAAAA TTTTCTGTCA CTCATTGTGT CTCACCCCAA TTAAAATGTG    2880

TACCGAAATC CGAAACTAGG GTATTTGACT AATATAGGAG TACGTAGACA AGATGGTACA    2940

ATAAAAAGGT GTACAATTTT AAAAGACAGT GGGATTTACC AATTCTACTT CTTGTGGGTT    3000

GGGGTCTGTG GGTACACAGG CATGTGTGGC CCAAACATTA TGTACCTCTG TATCATATGC    3060

TTTAGCATCT GATGCACAAA ATAGAGTGGT GGTTAAATGG TTAAGATGAA GAACACCCAA    3120

CCCCAGACAC CCATGTGTCC GTACACACCG GGTTTGTAAT ACATGGAGAC ATAGTATACG    3180

AAATCGTAGA CTACGTGTTT TATCTCACCA CCAGGTGCTT CTTTCCACAC AGGTACCCCA    3240

TAATAGACTG TGACCCACAA TTTTTCTGTA GCACTACAGA TCATCAACAT CCCAAGGAGC    3300

ATGGTGCCCC ATCTCCACCC CCATCTCCAC AAGTGACGAA GAAAGGTGTG TCCATGGGGT    3360

ATTATCTGAC ACTGGGTGTT AAAAAGACAT CGTGATGTCT AGTAGTTGTA GGGTTCCTCG    3420

TACCACGGGG TAGAGGTGGG GGTAGAGGTG TTCACGGCTG ATATTTCTCC TTCACTCTCA    3480

TTGCCACTGT CTTCTGCTCT TTCATATACG ATACAAACTT AACGCATATC GCGATAATGA    3540

AATAATTTAT GATTATTTCT CGCTTTCAAT TTAACACGAC TATAAAGAGG AAGTGAGAGT    3600

AACGGTGACA GAAGACGAGA AAGTATATGC TATGTTTGAA TTGCGTATAG CGCTATTACT    3660

TTATTAAATA CTAATAAAGA GCGAAAGTTA AATTGTGGGA CCATAACCCT CAAGAACCTT    3720

TGTATTTATT TTCACTTTTT AAGTATAGAA TAAAGAAGCT CTAATTAATT AAGCTACAAA    3780

TAGTTTCGTT TTCACCTTGT CTAATAACTA ATTAATTAAC CCGGTTGGGA GTTCTTGGAA    3840

ACATAAATAA AAGTGAAAAA TTCATATCTT ATTTCTTCGA GATTAATTAA TTCGATGTTT    3900

ATCAAAGCAA AAGTGGAACA GATTATTGAT TAATTAATTG GGCCACCATA TCTTGAGATA    3960
```

```
AAGTGAAAAT ATATATCATT ATATTACAAA GTACAATTAT TTAGGTTTAA TCATGGGTGC      4020

GAGAGCGTCA GTATTAAGCG GGGGAGAATT AGATCGATGG GAAAAAATTT AGAACTCTAT      4080

TTCACTTTTA TATATAGTAA TATAATGTTT CATGTTAATA AATCCAAATT AGTACCCACG      4140

CTCTCGCAGT CATAATTCGC CCCCTCTTAA TCTAGCTACC CTTTTTTAAA CCATGAGGCG      4200

GTTAAGGCCA GGGGGAAAGA AAAATATAAA ATTAAAACAT ATAGTATGGG CAAGCAGGGA      4260

GCTAGAACGA TTCGCAGTTA ATCCTGGCCT GTTAGAAACA TCAGAAGGCT GTAGACAAGC      4320

CAATTCCGGT CCCCCTTTCT TTTTTATATT TAATTTTGTA TATCATACCC GTTCGTCCCT      4380

CGATCTTGCT AAGCGTCAAT TAGGACCGGA CAATCTTTGT AGTCTTCCGA CATCTGTTGA      4440

GGATACTGGG ACAGCTACAA CCATCCCTTC AGACAGGATC AGAAGAACTT AGATCATTAT      4500

ATAATACAGT AGCAACCCTC TATTGTGTGC ATCAAAGGAT AGAGATAAAA GACACCAAGG      4560

AATATGACCC TGTCGATGTT GGTAGGGAAG TCTGTCCTAG TCTTCTTGAA TCTAGTAATA      4620

TATTATGTCA TCGTTGGGAG ATAACACACG TAGTTTCCTA TCTCTATTTT CTGTGGTTCC      4680

TTGAGGGCTT TAGACAAGAT AGAGGAAGAG CAAAACAAAA GTAAGAAAAA AGCACAGCAA      4740

GCAGCAGCTG ACACAGGACA CAGCAATCAG GTCAGCCAAA ATTACCCTAT AGTGCAGAAC      4800

ATCCAGCGAA ATCTGTTCTA TCTCCTTCTC GTTTTGTTTT CATTCTTTTT TCGTGTCGTT      4860

CGTCGTCGAC TGTGTCCTGT GTCGTTAGTC CAGTCGGTTT TAATGGGATA TCACGTCTTG      4920

TAGGTCGAGG GGGCAAATGG TACATCAGGC CATATCACCT AGAACTTTAA ATGCATGGGT      4980

AAAAGTAGTA GAAGAGAAGG CTTTCAGCCC AGAAGTGATA CCCATGTTTT CAGCATTATC      5040

AGAAGGAGCC CCCGTTTACC ATGTAGTCCG GTATAGTGGA TCTTGAAATT TACGTACCCA      5100

TTTTCATCAT CTTCTCTTCC GAAAGTCGGG TCTTCACTAT GGGTACAAAA GTCGTAATAG      5160

TCTTCCTCGG GAGGACCCCA CAAGATTTAA ACACCATGCT AAACACAGTG GGGGACATC      5220

AAGCAGCCAT GCAAATGTTA AAAGAGACCA TCAATGAGGA AGCTGCAGAA TGGGATAGAG      5280

TGCATCCAGT GCATTGGGGT GTTCTAAATT TGTGGTACGA TTTGTGTCAC CCCCCTGTAG      5340

TTCGTCGGTA CGTTTACAAT TTTCTCTGGT AGTTACTCCT TCGACGTCTT ACCCTATCTC      5400

ACGTAGGTCA CGTAGAGGGC AGGGCCTATT GCACCAGGCC AGATGAGAGA ACCAAGGGGA      5460

AGTGACATAG CAGGAACTAC TAGTACCCTT CAGGAACAAA TAGGATGGAT GACAAATAAT      5520

CCACCTATCC CAGTAGGACG TCCCGGATAA CGTGGTCCGG TCTACTCTCT TGGTTCCCCT      5580

TCACTGTATC GTCCTTGATG ATCATGGGAA GTCCTTGTTT ATCCTACCTA CTGTTTATTA      5640

GGTGGATAGG GTCATCCTGA GGGAAATTTA TAAAAGATGG ATAATCCTGG GATTAAATAA      5700

AATAGTAAGA ATGTATAGCC CTACCAGCAT TCTGGACATA AGACAAGGAC CAAAAGAACC      5760

CTTTAGAGAC TATGTAGACC GGCTTTAAAT ATTTTCTACC TATTAGGACC CTAATTTATT      5820

TTATCATTCT TACATATCGG GATGGTCGTA AGACCTGTAT TCTGTTCCTG GTTTTCTTGG      5880

GAAATCTCTG ATACATCTGG CCGAGGTTCT ATAAAACTCT AAGAGCCGAG CAAGCTTCAC      5940

AGGAGGTAAA AAATTGGATG ACAGAAACCT TGTTGGTCCA AAATGCGAAC CCAGATTGTA      6000

AGACTATTTT AAAAGCATTG GGACCAAAGA TATTTTGAGA TTCTCGGCTC GTTCGAAGTG      6060

TCCTCCATTT TTTAACCTAC TGTCTTTGGA ACAACCAGGT TTTACGCTTG GGTCTAACAT      6120

TCTGATAAAA TTTTCGTAAC CCTGGTGAGG GCGGCTACAC TAGAAGAAAT GATGACAGCA      6180

TGTCAGGGAG TAGGAGGACC CGGCCATAAG GCAAGAGTTT TGGCTGAAGC AATGAGCCAA      6240

GTAACAAATT CAGCTACCAT AATGATGCAG CGCCGATGTG ATCTTCTTTA CTACTGTCGT      6300
```

```
ACAGTCCCTC ATCCTCCTGG GCCGGTATTC CGTTCTCAAA ACCGACTTCG TTACTCGGTT      6360

CATTGTTTAA GTCGATGGTA TTACTACGTC GAGGAGAGGC AATTTTAGGA ACCAAAGAAA      6420

GATTGTTAAG TGTTTCAATT GTGGCAAAGA AGGGCACACA GCCAGAAATT GCAGGGCCCC      6480

TAGGAAAAAG GGCTGTTGGA AATGTGGAAA GGAATCTCCG TTAAAATCCT TGGTTTCTTT      6540

CTAACAATTC ACAAAGTTAA CACCGTTTCT TCCCGTGTGT CGGTCTTTAA CGTCCCGGGG      6600

ATCCTTTTTC CCGACAACCT TTACACCTTT CCTTGAGGGG ACACCAAATG AAAGATTGTA      6660

CTGAGAGACA GGCTAATTTT TTAGGGAAGA TCTGGCCTTC CTACAAGGGA AGGCCAGGGA      6720

ATTTTCTTCA GAGCAGACCA GAGCCAACAG CCCCACCACC TGTGGTTTAC TTTCTAACAT      6780

GACTCTCTGT CCGATTAAAA AATCCCTTCT AGACCGGAAG GATGTTCCCT TCCGGTCCCT      6840

TAAAAGAAGT CTCGTCTGGT CTCGGTTGTC GGGGTGGTGA GGGAAGAGAG CTTCAGGTCT      6900

GGGGTAGAGA CAACAACTCC CCCTCAGAAG CAGGAGCCGA TAGACAAGGA ACTGTATCCT      6960

TTAACTTCCC TCAGATCACT CTTTGGCAAC GACCCCTCGT CACTTCTCTC GAAGTCCAGA      7020

CCCCATCTCT GTTGTTGAGG GGGAGTCTTC GTCCTCGGCT ATCTGTTCCT TGACATAGGA      7080

AATTGAAGGG AGTCTAGTGA GAAACCGTTG CTGGGGAGCA GTGAGGCAAT AAAGATAGGG      7140

GGGCAACTAA AGGAAGCTCT ATTAGATACA GGAGCAGATG ATACAGTATT AGAAGAAATG      7200

AGTTTGCCAG GAAGATGGAA ACCAAAAATG ATAGGGGGAA TTGGAGGTTA TTTCTATCCC      7260

CCCGTTGATT TCCTTCGAGA TAATCTATGT CCTCGTCTAC TATGTCATAA TCTTCTTTAC      7320

TCAAACGGTC CTTCTACCTT TGGTTTTTAC TATCCCCCTT AACCTCGAGG GTTTTATCAA      7380

AGTAAGACAG TATGATCAGA TACTCATAGA AATCTGTGGA CATAAAGCTA TAGGTACAGT      7440

ATTAGTAGGA CCTACACCTG TCAACATAAT TGGAAGAAAT CTGTTGACTC CAAAATAGTT      7500

TCATTCTGTC ATACTAGTCT ATGAGTATCT TTAGACACCT GTATTTCGAT ATCCATGTCA      7560

TAATCATCCT GGATGTGGAC AGTTGTATTA ACCTTCTTTA GACAACTGAG GAGGAGATTG      7620

GTTGCACTTT AAATTTTTAA CCCGGGGGAT CCCGATTTTT ATGACTAGTT AATCAAATAA      7680

AAAGCATACA AGCTATTGCT TCTCTAACCA ACGTGAAATT TAAAAATTGG GCCCCCTAGG      7740

GCTAAAAATA CTGATCAATT AGTTTATTTT TCGTATGTTC GATAACGAAG GAGCAGA        7797

(2) INFORMATION FOR SEQ ID NO:8:

(i) SEQUENCE CHARACTERISTICS:
            (A) LENGTH: 19877 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

CGAGCTCGCG GCCGCCTATC AAAAGTCTTA ATGAGTTAGG TGTAGATAGT ATAGATATTA        60

CTACAAAGGT ATTCATATTT CCTATCAATT CTAAAGTAGA TGATATTAAT ACTCGAGCGC       120

CGGCGGATAG TTTTCAGAAT TACTCAATCC ACATCTATCA TATCTATAAT GATGTTTCCA       180

TAAGTATAAA GGATAGTTAA GATTTCATCT ACTATAATTA TACTCAAAGA TGATGATAGT       240

AGATAATAGA TACGCTCATA TAATGACTGC AAATTTGGAC GGTTCACATT TTAATCATCA       300

CGCGTTCATA AGTTTCAACT GCATAGATCA ATGAGTTTCT ACTACTATCA TCTATTATCT       360

ATGCGAGTAT ATTACTGACG TTTAAACCTG CCAAGTGTAA AATTAGTAGT GCGCAAGTAT       420

TCAAAGTTGA CGTATCTAGT TAATCTCACT AAAAAGATAG CCGATGTATT TGAGAGAGAT       480
```

```
TGGACATCTA ACTACGCTAA AGAAATTACA GTTATAAATA ATACATAATG GATTTTGTTA      540

TCATCAGTTA TTTAGAGTGA TTTTTCTATC GGCTACATAA ACTCTCTCTA ACCTGTAGAT      600

TGATGCGATT TCTTTAATGT CAATATTTAT TATGTATTAC CTAAAACAAT AGTAGTCAAT      660

AATTTAACAT AAGTACAATA AAAAGTATTA ATAAAAATA CTTACTTACG AAAAAATGAC       720

TAATTAGCTA TAAAAACCCA GATCTCTCGA GGTCGACGGT ATCGATAAGC TTAAATTGTA      780

TTCATGTTAT TTTTCATAAT TTATTTTTAT GAATGAATGC TTTTTTACTG ATTAATCGAT      840

ATTTTTGGGT CTAGAGAGCT CCAGCTGCCA TAGCTATTCG ATGATATCGA ATTCATAAAA      900

ATTATTGATG TCTACACATC CTTTTGTAAT TGACATCTAT ATATCCTTTT GTATAATCAA      960

CTCTAATCAC TTTACTATAG CTTAAGTATT TTTAATAACT ACAGATGTGT AGGAAAACAT     1020

TAACTGTAGA TATATAGGAA AACATATTAG TTGAGATTAG TGAAACGTAA CTTTTACAGT     1080

TTTCCCTACC AGTTTATCCC TATATTCAAC ATATCTATCC ATATGCATCT TAACACTCTC     1140

TGCCAAGATA GCTTCAGATT GAAAATGTCA AAAGGGATGG TCAAATAGGG ATATAAGTTG     1200

TATAGATAGG TATACGTAGA ATTGTGAGAG ACGGTTCTAT CGAAGTCTTG AAGTGAGGAT     1260

AGTCAAAAAG ATAAATGTAT AGAGCATAAT CCTTCTCGTA TACTCTGCCC TTTATTACAT     1320

CGCCCGCATT GGGCAACGAA TACACTCCTA TCAGTTTTTC TATTTACATA TCTCGTATTA     1380

GGAAGAGCAT ATGAGACGGG AAATAATGTA GCGGGCGTAA CCCGTTGCTT ATAGGAACAA     1440

AATGCAAGCA TACGATACAA ACTTAACGGA TATCGCGATA ATGAAATAAT TTATGATTAT     1500

TTCTCGCTTT CAATTTAACA CAACCCTCAA GAACTGTTTT ACGTTCGTAT GCTATGTTTG     1560

AATTGCCTAT AGCGCTATTA CTTTATTAAA TACTAATAAA GAGCGAAAGT TAAATTGTGT     1620

TGGGAGTTCT TGCACTTTGT ATTTATTTTC ACTTTTTAAG TATAGAATAA AGAAAGCTCT     1680

AATTAATTAA TGAACAGATT GTTTCGTTTT CCCCTTGGCG TATCACTAAT TAATTAACCC     1740

GGGCGAAACA TAAATAAAAG TGAAAAATTC ATATCTTATT TCTTTCGAGA TTAATTAATT     1800

ACTTGTCTAA CAAAGCAAAA GGGGAACCGC ATAGTGATTA ATTAATTGGG CCCGTGCAGC     1860

TCGAGGAATT CAACTATATC GACATATTTC ATTTGTATAC ACATAACCAT TACTAACGTA     1920

GAATGTATAG AAGAGATGT AACGGGAACA GGGTTTGTTG ATTCACGTCG AGCTCCTTAA      1980

GTTGATATAG CTGTATAAAG TAAACATATG TGTATTGGTA ATGATTGCAT CTTACATATC     2040

CTTCTCTACA TTGCCCTTGT CCCAAACAAC TAAGGCAAAC TATTCTAATA CATAATTCTT     2100

CTGTTAATAC GTCTTGCACG TAATCTATTA TAGATGCCAA GATATCTATA TAATTATTTT     2160

GTAAGATGAT GTTAACTATG TGATCGTTTG ATAAGATTAT GTATTAAGAA GACAATTATG     2220

CAGAACGTGC ATTAGATAAT ATCTACGGTT CTATAGATAT ATTAATAAAA CATTCTACTA     2280

CAATTGATAC ACTACTATAT AAGTAGTGTA ATAATTCATG TATTTCGATA TATGTTCCAA     2340

CTCTGTCTTT GTGATGTCTA GTTTCGTAAT ATCTATAGCA TCCTCAAAAA ATATATTCGC     2400

ATATGATATA TTCATCACAT TATTAAGTAC ATAAAGCTAT ATACAAGGTT GAGACAGAAA     2460

CACTACAGAT CAAAGCATTA TAGATATCGT AGGAGTTTTT TATATAAGCG TATAATTCCC     2520

AAGTCTTCAG TTCTATCTTC TAAAAAATCT TCAACGTATG GAATATAATA ATCTATTTTA     2580

CCTCTTCTGA TATCATTAAT GATATAGTTT TTGACACTAT CTTCTAAGGG TTCAGAAGTC     2640

AAGATAGAAG ATTTTTTAGA AGTTGCATAC CTTATATTAT TAGATAAAAT GGAGAAGACT     2700

ATAGTAATTA CTATATCAAA AACTGTGATA GAAGTGTCAA TTGATTCTTA TTCACTATAT     2760

CTAAGAAACG GATAGCGTCC CTAGGACGAA CTACTGCCAT AATATCTCT ATTATAGCTT      2820

CTGGACATAA TTCATCTATT ATACACAGTT AACTAAGAAT AAGTGATATA GATTCTTTGC     2880
```

-continued

```
CTATCGCAGG GATCCTGCTT GATGACGGTA ATTATAGAGA TAATATCGAA GACCTGTATT      2940

AAGTAGATAA TATGCAGAAT TAATGGGAAC TATTCCGTAT CTATCTAACA TAGTTTTAAG      3000

AAAGTCAGAA TCTAAGACCT GATGTTCATA TATTGGTTCA TACATGAAAT GATCTCTATT      3060

GATGGTCTTA ATTACCCTTG ATAAGGCATA GATAGATTGT ATCAAAATTC TTTCAGTCTT      3120

AGATTCTGGA CTACAAGTAT ATAACCAAGT ATGTACTTTA CTAGAGATAA CTACATAGTG      3180

ACTATTTCAT TCTCTGAAAA TTGGTAACTC ATTCTATATA TGCTTTCCTT GTTGATGAAG      3240

GATAGAATAT ACTCAATAGA ATTTGTACCA ACAAACTGTT CTCTTATCAC TGATAAAGTA      3300

AGAGACTTTT AACCATTGAG TAAGATATAT ACGAAAGGAA CAACTACTTC CTATCTTATA      3360

TGAGTTATCT TAAACATGGT TGTTTGACAA GAGATATGAA TCGTATATCA TCATCTGAAA      3420

TAATCATGTA AGGCATACAT TTAACAATTA GAGACTTGTC TCCTGTTATC AATATACTAT      3480

TCTTGTGATA ATTTATGTGT GAGGATACTT AGCATATAGT AGTAGACTTT ATTAGTACAT      3540

TCCGTATGTA AATTGTTAAT CTCTGAACAG AGGACAATAG TTATATGATA AGAACACTAT      3600

TAAATACACA CTCCCAAATT TGTCCACGTT CTTTAATTTT GTTATAGTAG ATATCAAATC      3660

CAATGGAGCT ACAGTTCTTG GCTTAAACAG ATATAGTTTT TCTGGAACAA ATTCTACAAC      3720

ATTAGTTTAA ACAGGTGCAA GAAATTAAAA CAATATCATC TATAGTTTAG GTTACCTCGA      3780

TGTCAAGAAC CGAATTTGTC TATATCAAAA AGACCTTGTT TAAGATGTTG TAATTTATAA      3840

AGGACTTTGG GTAGATAAGT GGGATGAAAT CCTATTTTAA TTAATGCTAT CGCATTGTCC      3900

TCGTGCAAAT ATCCAAACGC TTTTGTGATA GTATGGCATT CATTAATATT TCCTGAAACC      3960

CATCTATTCA CCCTACTTTA GGATAAAATT AATTACGATA GCGTAACAGG AGCACGTTTA      4020

TAGGTTTGCG AAAACACTAT CATACCGTAA GTAAGTCTAG AAACGCTCTA CGAATATCTG      4080

TGACAGATAT CATCTTTAGA GAATACTACTA GTCGCGTTAA TAGTACTACA ATTTGTATTT      4140

TTTAATCTAT CTCAATAAAA AAATCAGATC TTTGCGAGAT GCTTATAGAC ACTGTCTATA      4200

GTAGAAATCT CTTATATGAT CAGCGCAATT ATCATGATGT TAAACATAAA AAATTAGATA      4260

GAGTTATTTT TTTATAATAT GTATGATTCA ATGTATAACT AAACTACTAA CTGTTATTGA      4320

TAACTAGAAT CAGAATCTAA TGATGACGTA ACCAAGAAGT TTATCTACTG CCAAATTATA      4380

CATACTAAGT TACATATTGA TTTGATGATT GACAATAACT ATTGATCTTA GTCTTAGATT      4440

ACTACTGCAT TGGTTCTTCA AATAGATGAC GGTTGATTTA GCTGCATTAT TTTTAGCATC      4500

TCGTTTAGAT TTTCCATCTG CCTTATCGAA TACTCTTCCG TCGATGTCTA CACAGGCATA      4560

AAATGTAAAT CGACGTAATA AAAATCGTAG AGCAAATCTA AAAGGTAGAC GGAATAGCTT      4620

ATGAGAAGGC AGCTACAGAT GTGTCCGTAT TTTACAAAAG AGCATAGGAG AGTTACTAGG      4680

CCCAACTGAT TCAATACGAA AAGACCAATC TCTCTTAGTT ATTTGGCAGT ACTCATTAAT      4740

AATGGTGACA GGGTTTCCTC TCAATGATCC GGGTTGACTA AGTTATGCTT TTCTGGTTAG      4800

AGAGAATCAA TAAACCGTCA TGAGTAATTA TTACCACTGT CCCAAGTCTA GCATCTTTCC      4860

AATCAATAAT TTTTTTAGCC GGAATAACAT CATCAAAAGA CTTATGATCC TCTCTCATTG      4920

ATTTTTCGCG GGATACATCT CGTAGAAAGG TTAGTTATTA AAAAAATCGG CCTTATTGTA      4980

GTAGTTTTCT GAATACTAGG AGAGAGTAAC TAAAAAGCGC CCTATGTAGA AATCTATTAT      5040

GACGTCAGCC ATAGCATCAG CATCCGGCTT ATCCGCCTCC GTTGTCATAA ACCAACGAGG      5100

AGGAATATCG TCGGAGCTGT ATAGATAATA CTGCAGTCGG TATCGTAGTC GTAGGCCGAA      5160

TAGGCGGAGG CAACAGTATT TGGTTGCTCC TCCTTATAGC AGCCTCGACA TAAAATTCAC      5220
```

-continued

```
CATAGCACTA CGTTGAAGAT CGTACAGAGC TTTATTAACT TCTCGCTTCT CCATATTAAG    5280

TTGTCTAGTT AGTTGTGCAG CAGTAGCGTG GTATCGTGAT GCAACTTCTA GCATGTCTCG    5340

AAATAATTGA AGAGCGAAGA GGTATAATTC AACAGATCAA TCAACACGTC GTCATCGAAT    5400

AATATCCTTC GATTCCAATG TTTTTAATAG CCGCACACAC AATCTCTGCG TCAGAACGCT    5460

CGTCAATATA GATCTTAGAC ATTTTTAGAG AGAAAGGAAG CTAAGGTTAC AAAAATTATC    5520

GGCGTGTGTG TTAGAGACGC AGTCTTGCGA GCAGTTATAT CTAGAATCTG TAAAAATCTC    5580

TCTTGGAACA CTAACACAAC CAGCAATAAA ACTGAACCTA CTTTATCATT TTTTTATTCA    5640

TCATCCTCTG GTGGTTCGTC GTTTCTATCG AATGTAGCTC TGATTAACCC GTCATCTATA    5700

GATTGTGTTG GTCGTTATTT TGACTTGGAT GAAATAGTAA AAAAATAAGT AGTAGGAGAC    5760

CACCAAGCAG CAAAGATAGC TTACATCGAG ACTAATTGGG CAGTAGATAT GGTGATGCTG    5820

GTTCTGGAGA TTCTGGAGGA GATGGATTAT TATCTGGAAG AATCTCTGTT ATTTCCTTGT    5880

TTTCATGTAT CGATTGCGTT GTAACATTAA GATTGCGAAA CCACTACGAC CAAGACCTCT    5940

AAGACCTCCT CTACCTAATA ATAGACCTTC TTAGAGACAA TAAAGGAACA AAAGTACATA    6000

GCTAACGCAA CATTGTAATT CTAACGCTTT TGCTCTAAAT TTGGGAGGCT TAAAGTGTTG    6060

TTTGCAATCT CTACACGCGT GTCTAACTAG TGGAGGTTCG TCAGCTGCTC TAGTTTGAAT    6120

CATCATCGGC GTAGTATTCC ACGAGATTTA AACCCTCCGA ATTCACAAC AAACGTTAGA     6180

GATGTGCGCA CAGATTGATC ACCTCCAAGC AGTCGACGAG ATCAAACTTA GTAGTAGCCG    6240

CATCATAAGG TACTTTTACA GTTAGGACAC GGTGTATTGT ATTTCTCGTC GAGAACGTTA    6300

AAATAATCGT TGTAACTCAC ATCCTTTATT TTATCTATAT TGTATTCTAC TCCTTTCTTA    6360

ATGAAAATGT CAATCCTGTG CCACATAACA TAAAGAGCAG CTCTTGCAAT TTTATTAGCA    6420

ACATTGAGTG TAGGAAATAA AATAGATATA ACATAAGATG AGGAAAGAAT ATGCATTTTA    6480

TACCGAATAA GAGATAGCGA AGGAATTCTT TTTATTGATT AACTAGTCAA ATGAGTATAT    6540

ATAATTGAAA AAGTAAAATA TAAATCATAT AATAATGAAA TACGTAAAAT ATGGCTTATT    6600

CTCTATCGCT TCCTTAAGAA AAATAACTAA TTGATCAGTT TACTCATATA TATTAACTTT    6660

TTCATTTTAT ATTTAGTATA TTATTACTTT CGAAATATCA GTAATAGACA GGAACTGGCA    6720

GATTCTTCTT CTAATGAAGT AAGTACTGCT AAATCTCCAA AATTAGATAA AAATGATACA    6780

GCAAATACAG CTTCATTCAA GCTTTATAGT CATTATCTGT CCTTGACCGT CTAAGAAGAA    6840

GATTACTTCA TTCATGACGA TTTAGAGGTT TTAATCTATT TTTACTATGT CGTTTATGTC    6900

GAAGTAAGTT CGAATTACCT TTTAATTTTT TCAGACACAC CTTATTACAA ACTAACTAAG    6960

TCAGATGATG AGAAAGTAAA TATAAATTTA ACTTATGGGT ATAATATAAT AAAGATTCAT    7020

GCTTAATGGA AAATTAAAAA AGTCTGTGTG GAATAATGTT TGATTGATTC AGTCTACTAC    7080

TCTTTCATTT ATATTTAAAT TGAATACCCA TATTATATTA TTTCTAAGTA GATATTAATA    7140

ATTTACTTAA CGATGTTAAT AGACTTATTC CATCAACCCC TTCAAACCTT TCTGGATATT    7200

ATAAAATACC AGTAATGAT ATTAAAATAG ATTGTTTAAG CTATAATTAT TAAATGAATT     7260

GCTACAATTA TCTGAATAAG GTAGTTGGGG AAGTTTGGAA AGACCTATAA TATTTTATGG    7320

TCAATTACTA TAATTTTATC TAACAAATTC AGATGTAAAT AATTATTTGG AGGTAAAGGA    7380

TATAAAATTA GTCTATCTTT CACATGGAAA TGAATTACCT AATATTAATA ATTATGATAG    7440

GAATTTTTA GGATTACAG TCTACATTTA TTAATAAACC TCCATTTCCT ATATTTTAAT      7500

CAGATAGAAA GTGTACCTTT ACTTAATGGA TTATAATTAT TAATACTATC CTTAAAAAAT    7560

CCTAAATGTC CTGTTATATG TATCAACAAT ACAGGCAGAT CTATGGTTAT GGTAAAACAC    7620
```

-continued

```
TGTAACGGGA AGCAGCATTC TATGGTAACT GGCCTATGTT TAATAGCCAG ATCATTTTAC    7680

GACAATATAC ATAGTTGTTA TGTCCGTCTA GATACCAATA CCATTTTGTG ACATTGCCCT    7740

TCGTCGTAAG ATACCATTGA CCGGATACAA ATTATCGGTC TAGTAAAATG TCTATAAACA    7800

TTTTACCACA AATAATAGGA TCCTCTAGAT ATTTAATATT ATATCTAACA ACAACAAAAA    7860

AATTTAACGA TGTATGGCCA GAAGTATTTT CTACTAATAA AGATATTTGT AAAATGGTGT    7920

TTATTATCCT AGGAGATCTA TAAATTATAA TATAGATTGT TGTTGTTTTT TTAAATTGCT    7980

ACATACCGGT CTTCATAAAA GATGATTATT AGATAAAGAT AGTCTATCTT ATCTACAAGA    8040

TATGAAAGAA GATAATCATT TAGTAGTAGC TACTAATATG GAAAGAAATG TATACAAAAA    8100

CGTGGAAGCT TTTATATTAA TCTATTTCTA TCAGATAGAA TAGATGTTCT ATACTTTCTT    8160

CTATTAGTAA ATCATCATCG ATGATTATAC CTTTCTTTAC ATATGTTTTT GCACCTTCGA    8220

AAATATAATT ATAGCATATT ACTAGAAGAT TTAAAATCTA GACTTAGTAT AACAAAACAG    8280

TTAAATGCCA ATATCGATTC TATATTTCAT CATAACAGTA GTACATTAAT CAGTGATATA    8340

TATCGTATAA TGATCTTCTA AATTTTAGAT CTGAATCATA TTGTTTTGTC AATTTACGGT    8400

TATAGCTAAG ATATAAAGTA GTATTGTCAT CATGTAATTA GTCACTATAT CTGAAACGAT    8460

CTACAGACTC AACTATGCAA GGAATAAGCA ATATGCCAAT TATGTCTAAT ATTTTAACTT    8520

TAGAACTAAA ACGTTCTACC AATACTAAAA ATAGGATACG GACTTTGCTA GATGTCTGAG    8580

TTGATACGTT CCTTATTCGT TATACGGTTA ATACAGATTA TAAATTGAA ATCTTGATTT    8640

TGCAAGATGG TTATGATTTT TATCCTATGC TGATAGGCTG TTAAAAGCTG CAATAAATAG    8700

TAAGGATGTA GAAGAAATAC TTTGTTCTAT ACCTTCGGAG GAAAGAACTT TAGAACAACT    8760

TAAGTTTAAT CAAACTTGTA ACTATCCGAC AATTTTCGAC GTTATTTATC ATTCCTACAT    8820

CTTCTTTATG AAACAAGATA TGGAAGCCTC CTTTCTTGAA ATCTTGTTGA ATTCAAATTA    8880

GTTTGAACAT TTTATGAAGG TACCAAATAC TTCCATGGTT TTTTTTCATT ATTTAGAAAT    8940

TATGCATTTT AGATCTTTAT AAGCGGCCGT GATTAACTAG TCATAAAAAC CCGGGATCGA    9000

TTCTAGACTC GAGGGTACCG GATCTTAATA AAAAAAGTAA TAAATCTTTA ATACGTAAAA    9060

TCTAGAAATA TTCGCCGGCA CTAATTGATC AGTATTTTTG GGCCCTAGCT AAGATCTGAG    9120

CTCCCATGGC CTAGAATTAT AATTAGTCAT CAGGCAGGGC GAGAACGAGA CTATCTGCTC    9180

GTTAATTAAT TAGGTCGACG GATCCCCCAA CAAAAACTAA TCAGCTATCG GGGTTAATTA    9240

ATTAGTTATA TTAATCAGTA GTCCGTCCCG CTCTTGCTCT GATAGACGAG CAATTAATTA    9300

ATCCAGCTGC CTAGGGGGTT GTTTTTGATT AGTCGATAGC CCCAATTAAT TAATCAATAT    9360

AGACAAGGTG AAAACGAAAC TATTTGTAGC TTAATTAATT AGAGCTTCTT TATTCTATAC    9420

TTAAAAAGTG AAAATAAATA CAAAGGTTCT TGAGGGTTGT GTTAAATTGA TCTGTTCCAC    9480

TTTTGCTTTG ATAAACATCG AATTAATTAA TCTCGAAGAA ATAAGATATG AATTTTTCAC    9540

TTTTATTTAT GTTTCCAAGA ACTCCCAACA CAATTTAACT AAAGCGAGAA ATAATCATAA    9600

ATTATTTCAT TATCGCGATA TCCGTTAAGT TTGTATCGTA ATGCCACTAA CAGAAGAAGC    9660

AGAGCTAGAA CTGGCAGAAA ACTTTCGCTC TTTATTAGTA TTTAATAAAG TAATAGCGCT    9720

ATAGGCAATT CAAACATAGC ATTACGGTGA TTGTCTTCTT CGTCTCGATC TTGACCGTCT    9780

TTTGTTTGGA AGGAAGATAG AGAGATTCTA AAAGAACCAG TACATGGAGT GTATTATGAC    9840

CCATCAAAAG ACTTAATAGC AGAAATACAG AAGCAGGGGC AAGGCCAATC TCTCTAAGAT    9900

TTTCTTGGTC ATGTACCTCA CATAATACTG GGTAGTTTTC TGAATTATCG TCTTTATGTC    9960
```

```
TTCGTCCCCG TTCCGGTTAG GGAGATTAAA AGGGGGGGTT GGACATATCA AATTTATCAA    10020

GAGCCATTTA AAAATCTGAA AACAGGAATG GAGTGGAGAT TTGATTCTAG ATTAGCATTT    10080

CATCACGTAA CCTGTATAGT TTAAATAGTT CTCGGTAAAT TTTTAGACTT TTGTCCTTAC    10140

CTCACCTCTA AACTAAGATC TAATCGTAAA GTAGTGCATT TTGTGGATGT GTAGAAGAAA    10200

TGCTAGAGAA TTACATCCTG AATATTTTAA AAATTGTAAG CTTATGGCAA TATTCCAAAG    10260

TAGCATGACA AAAATCTTAG AGCCTTTTAG ACGATCTCTT AATGTAGGAC TTATAAAATT    10320

TTTAACATTC GAATACCGTT ATAAGGTTTC ATCGTACTGT TTTTAGAATC TCGGAAAATC    10380

TAAAGGGTAC TAAGTTGAGT AAACAAAATC CAGACATAGT TATCTATCAA TACATGGATG    10440

ATTTGTATGT AGGATCTGAC TTAGAAATAG GGCAGCATAG AACAAAAATA TTTGTTTTAG    10500

GTCTGTATCA ATAGATAGTT ATGTACCTAC TAAACATACA TCCTAGACTG AATCTTTATC    10560

CCGTCGTATC TTGTTTTTAT GAAATGTTAA TAGAGGGAGT TGAGGAGCTG AGACAACATC    10620

TGTTGAGGTG GGGACTTACA ACCATGGTAG GTTTTCCAGT AACACCTCAA GTACCTTTAA    10680

GACCAATGAC TCTCCTCGAC TCTGTTGTAG ACAACTCCAC CCCTGAATGT TGGTACCATC    10740

CAAAAGGTCA TTGTGGAGTT CATGGAAATT CTGGTTACTG AGGAGGAGTG TTTAGATGAA    10800

GTTTTACAAA GCAGCTGTAG ATCTTTCTCA CTTTTTAAAA GAAAAAGGAG GTTTAGAAGG    10860

GCTAATTCAT TCTCAACGAA GACAAGATAT TCTTATGTTT CGTCGACATC TAGAAAGAGT    10920

GAAAAATTTT CTTTTTCCTC CAAATCTTCC CGATTAAGTA AGAGTTGCTT CTGTTCTATA    10980

AGAATAAAAA AGGGGGGAGA GGATGATTTG TGGATTTATC ATACACAAGG ATATTTTCCT    11040

GATTGGCAGA ATTACACACC AGGACCAGGA GTCAGATACC CATTAACCTT TGGTCTAAAC    11100

ACCTAAATAG TATGTGTTCC TATAAAAGGA CTAACCGTCT TAATGTGTGG TCCTGGTCCT    11160

CAGTCTATGG GTAATTGGAA ACCAATTTGG TATGATTGGA AGTTGTTGGT GCTACAAGCT    11220

AGTACCAATG ATTGAGACTG TACCAGTAAA ATTAAAGCCA GGAATGGATG GCCCAAAAGT    11280

TAAACAATGG CCATTGACCA CGATGTTCGA TCATGGTTAC TAACTCTGAC ATGGTCATTT    11340

TAATTTCGGT CCTTACCTAC CGGGTTTTCA ATTTGTTACC GGTAACTCTA TGTAAGTAGA    11400

GTTACAGAAG AAAAAATAAA AGCATTAGTA GAAATTTGTA CAGAGATGGA AAAGGAAGGG    11460

AAAATTTCAA AAATTGGGCC TTAATTTTTC TTGTCTTCTT TTTTATTTTC GTAATCATCT    11520

TTAAACATGT CTCTACCTTT TCCTTCCCTT TTAAAGTTTT TAACCCGGAA TTAAAAGAT    11580

GGAAAGCTGT GGGGTGCAGC CCGGGGGATC CTTTTTATAG CTAATTAGTC ACGTACCTTT    11640

GAGAGTACCA CTTCAGCTAC CTCTTTTGTG TCTCAGAGTA ACTTTCTTTA ATCAATTCCA    11700

AAACACGTCG GGCCCCCTAG GAAAAATATC GATTAATCAG TGCATGGAAA CTCTCATGGT    11760

GAAGTCGATG GAGAAAACAC AGAGTCTCAT TGAAAGAAAT TAGTTAAGGT TTTGTGAGAG    11820

TAAATTACTA GCAGAAGCTA AGAGCGGAGC ACCATAGACC ATAGGAGGAG CAGATAATGT    11880

AGTATACTAA TATTAACTCA CATTTGACTA ATTAGCTATA AAACCCGGG ATCGATTCTA    11940

GAATAAAAAT TATCCCTGCC TAACTCTATT CACTACAGAG AGTACAGCAA AAACATTACA    12000

TCATATGATT ATAATTGAGT GTAAACTGAT TAATCGATAT TTTTGGGCCC TAGCTAAGAT    12060

CTTATTTTTA ATAGGGACGG ATTGAGATAA GTGATGTCTC TCATGTCGTT TTTGCAGAGA    12120

TAAGTATTCT TAAACCTACC AAGCCTCCTA CTATCATTAT GAATAATCTT TTTTCTCTCT    12180

GCACCACTCT TCTCTTTGCC TTGGTGGGTG CTACTCCTAA TGGTTCAATT GTTACTACTT    12240

TATAATAAGA ATTTGGATGG TTCGGAGGAT GATAGTAATA CTTATTAGAA AAAAGAGAGA    12300

CGTGGTGAGA AGAGAAACGG AACCACCCAC GATGAGGATT ACCAAGTTAA CAATGATGAA    12360
```

-continued

```
ATATGGGATA GTTAAGGGTT TATATAATTC ACTTCTCCAA TTGTCCCTCA TATCTCCTCC    12420

TCCAGGTCTG AAGATCTCGG TGTCGTTCGT GTCCGTGTCC TTACCACCAT CTCTTGTTAA    12480

TAGTAGCCCT GTAATATTAA ATATATTAAG TGAAGAGGTT AACAGGGAGT ATAGAGGAGG    12540

AGGTCCAGAC TTCTAGAGCC ACAGCAAGCA CAGGCACAGG AATGGTGGTA GAGAACAATT    12600

ATCATCGGGA CATTATAAGG GTTTGGTGTG GTGATGAACA TCTAATTTGT CCTTCAATGG    12660

GAGGGGCATA TATTGCTTTT CCTACTTCCT GCCACATGTT TATAATTTGT TTTATTTTGC    12720

ATTGAAGTGT GATATTGTTA TTTGACCCTG TACTACTTGT AGATTAAACA GGAAGTTACC    12780

CTCCCCGTAT ATAACGAAAA GGATGAAGGA CGGTGTACAA ATATTAAACA AAATAAAACG    12840

TAACTTCACA CTATAACAAT AAACTGGGAC ACGAAGCTGT GGAGTATTAT TCCAAGTATT    12900

ATTACCATTC CAAGTACTAT TAAACAGTGG TGATGAATTA CAGTAGAAGA ATTCCCCTCC    12960

ACAATTAAAA CTGTGCATTA CAATTTCTGG GTCCCCTCCT GATCATAATA AGGTTCATAA    13020

TAATGGTAAG GTTCATGATA ATTTGTCACC ACTACTTAAT GTCATCTTCT TAAGGGGAGG    13080

TGTTAATTTT GACACGTAAT GTTAAAGACC CAGGGGAGGA CTTTGTCGGC GGGGGGATTG    13140

ATTAAAGACT ATTGTTTTAT TCTTAAATTG TTCTTTTAAT TTGCTAACTA TCTGTCTTAA    13200

AGTGTCATTC CATTTGCTC TACTAATGTT ACAATGTGCT TGTCTTATAG TTCCCCTAAC    13260

TAATTTCTGA TAACAAAATA AGAATTTAAC AAGAAAATTA AACGATTGAT AGACAGAATT    13320

TCACAGTAAG GTAAAACGAG ATGATTACAA TGTTACACGA ACAGAATATC AAGGTTACAT    13380

GGGTATTATA TTTTTTGTTG TATAAAATGC TCTCCCTGGT CCTATATGTA TCCTTTTTCT    13440

TTTATTGTAG TTGGGTCTTG TACAATTAAT TTGTACAGAT TCATTCAGAT GTACTATGAT    13500

GGTATAATAT AAAAAACAAC ATATTTTACG AGAGGGACCA GGATATACAT AGGAAAAAGA    13560

AAATAACATC AACCCAGAAC ATGTTAATTA AACATGTCTA AGTAAGTCTA CATGACACTA    13620

CCATTAGGTC TGGTTTAGCA TTATCATTGA AATTCTCAGA TCTAATTACT ACCTCTTCTT    13680

CTGCTAGACT GCCATTTAAC AGCAGTTGAG TTGATACTAC TGGCCTAATT CCATGTGTAC    13740

ATTGTACTGT GCTAAATCGT AATAGTAACT TTAAGAGTCT AGATTAATGA TGGAGAAGAA    13800

GACGATCTGA CGGTAAATTG TCGTCAACTC AACTATGATG ACCGGATTAA GGTACACATG    13860

TAACATGACA CGAAAGTGTC TGGGACATTT TTACATGATC CTTTTCCACT GAACTTTTTA    13920

TCGTTACACT TTAGAATCGC AAAACCAGCC GGGGCACAAT AGTGTATGGG AATTGGCTCA    13980

AAGGATATCT TTGGACAAGC TTGCTGTAAA AATGTACTAG GAAAAGGTGA CTTGAAAAAT    14040

AGCAATGTGA AATCTTAGCG TTTTGGTCGG CCCCGTGTTA TCACATACCC TTAACCGAGT    14100

TTCCTATAGA AACCTGTTCG AACCGGCAGA ACCAGGTGTA ATGACTGAGG TATTACAACT    14160

TATCAACCTA TAGCTGGTAC TATCATTATT TATTGATACT ATATCAAGTT TATAAAGAAG    14220

TGCATATTCT TTCTGCATCT TATCTCTTAT GCTTGTACAT TACTGACTCC ATAATGTTGA    14280

ATAGTTGGAT ATCGACCATG ATAGTAATAA ATAACTATGA TATAGTTCAA ATATTTCTTC    14340

ACGTATAAGA AAGACGTAGA ATAGAGAATA CGAACATTCT ATGGGGTGAT ATTGAAAGAG    14400

CAGTTTTTCA TTTCTCCTCC CTTTATTGTT CCCTCGCTAT TACTATTGTT ATTAGCAGTA    14460

CTATTATTGG TATTAGTAGT ATTCCTCAAA TCAGTGCAAT TTAACCACTA TAACTTTCTC    14520

GTCAAAAAGT AAAGAGGAGG GAAATAACAA GGGAGCGATA ATGATAACAA TAATCGTCAT    14580

GATAATAACC ATAATCATCA TAAGGAGTTT AGTCACGTTA AATTTCGGTG ATTTTTCGGA    14640

GTAACACAGA GTGGGGTTAA TTTTACACAT GGCTTTAGGC TTTGATCCCA TAAACTGATT    14700
```

-continued

```
ATATCCTCAT GCATCTGTTC TACCATGTTA TTTTTCCACA TGTTAAAATT TTCTGTCACT    14760

CATTGTGTCT CACCCCAATT AAAATGTGTA CCGAAATCCG AAACTAGGGT ATTTGACTAA    14820

TATAGGAGTA CGTAGACAAG ATGGTACAAT AAAAAGGTGT ACAATTTTAA AAGACAGTGT    14880

CTCTGGATTT ACCAATTCTA CTTCTTGTGG GTTGGGGTCT GTGGGTACAC AGGCATGTGT    14940

GGCCCAAACA TTATGTACCT CTGTATCATA TGCTTTAGCA TCTGATGCAC AAAATAGAGT    15000

GGTGGTTAAA TGGTTAAGAT GAAGAACACC CAACCCCAGA CACCCATGTG TCCGTACACA    15060

CCGGGTTTGT AATACATGGA GACATAGTAT ACGAAATCGT AGACTACGTG TTTTATCTCA    15120

CCACCATCAT ATAAACTTTG GTGCTTCTTT CCACACAGGT ACCCCATAAT AGACTGTGAC    15180

CCACAATTTT TCTGTAGCAC TACAGATCAT CAACATCCCA AGGAGCATGG TGCCCCATCT    15240

CCACCCCCAT CTCCACAAGT GACGAAGAAA GGTGTGTCCA TGGGGTATTA TCTGACACTG    15300

GGTGTTAAAA AGACATCGTG ATGTCTAGTA GTTGTAGGGT TCCTCGTACC ACGGGGTAGA    15360

GGTGGGGGTA GAGGTGTTCA CAGTTACGTG GGGCTGATAT TTCTCCTTCA CTCTCATTGC    15420

CACTGTCTTC TGCTCTTTCA TATACGATAC AAACTTAACG CATATCGCGA TAATGAAATA    15480

ATTTATGATT ATTTCTCGCT TTCAATTTAA CACGACTATA AAGAGGAAGT GAGAGTAACG    15540

GTGACAGAAG ACGAGAAAGT ATATGCTATG TTTGAATTGC GTATAGCGCT ATTACTTTAT    15600

TAAATACTAA TAAAGAGCGA AAGTTAAATT GTGATGGACC ATAACCCTCA AGAACCTTTG    15660

TATTTATTTT CACTTTTTAA GTATAGAATA AAGAAGCTCT AATTAATTAA GCTACAAATA    15720

GTTTCGTTTT CACCTTGTCT AATAACTAAT TAATTAACCC GGTTGGGAGT TCTTGGAAAC    15780

ATAAATAAAA GTGAAAAATT CATATCTTAT TTCTTCGAGA TTAATTAATT CGATGTTTAT    15840

CAAAGCAAAA GTGGAACAGA TTATTGATTA ATTAATTGGG CCACCATATC TTGAGATAAA    15900

GTGAAAATAT ATATCATTAT ATTACAAAGT ACAATTATTT AGGTTTAATC ATGGGTGCGA    15960

GAGCGTCAGT ATTAAGCGGG GGAGAATTAG ATCGATGGGA AAAAATTTAG AACTCTATTT    16020

CACTTTTATA TATAGTAATA TAATGTTTCA TGTTAATAAA TCCAAATTAG TACCCACGCT    16080

CTCGCAGTCA TAATTCGCCC CCTCTTAATC TAGCTACCCT TTTTTAAACC ATGAAGGGAG    16140

GCGGTTAAGG CCAGGGGGAA AGAAAAAATA TAAATTAAAA CATATAGTAT GGGCAAGCAG    16200

GGAGCTAGAA CGATTCGCAG TTAATCCTGG CCTGTTAGAA ACATCAGAAG GCTGTAGACA    16260

AGCCAATTCC GGTCCCCCTT TCTTTTTTAT ATTTAATTTT GTATATCATA CCCGTTCGTC    16320

CCTCGATCTT GCTAAGCGTC AATTAGGACC GGACAATCTT TGTAGTCTTC CGACATCTGT    16380

TGGAAGTGCG AGGATACTGG GACAGCTACA ACCATCCCTT CAGACAGGAT CAGAAGAACT    16440

TAGATCATTA TATAATACAG TAGCAACCCT CTATTGTGTG CATCAAAGGA TAGAGATAAA    16500

AGACACCAAG GAATATGACC CTGTCGATGT TGGTAGGGAA GTCTGTCCTA GTCTTCTTGA    16560

ATCTAGTAAT ATATTATGTC ATCGTTGGGA GATAACACAC GTAGTTTCCT ATCTCTATTT    16620

TCTGTGGTTC CTTGTGTATC TGAGGGCTTT AGACAAGATA GAGGAAGAGC AAAACAAAAG    16680

TAAGAAAAAA GCACAGCAAG CAGCAGCTGA CACAGGACAC AGCAATCAGG TCAGCCAAAA    16740

TTACCCTATA GTGCAGAACA TCCAGCGAAA TCTGTTCTAT CTCCTTCTCG TTTTGTTTTC    16800

ATTCTTTTTT CGTGTCGTTC GTCGTCGACT GTGTCCTGTG TCGTTAGTCC AGTCGGTTTT    16860

AATGGGATAT CACGTCTTGT AGGTCAAAAA TGGAGGGGGC AAATGGTACA TCAGGCCATA    16920

TCACCTAGAA CTTTAAATGC ATGGGTAAAA GTAGTAGAAG AGAAGGCTTT CAGCCCAGAA    16980

GTGATACCCA TGTTTTCAGC ATTATCAGAA GGAGCCCCCG TTTACCATGT AGTCCGGTAT    17040

AGTGGATCTT GAAATTTACG TACCCATTTT CATCATCTTC TCTTCCGAAA GTCGGGTCTT    17100
```

-continued

```
CACTATGGGT ACAAAAGTCG TAATAGTCTT CCTCGGGATA AAGAGAGGAC CCCACAAGAT    17160

TTAAACACCA TGCTAAACAC AGTGGGGGGA CATCAAGCAG CCATGCAAAT GTTAAAAGAG    17220

ACCATCAATG AGGAAGCTGC AGAATGGGAT AGAGTGCATC CAGTGCATTG GGGTGTTCTA    17280

AATTTGTGGT ACGATTTGTG TCACCCCCCT GTAGTTCGTC GGTACGTTTA CAATTTTCTC    17340

TGGTAGTTAC TCCTTCGACG TCTTACCCTA TCTCACGTAG GTCACGTATT TGGAATAAGA    17400

GGGCAGGGCC TATTGCACCA GGCCAGATGA GAGAACCAAG GGGAAGTGAC ATAGCAGGAA    17460

CTACTAGTAC CCTTCAGGAA CAAATAGGAT GGATGACAAA TAATCCACCT ATCCCAGTAG    17520

GACGTCCCGG ATAACGTGGT CCGGTCTACT CTCTTGGTTC CCCTTCACTG TATCGTCCTT    17580

GATGATCATG GGAAGTCCTT GTTTATCCTA CCTACTGTTT ATTAGGTGGA TAGGGTCATC    17640

CTAGAGGAGT TTGTGGAGGG AAATTTATAA AAGATGGATA ATCCTGGGAT TAAATAAAAT    17700

AGTAAGAATG TATAGCCCTA CCAGCATTCT GGACATAAGA CAAGGACCAA AAGAACCCTT    17760

TAGAGACTAT GTAGACCGGC TTTAAATATT TTCTACCTAT TAGGACCCTA ATTTATTTTA    17820

TCATTCTTAC ATATCGGGAT GGTCGTAAGA CCTGTATTCT GTTCCTGGTT TTCTTGGGAA    17880

ATCTCTGATA CATCTGGCCG TGGAGGTTCT ATAAAACTCT AAGAGCCGAG CAAGCTTCAC    17940

AGGAGGTAAA AAATTGGATG ACAGAAACCT TGTTGGTCCA AAATGCGAAC CCAGATTGTA    18000

AGACTATTTT AAAAGCATTG GGACCAAAGA TATTTTGAGA TTCTCGGCTC GTTCGAAGTG    18060

TCCTCCATTT TTTAACCTAC TGTCTTTGGA ACAACCAGGT TTTACGCTTG GGTCTAACAT    18120

TCTGATAAAA TTTTCGTAAC CCTGGTTAAT TACTAGGAGG GCGGCTACAC TAGAAGAAAT    18180

GATGACAGCA TGTCAGGGAG TAGGAGGACC CGGCCATAAG GCAAGAGTTT TGGCTGAAGC    18240

AATGAGCCAA GTAACAAATT CAGCTACCAT AATGATGCAG CGCCGATGTG ATCTTCTTTA    18300

CTACTGTCGT ACAGTCCCTC ATCCTCCTGG GCCGGTATTC CGTTCTCAAA ACCGACTTCG    18360

TTACTCGGTT CATTGTTTAA GTCGATGGTA TTACTACGTC AATTACGGGG AAATATGAGG    18420

AGAGGCAATT TTAGGAACCA AAGAAAGATT GTTAAGTGTT TCAATTGTGG CAAAGAAGGG    18480

CACACAGCCA GAAATTGCAG GGCCCCTAGG AAAAAGGGCT GTTGGAAATG TGGAAAGGAA    18540

TCTCCGTTAA AATCCTTGGT TTCTTTCTAA CAATTCACAA AGTTAACACC GTTTCTTCCC    18600

GTGTGTCGGT CTTTAACGTC CCGGGGATCC TTTTTCCCGA CAACCTTTAC ACCTTTCCTT    18660

GCCGGTACAG CCGGAGGGGA CACCAAATGA AAGATTGTAC TGAGAGACAG GCTAATTTTT    18720

TAGGGAAGAT CTGGCCTTCC TACAAGGGAA GGCCAGGGAA TTTTCTTCAG AGCAGACCAG    18780

AGCCAACAGC CCCACCACCT GTGGTTTACT TTCTAACATG ACTCTCTGTC CGATTAAAAA    18840

ATCCCTTCTA GACCGGAAGG ATGTTCCCTT CCGGTCCCTT AAAAGAAGTC TCGTCTGGTC    18900

TCGGTTGTCG GGGTGGTGCT AGGGTAGAGG GAAGAGAGCT TCAGGTCTGG GGTAGAGACA    18960

ACAACTCCCC CTCAGAAGCA GGAGCCGATA GACAAGGAAC TGTATCCTTT AACTTCCCTC    19020

AGATCACTCT TTGGCAACGA CCCCTCGTCA CTTCTCTCGA AGTCCAGACC CCATCTCTGT    19080

TGTTGAGGGG GAGTCTTCGT CCTCGGCTAT CTGTTCCTTG ACATAGGAAA TTGAAGGGAG    19140

TCTAGTGAGA AACCGTTGCT GGGGAGCAGT GTTTTGTGAG GCAATAAAGA TAGGGGGGCA    19200

ACTAAAGGAA GCTCTATTAG ATACAGGAGC AGATGATACA GTATTAGAAG AAATGAGTTT    19260

GCCAGGAAGA TGGAAACCAA AAATGATAGG GGGAATTGGA GGTTATTTCT ATCCCCCCGT    19320

TGATTTCCTT CGAGATAATC TATGTCCTCG TCTACTATGT CATAATCTTC TTTACTCAAA    19380

CGGTCCTTCT ACCTTTGGTT TTTACTATCC CCCTTAACCT CTGGATGATG GGGAGGGTT    19440
```

```
TTATCAAAGT AAGACAGTAT GATCAGATAC TCATAGAAAT CTGTGGACAT AAAGCTATAG    19500

GTACAGTATT AGTAGGACCT ACACCTGTCA ACATAATTGG AAGAAATCTG TTGACTCCAA    19560

AATAGTTTCA TTCTGTCATA CTAGTCTATG AGTATCTTTA GACACCTGTA TTTCGATATC    19620

CATGTCATAA TCATCCTGGA TGTGGACAGT TGTATTAACC TTCTTTAGAC AACTGAGGCG    19680

AGTGTGTGAG GAGATTGGTT GCACTTTAAA TTTTTAACCC GGGGGATCCC GATTTTTATG    19740

ACTAGTTAAT CAAATAAAAA GCATACAAGC TATTGCTTCT CTAACCAACG TGAAATTTAA    19800

AAATTGGGCC CCCTAGGGCT AAAAATACTG ATCAATTAGT TTATTTTTCG TATGTTCGAT    19860

AACGAAGGCT CAGAGAG                                                  19877
```

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
GAAATAGTTA GCGTCAAC                                                 18
```

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
TGTCTAATGT GTTGAAGAAA AGATCATACA AGTTATAC                           38
```

(2) INFORMATION FOR SEQ ID NO:11:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
AACTTGTATG ATCTTTTCTT CAACACATTA GACATGTATT TAC                     43
```

(2) INFORMATION FOR SEQ ID NO:12:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TAAGTTTGTA TCGTAATGGA CTCTAAAGAG ACTATTC                            37
```

(2) INFORMATION FOR SEQ ID NO:13:

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGTCTCTTTA GAGTCCATTA CGATACAAAC TTAAC                                   35

(2) INFORMATION FOR SEQ ID NO:14:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CCGACGATTT TAAAACGCCA CCGTCAGGGA AAGTTTCATA AGAAGCACCG GAAGAGAAGA        60

GAATTCTCGG GACAATTGGA TC                                                 82

(2) INFORMATION FOR SEQ ID NO:15:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GTCTAGCTGG TGCTGAGTTT CTACGTGAGT TGATTCGTCT CTTGCGTGCC TCTCGTGATC        60

CAATTGTCCC GAGATATTCT C                                                  81

(2) INFORMATION FOR SEQ ID NO:16:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTAGAAACTC AGCACCAGCT AGACAAGCTT CTTTATTCTA TACTTAAAAA GTGAAAATAA        60

ATAC                                                                     64

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

ACTACTAATT AGCTATAAAA ACCCGGGATT AGTTTTTATT ACTAACTAAT TACTATACTG        60
```

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

ATCATCGGAT CCTTTAATAA TCTTATGAAC TTTTATAAAT ATGAG          45

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ATCATCGAAG AGCTTCCGCT ATCTGCATTA AAGTTT          36

(2) INFORMATION FOR SEQ ID NO:20:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

ATCATCCCCG GGAAGCTTTT AGTTATTGAA ATTAATCATA TA          42

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CATCATGAGC TCACTTATTA CATCCTACT          29

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TACTACGGTA CCTTTAATAA GCAATCACT          29

(2) INFORMATION FOR SEQ ID NO:23:

(i) SEQUENCE CHARACTERISTICS:
        (A) LENGTH: 59 base pairs (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:23:

CCCTCTAGAT CGCGATATCC GTTAAGTTTG TATCGTAATG CTTGCATTTT GTTATTCGT        59

(2) INFORMATION FOR SEQ ID NO:24:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:24:

CCCGAATTCA TAAAAATTAT TGATGTCTAC A        31

(2) INFORMATION FOR SEQ ID NO:25:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:25:

GGCCGCGTCG ACATGCA        17

(2) INFORMATION FOR SEQ ID NO:26:

(i) SEQUENCE CHARACTERISTICS:
    (A) LENGTH: 9 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

TGTCGACGC        9

(2) INFORMATION FOR SEQ ID NO:27:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:27:

TTTCATTATC GCGATATCCG TTAAGTTTGT ATCGTAATGT CCACTCGTGG CGATC        55

(2) INFORMATION FOR SEQ ID NO:28:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:28:

GGAGGGTTTC AGAGGCAG                                                  18

(2) INFORMATION FOR SEQ ID NO:29:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CCCCTCGAGT CGCGATATCC GTTAAGTTTG TATCGTAATG CCACTAACAG AAGAAGCA     58

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

AAATCTCCAC TCCATCCTTG TTTTCAGATT TTTAAA                              36

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

AATCTGAAAA CAGGAATGGA GTGGAGATTT GATTCT                              36

(2) INFORMATION FOR SEQ ID NO:32:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CCCAAGCTTA CAATTTTTAA AATATTCAGG                                     30

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CCCAAGCTTA TGGCAATATT CCAAAGTAGC                                    30

(2) INFORMATION FOR SEQ ID NO:34:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

TGGAAAACCT ACCATGGTTG TAAGTCCCCA CCTCAA                             36

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

TGGGGACTTA CAACCATGGT AGGTTTTCCA GTAACA                             36

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

TACAGTCTCA ATCATTGGTA CTAGCTTGTA GCACCA                             36

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

TACAAGCTAG TACCAATGAT TGAGACTGTA CCAGTA                             36

(2) INFORMATION FOR SEQ ID NO:38:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CCCCCTGCAG AAAAATTAAG GCCCAATTTT TGAAAT                             36

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TAGGAAGATA CGTATTATTT TATAC                                              25

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

ATCCCATTAT GAAAGCTTAT AG                                                 22

(2) INFORMATION FOR SEQ ID NO:41:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

CTCGAGCTGC AGGATATCAT CGATGGATCC TTTTTATAGC TAATTAGTCA CGTACCTTTA        60

TCATTAGTAA CAAAT                                                         75

(2) INFORMATION FOR SEQ ID NO:42:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GGATCCATCG ATGATATCCT GCAGCTCGAG TTTTTATGAC TAGTTAATCA CGGCCGCTCA        60

ATATTGTATT GGATGGTTAG                                                    80

(2) INFORMATION FOR SEQ ID NO:43:

(i) SEQUENCE CHARACTERISTICS:
        (A) LENGTH: 280 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:43:

Met Pro Leu Thr Glu Glu Ala Glu Leu Glu Leu Ala Glu Asn Arg Glu
1               5                   10                  15

Ile Leu Lys Glu Pro Val His Gly Val Tyr Tyr Asp Pro Ser Lys Asp

```
                    20                  25                  30
Leu Ile Ala Glu Ile Gln Lys Gln Gly Gln Gly Gln Trp Thr Tyr Gln
                35                  40                  45
Ile Tyr Gln Glu Pro Phe Lys Asn Leu Lys Thr Gly Met Glu Trp Arg
 50                  55                  60
Phe Asp Ser Arg Leu Ala Phe His His Val Ala Arg Glu Leu His Pro
 65                  70                  75                  80
Glu Tyr Phe Lys Asn Cys Lys Leu Met Ala Ile Phe Gln Ser Ser Met
                85                  90                  95
Thr Lys Ile Leu Glu Pro Phe Arg Lys Gln Asn Pro Asp Ile Val Ile
                100                 105                 110
Tyr Gln Tyr Met Asp Asp Leu Tyr Val Gly Ser Asp Leu Glu Ile Gly
                115                 120                 125
Gln His Arg Thr Lys Ile Glu Glu Leu Arg Gln His Leu Leu Arg Trp
                130                 135                 140
Gly Leu Thr Thr Met Val Gly Phe Pro Val Thr Pro Gln Val Pro Leu
145                 150                 155                 160
Arg Pro Met Thr Tyr Lys Ala Ala Val Asp Leu Ser His Phe Leu Lys
                165                 170                 175
Glu Lys Gly Gly Leu Glu Gly Leu Ile His Ser Gln Arg Arg Gln Asp
                180                 185                 190
Ile Leu Asp Leu Trp Ile Tyr His Thr Gln Gly Tyr Phe Pro Asp Trp
                195                 200                 205
Gln Asn Tyr Thr Pro Gly Pro Gly Val Arg Tyr Pro Leu Thr Phe Gly
                210                 215                 220
Trp Cys Tyr Lys Leu Val Pro Met Ile Glu Thr Val Pro Val Lys Leu
225                 230                 235                 240
Lys Pro Gly Met Asp Gly Pro Lys Val Lys Gln Trp Pro Leu Thr Glu
                245                 250                 255
Glu Lys Ile Lys Ala Leu Val Glu Ile Cys Thr Glu Met Glu Lys Glu
                260                 265                 270
Gly Lys Ile Ser Lys Ile Gly Pro
                275                 280

(2) INFORMATION FOR SEQ ID NO:44:

(i) SEQUENCE CHARACTERISTICS:
        (A) LENGTH: 550 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:44:

Gly Gln Arg Val Arg Asn Val Val Ser Leu Val Ala Phe Val Ile Arg
 1                   5                  10                  15
Leu Gly Val Leu Gly Gly Val Ile Met Ile Phe Leu Arg Lys Glu Arg
                20                  25                  30
Gln Val Val Arg Arg Lys Ala Lys Thr Pro Ala Val Gly Leu Pro Glu
                35                  40                  45
Ile Thr Val Val Lys Tyr Lys Tyr Leu Glu Ser Arg Trp Asn Asp Arg
 50                  55                  60
Met Asp Gly Gly Gly Pro Arg Phe Ile Glu Thr Asp Asn Thr Asp Thr
 65                  70                  75                  80
Asp Lys Gly Gly Asp Arg Thr Leu Leu Leu Gly Thr Ile Asn Ser Ser
```

-continued

```
                        85                  90                  95
Cys Arg Ile Gln Gly Glu Ile Pro Pro Ala Tyr Ile Ala Lys Gly Val
                    100                 105                 110

Glu Gln Trp Met Asn Ile Ile Gln Lys Ile Lys Cys Gln Leu Thr Ile
            115                 120                 125

Asn Asn Asn Ser Gly Thr Thr Asn Asn Trp Thr Asn Asn Gly Asn Trp
        130                 135                 140

Thr Ser Asn Phe Leu Pro Ser Ser Asn Cys Tyr Phe Glu Gly Gly
145                 150                 155                 160

Cys Asn Phe Ser His Met Val Ile Glu Pro Asp Gly Gly Ser Ser Gln
                165                 170                 175

Asn Phe Val Ile Thr Lys Asn Lys Phe Gln Glu Lys Leu Lys Ser Val
            180                 185                 190

Ile Gln Arg Leu Thr Asp Asn Trp Lys Ala Arg Ser Ile Asn Cys His
        195                 200                 205

Ala Gln Arg Ile Thr Gly Ile Ile Asn Lys Thr Thr Tyr Phe Ala Arg
    210                 215                 220

Gly Pro Gly Ile His Ile Arg Lys Arg Lys Asn Tyr Asn Pro Arg Thr
225                 230                 235                 240

Cys Asn Ile Gln Val Ser Glu Asn Leu His Val Ile Ile Thr Lys Ala
                245                 250                 255

Asn Asp Asn Phe Asn Glu Ser Arg Ile Val Val Glu Glu Ala Leu
            260                 265                 270

Ser Gly Asn Leu Leu Leu Gln Thr Ser Val Val Pro Arg Ile Gly His
        275                 280                 285

Thr Cys Gln Val Thr Ser Val Asn Lys Cys Ser Gly Lys Gly Ser Phe
    290                 295                 300

Lys Lys Asp Asn Cys Lys Leu Ile Ala Phe Gly Ala Pro Ala Cys Tyr
305                 310                 315                 320

His Ile Pro Ile Pro Glu Phe Ser Ile Lys Pro Cys Ala Gln Thr Ile
                325                 330                 335

Val Ser Thr Asn Cys Ser Ile Leu Arg Tyr Ser Thr Ser Asp Asn Asn
            340                 345                 350

Ile Ser Val Ile Asp Leu Lys Tyr Leu Leu Ala Tyr Glu Lys Gln Met
        355                 360                 365

Lys Asp Arg Ile Ser Thr Thr Ile Asn Phe Ser Cys Asn Lys Met Glu
    370                 375                 380

Gly Gly Lys Ile Thr Gly Glu Ser Asn Ser Asn Asn Ala Thr Ser
385                 390                 395                 400

Asn Asn Thr Asn Thr Thr Asn Arg Leu Asp Thr Cys Asn Leu Thr Val
                405                 410                 415

Cys Leu Pro Thr Leu Lys Val Cys Pro Lys Leu Ser Gln Asp Trp Leu
            420                 425                 430

Ser Ile Ile Asp Glu His Met Gln Glu Val Met Asn Asn Lys Trp Met
        435                 440                 445

Asn Phe Asn Glu Thr Val Asn Val Leu Glu Val Gln Pro Asn Pro
    450                 455                 460

Asp Thr Pro Val Cys Ala His Thr Ala Trp Val Asn His Val Glu Thr
465                 470                 475                 480

Asp Tyr Ala Lys Ala Asp Ser Ala Cys Phe Leu Thr Thr Ala Glu
                485                 490                 495

Lys Trp Val Pro Val Gly Tyr Tyr Val Thr Val Trp Leu Lys Glu Thr
            500                 505                 510
```

```
Ala Ser Cys Ile Met Leu Met Gly Leu Leu Met Thr Gly Trp Arg Trp
    515                 520                 525

Gly Trp Arg Trp Leu His Gln Tyr Lys Glu Lys Val Arg Met Ala Val
    530                 535                 540

Thr Lys Gln Glu Lys Met
545                 550
```

(2) INFORMATION FOR SEQ ID NO:45:

(i) SEQUENCE CHARACTERISTICS:
        (A) LENGTH: 500 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:45:

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
                20                  25                  30

His Ile Val Trp Ala Ser Arg Glu Leu Glu Arg Phe Ala Val Asn Pro
            35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
                100                 105                 110

Lys Lys Ala Gln Gln Ala Ala Ala Asp Thr Gly His Ser Asn Gln Val
            115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
    195                 200                 205

Ala Ala Glu Trp Asp Arg Val His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
    275                 280                 285

Pro Lys Glu Pro Phe Arg Asp Tyr Val Asp Arg Phe Tyr Lys Thr Leu
290                 295                 300
```

-continued

```
Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Ser Ala Thr Ile Met Met Gln Arg Gly Asn Phe Arg
370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
            435                 440                 445

Leu Gln Ser Arg Pro Glu Pro Thr Ala Pro Pro Glu Glu Ser Phe Arg
450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500
```

(2) INFORMATION FOR SEQ ID NO:46:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:46:

```
Pro Gln Ile Thr Leu Trp Gln Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Ser Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe
```

(2) INFORMATION FOR SEQ ID NO:47:

(i) SEQUENCE CHARACTERISTICS:
        (A) LENGTH: 88 amino acids
        (B) TYPE: amino acid (C) STRANDEDNESS: Not Relevant
(D) TOPOLOGY: linear (ii) MOLECULE TYPE: amino acid (xi) SEQUENCE DESCRIPTION: SEQ ID NO:47:

Gln His Arg Cys Met Arg Lys Tyr Asn Val Asp Ile Tyr Gly Lys Thr
1               5                   10                  15

Tyr Asp Val Arg Ile Val Lys Val Lys Val Thr Lys Gly Val Leu Lys
                20                  25                  30

Asp Arg Tyr Glu Val Tyr Arg Asp Met His Met Lys Val Ser Glu Ala
            35                  40                  45

Leu Ile Ala Glu Ser His Pro Tyr Asp Phe Leu Tyr Ile Tyr Leu Ala
50                      55                  60

Tyr Asp Lys Glu Tyr Val Arg Gly Lys Ile Val Asp Gly Ala Asn Pro
65                  70                  75                  80

Leu Ser Tyr Cys Phe Ala Leu Met
                85

(2) INFORMATION FOR SEQ ID NO:48:

(i) SEQUENCE CHARACTERISTICS:
        (A) LENGTH: 190 amino acids
        (B) TYPE: amino acid
        (C) STRANDEDNESS: Not Relevant
        (D) TOPOLOGY: linear (ii) MOLECULE TYPE: amino acid (xi) SEQUENCE DESCRIPTION: SEQ ID NO:48:

Phe Arg Ile Ile Val Tyr Gly Leu Leu Lys Asp Val Ala Leu Lys Ala
1               5                   10                  15

Ala Asn Asn Lys Ala Asp Arg Lys Ser Lys Gly Asp Ala Lys Asp Phe
                20                  25                  30

Val Arg Gly Asp Ile Asp Val Cys Ala Tyr Phe Thr Pro Ser Asn Ser
            35                  40                  45

Pro Gly Val Ser Glu Ile Arg Phe Ser Trp Asp Arg Lys Thr Ile Gln
    50                  55                  60

Cys Tyr Glu Asn Ile Ile Thr Val Pro Asn Ala Asp Lys Trp Asp Ile
65                  70                  75                  80

Ile Lys Lys Ala Pro Ile Val Asp Asp Phe Ser Lys His Asp Glu Arg
                85                  90                  95

Met Ser Lys Glu Arg Ser Val Asp Asp Ile Ile Val Asp Ala Met Ala
                100                 105                 110

Asp Ala Asp Pro Lys Asp Ala Glu Thr Thr Met Phe Trp Arg Pro Pro
            115                 120                 125

Ile Asp Asp Ser Ser Tyr Val Met Ala Ser Arg Gln Leu Asp Tyr Leu
130                 135                 140

Ala Lys Asn Val Glu Arg Lys Glu Met Asn Leu Gln Arg Thr Leu Gln
145                 150                 155                 160

Ala Ala Thr Ala Gly Glu Ile Gly Ile Asn Lys Ile Ala Ala Cys Val
                165                 170                 175

Ile Glu Ala Asp Ser Arg Glu Asp Ile Tyr Ile Lys Ser Met
                180                 185                 190